(12) United States Patent
Parham et al.

(10) Patent No.: US 11,530,224 B2
(45) Date of Patent: Dec. 20, 2022

(54) COMPOUNDS WITH DIAZADIBENZOFURANE OR DIAZADIBENZOTHIOPHENE STRUCTURES

(71) Applicant: Merck Patent GmbH, Darmstadt (DE)

(72) Inventors: Amir Parham, Frankfurt am Main (DE); Thomas Eberle, Landau (DE); Anja Jatsch, Frankfurt am Main (DE); Tobias Grossmann, Darmstadt (DE); Jonas Kroeber, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 434 days.

(21) Appl. No.: 16/338,309

(22) PCT Filed: Sep. 28, 2017

(86) PCT No.: PCT/EP2017/074585
§ 371 (c)(1),
(2) Date: Mar. 29, 2019

(87) PCT Pub. No.: WO2018/060307
PCT Pub. Date: Apr. 5, 2018

(65) Prior Publication Data
US 2020/0024282 A1    Jan. 23, 2020

(30) Foreign Application Priority Data

Sep. 30, 2016   (EP) .................................... 16191703

(51) Int. Cl.
  *C07D 491/048* (2006.01)
  *C07D 495/04* (2006.01)
  *H01L 51/00* (2006.01)
  *H01L 51/50* (2006.01)

(52) U.S. Cl.
  CPC ....... *C07D 491/048* (2013.01); *C07D 495/04* (2013.01); *H01L 51/0034* (2013.01); *H01L 51/0072* (2013.01); *H01L 51/0073* (2013.01); *H01L 51/0074* (2013.01); *H01L 51/5024* (2013.01)

(58) Field of Classification Search
  None
  See application file for complete search history.

(56) References Cited

U.S. PATENT DOCUMENTS

| 4,539,507 A | 9/1985 | VanSlyke et al. |
| 5,151,629 A | 9/1992 | VanSlyke |
| 5,840,217 A | 11/1998 | Lupo et al. |
| 6,458,909 B1 | 10/2002 | Spreitzer et al. |
| 2012/0223276 A1 | 9/2012 | Parham et al. |
| 2014/0225046 A1 | 8/2014 | Jatsch et al. |
| 2014/0291645 A1 | 10/2014 | Inoue et al. |
| 2015/0207082 A1 | 7/2015 | Dyatkin et al. |
| 2015/0243893 A1 | 8/2015 | Joseph et al. |
| 2015/0322198 A1* | 11/2015 | Hayer ..................... C08L 65/02 252/500 |
| 2015/0325799 A1 | 11/2015 | Hwang et al. |
| 2016/0308143 A1 | 10/2016 | Kim et al. |
| 2017/0186971 A1* | 6/2017 | Kanamoto .......... H01L 51/0074 |
| 2017/0200903 A1 | 7/2017 | Park et al. |
| 2019/0044071 A1 | 2/2019 | Parham et al. |
| 2020/0055865 A1 | 2/2020 | Kim et al. |
| 2020/0161564 A1 | 5/2020 | Kim et al. |
| 2021/0151689 A1 | 5/2021 | Hara et al. |

FOREIGN PATENT DOCUMENTS

| CN | 105849112 A | 8/2016 |
| CN | 109071580 A | 12/2018 |
| CN | 110099895 A | 8/2019 |
| CN | 110785421 A | 2/2020 |
| CN | 111094297 A | 5/2020 |
| CN | 111108108 A | 5/2020 |
| EP | 0676461 A2 | 10/1995 |
| EP | 3056498 A1 | 8/2016 |
| JP | 2011084531 A | 4/2011 |
| JP | 2013-510803 A | 3/2013 |
| JP | 5604848 B2 | 10/2014 |
| JP | 2015-157808 A | 9/2015 |
| JP | 2016-147851 A | 8/2016 |
| TW | 201326360 A | 7/2013 |
| WO | 9827136 A1 | 6/1998 |
| WO | 2014157599 A1 | 10/2014 |
| WO | WO-2015/108301 A1 * | 7/2015 |
| WO | 2015182872 A1 | 12/2015 |
| WO | 2016/102040 A1 | 6/2016 |
| WO | 2017/186760 A1 | 11/2017 |

OTHER PUBLICATIONS

International Search Report dated Nov. 20, 2017 in International Application No. PCT/EP2017/074585.
International Preliminary Reporton Patentability received for PCT Patent Application No. PCT/EP2017/074585, dated Apr. 11, 2019, 13 pages (8 pages of English Translation and 5 pages of Original Document).

* cited by examiner

*Primary Examiner* — Jay Yang
(74) *Attorney, Agent, or Firm* — Faegre Drinker Biddle & Reath LLP

(57) ABSTRACT

The present invention describes diazadibenzofuran or diazadibenzothiophene derivatives substituted by carbazole, fluorene, phenanthrene, benzofuran and/or benzothiophene groups, especially for use in electronic devices. The invention further relates to a process for preparing the compounds of the invention and to electronic devices comprising these.

52 Claims, No Drawings

COMPOUNDS WITH DIAZADIBENZOFURANE OR DIAZADIBENZOTHIOPHENE STRUCTURES

RELATED APPLICATIONS

This application is a national stage entry, filed pursuant to 35 U.S.C. § 371, of PCT/EP2017/074585, filed Sep. 28, 2017, which claims the benefit of European Patent Application No. 16191703.4, filed Sep. 30, 2016, which is incorporated herein by reference in its entirety.

The present invention describes diazadibenzofuran or diazadibenzothiophene derivatives, especially for use in electronic devices. The invention further relates to a process for preparing the compounds of the invention and to electronic devices comprising these compounds.

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime.

The properties of organic electroluminescent devices are not only determined by the emitters used. Also of particular significance here are especially the other materials used, such as host and matrix materials, hole blocker materials, electron transport materials, hole transport materials and electron or exciton blocker materials. Improvements to these materials can lead to distinct improvements to electroluminescent devices.

According to the prior art, heteroaromatic compounds, for example diazabenzofuran derivatives, are frequently used as matrix materials for phosphorescent compounds and as electron transport materials. In addition, carbazole derivatives are also used as matrix materials. Examples that are known for this function include diazadibenzofuran derivatives substituted by carbazole groups, as disclosed in JP 5604848 B2, WO 2015/182872 A1. In addition, WO 2014/157599 A1 and WO 2015/182872 A1 describe diazadibenzofuran derivatives which are substituted with fluorene, phenanthrene, triphenylene groups or dibenzothiophene groups. However, the diazadibenzofuran groups do not necessarily have twin substitution in the diazaphenyl radical of the diazadibenzofuran group by aryl or heteroaryl groups. Moreover, some of the compounds detailed have two diazaphenyl radicals in the diazadibenzofuran group.

In general terms, in the case of these materials, for example for use as matrix materials, there is still a need for improvement, particularly in relation to the lifetime, but also in relation to the efficiency and operating voltage of the device.

The problem addressed by the present invention is therefore that of providing compounds which are suitable for use in an organic electronic device, especially in an organic electroluminescent device, and which lead to good device properties when used in this device, and that of providing the corresponding electronic device.

More particularly, the problem addressed by the present invention is that of providing compounds which lead to a high lifetime, good efficiency and low operating voltage. Particularly the properties of the matrix materials too have an essential influence on the lifetime and efficiency of the organic electroluminescent device.

A further problem addressed by the present invention can be considered that of providing compounds suitable for use in a phosphorescent or fluorescent OLED, especially as a matrix material. It is a particular object of the present invention to provide matrix materials suitable for red-, yellow- and green-phosphorescing OLEDs and possibly also for blue-phosphorescing OLEDs.

Moreover, a further problem addressed by the present invention can be considered that of providing compounds suitable for use in a phosphorescent or fluorescent OLED, especially as electron transport materials.

Moreover, the compounds should be processible in a very simple manner, and especially exhibit good solubility and film formation. For example, the compounds should exhibit elevated oxidation stability and an improved glass transition temperature.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, particular compounds that are described in detail hereinafter solve these problems and eliminate the disadvantage from the prior art. The use of the compounds leads to very good properties of organic electronic devices, especially of organic electroluminescent devices, especially with regard to lifetime, efficiency and operating voltage. Electronic devices, especially organic electroluminescent devices, containing such compounds, and the corresponding preferred embodiments, are therefore provided by the present invention.

The present invention therefore provides a compound comprising structures of the following formula (A):

Formula (A)

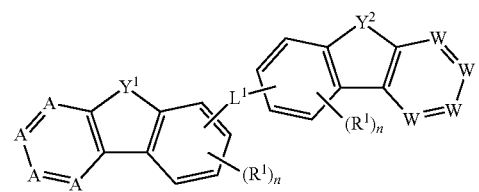

where the symbols used are as follows:
$Y^1$ is O or S;
$Y^2$ is $N(Ar)$, O, S, $C(R^1)_2$ or $—R^1C=CR^1—$;
W is the same or different at each instance and is N or $CR^1$, preferably $CR^1$, with the proviso that not more than two of the W groups in one cycle are N;
$L^1$ is a bond or an aromatic or heteroaromatic ring system which has 5 to 30 aromatic ring atoms and may be substituted by one or more $R^1$ radicals;
A is the same or different at each instance and is N, $CAr^a$ or $CAr^b$, where exactly two A are N separated by at least one $CAr^a$ or $CAr^b$ group, with the proviso that A is $CAr^b$ if two N are adjacent to this A;
Ar is the same or different at each instance and is an aromatic or heteroaromatic ring system which has 5 to 30 aromatic ring atoms and may be substituted by one or more $R^1$ radicals;

Ar$^a$ is the same or different at each instance and is an aromatic or heteroaromatic ring system which has 5 to 30 aromatic ring atoms and may be substituted by one or more R$^1$ radicals;

Ar$^b$ is the same or different at each instance and is an aromatic or heteroaromatic ring system which has 5 to 30 aromatic ring atoms and may be substituted by one or more R$^1$ radicals;

R$^1$ is the same or different at each instance and is H, D, F, Cl, Br, I, CN, NO$_2$, N(Ar$^1$)$_2$, N(R$^2$)$_2$, C(=O)Ar$^1$, C(=O)R$^2$, P(=O)(Ar$^1$)$_2$, P(Ar$^1$)$_2$, B(Ar$^1$)$_2$, Si(Ar$^1$)$_3$, Si(R$^2$)$_3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^2$ radicals, where one or more nonadjacent CH$_2$ groups may be replaced by —R$^2$C=CR$^2$—, —C≡C—, Si(R$^2$)$_2$, C=O, C=S, C=NR$^2$, —C(=O)O—, —C(=O)NR$^2$—, NR$^2$, P(=O)(R$^2$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a combination of these systems; at the same time, two or more substituents R$^1$ together may also form a mono- or polycyclic, aliphatic or aromatic ring system;

Ar$^1$ is the same or different at each instance and is an aromatic or heteroaromatic ring system which has 5 to 30 aromatic ring atoms and may be substituted by one or more nonaromatic R$^2$ radicals; at the same time, it is possible for two Ar$^1$ radicals bonded to the same silicon atom, nitrogen atom, phosphorus atom or boron atom also to be joined together via a bridge by a single bond or a bridge selected from B(R$^2$), C(R$^2$)$_2$, Si(R$^2$)$_2$, C=O, C=NR$_2$, C=C(R$^2$)$_2$, O, S, S=O, SO$_2$, N(R$^2$), P(R$^2$) and P(=O)R$^2$;

R$^2$ is the same or different at each instance and is H, D, F, Cl, Br, I, CN, B(OR$^3$)$_2$, CHO, C(=O)R$^3$, CR$^3$=C(R$^3$)$_2$, C(=O)OR$^3$, C(=O)N(R$^3$)$_2$, Si(R$^3$)$_3$, P(R$^3$)$_2$, B(R$^3$)$_2$, N(R$^3$)$_2$, NO$_2$, P(=O)(R$^3$)$_2$, OSO$_2$R$^3$, OR$^3$, S(=O)R$^3$, S(=O)$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by —R$^3$C=CR$^3$—, —C≡C—, Si(R$^3$)$_2$, C=O, C=S, C=NR$^3$, —C(=O)O—, —C(=O)NR$^3$—, NR$^3$, P(=O)(R$^3$), —O—, —S—, SO or SO$_2$ and where one or more hydrogen atoms may be replaced by D, F, Cl, Br, I, CN or NO$_2$, or an aromatic or heteroaromatic ring system which has 5 to 40 aromatic ring atoms and may be substituted in each case by one or more R$^3$ radicals, or an aryloxy or heteroaryloxy group which has 5 to 40 aromatic ring atoms and may be substituted by one or more R$^3$ radicals, or a combination of these systems; at the same time, two or more adjacent R$^2$ substituents together may also form a mono- or polycyclic, aliphatic or aromatic ring system;

R$^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent R$^3$ substituents together may also form a mono- or polycyclic, aliphatic or aromatic ring system;

n is 0, 1, 2 or 3, preferably 0, 1 or 2, more preferably 0 or 1, especially preferably 0;

with the proviso that, if the Y$^2$ group is N(Ar), O or S, the Ar$^a$ radical does not compromise any carbazole group, including R$^1$, R$^2$ and R$^3$ substituents that may be bonded to the Ar$^a$ radical.

Adjacent carbon atoms in the context of the present invention are carbon atoms bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

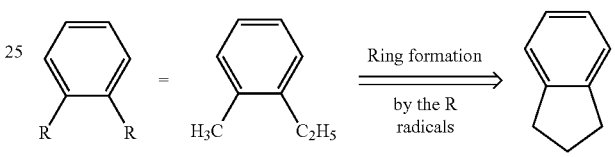

In addition, however, the abovementioned wording shall also be understood to mean that, if one of the two radicals is hydrogen, the second radical binds to the position to which the hydrogen atom was bonded, forming a ring. This shall be illustrated by the following scheme:

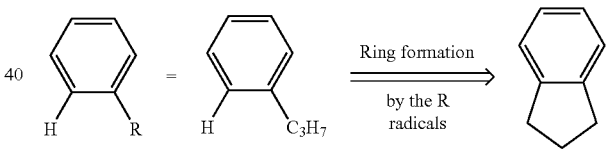

A fused aryl group, a fused aromatic ring system or a fused heteroaromatic ring system in the context of the present invention is a group in which two or more aromatic groups are fused, i.e. annelated, to one another along a common edge, such that, for example, two carbon atoms belong to the at least two aromatic or heteroaromatic rings, as, for example, in naphthalene. By contrast, for example, fluorene is not a fused aryl group in the context of the present invention, since the two aromatic groups in fluorene do not have a common edge. Corresponding definitions apply to heteroaryl groups and to fused ring systems which may but need not also contain heteroatoms.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred configuration, the compounds of the invention may form a structure of the formula (I), (II) or (III)

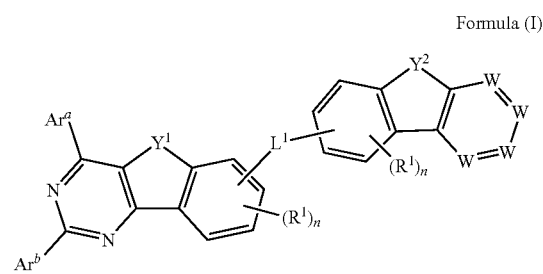

Formula (I)

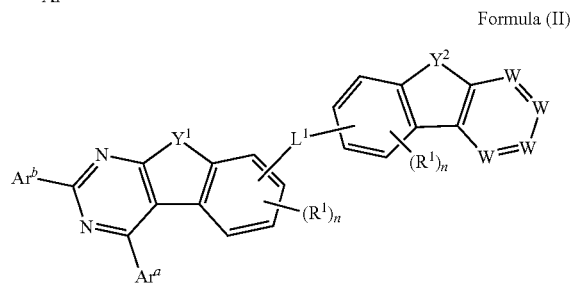

Formula (II)

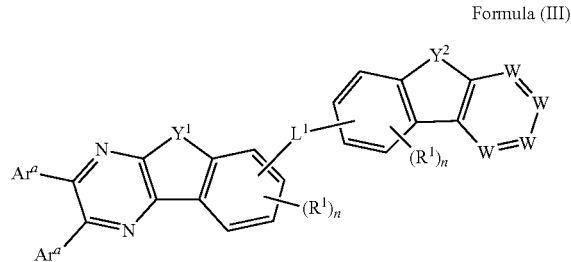

Formula (III)

in which the symbols $Ar^a$, $Ar^b$, $Y^1$, $L^1$, $Y^2$, $R^1$, n and W have the definition set out above for formula (A). Preference is given to compounds having structures of the formula (I) and/or (II).

Preferably, the compounds of the invention may comprise structures of formulae (Ia), (IIa) and/or (IIIa)

Formula (Ia)

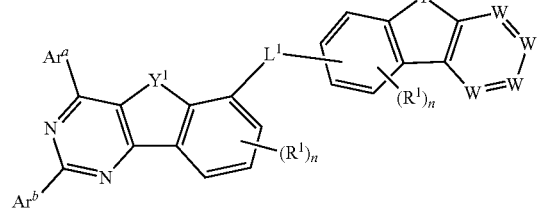

Formula (IIa)

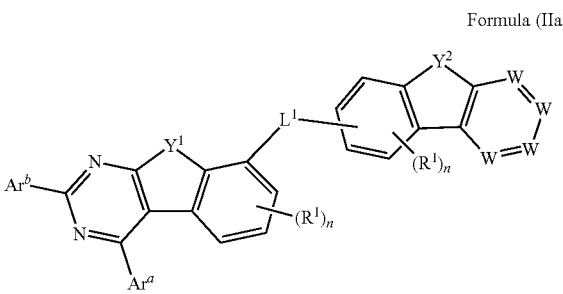

Formula (IIIa)

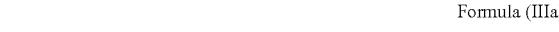

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (Ia) and/or (IIa).

Preferably, the compounds of the invention may comprise structures of at least one of the formulae (Ib), (IIb) and/or (IIIb)

Formula (Ib)

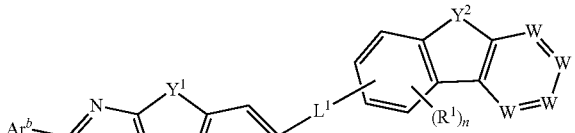

Formula (IIb)

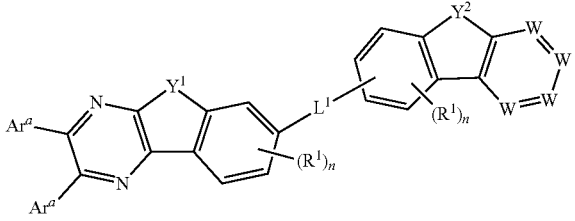

Formula (IIIb)

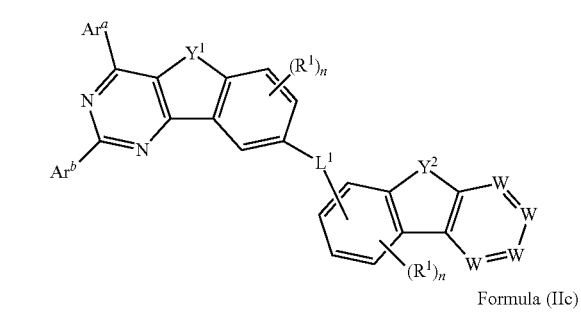

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (Ib) and/or (IIb).

Preferably, the compounds of the invention may comprise structures of at least one of the formulae (Ic), (IIc) and/or (IIIc)

Formula (Ic)

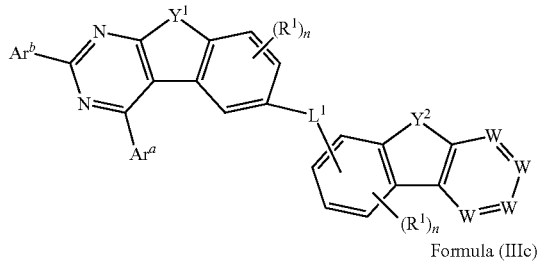

Formula (IIc)

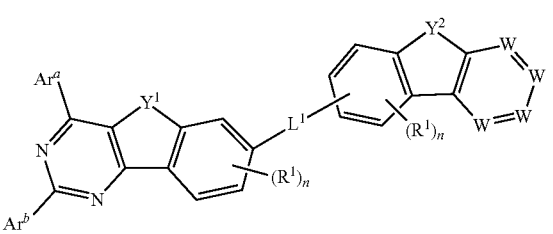

Formula (IIIc)

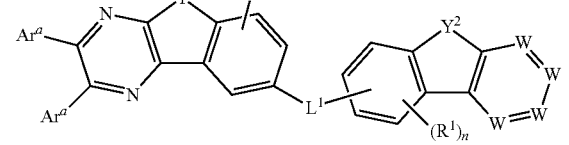

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (Ic) and/or (IIc).

It may also be the case that the compound comprises at least one of the structures of the formulae (Id), (IId) and/or (IIId)

Formula (Id)

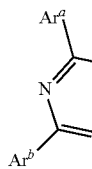

Formula (IId)


Formula (IIId)

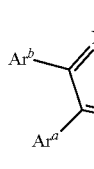

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (Id) and/or (IId).

Of the above-detailed compounds comprising structures of the formulae (Ia) to (IIId), preference is given to those compounds containing structures of the formulae (Ic), (IIc), (IIIc), (Id), (IId) and/or (IIId), particular preference being given to compounds having structures of the formulae (Ic), (IIc) and/or (IIIc).

It may additionally be the case that the compound comprises at least one of the structures of the formulae (Ie), (IIe) and/or (IIIe)

Formula (Ie)


Formula (IIe)

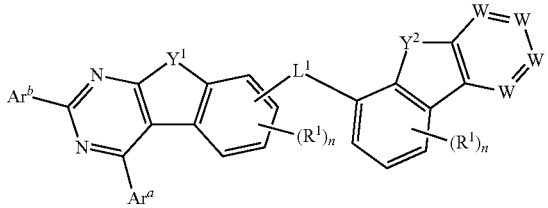

Formula (IIIe)

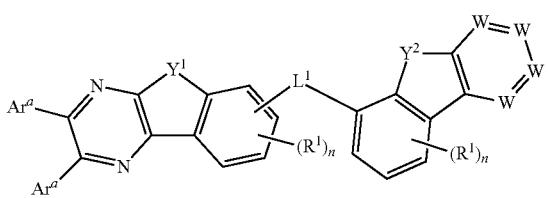

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (Ie) and/or (IIe).

It may further be the case that the compound comprises at least one of the structures of the formulae (If), (IIf) and/or (IIIf)

Formula (If)

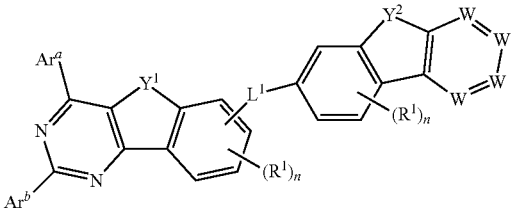

Formula (IIf)

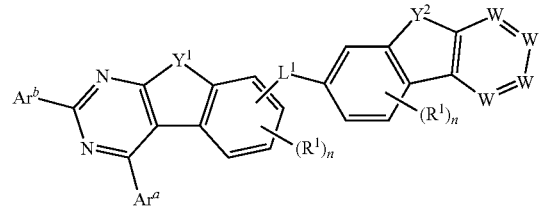

Formula (IIIf)

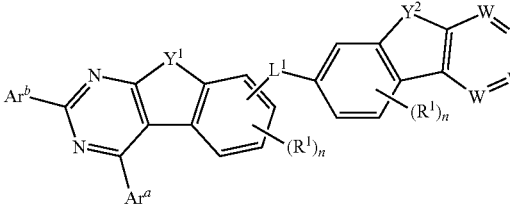

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (If) and/or (IIf).

Preferably, the compounds of the invention may comprise structures of at least one of the formulae (Ig), (IIg) and/or (IIIg)

Formula (Ig)

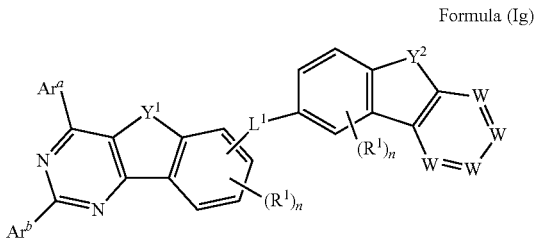

Formula (IIg)

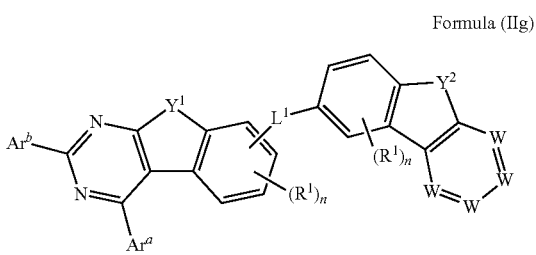

Formula (IIIg)

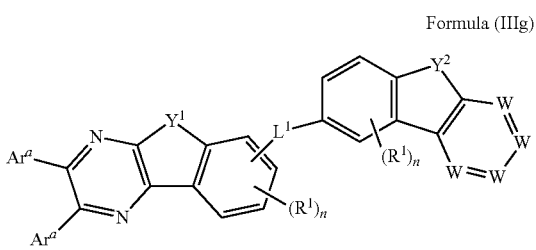

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (Ig) and/or (IIg).

It may also be the case that the compound of the invention comprises at least one of the structures of the formulae (Ih), (IIh) and/or (IIIh)

Formula (Ih)

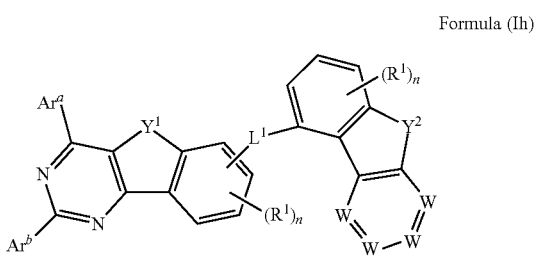

Formula (IIh)

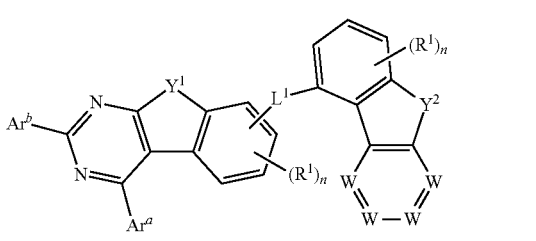

Formula (IIIh)

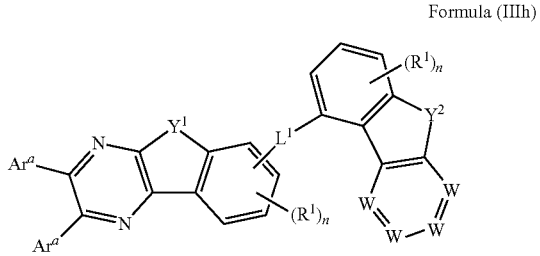

in which the symbols $Ar^a$, $Ar^b$, $Y^1$, $L^1$, $Y^2$, $R^1$, n and W have the definition set out above, especially for formula (A), (I), (II) or (III), preference being given to structures of the formula (Ih) and/or (IIh).

Of the above-detailed compounds comprising structures of the formulae (Ie) to (IIIh), preference is given to those compounds containing structures of the formulae (Ig), (IIg), (IIIg), (Ih), (ah) and/or (IIIh), particular preference being given to compounds having structures of the formulae (Ig), (IIg) and/or (IIIg).

It may additionally be the case that the substituents $R^1$ of the structures of one of the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) that are not part of a $CR^1$ group represented by the symbol W do not form a fused aromatic or heteroaromatic ring system with the ring atoms of the respective ring structure, and preferably do not form any fused ring system. This includes the formation of a fused ring system with possible $R^2$, $R^3$ substituents which may be bonded to the $R^1$ radicals. It may preferably be the case that the substituents $R^1$ of the structures of one of the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) that are not part of a $CR^1$ group represented by the symbol W do not form any ring system with the ring atoms of the respective ring structure. This includes the formation of a ring system with possible $R^2$, $R^3$ substituents which may be bonded to the $R^1$ radicals.

It may also be the case that the sum total of the indices n in the structures of the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) in each case is not more than 3, preferably not more than 2 and more preferably not more than 1.

In the structures of the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), it is possible that two adjacent W groups are each $CR^1$ and together form a group of the formula (W-1)

Formula (W-1)

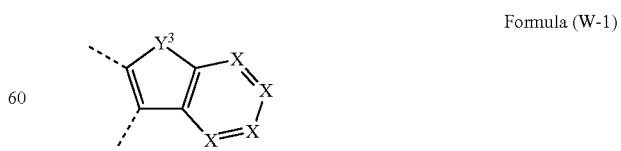

in which
$Y^3$ is N(Ar), O, S or $C(R^2)_2$, preferably $C(R^2)_2$,
X is the same or different at each instance and is N or $CR^2$, preferably $CR^2$, with the proviso that not more than two of the X groups in one cycle are N, where Ar and $R^2$ may have the definition given above, especially for formula (A), and the dotted lines represent the bonds to the adjacent atoms. Preferably, the compounds comprising structures of the formula (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) preferably have not more than one group of the formula (W-1) per structure.

Preference is further given to compounds which are characterized in that, in formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), not more than two W groups are N, preferably not more than one W group is N, and preferably all W are $CR^1$, where preferably not more than 4, more preferably not more than 3 and especially preferably not more than 2 of the $CR^1$ groups that W represents are not the CH group.

It may also be the case that the $R^1$ radicals of the W groups in the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) do not form a fused aromatic or heteroaromatic ring system with the ring atoms of the ring structure, and preferably do not form any fused ring system. This includes the formation of a fused ring system with possible $R^2$, $R^3$ substituents which may be bonded to the $R^1$ radicals. It may preferably be the case that the $R^1$ radicals of the W groups in the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) do not form any ring system with the ring atoms of the ring structure. This includes the formation of a ring system with possible $R^2$, $R^3$ substituents which may be bonded to the $R^1$ radicals.

In a preferred embodiment of the compounds according to the invention, comprising structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) the symbol $Y^2$ is $C(R^1)$ and $R^1$ is the same or different in each case and is an aromatic or heteroaromatic ring system which has 5 to 40 aromatic ring atoms and may be substituted in each case by one or more $R^2$ radicals.

It may additionally be the case that, in the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), the symbol $Y^2$ is a group of the formula ($Y^2$-1)

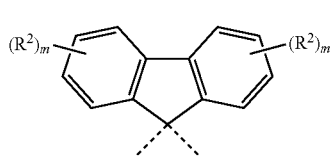

Formula ($Y^2$-1)

in which the dotted lines represent the bonds to the adjacent atoms, $R^2$ has the definition given above, especially for formula (A), and m is 0, 1, 2, 3 or 4, preferably 0, 1 or 2.

It may also be the case that, in the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), the symbol $Y^2$ is a group of the formula ($Y^2$-2)

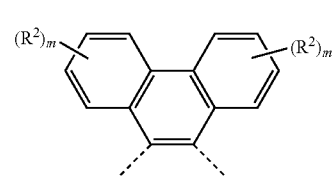

Formula ($Y^2$-2)

in which the dotted lines represent the bonds to the adjacent atoms, $R^2$ has the definition given above, especially for formula (A), and m is 0, 1, 2, 3 or 4, preferably 0, 1 or 2.

It may preferably be the case that the sum total of the indices m in the structures of the formula ($Y^2$-1) and/or ($Y^2$-2) in each case is not more than 3, preferably not more than 2 and especially preferably not more than 1.

It may also be the case that the $R^1$ radicals in the structures of the formula ($Y^2$-1) and/or ($Y^2$-2) do not form any fused aromatic or heteroaromatic ring system with the ring atoms of the ring structure, preferably any fused ring system. This includes the formation of a fused ring system with possible $R^2$, $R^3$ substituents that may be bonded to the $R^1$ radicals. It may preferably be the case that the $R^1$ radicals in the structures of the formula ($Y^2$-1) and/or ($Y^2$-2) do not form any ring system with the ring atoms of the ring structure. This includes the formation of a ring system with possible $R^2$, $R^3$ substituents that may be bonded to the $R^1$ radicals.

In a further preferred configuration, in structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), the symbol $Y^1$ may be O or S and symbol $Y^2$ may be N(Ar).

Preferably, in the structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) one of the Ar, $Ar^a$ and/or $Ar^b$ groups has not more than 5 heteroatoms, preferably not more than 3 heteroatoms and more preferably not more than 1 heteroatom, where this includes $R^1$, $R^2$ and $R^3$ substituents that may be bonded to these groups. Especially preferably, the Ar, $Ar^a$ and/or $Ar^b$ groups do not have any heteroatom, where this includes $R^1$, $R^2$ and $R^3$ substituents that may be bonded to these groups.

It may also be the case that the Ar, $Ar^a$ and/or $Ar^b$ groups in structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) have a total of not more than 5 heteroatoms, preferably not more than 3 heteroatoms and more preferably not more than 1 heteroatom, where this includes $R^1$, $R^2$ and $R^3$ substituents that may be bonded to these groups.

It may additionally be the case that the Ar, $Ar^a$ and/or $Ar^b$ groups in structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) have a total of not more than 50, preferably not more than 40 and more preferably not more than 22 aromatic ring atoms, where this includes $R^1$, $R^2$ and $R^3$ substituents that may be bonded to these groups.

It may further be the case that the Ar radical in structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) does not comprise any carbazole group, where this includes $R^1$, $R^2$ and $R^3$ substituents that may be bonded to the Ar radical.

Preferably, the $Ar^a$ radical in structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) does not comprise any carbazole group, where this includes $R^1$, $R^2$ and $R^3$ substituents that may be bonded to the $Ar^a$ radical.

In a further-preferred configuration, the $Ar^b$ group in structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) may be a group of the formula ($Ar^b$-1).

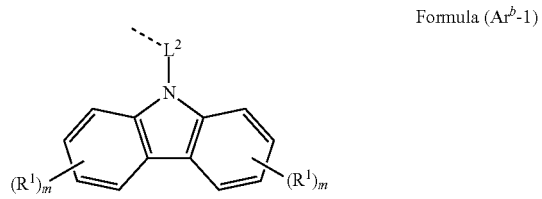

Formula ($Ar^b$-1)

in which $L^2$ is a bond or an aromatic or heteroaromatic ring system which has 5 to 30 aromatic ring atoms and may be substituted by one or more $R^1$ radicals, the symbol $R^1$ has the definition given above, especially for formula (A), m is 0, 1, 2, 3 or 4, preferably 0, 1 or 2, and the dotted line represents the bond to the diazadibenzofuran or diazadibenzothiophene group.

Preference is given inter alia to compounds comprising structures of the formula (IV) and/or (V)

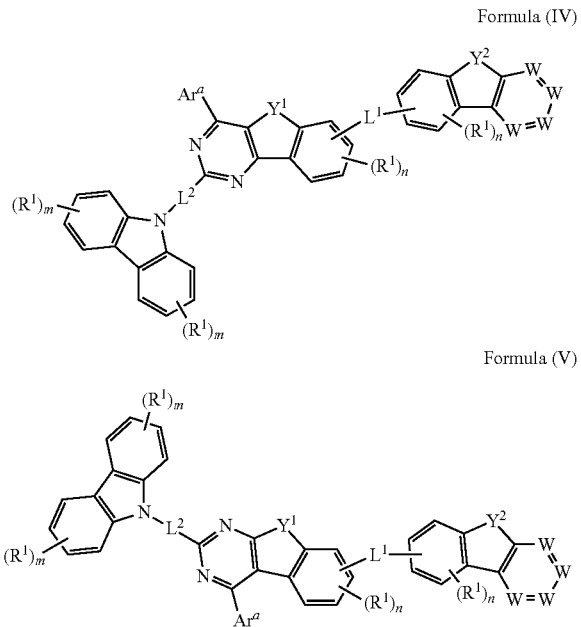

Formula (IV)

Formula (V)

in which $L^2$ is a bond or an aromatic or heteroaromatic ring system which has 5 to 30 aromatic ring atoms and may be substituted by one or more $R^1$ radicals, the symbols $Ar^a$, $Y^1$, $L^1$, $Y^2$, $R^1$, n and W have the definition given above, especially for formula (A), m is 0, 1, 2, 3 or 4, preferably 0, 1 or 2, and the dotted line represents the bond.

It may preferably be the case that the sum total of the indices m in the structures of the formulae ($Ar^b$-1), (IV) and/or (V) in each case is not more than 3, preferably not more than 2 and more preferably not more than 1.

It may also be the case that the $R^1$ radicals in the structures of the formulae ($Ar^b$-1), (IV) and/or (V) do not form a fused aromatic or heteroaromatic ring system with the ring atoms of the ring structure to which the $R^1$ radical binds, and preferably do not form any fused ring system. This includes the formation of a fused ring system with possible $R^2$, $R^3$ substituents which may be bonded to the $R^1$ radicals. It may preferably be the case that the $R^1$ radicals in the structures of the formulae ($Ar^b$-1), (IV) and/or (V) do not form a ring system with the ring atoms of the ring structure. This includes the formation of a ring system with possible $R^2$, $R^3$ substituents which may be bonded to the $R^1$ radicals.

For structures of the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) in which $Y^2$ is $C(R^1)_2$ or $-R^1C=CR^1-$, the $Ar^a$ radical may likewise be a group of the formula ($Ar^b$-1).

It may also be the case that the Ar, $Ar^a$ and/or $Ar^b$ radical is selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, spirobifluorenyl, fluorenyl, dibenzofuranyl, dibenzothiophenyl, anthracenyl, phenanthrenyl and/or triphenylenyl, each of which may be substituted by one or more $R^2$ radicals, but are preferably unsubstituted, particular preference being given to spirobifluorene, fluorene, dibenzofuran, dibenzothiophene, anthracene, phenanthrene, triphenylene groups.

In a further embodiment neither $Ar^a$ nor $Ar^b$ of the above mentioned compounds comprise a carbazole group, a dibenzofurane group or dibenzothiophene group. Particular preferred is if neither $Ar^a$ nor $Ar^b$ of the above mentioned compounds comprise a condensed heteroaromaatic group. Very particularly preferred is if neither $Ar^a$ nor $Ar^b$ of the above mentioned compounds comprise a heteroaromatic group.

In a preferred configuration, compounds comprising structures of formula (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) can be represented by structures of the formula (A), (I), (ii), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V). Preferably, compounds comprising structures of formula (A), (I), (ii), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V), (VII) and/or (VIII) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

When W is $CR^1$ or when the aromatic and/or heteroaromatic groups are substituted by $R^1$ substituents, these $R^1$ substituents are preferably selected from the group consisting of H, D, F, CN, N(Ar$^1$)$_2$, C(=O)Ar$^1$, P(=O)(Ar$^1$)$_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more R$^2$ radicals, where one or more nonadjacent CH$_2$ groups may be replaced by 0 and where one or more hydrogen atoms may be replaced by D or F, an aromatic or heteroaromatic ring system which has 5 to 24 aromatic ring atoms and may be substituted in each case by one or more R$^2$ radicals, but is preferably unsubstituted, or an aralkyl or heteroaralkyl group which has 5 to 25 aromatic ring atoms and may be substituted by one or more R$^2$ radicals; at the same time, it is optionally possible for two R$^1$ substituents bonded to the same carbon atom or to adjacent carbon atoms to form a monocyclic or polycyclic, aliphatic, aromatic or heteroaromatic ring system which may be substituted by one or more R$^1$ radicals, where Ar$^1$ is the same or different at each instance and represents an aromatic or heteroaromatic ring system which has 6 to 40 carbon atoms and may be substituted in each case by one or more R$^2$ radicals, an aryloxy group which has 5 to 60 aromatic ring atoms and may be substituted by one or more R$^2$ radicals, or an aralkyl group which has 5 to 60 aromatic ring atoms and may be substituted in each case by one or more R$^2$ radicals, where two or more adjacent R$^2$ substituents may optionally form a mono- or polycyclic aliphatic ring system which may be substituted by one or more R$^3$ radicals, where the symbol R$^2$ has the definition given above, especially for formula (A). Preferably, Ar$^1$ is the same or different at each instance and is an aryl or heteroaryl group which has 5 to 24 and preferably 5 to 12 aromatic ring atoms, and which may be substituted in each case by one or more R$^2$ radicals, but is preferably unsubstituted.

Examples of suitable Ar$^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R$^2$ radicals, but are preferably unsubstituted.

More preferably, these R$^1$ substituents are selected from the group consisting of H, D, F, CN, N(Ar$^1$)$_2$, a straight-chain alkyl group having 1 to 8 carbon atoms, preferably having 1, 2, 3 or 4 carbon atoms, or a branched or cyclic alkyl group having 3 to 8 carbon atoms, preferably having 3 or 4 carbon atoms, or an alkenyl group having 2 to 8 carbon atoms, preferably having 2, 3 or 4 carbon atoms, each of which may be substituted by one or more R$^2$ radicals, but is preferably unsubstituted, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more nonaromatic R$^1$ radicals, but is preferably unsubstituted; at the same time, it is optionally possible for two R$^1$ substituents bonded to the same carbon atom or to adjacent carbon atoms to form a monocyclic or polycyclic aliphatic ring system which may be substituted by one or more R$^2$ radicals, but is preferably unsubstituted, where Ar$^1$ may have the definition set out above.

Most preferably, the R$^1$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic R$^2$ radicals, but is preferably unsubstituted. Examples of suitable R$^1$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R$^2$ radicals, but are preferably unsubstituted.

It may additionally be the case that, in a structure of formula (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V), at least one R$^1$, Ar, Ar$^1$, Ar$^a$ or Ar$^b$ radical is a group selected from the formulae (R$^1$-1) to (R$^1$-87):

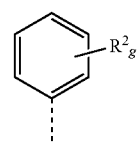

Formula (R$^1$-1)

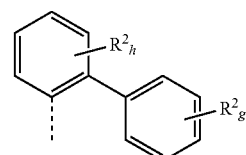

Formula (R$^1$-2)

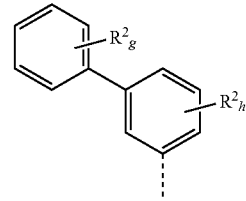

Formula (R$^1$-3)

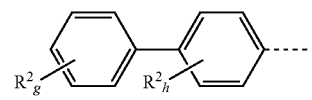

Formula (R$^1$-4)

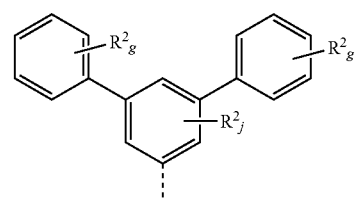

Formula (R$^1$-5)

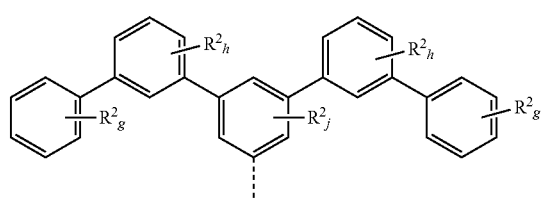

Formula (R$^1$-6)

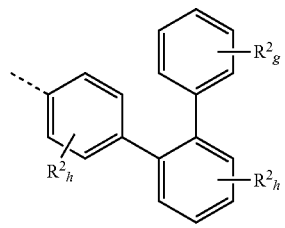
Formula (R¹-7)
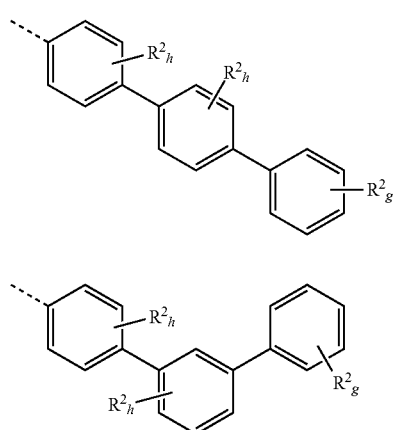
Formula (R¹-8)
Formula (R¹-9)
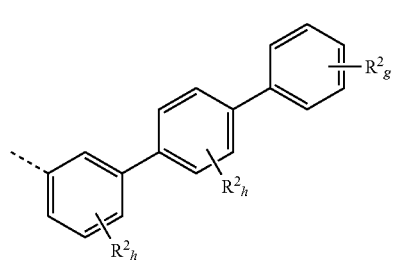
Formula (R¹-10)
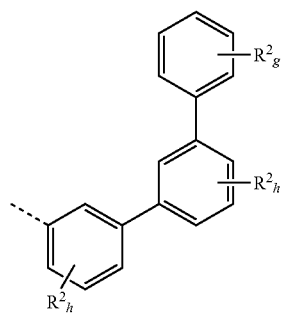
Formula (R¹-11)
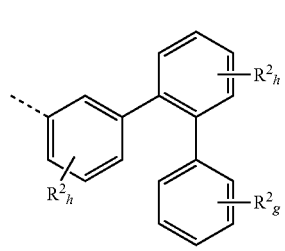
Formula (R¹-12)
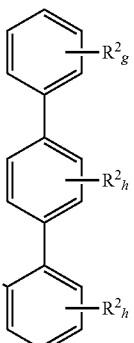
Formula (R¹-13)
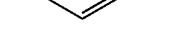
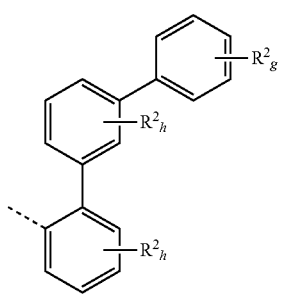
Formula (R¹-14)
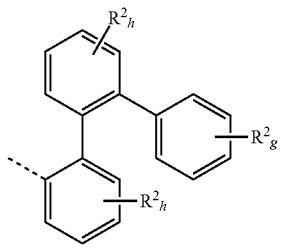
Formula (R¹-15)
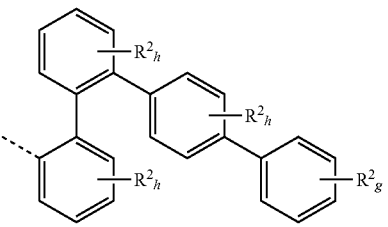
Formula (R¹-16)
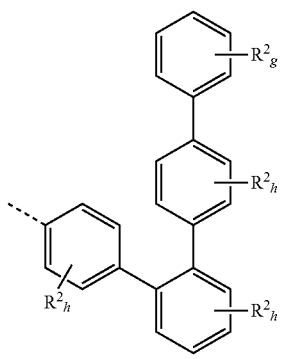
Formula (R¹-17)

Formula (R¹-18)
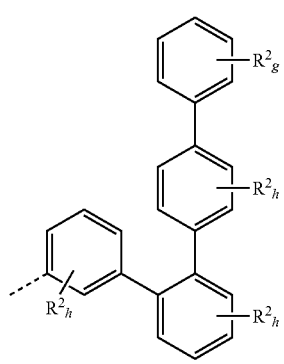
Formula (R¹-19)
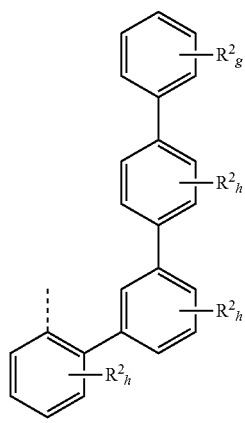
Formula (R¹-20)
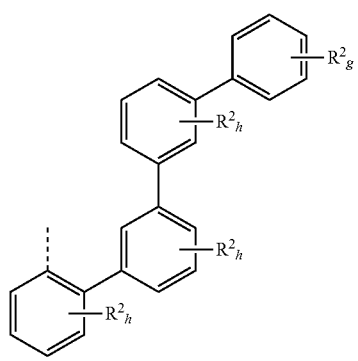
Formula (R¹-21)
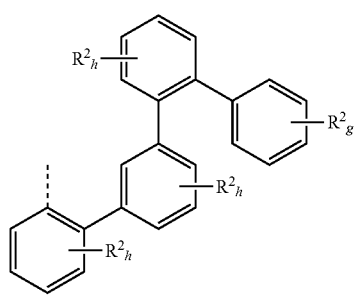
Formula (R¹-22)
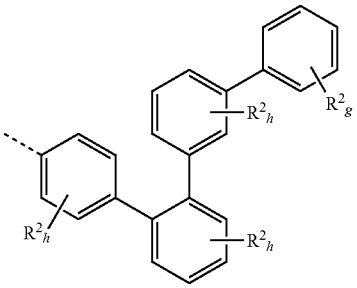
Formula (R¹-23)
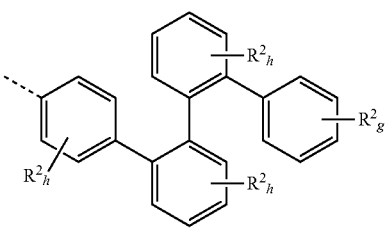
Formula (R¹-24)
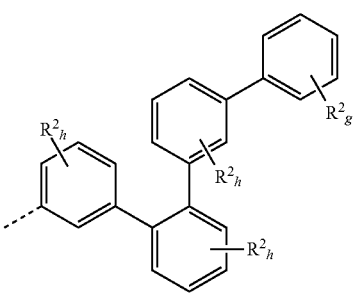
Formula (R¹-25)
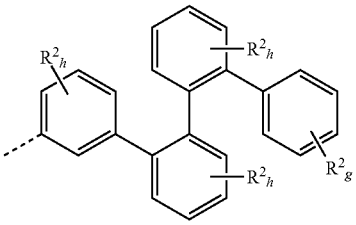
Formula (R¹-26)
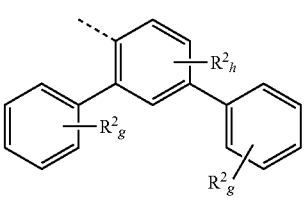
Formula (R¹-27)
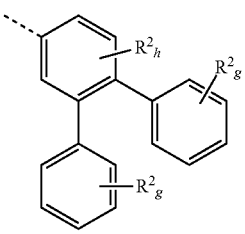

Formula (R¹-28)
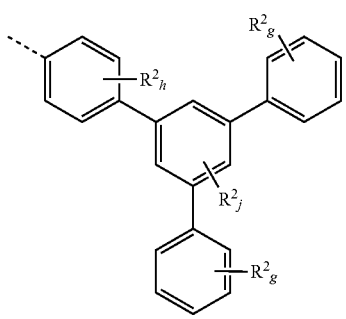
Formula (R¹-29)
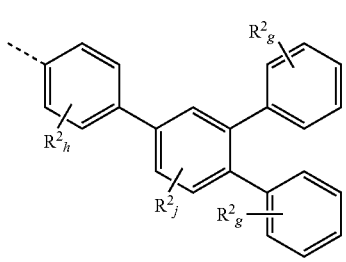
Formula (R¹-30)
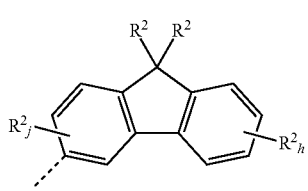
Formula (R¹-31)
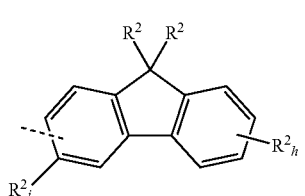
Formula (R¹-32)
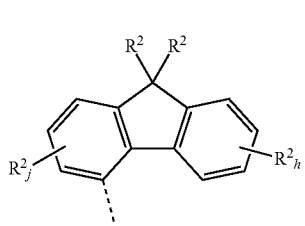
Formula (R¹-33)
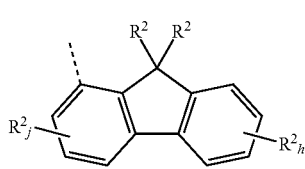
Formula (R¹-34)
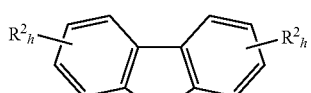
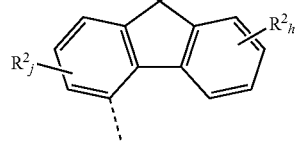
Formula (R¹-35)
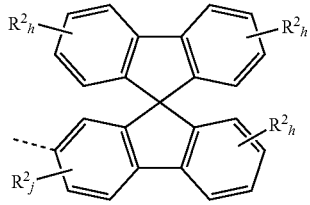
Formula (R¹-36)
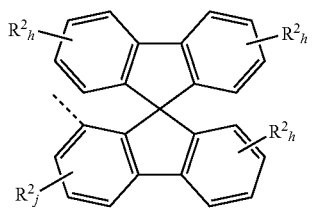
Formula (R¹-37)
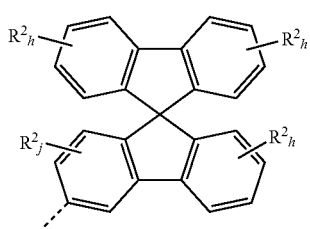
Formula (R¹-38)
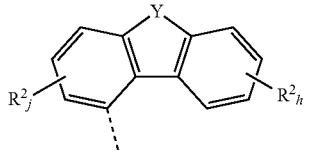
Formula (R¹-39)
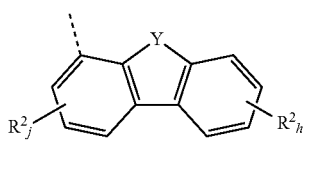
Formula (R¹-40)
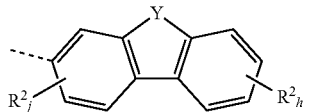
Formula (R¹-41)
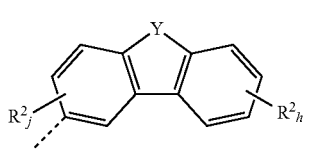
Formula (R¹-42)
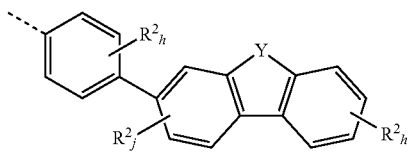

Formula (R¹-43)
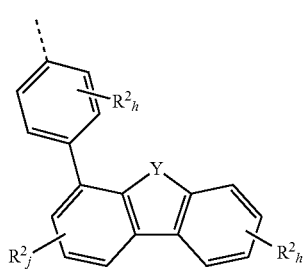
Formula (R¹-44)
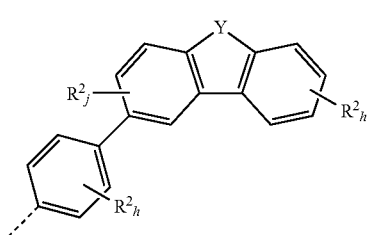
Formula (R¹-45)
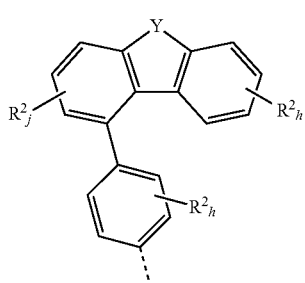
Formula (R¹-46)
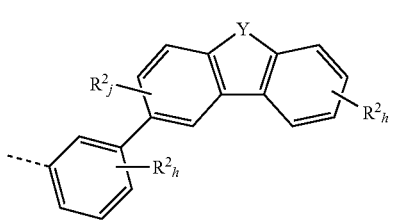
Formula (R¹-47)
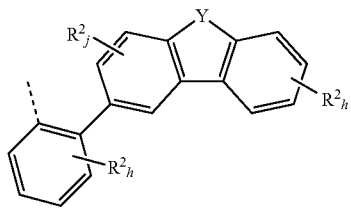
Formula (R¹-48)
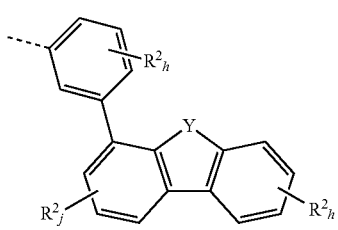
Formula (R¹-49)
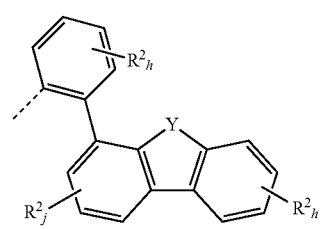
Formula (R¹-50)
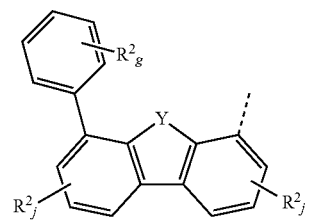
Formula (R¹-51)
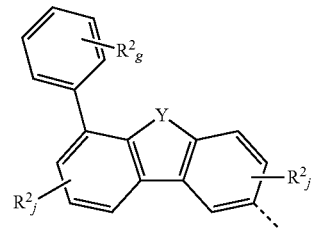
Formula (R¹-52)
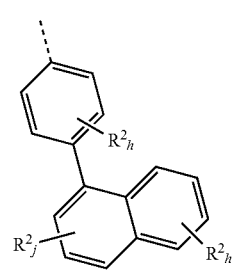
Formula (R¹-53)
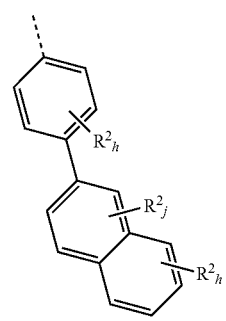
Formula (R¹-54)
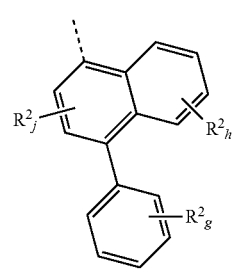

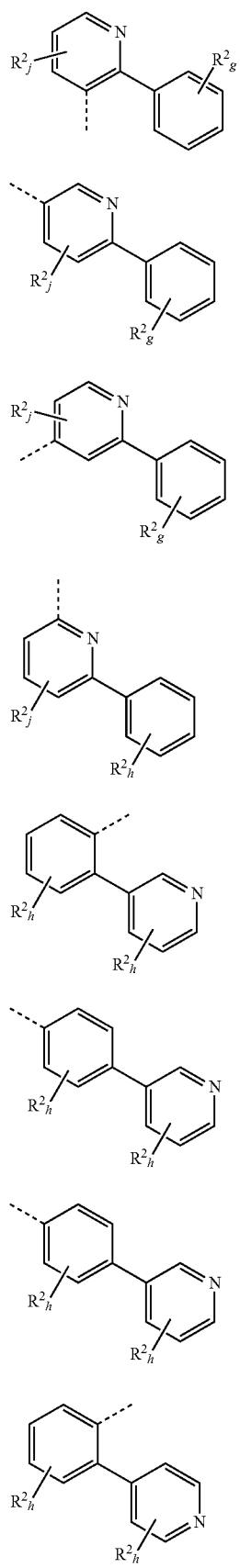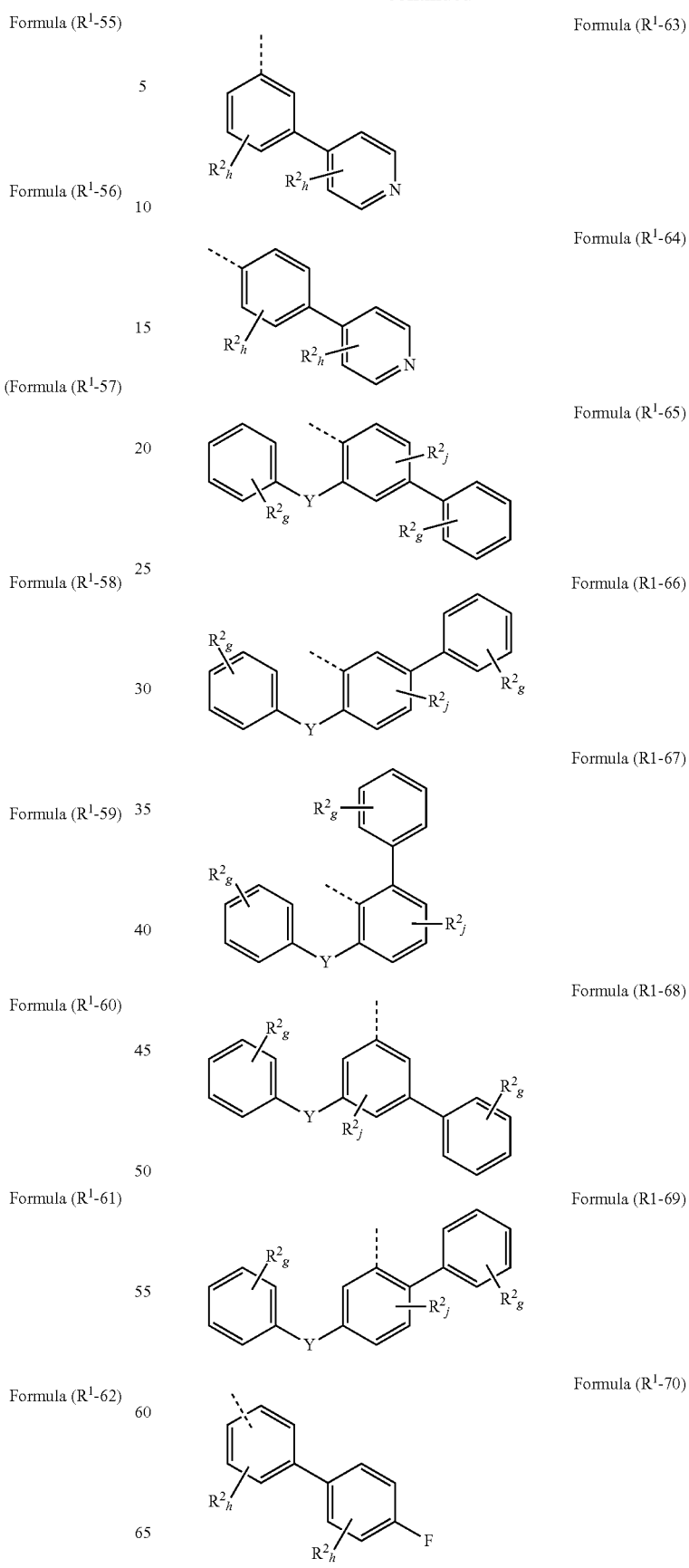

Formula (R¹-71)
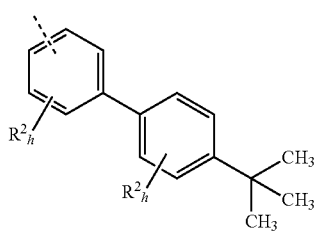

Formula (R¹-72)
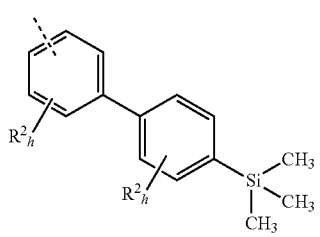

Formula (R¹-73)
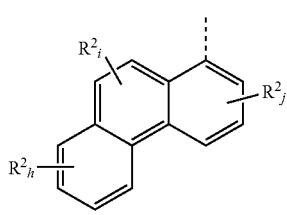

Formula (R¹-74)
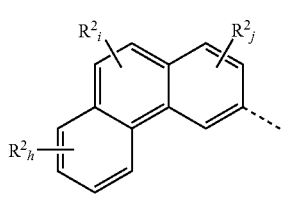

Formula (R¹-75)
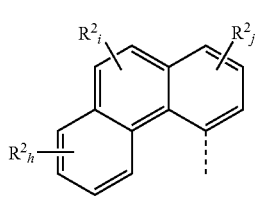

Formula (R¹-76)
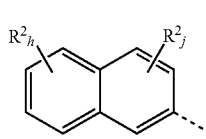

Formula (R¹-77)
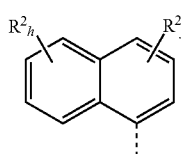

Formula (R¹-78)
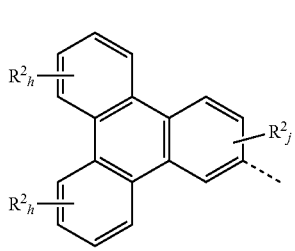

Formula (R¹-79)
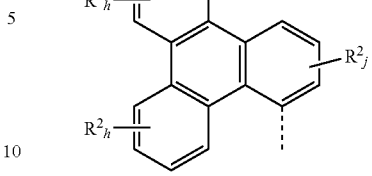

Formula (R¹-80)
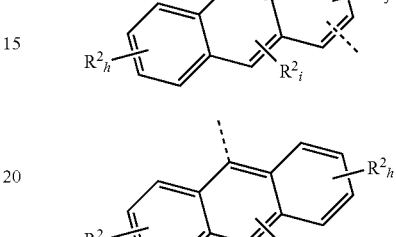

Formula (R¹-81)
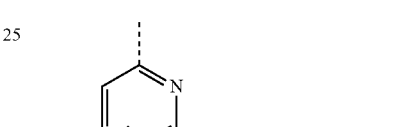

Formula (R¹-82)
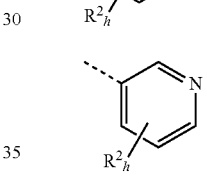

Formula (R¹-83)
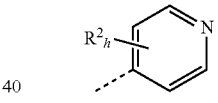

Formula (R¹-84)
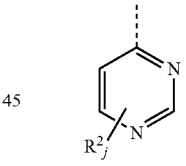

Formula (R¹-85)
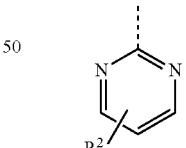

Formula (R¹-86)
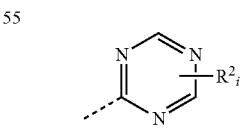

Formula (R¹-87)

where the symbols used are as follows:
Y is O, S or NR², preferably O or S;
k at each instance is independently 0 or 1,
i at each instance is independently 0, 1, or 2, preferably 0 or 1;
j at each instance is independently 0, 1, 2 or 3, preferably 0, 1 or 2, more preferably 0 or 1;

h at each instance is independently 0, 1, 2, 3 or 4, preferably 0, 1 or 2;

g at each instance is independently 0, 1, 2, 3, 4 or 5, preferably 0, 1 or 2;

$R^2$ may have the definition given above, especially for formula (A), and the dotted bond marks the attachment position.

It may preferably be the case that the sum total of the indices k, i, j, h and g in the structures of the formula ($R^1$-1) to ($R^1$-87) in each case is not more than 3, preferably not more than 2 and more preferably not more than 1.

Preferably, the $R^2$ radicals in the formulae ($R^1$-1) to ($R^1$-87) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

More preferably, the $Ar^a$ and/or $Ar^b$ radicals in the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) are selected from a group of the formulae ($R^1$-1) to ($R^1$-48) and ($R^1$-73) to ($R^1$-87), especially preferably ($R^1$-1), ($R^1$-38) to ($R^1$-48) and ($R^1$-73) to ($R^1$-81). In this context, the preferences detailed above for the groups of the formulae ($R^1$-1) to ($R^1$-87) with regard to the sum total of the indices and the $R^2$ radicals bonded to these groups are applicable.

More preferably, the Ar and/or $Ar^1$ radicals in the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) are selected from a group of the formulae ($R^1$-1) to ($R^1$-54), particularly preferably ($R^1$-1) to ($R^1$-51), especially preferably ($R^1$-1) to ($R^1$-37), very particular preference being given to radicals according to ($R^1$-1). In this context, the preferences detailed above for the groups of the formulae ($R^1$-1) to ($R^1$-87) with regard to the sum total of the indices and the $R^2$ radicals bonded to these groups are applicable.

Preferably, the $L^1$ or $L^2$ group together with the two aryl or heteroaryl groups to which the $L^1$ or $L^2$ group of formula (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), ($Ar^b$-1), (IV) and/or (V) is bonded form through-conjugation. Through-conjugation of the aromatic or heteroaromatic systems is formed as soon as direct bonds are formed between adjacent aromatic or heteroaromatic rings. A further bond between the aforementioned conjugated groups, for example via a sulphur, nitrogen or oxygen atom or a carbonyl group, is not detrimental to conjugation. In the case of a fluorene system, the two aromatic rings are bonded directly, where the spa-hybridized carbon atom in position 9 does prevent fusion of these rings, but conjugation is possible, since this $sp^3$-hybridized carbon atom in position 9 does not necessarily lie between the two aryl or heteroaryl groups. In contrast, in the case of a second spirobifluorene structure, through-conjugation can be formed if the bond between the two aryl or heteroaryl groups is via the same phenyl group in the spirobifluorene structure or via phenyl groups in the spirobifluorene structure that are bonded directly to one another and are in one plane. If the bond between the two aryl or heteroaryl groups is via different phenyl groups in the second spirobifluorene structure bonded via the $sp^3$-hybridized carbon atom in position 9, the conjugation is interrupted.

In a further preferred embodiment of the invention, $L^1$ and/or $L^2$ is a bond.

In a further preferred embodiment of the invention, $L^1$ and/or $L^2$ is an aromatic or heteroaromatic ring system which has 5 to 14 aromatic or heteroaromatic ring atoms, preferably an aromatic ring system which has 6 to 12 carbon atoms, and which may be substituted by one or more $R^1$ radicals, but is preferably unsubstituted, where $R^1$ may have the definition given above, especially for formula (A). More preferably, $L^1$ and/or $L^2$ is an aromatic ring system having 6 to 10 aromatic ring atoms or a heteroaromatic ring system having 6 to 13 heteroaromatic ring atoms, each of which may be substituted by one or more $R^2$ radicals, but is preferably unsubstituted, where $R^2$ may have the definition given above, especially for formula (A).

Additionally preferably, the symbol $L^1$ and/or $L^2$ detailed in the structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), ($Ar^b$-1), (IV) and/or (V) inter alia is the same or different at each instance and is an aryl or heteroaryl radical having 5 to 24 ring atoms, preferably 6 to 13 ring atoms, more preferably 6 to 10 ring atoms, such that an aromatic or heteroaromatic group of an aromatic or heteroaromatic ring system is bonded directly, i.e. via an atom of the aromatic or heteroaromatic group, to the respective atom of the further group.

It may additionally be the case that the $L^1$ and/or $L^2$ group detailed in the structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), ($Ar^b$-1), (IV) and/or (V) inter alia comprises an aromatic ring system having not more than two fused aromatic and/or heteroaromatic rings, and preferably does not comprise any fused aromatic or heteroaromatic system. Accordingly, naphthyl structures are preferred over anthracene structures. In addition, fluorenyl, spirobifluorenyl, dibenzofuranyl and/or dibenzothienyl structures are preferred over naphthyl structures.

Particular preference is given to structures having no fusion, for example phenyl, biphenyl, terphenyl and/or quaterphenyl structures.

Examples of suitable aromatic or heteroaromatic ring systems $L^1$ and/or $L^2$ are selected from the group consisting of ortho-, meta- or para-phenylene, ortho-, meta- or para-biphenylene, terphenylene, especially branched terphenylene, quaterphenylene, especially branched quaterphenylene, fluorenylene, spirobifluorenylene, dibenzofuranylene, dibenzothienylene and carbazolylene, each of which may be substituted by one or more $R^2$ radicals, but are preferably unsubstituted.

It may also be the case that the $L^1$ and/or $L^2$ group detailed in the structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh) ($Ar^b$-1), (IV) and/or (V) inter alia has not more than 1 nitrogen atom, preferably not more than 2 heteroatoms, especially preferably not more than one heteroatom and more preferably no heteroatom.

Preference is given to compounds comprising structures of the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) in which the $L^1$ and/or $L^2$ group of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh) and/or (IIIh), (Ar$^b$-1), (IV) and/or (V) is a group selected from the formulae (L$^1$-1) to (L$^1$-108)
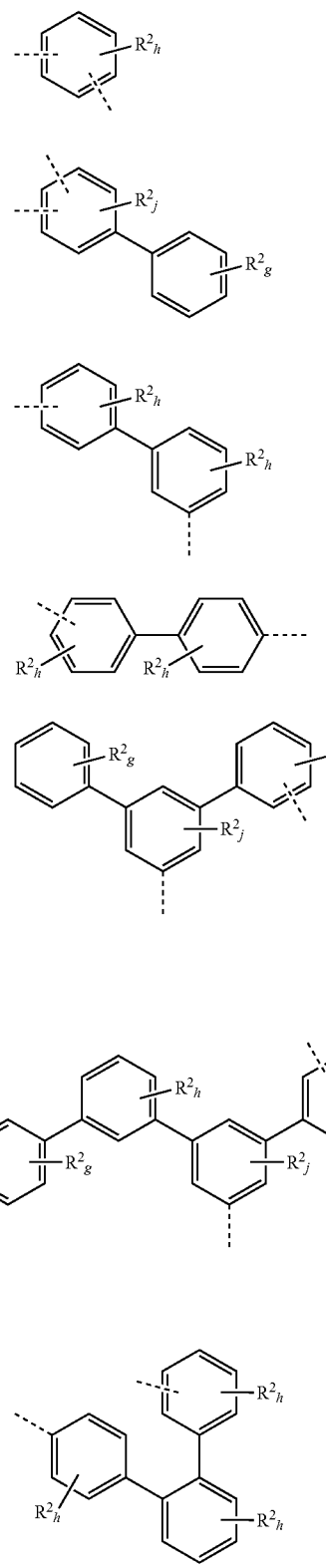
Formula (L$^1$-1)
Formula (L$^1$-2)
Formula (L$^1$-3)
Formula (L$^1$-4)
Formula (L$^1$-5)
Formula (L$^1$-6)
Formula (L$^1$-7)
-continued
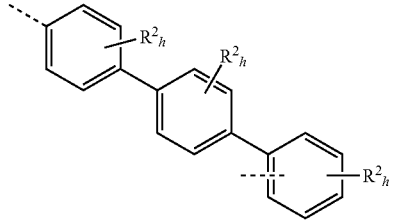
Formula (L$^1$-8)
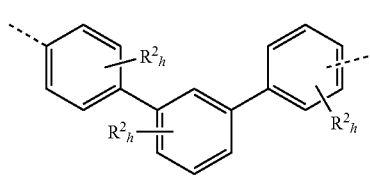
Formula (L$^1$-9)
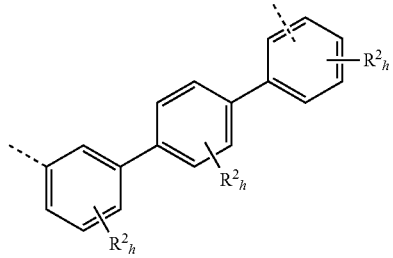
Formula (L$^1$-10)
Formula (L$^1$-11)
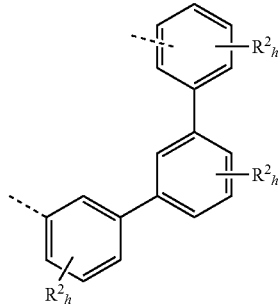
Formula (L$^1$-12)
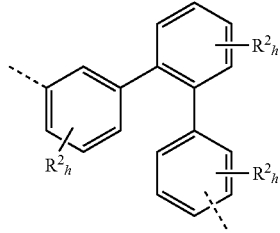
Formula (L$^1$-13)
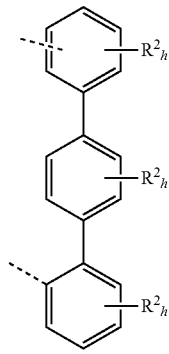

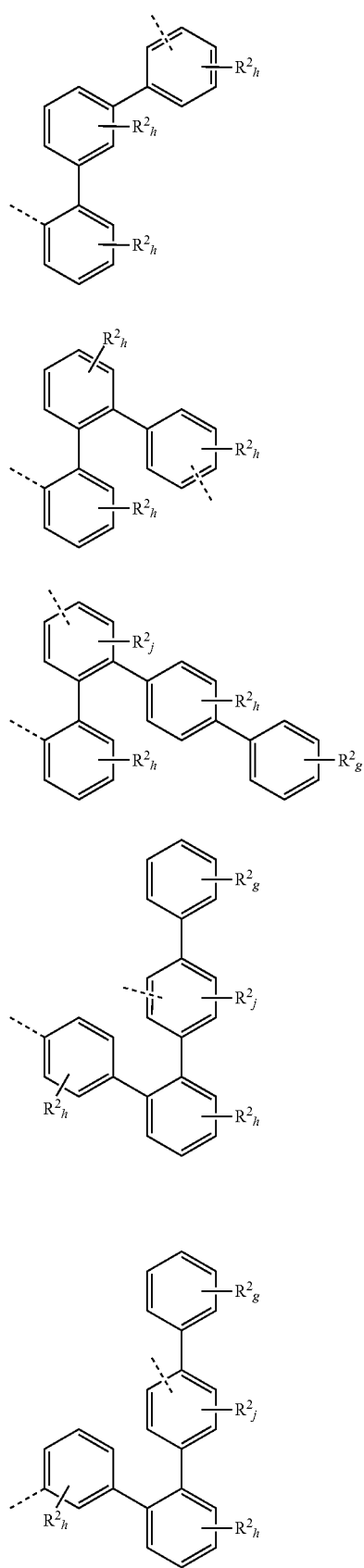
Formula (L¹-14)
Formula (L¹-15)
Formula (L¹-16)
Formula (L¹-17)
Formula (L¹-18)
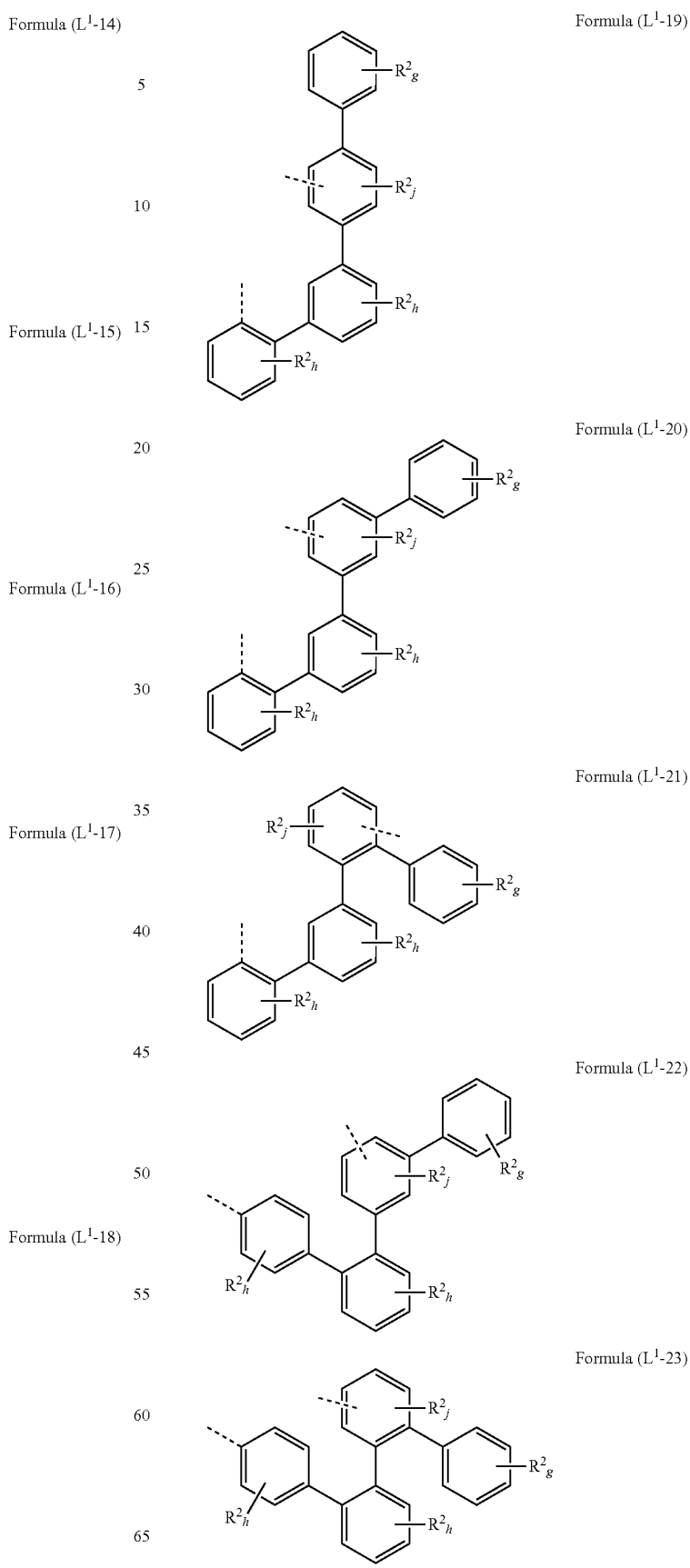
Formula (L¹-19)
Formula (L¹-20)
Formula (L¹-21)
Formula (L¹-22)
Formula (L¹-23)

Formula (L¹-24)
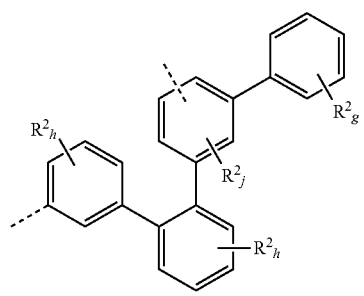
Formula (L¹-25)
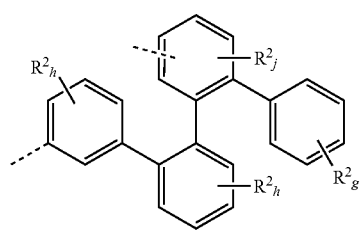
Formula (L¹-26)
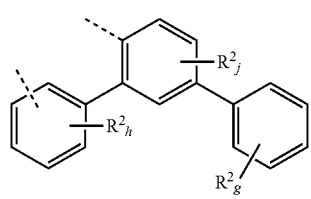
Formula (L¹-27)
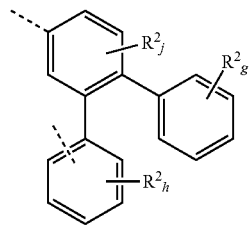
Formula (L¹-28)
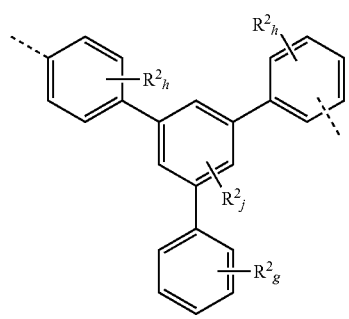
Formula (L¹-29)
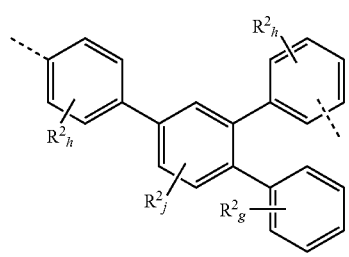
Formula (L¹-30)
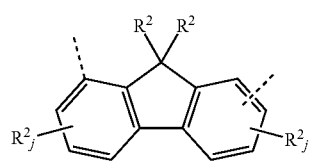
Formula (L¹-31)
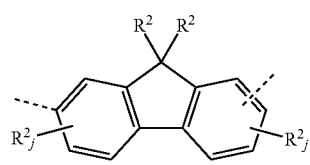
Formula (L¹-32)
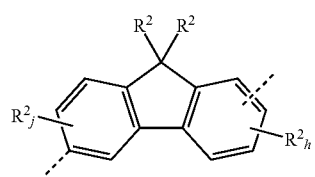
Formula (L¹-33)
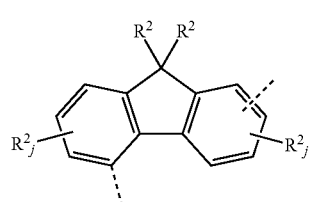
Formula (L¹-34)
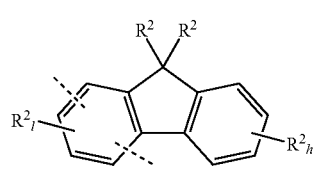
Formula (L¹-35)
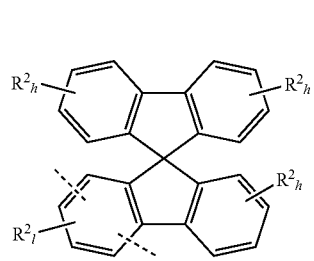
Formula (L¹-36)
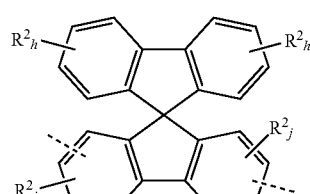
Formula (L¹-37)
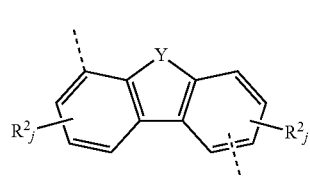

Formula (L¹-38)
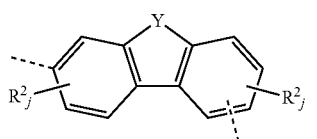
Formula (L¹-39)
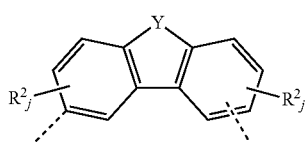
Formula (L¹-40)
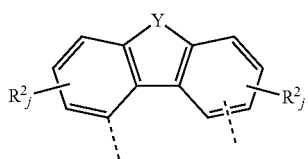
Formula (L¹-41)
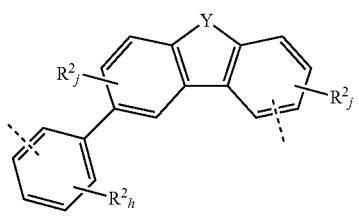
Formula (L¹-42)
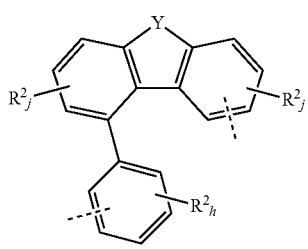
Formula (L¹-43)
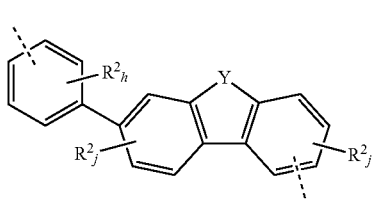
Formula (L¹-44)
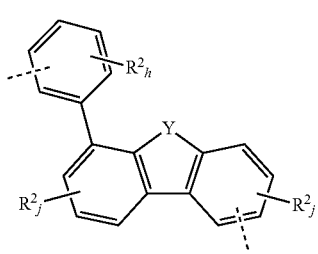
Formula (L¹-45)
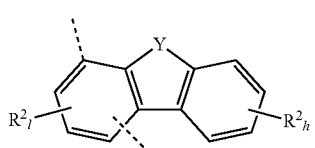
Formula (L¹-46)
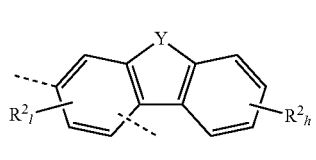
Formula (L¹-47)
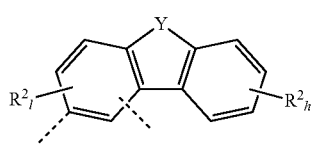
Formula (L¹-48)
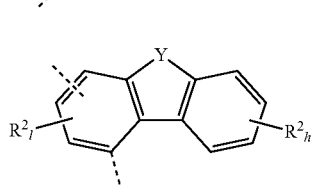
Formula (L¹-49)
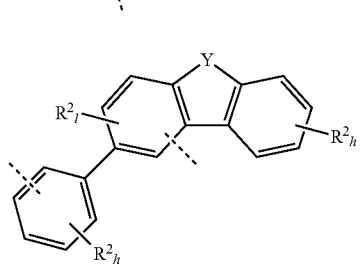
Formula (L¹-50)
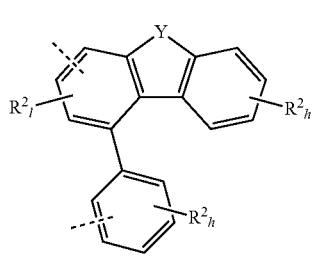
Formula (L¹-51)
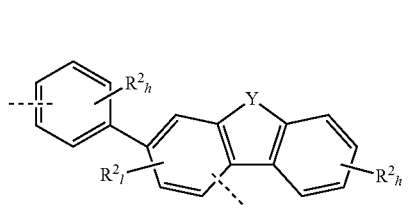
Formula (L¹-52)
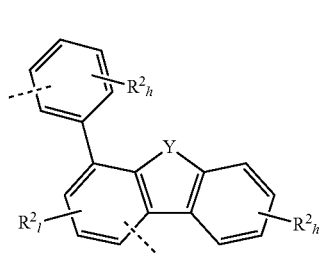
Formula (L¹-53)
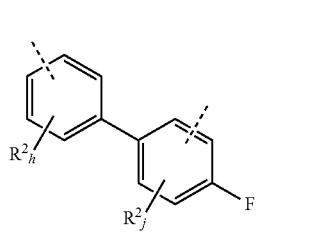

-continued
Formula (L¹-54)
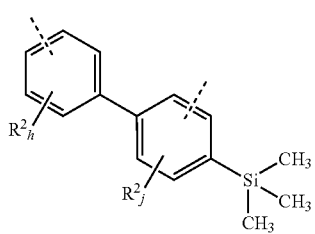
Formula (L¹-55)
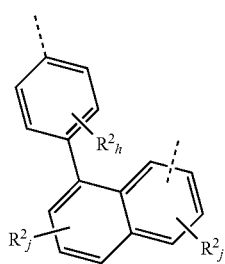
Formula (L¹-56)
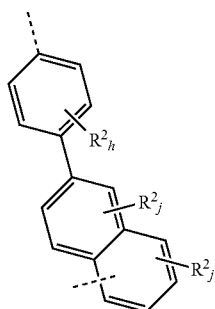
Formula (L¹-57)
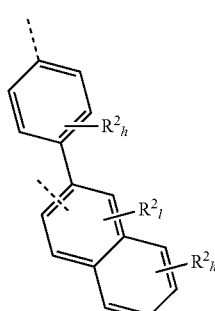
Formula (L¹-58)
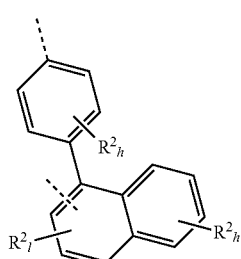
Formula (L¹-59)
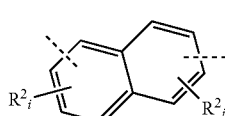
Formula (L¹-60)
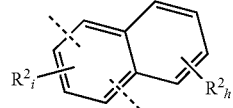
Formula (L¹-61)
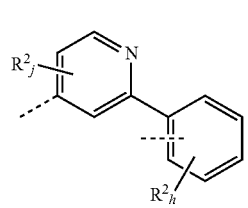
Formula (L¹-62)
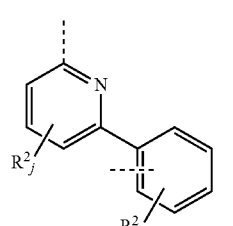
Formula (L¹-63)
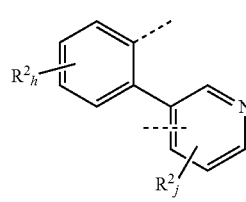
Formula (L¹-64)
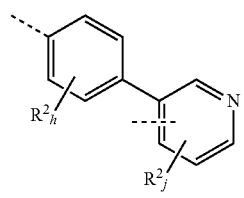
Formula (L¹-65)
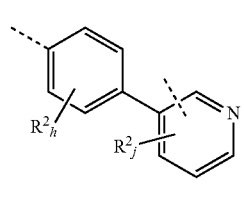
Formula (L¹-66)
Formula (L¹-67)

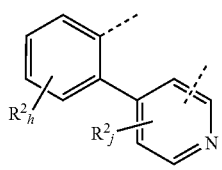
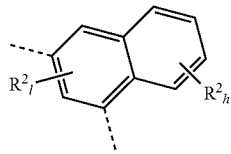

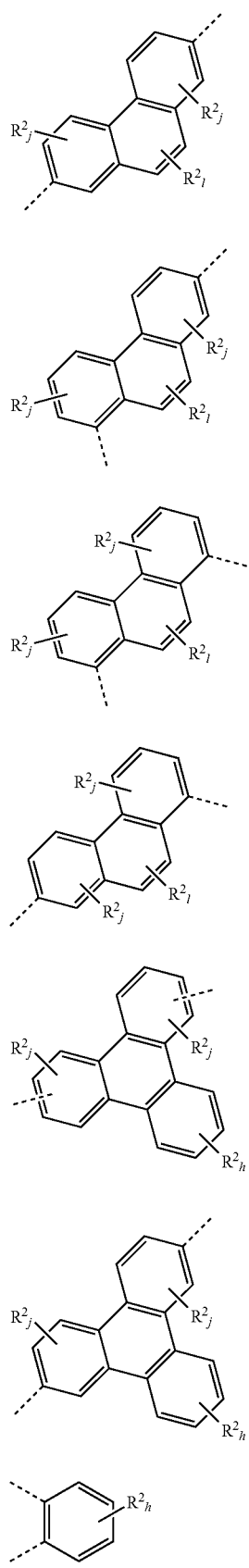
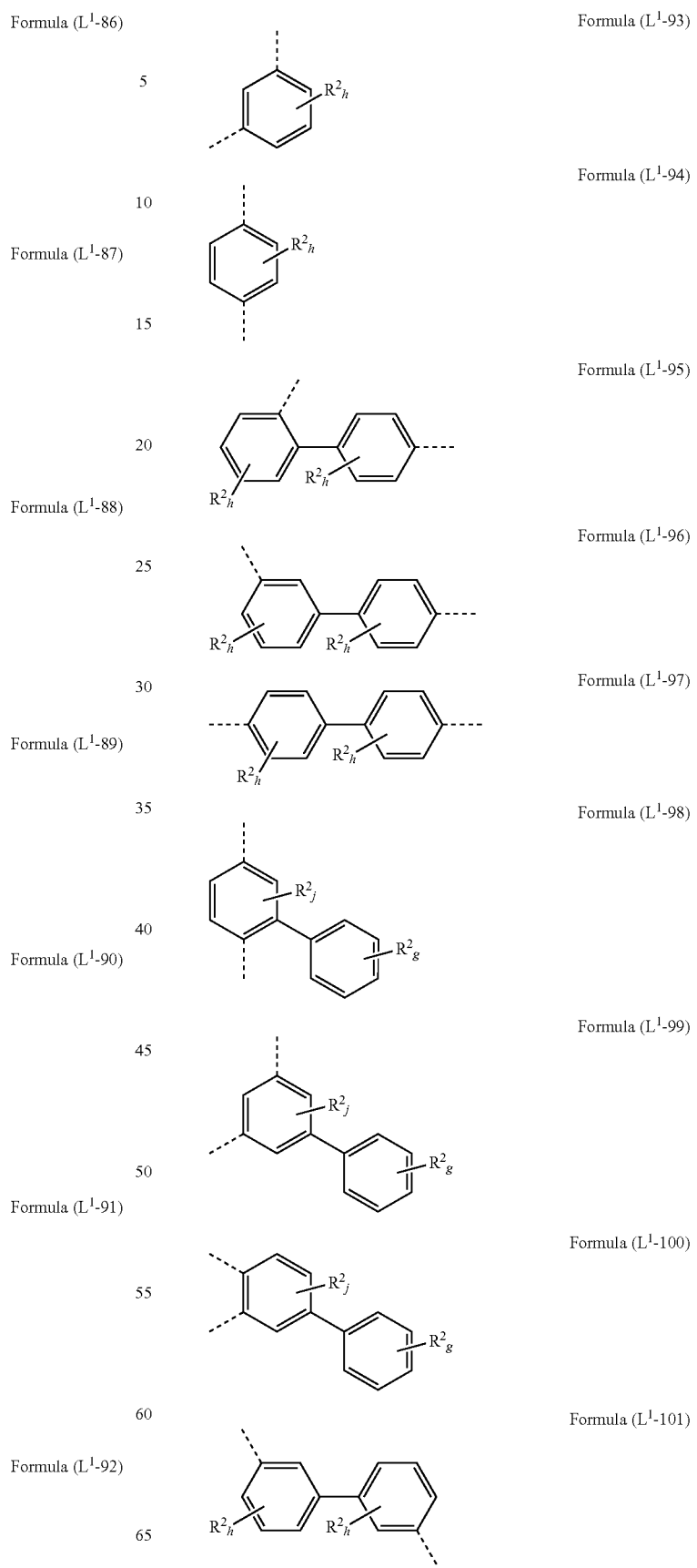

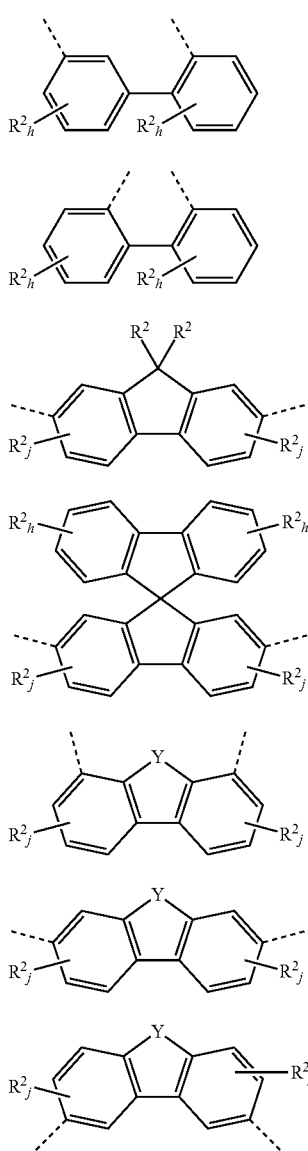

Formula (L¹-102)
Formula (L¹-103)
Formula (L¹-104)
Formula (L¹-105)
Formula (L¹-106)
Formula (L¹-107)
Formula (L¹-108)

where the dotted bonds in each case mark the attachment positions, the index k is 0 or 1, the index l is 0, 1 or 2, the index j at each instance is independently 0, 1, 2 or 3; the index h at each instance is independently 0, 1, 2, 3 or 4, the index g is 0, 1, 2, 3, 4 or 5; the symbol Y is O, S or $NR^2$, preferably O or S; and the symbol $R^2$ has the definition given above, especially for formula (A).

It may preferably be the case that the sum total of the indices k, l, g, h and j in the structures of the formula (L¹-1) to (L¹-108) is at most 3 in each case, preferably at most 2 and more preferably at most 1.

It may also be the case that one of the L¹ and/or L² groups in structures of the formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) has not more than 5 heteroatoms, preferably not more than 3 heteroatoms and more preferably not more than 1 heteroatom, where this includes $R^1$, $R^2$ and $R^3$ substituents that may be bonded to these groups.

It may additionally be the case that the L¹ and/or L² groups overall in structures of formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) have not more than 5 heteroatoms, preferably not more than 3 heteroatoms and more preferably not more than 1 heteroatom, where this includes $R^1$, $R^2$ and $R^3$ substituents that may be bonded to these groups.

Preferred compounds according to the invention comprise an L¹ group selected from one of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103). Advantageously, the sum total of the indices k, l, g, h and j in the structures of the formulae (L¹-1) to (L¹-78) and/or (L¹-92) to (L¹-108), preferably of the formula (L¹-1) to (L¹-54) and/or (L¹-92) to (L¹-108), especially preferably of the formula (L¹-1) to (L¹-29) and/or (L¹-92) to (L¹-103), may in each case be not more than 3, preferably not more than 2 and more preferably not more than 1.

Preferably, the $R^2$ radicals in the formulae (L¹-1) to (L¹-108) do not form a fused aromatic or heteroaromatic ring system, and preferably do not form any fused ring system, with the ring atoms of the aryl group or heteroaryl group to which the $R^2$ radicals are bonded. This includes the formation of a fused ring system with possible $R^3$ substituents which may be bonded to the $R^2$ radicals.

In a further preferred embodiment of the invention, $R^2$, for example in a structure of formula (A) and preferred embodiments of this structure or the structures where reference is made to these formulae, is the same or different at each instance and is selected from the group consisting of H, D, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

In a further preferred embodiment of the invention, $R^3$, for example in a structure of formula (A) and preferred embodiments of this structure or the structures where reference is made to these formulae, is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system which has 5 to 30 aromatic ring atoms, preferably 5 to 24 aromatic ring atoms, more preferably 5 to 13 aromatic ring atoms, and may be substituted by one or more alkyl groups each having 1 to 4 carbon atoms, but is preferably unsubstituted.

When the compound of the invention is substituted by aromatic or heteroaromatic $R^1$ or $R^2$ groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

Particular preference is given to compounds of the invention having the following properties:

| $Ar^a$ and $Ar^b$ | $L^1$ | Position of $L^1$ on phenyl ring with $Y^1$ | Position of $L^1$ on phenyl ring with $Y^2$ | Index n for $R^1$ |
|---|---|---|---|---|
| $R^1$-1 to $R^1$-87 | bond or $L^1$-1 | (Ic), (IIc), (IIIc), (Id), (IId), (IIId) | (Ig), (IIg), (IIIg), (Ih), (IIh), (IIIh) | 0, 1, 2 |
| $R^1$-1 | $L^1$-94 | (Ic), (IIc), (IIIc) | (Ig), (IIg), (IIIg) | 0, 1 |
| $R^1$-1 | $L^1$-94 | (Id), (IId), (IIId) | (Ig), (IIg), (IIIg) | 0, 1 |
| $R^1$-1 | bond | (Ic), (IIc), (IIIc) | (Ig), (IIg), (IIIg) | 0, 1 |
| $R^1$-1 | bond | (Id), (IId), (IIId) | (Ig), (IIg), (IIIg) | 0, 1 |

Particular preference is given to compounds having a structure of the formula (W-1) where $Y^3$ is a group of the formula $C(R^2)_2$ and the compounds have the following properties:

| $Ar^a$ and $Ar^b$ | $L^1$ | Position of $L^1$ on phenyl ring with $Y^1$ | Position of $L^1$ on phenyl ring with $Y^2$ | Index n for $R^1$ |
|---|---|---|---|---|
| $R^1$-1 to $R^1$-87 | bond or $L^1$-1 | (Ic), (IIc), (IIIc), (Id), (IId), (IIId) | (Ig), (IIg), (IIIg), (Ih), (IIh), (IIIh) | 0, 1, 2 |
| $R^1$-1 | $L^1$-94 | (Ic), (IIc), (IIIc) | (Ig), (IIg), (IIIg) | 0, 1 |
| $R^1$-1 | $L^1$-94 | (Id), (IId), (IIId) | (Ig), (IIg), (IIIg) | 0, 1 |
| $R^1$-1 | bond | (Ic), (IIc), (IIIc) | (Ig), (IIg), (IIIg) | 0, 1 |
| $R^1$-1 | bond | (Id), (IId), (IIId) | (Ig), (IIg), (IIIg) | 0, 1 |

In addition, particular preference is given to compounds in which $Y^2$ is a group of the formula N(Ar) and the compounds have the following properties:

| $Ar^a$ and $Ar^b$ | $L^1$ | Position of $L^1$ on phenyl ring with $Y^1$ | Position of $L^1$ on phenyl ring with $Y^2$ | Index n for $R^1$ |
|---|---|---|---|---|
| $R^1$-1 to $R^1$-87 | bond or $L^1$-1 | (Ic), (IIc), (IIIc), (Id), (IId), (IIId), | (Ig), (IIg), (IIIg), (Ih), (IIh), (IIIh), | 0, 1 or 2 |
| $R^1$-1 | $L^1$-94 | (Ic), (IIc), (IIIc), | (Ig), (IIg), (IIIg) | 0, 1 |
| $R^1$-1 | $L^1$-94 | (Id), (IId), (IIId), | (Ig), (IIg), (IIIg) | 0, 1 |
| $R^1$-1 | bond | (Ic), (IIc), (IIIc), | (Ig), (IIg), (IIIg) | 0, 1 |
| $R^1$-1 | bond | (Id), (IId), (IIId), | (Ig), (IIg), (IIIg) | 0, 1 |

The index g in formula $R^1$-1 in the aforementioned tables is preferably 0, 1, 2 or 3, more preferably 0 or 1, especially preferably 0; the index h in formula $L^1$-1 or $L^1$-94 in the aforementioned tables is preferably 0, 1, 2 or 3, more preferably 0 or 1, especially preferably 0.

In the tables set out above, the assignment that $Ar^a$ and $Ar^b$ is $R^1$-1 to $R^1$-87 means that both the $Ar^a$ group and the $Ar^b$ group is selected from the radicals of the above-detailed formulae $R^1$-1 to $R^1$-87, preferably $R^1$-1. The assignment that $L^1$ is a bond or $L^1$-1 means that the $L^1$ group in the above-detailed formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) in each case is a bond or a radical of the above-detailed formula $L^1$-1, preferably $L^1$-94. The assignment that the position $L^1$ on the phenyl ring with $Y^1$ preferably corresponds to the formula (Ic), (IIc), (IIIc), (Id), (IId), (IIId) means that the $L^1$ group is preferably in the para or meta position to the $Y^1$ group, as shown in formula (Ic), (IIc), (IIIc), (Id), (IId), (IIId). The assignment that the position $L^1$ on the phenyl ring with $Y^2$ preferably corresponds to the formula (Ig), (IIg), (IIIg), (Ih), (IIh), (IIIh) means that the $L^1$ group is preferably in the para or meta position to the $Y^2$ group, as shown in formula (Ig), (IIg), (IIIg), (Ih), (IIh), (IIIh). The assignment that the index n for $R^1$ is 0, 1, 2 means that, in the above-detailed formulae (A), (I), (II), (III), (Ia), (IIa), (IIIa), (Ib), (IIb), (IIIb), (Ic), (IIc), (IIIc), (Id), (IId), (IIId), (Ie), (IIe), (IIIe), (If), (IIf), (IIIf), (Ig), (IIg), (IIIg), (Ih), (IIh), (IIIh), (IV) and/or (V) the index n in each case is 0, 1 or 2, preferably 0 or 1 and especially preferably 0.

Examples of suitable compounds of the invention are the structures of the following formulae 1 to 217 shown below:

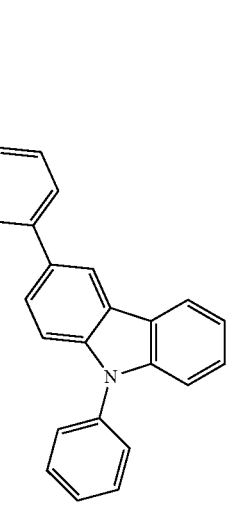

Formula 1

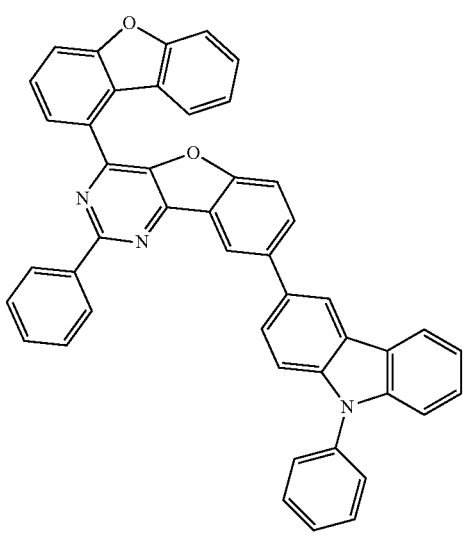

Formula 2

Formula 3
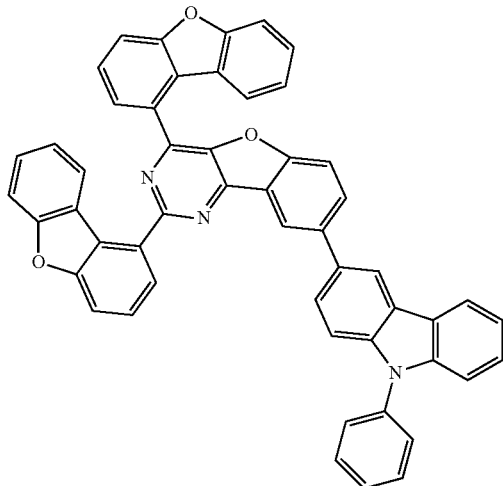
Formula 4
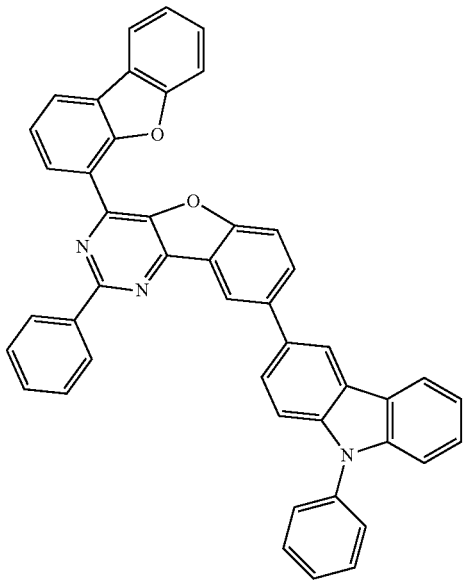
Formula 5
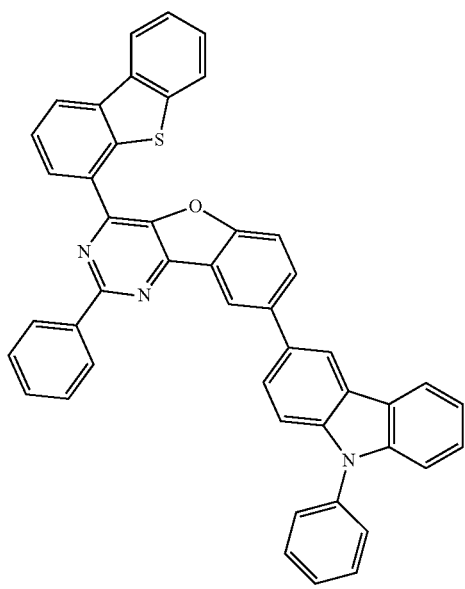
Formula 6
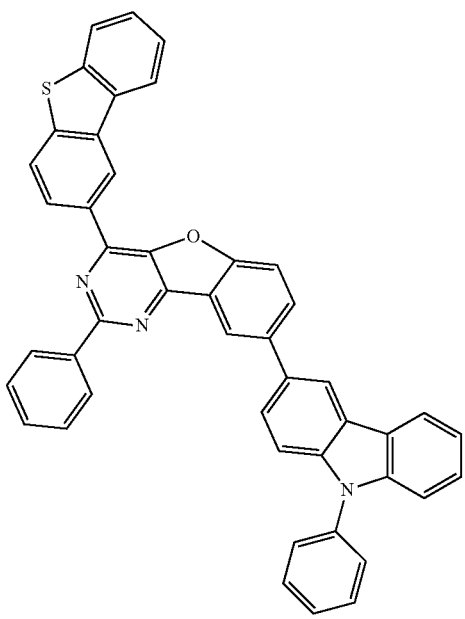

-continued
Formula 7
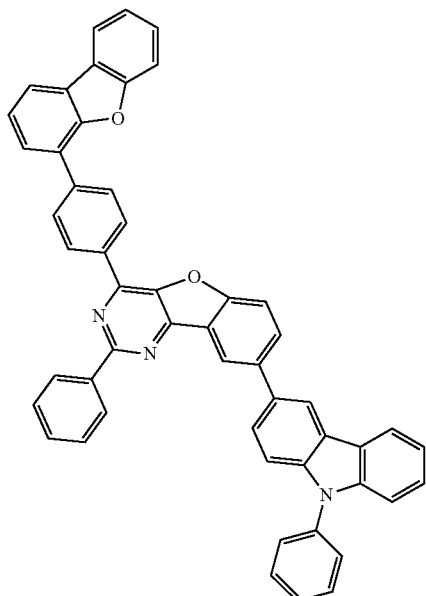
Formula 8
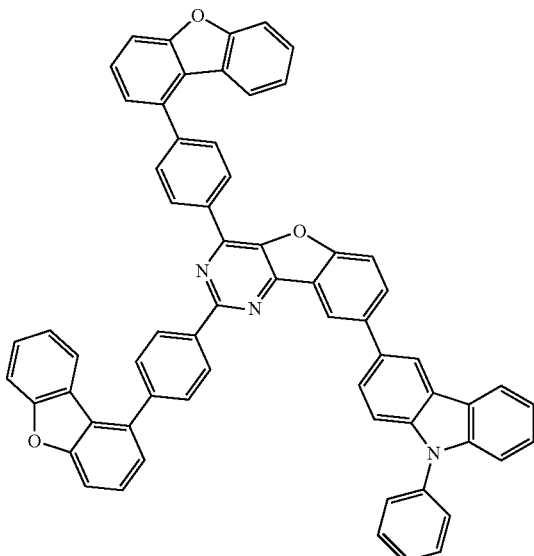
Formula 9
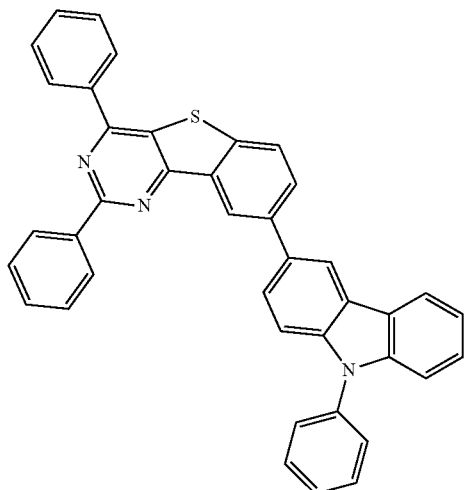
Formula 10
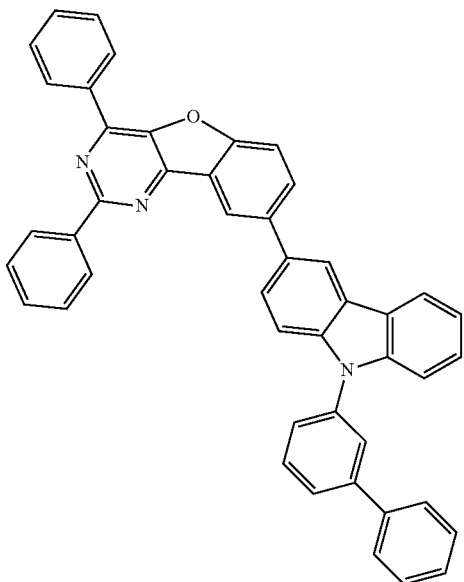
Formula 11
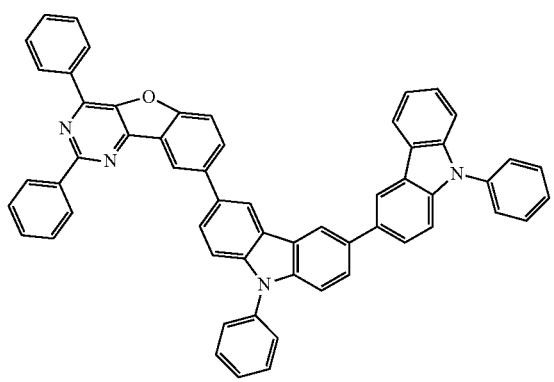
Formula 12
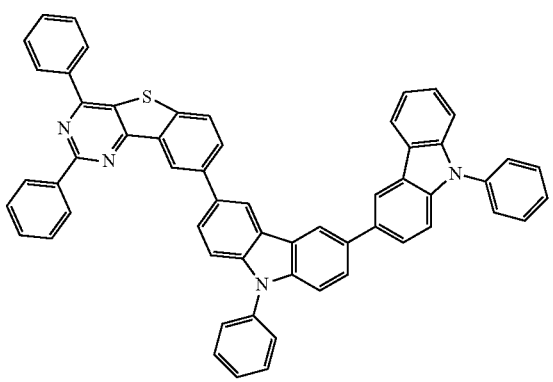

-continued
Formula 13
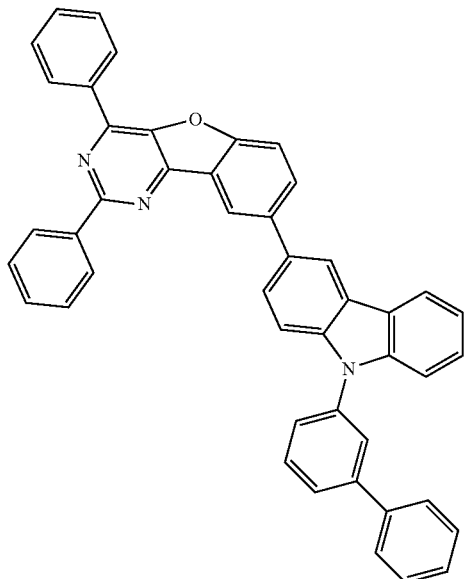
Formula 14
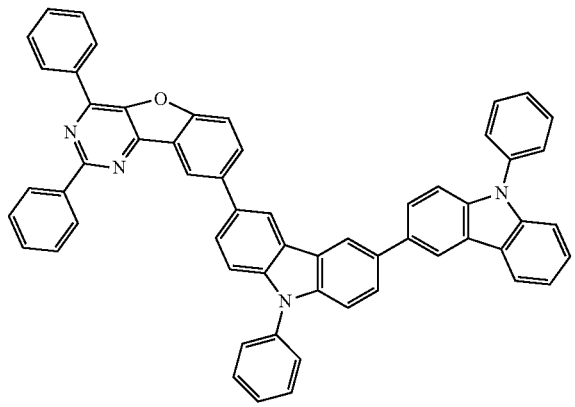
Formula 15
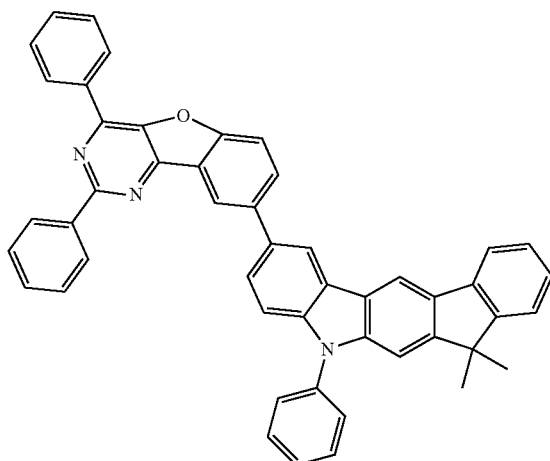
Formula 16
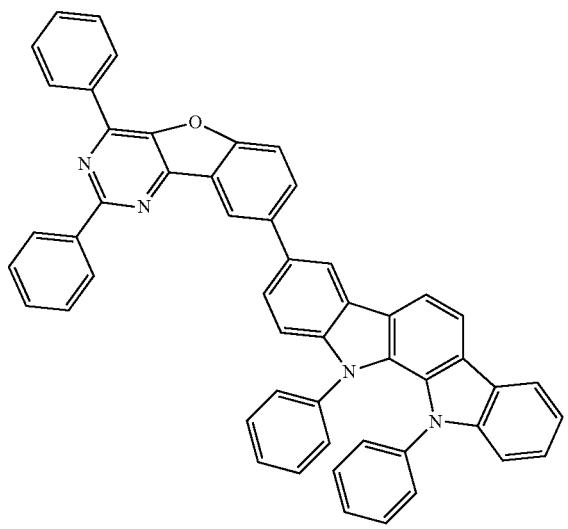
Formula 17
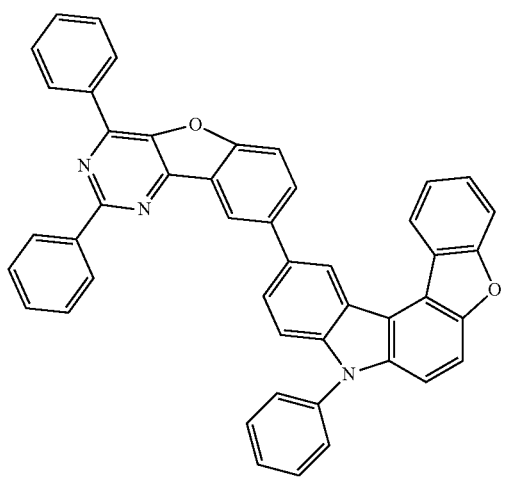
Formula 18
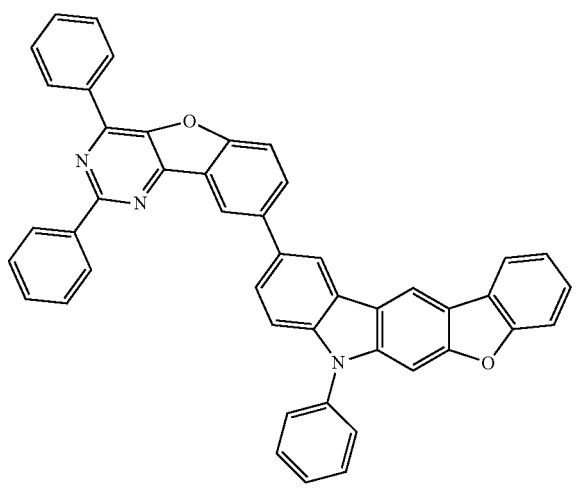

-continued
Formula 19
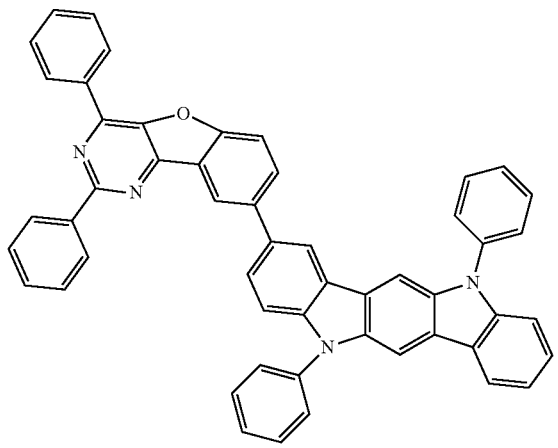
Formula 20
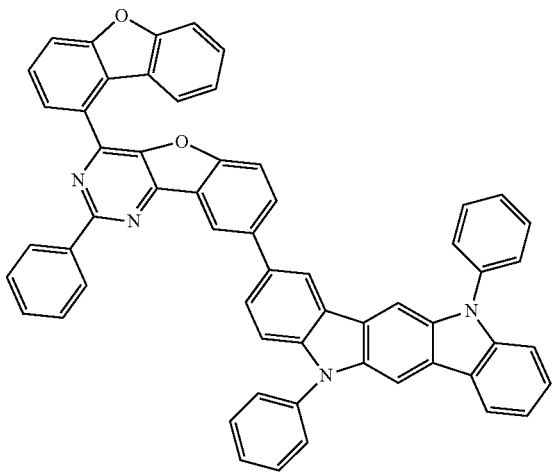
Formula 21
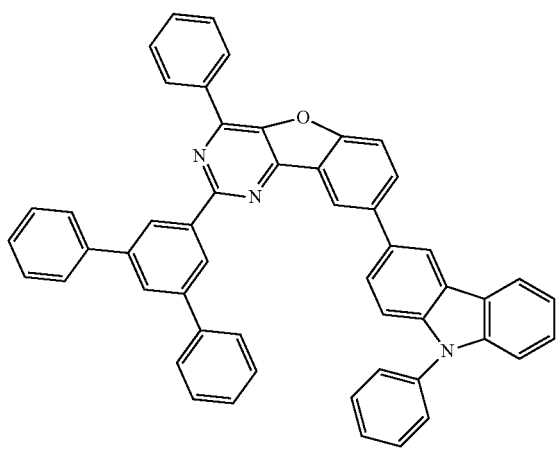
Formula 22
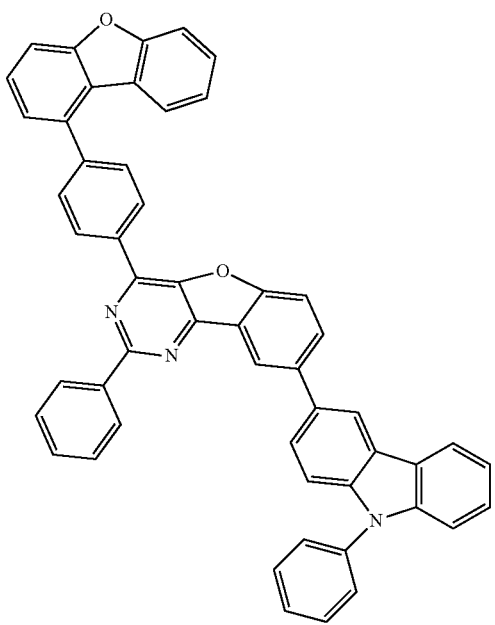

-continued
Formula 23
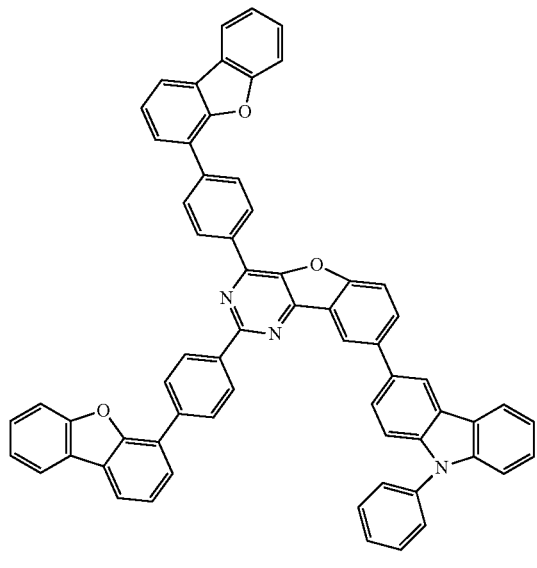
Formula 24
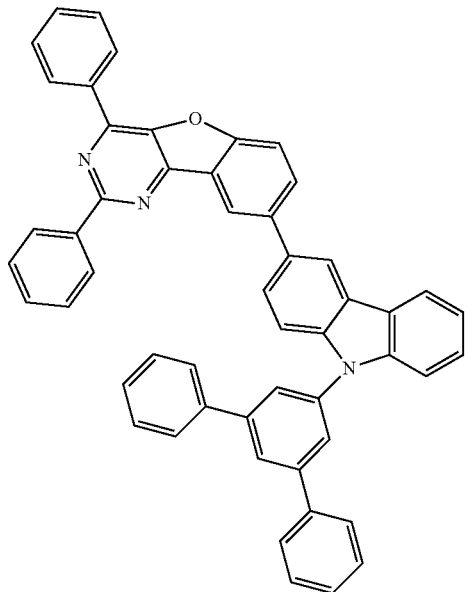
Formula 25
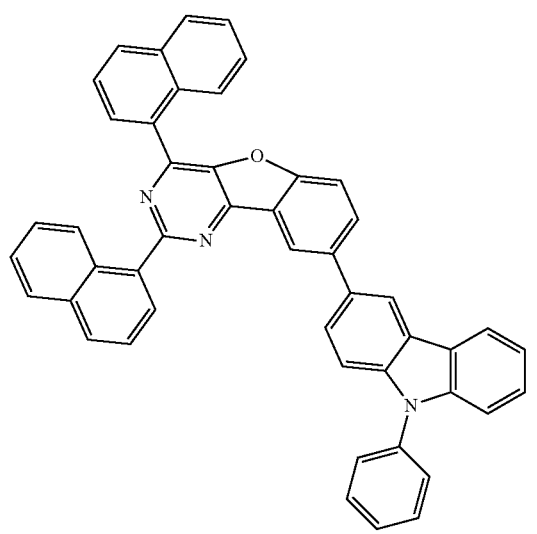
Formula 26
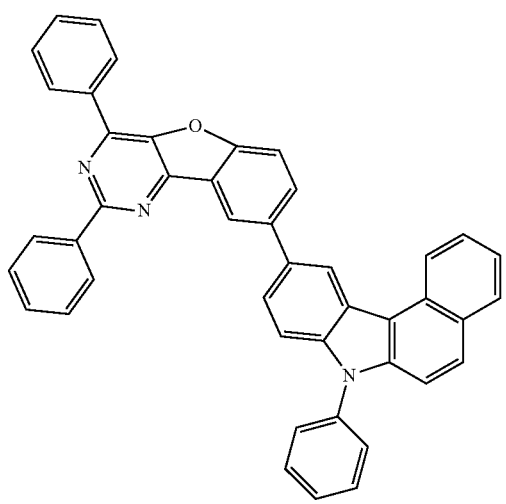

-continued
Formula 27
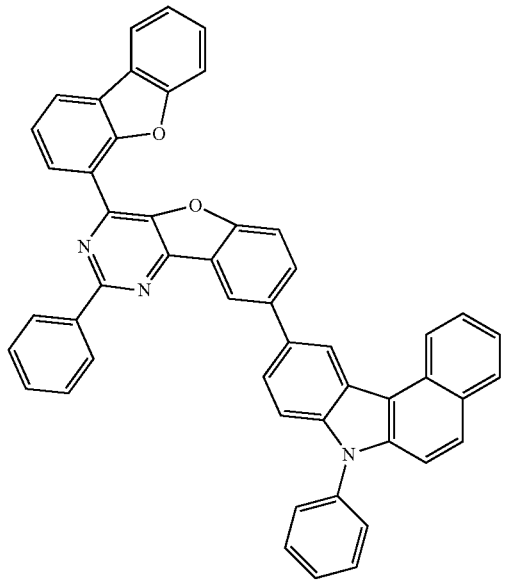
Formula 28
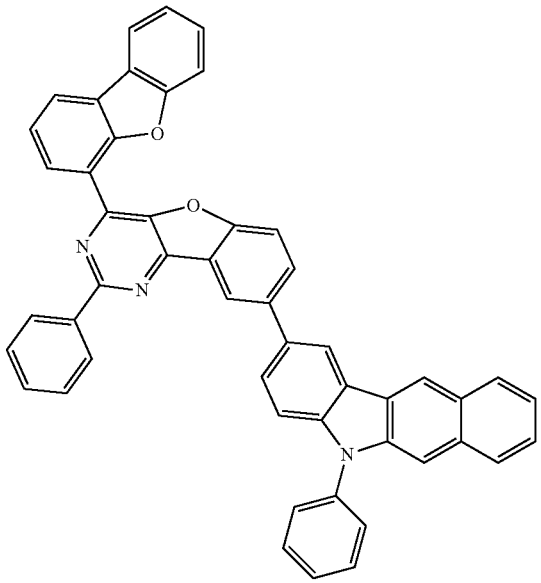
Formula 29
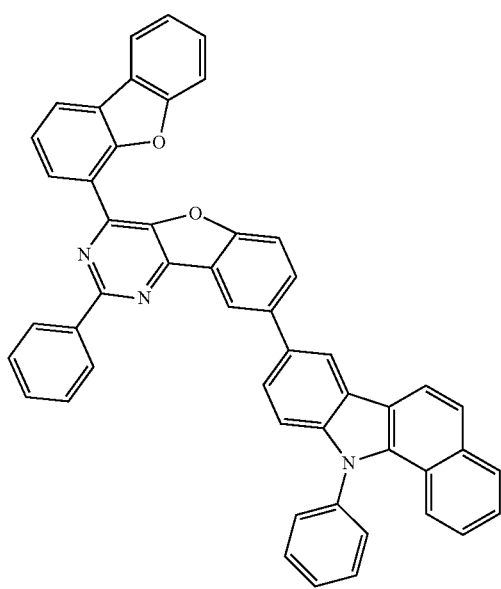
Formula 30
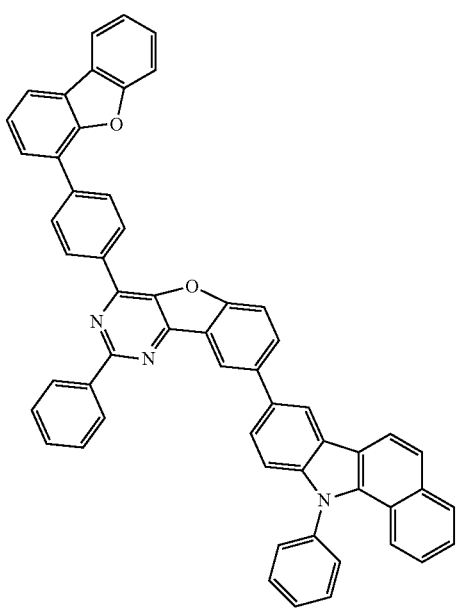

-continued
Formula 31
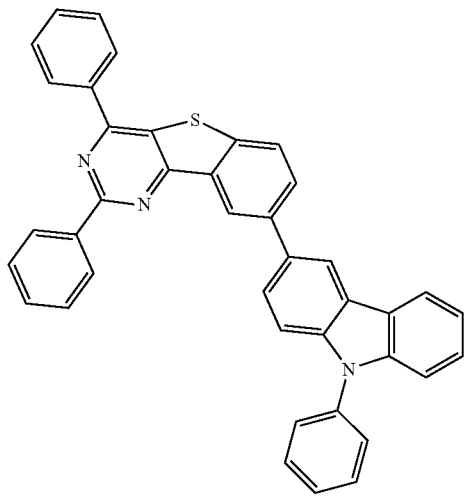
Formula 32
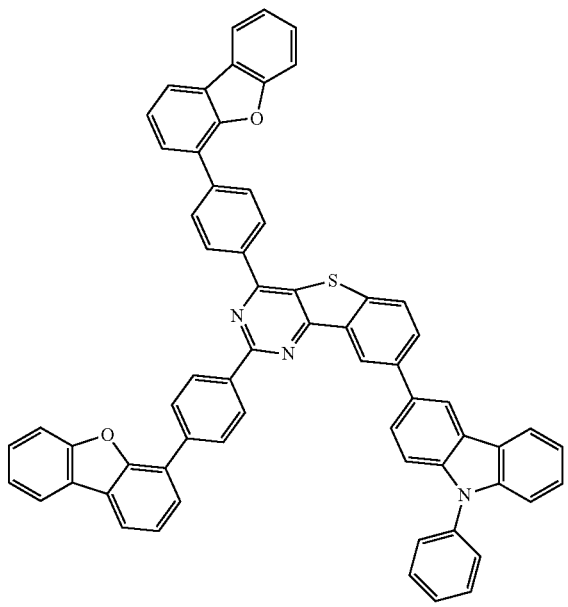
Formula 33
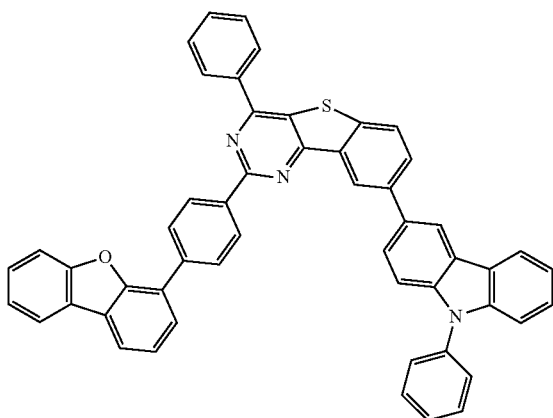
Formula 34
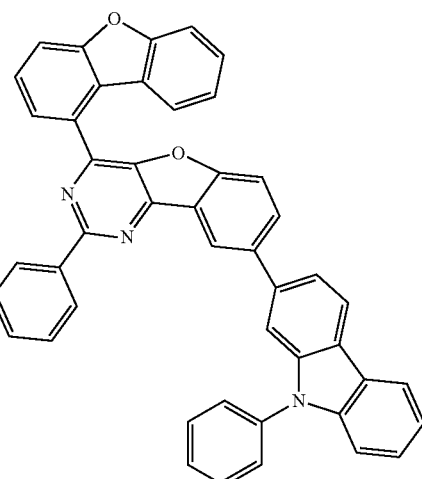
Formula 35
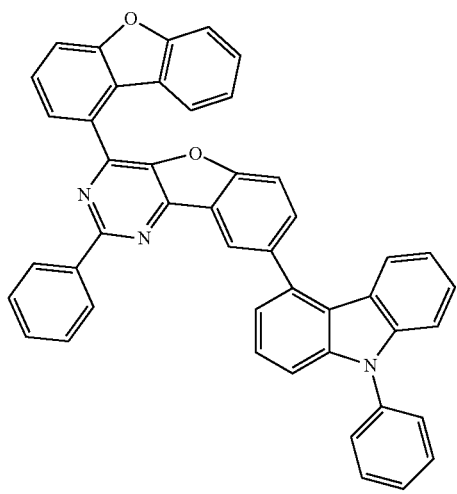
Formula 36
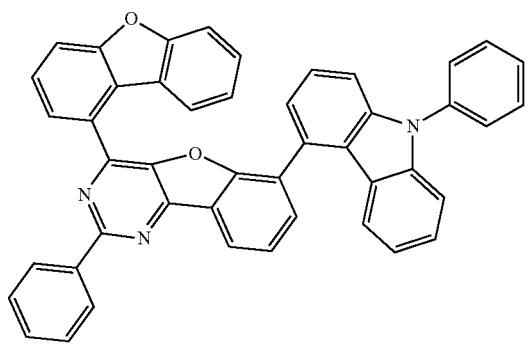

-continued
Formula 37
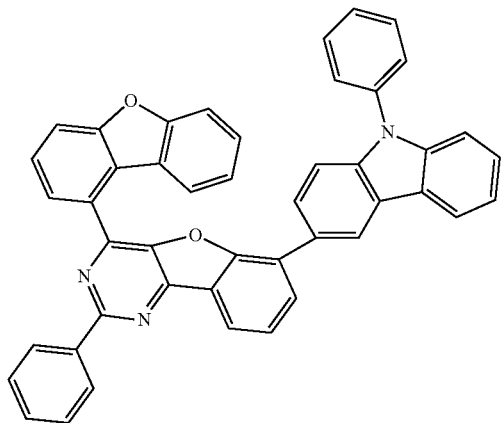
Formula 38
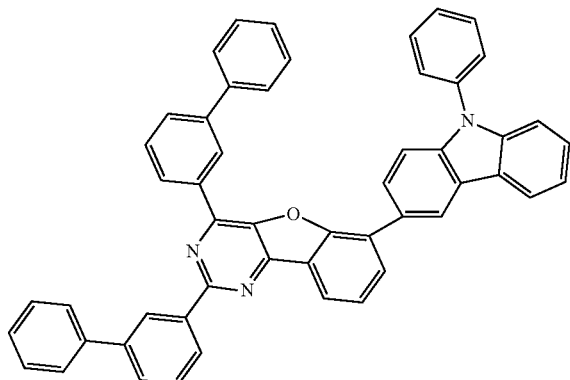
Formula 39
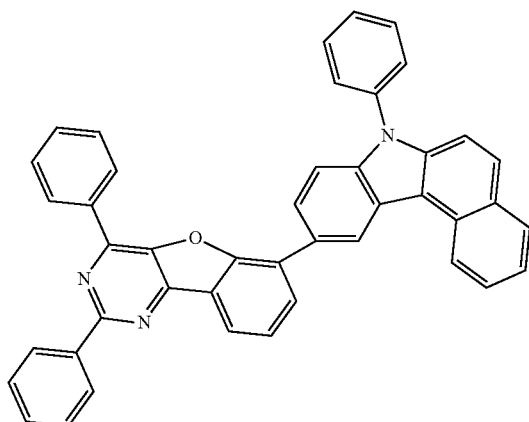
Formula 40
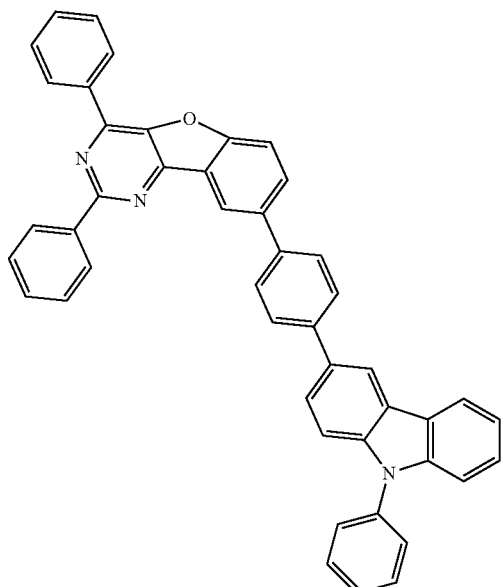
Formula 41
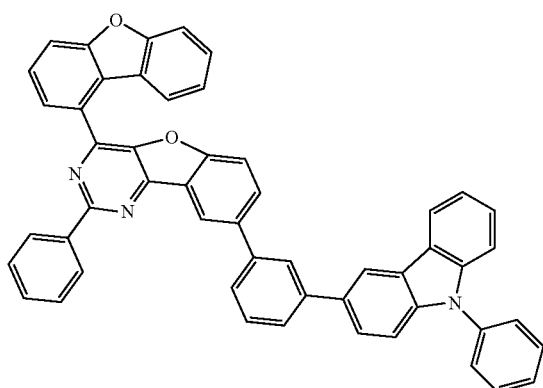
Formula 42
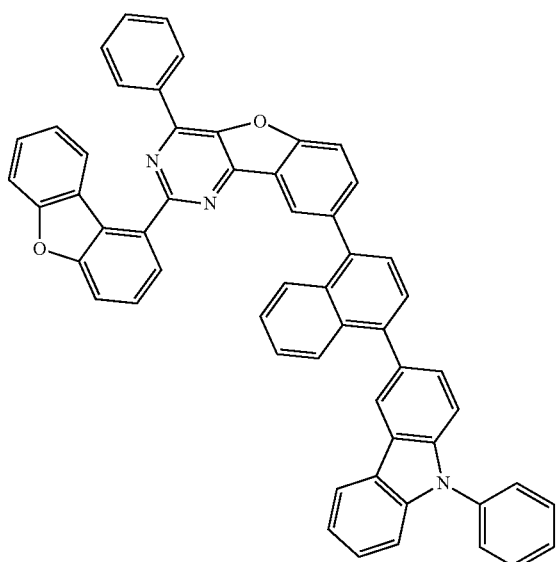

-continued
Formula 43
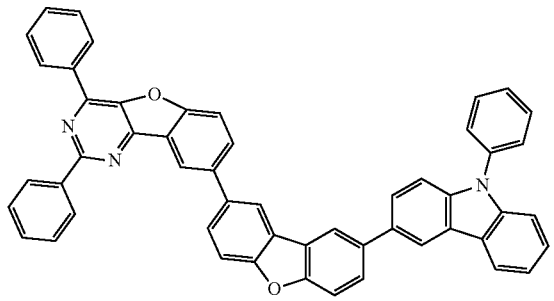
Formula 44
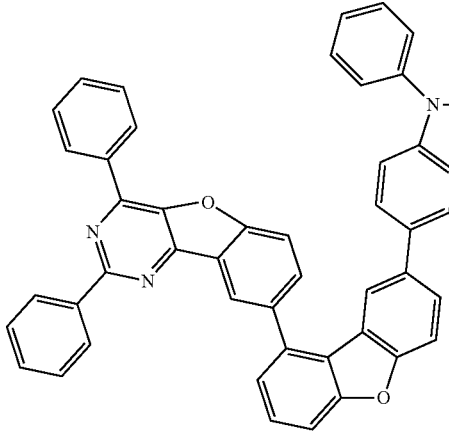
Formula 45
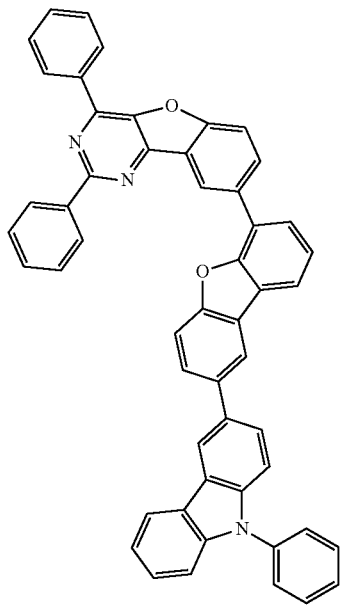
Formula 46
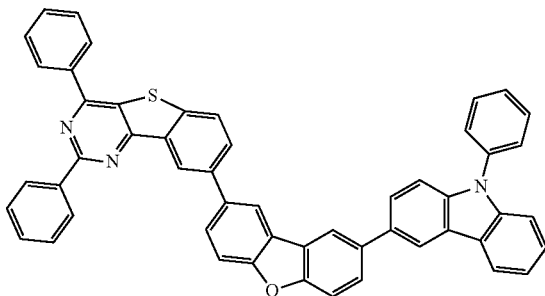
Formula 47
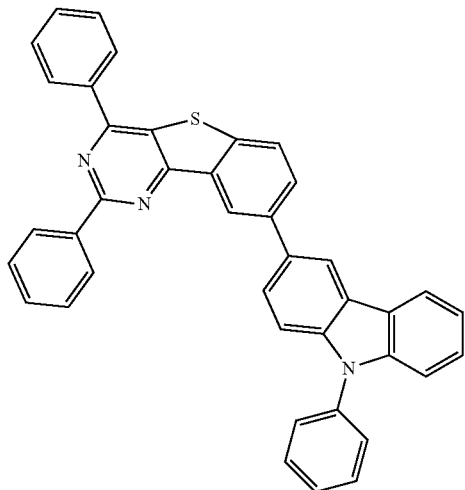
Formula 48
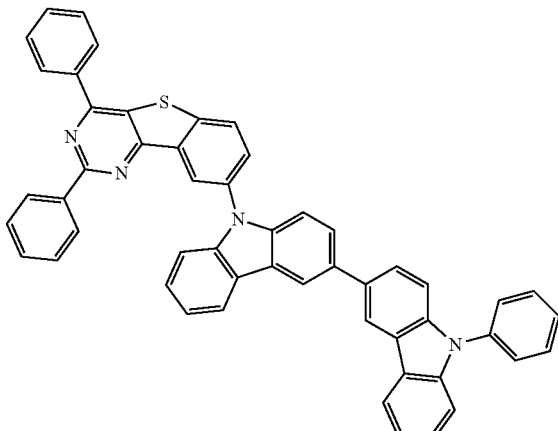

-continued
Formula 49
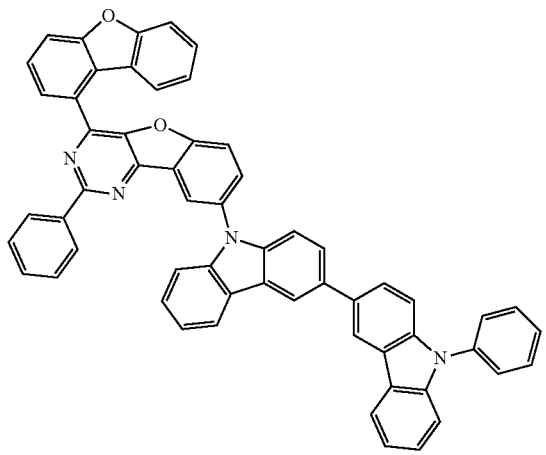
Formula 50
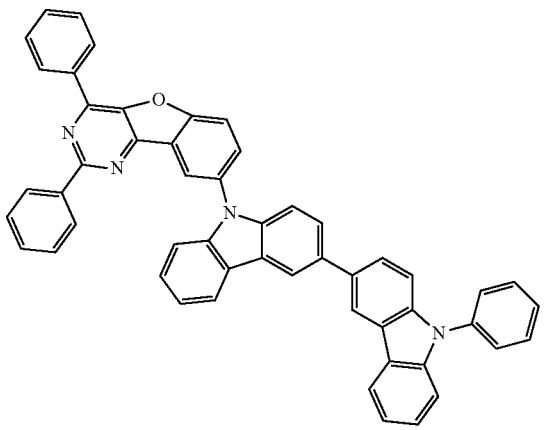
Formula 51
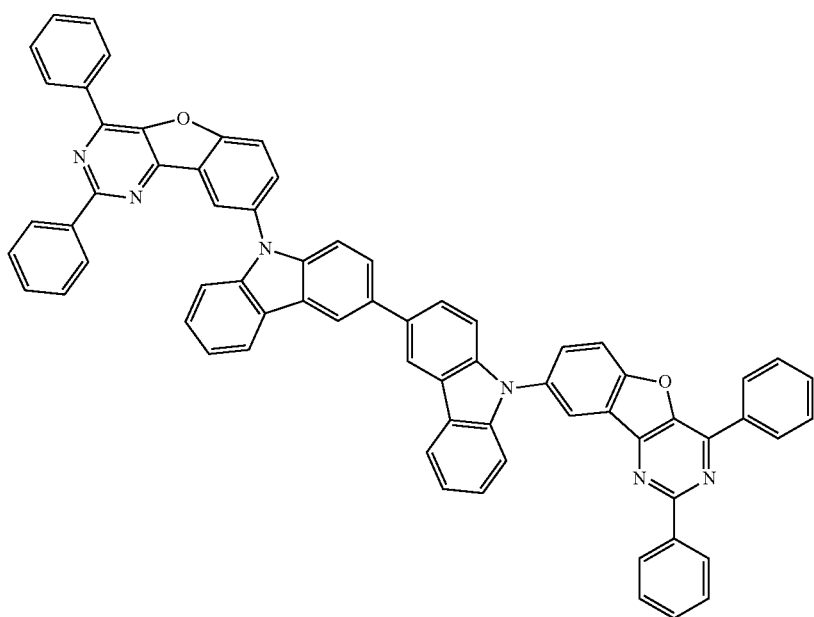
Formula 52
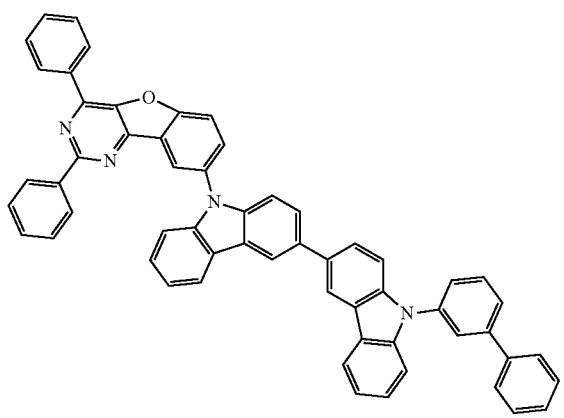
Formula 53
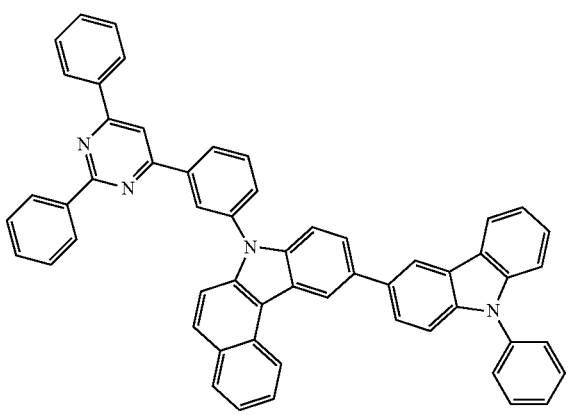

-continued
Formula 54
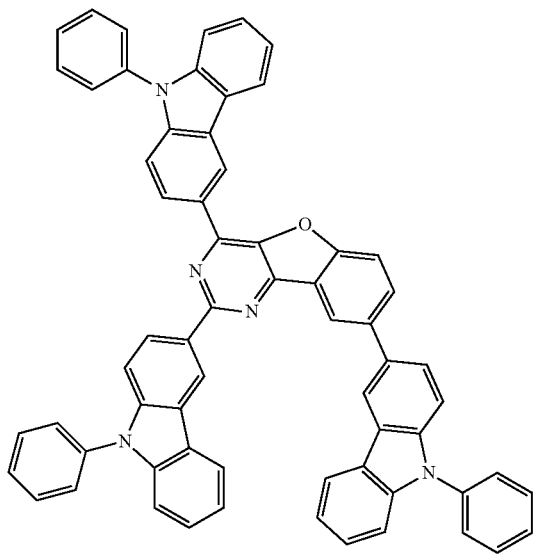
Formula 55
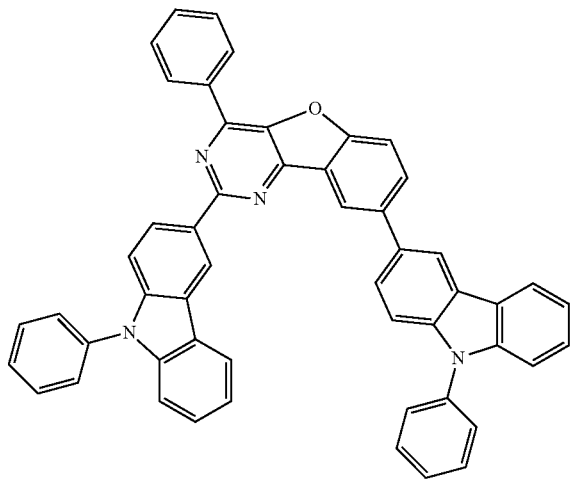
Formula 56
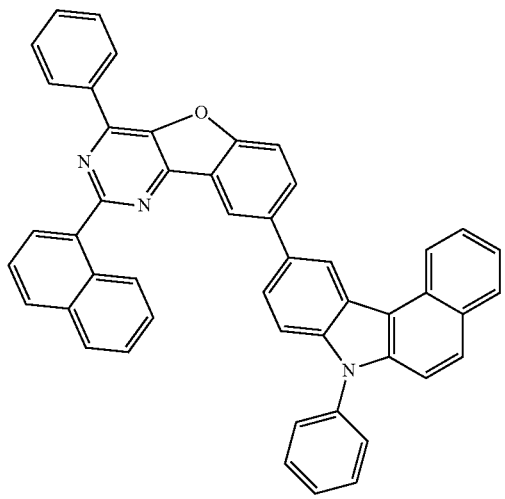
Formula 57
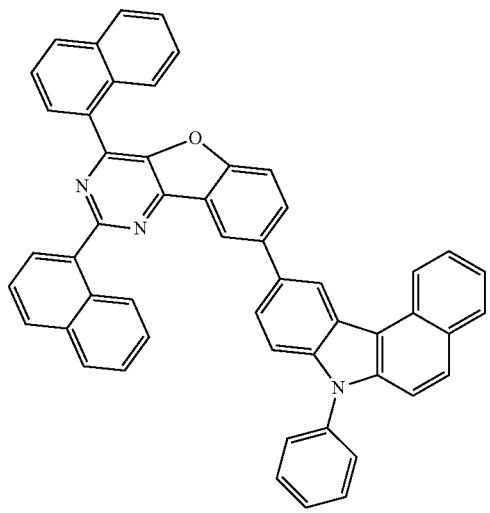
Formula 58
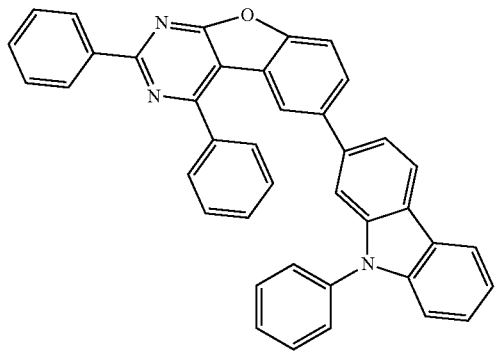
Formula 59
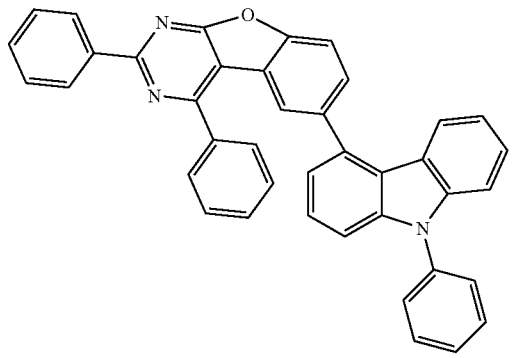

-continued
Formula 60
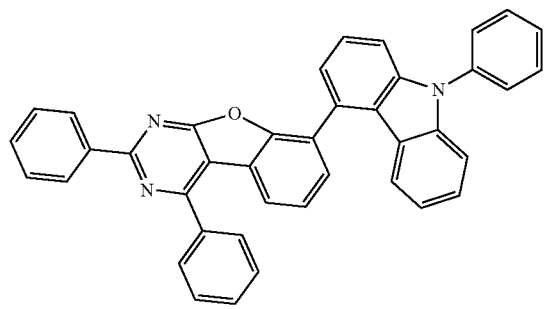
Formula 61
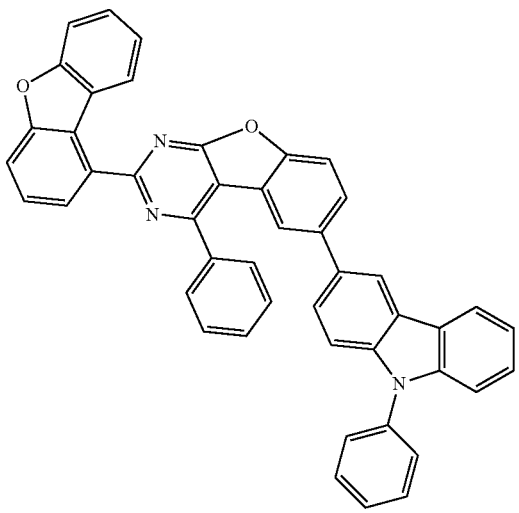
Formula 62
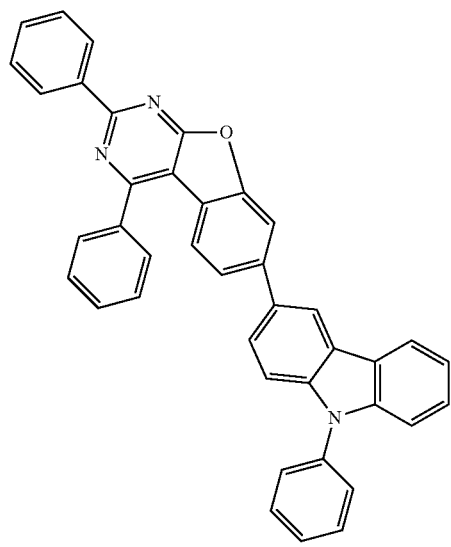
Formula 63
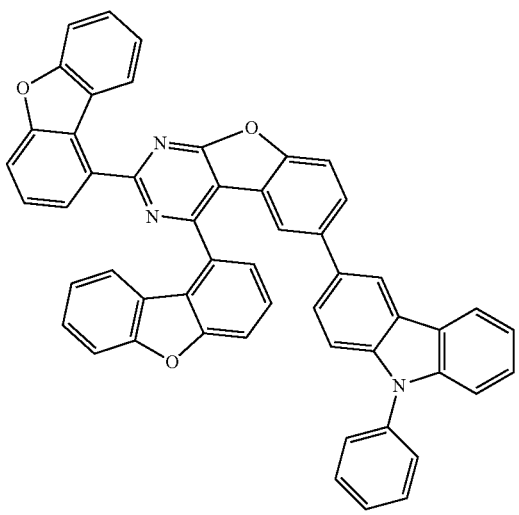
Formula 64
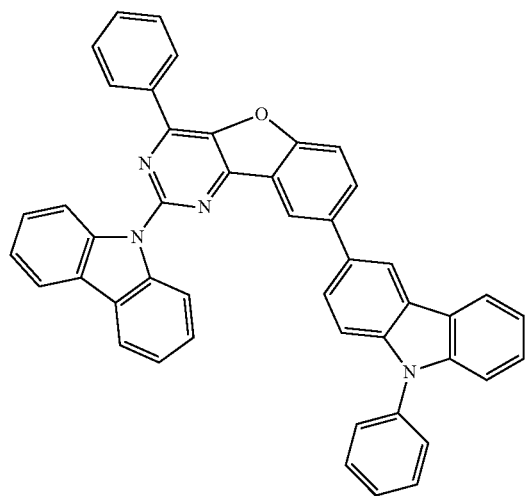
Formula 65
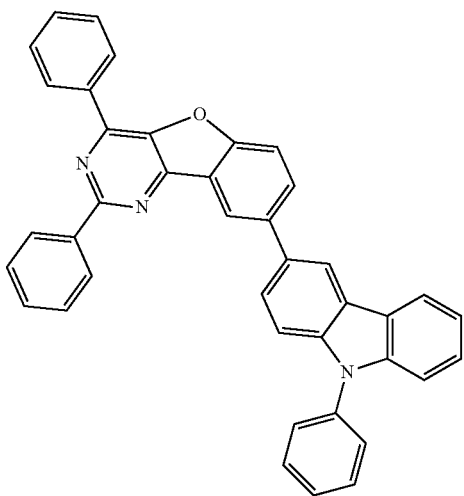

Formula 66
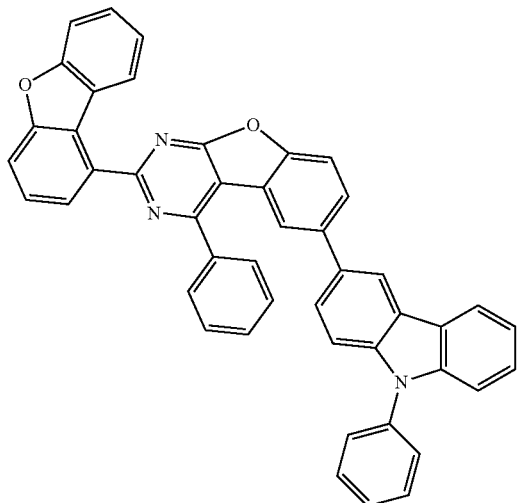
Formula 67
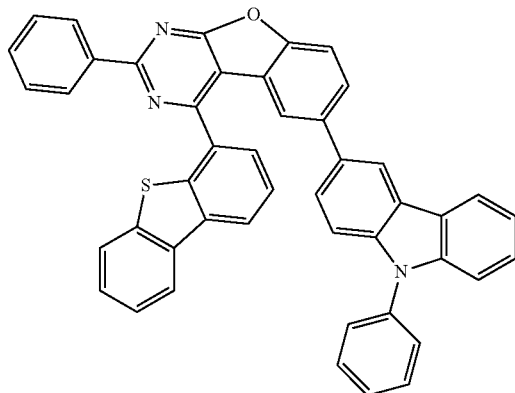
Formula 68
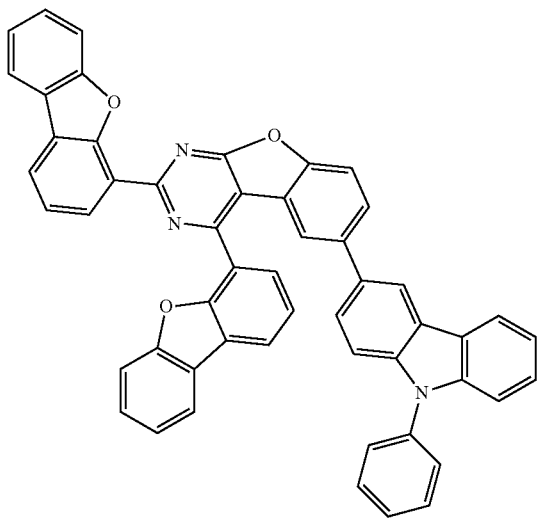
Formula 69
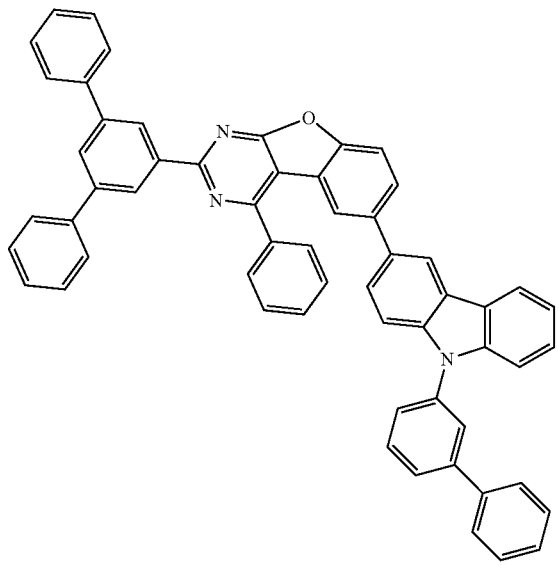
Formula 70
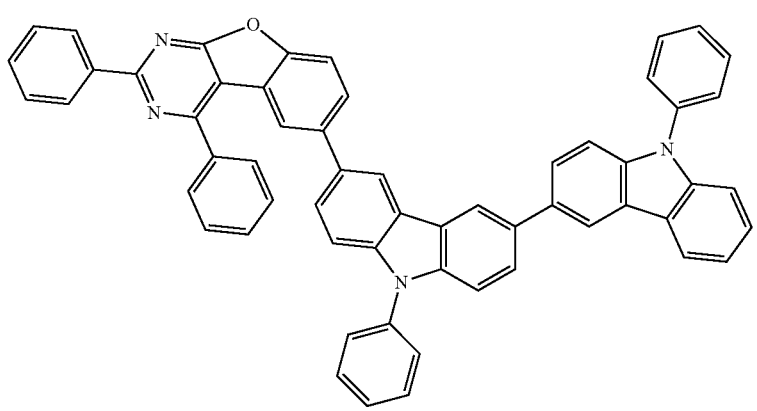

-continued
Formula 71
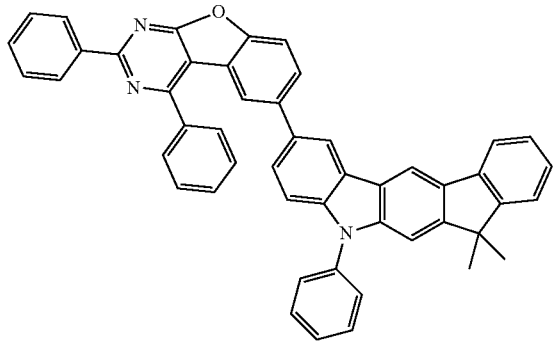
Formula 72
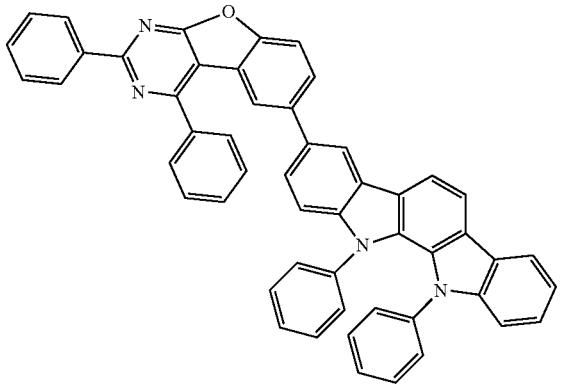
Formula 73
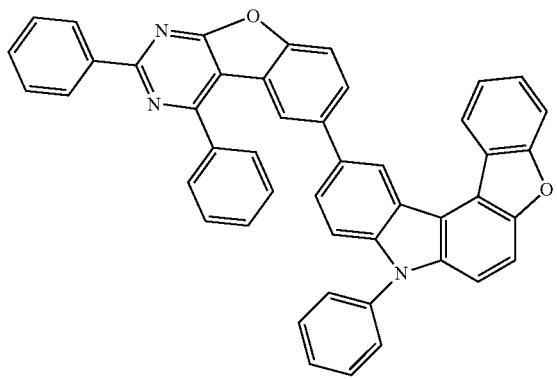
Formula 74
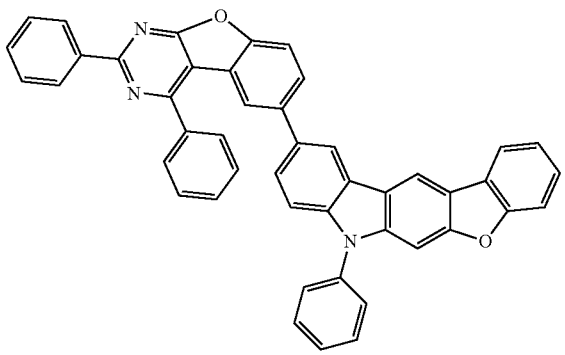
Formula 75
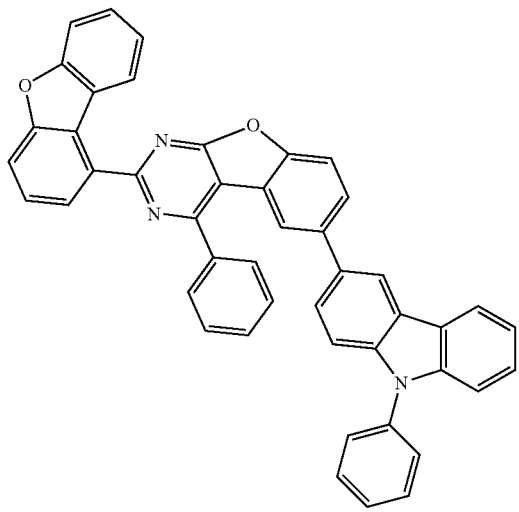
Formula 76
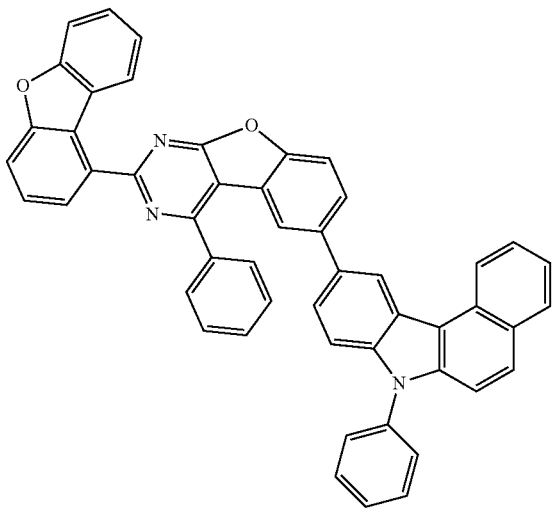

-continued
Formula 77
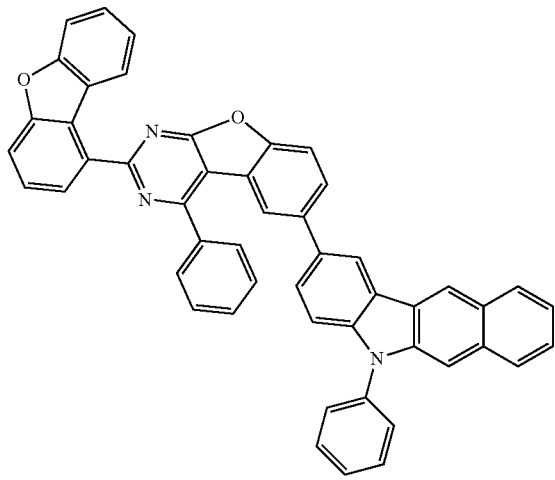
Formula 78
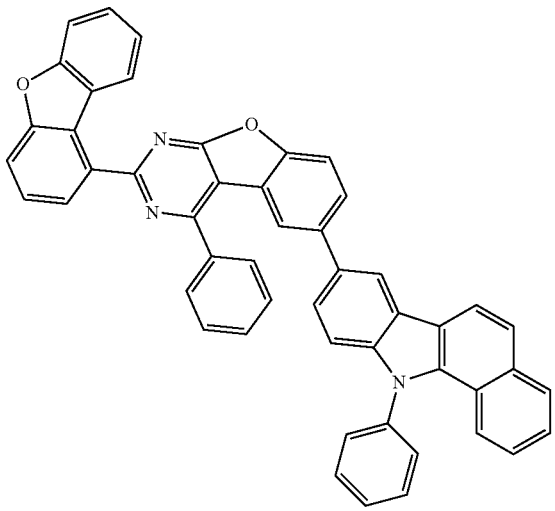
Formula 79
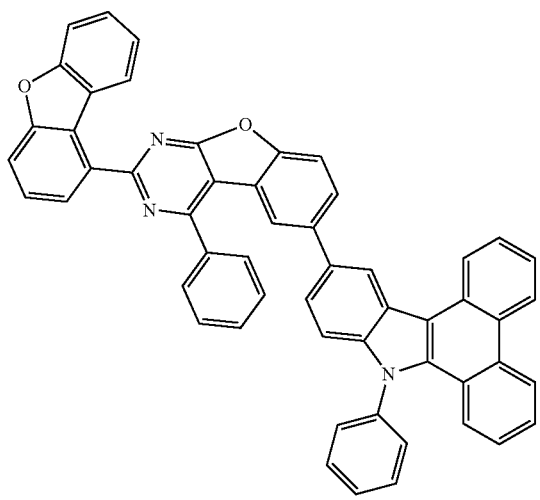
Formula 80
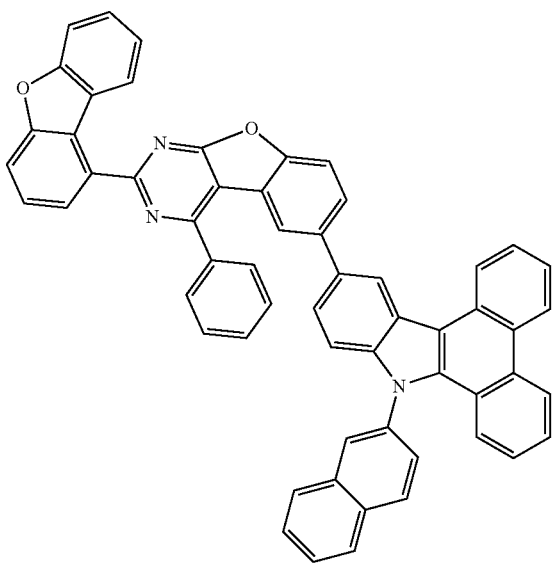
Formula 81
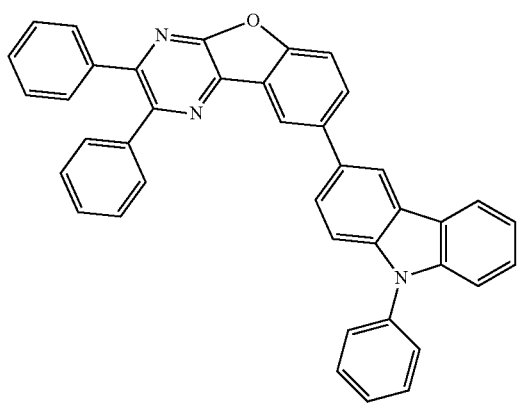
Formula 82
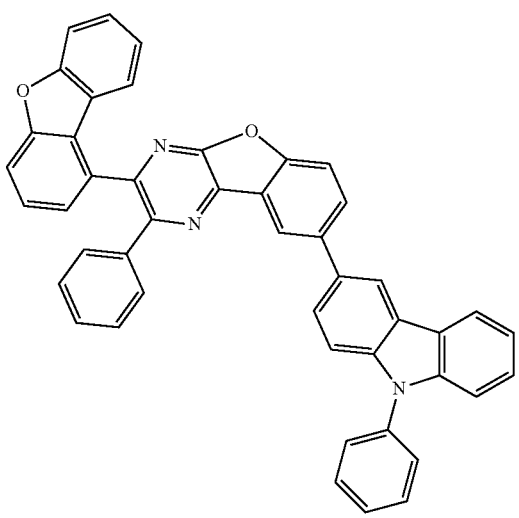

-continued
Formula 83
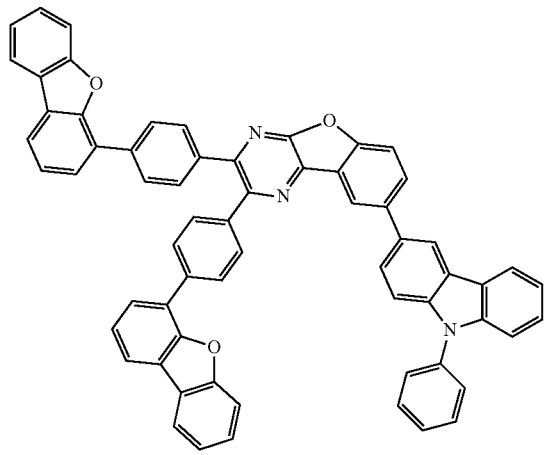
Formula 84
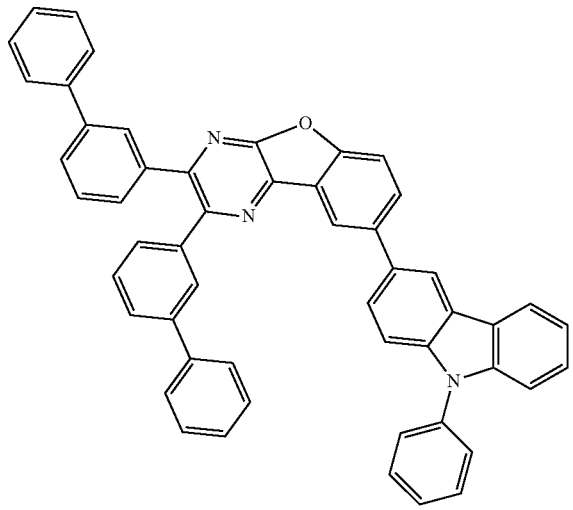
Formula 85
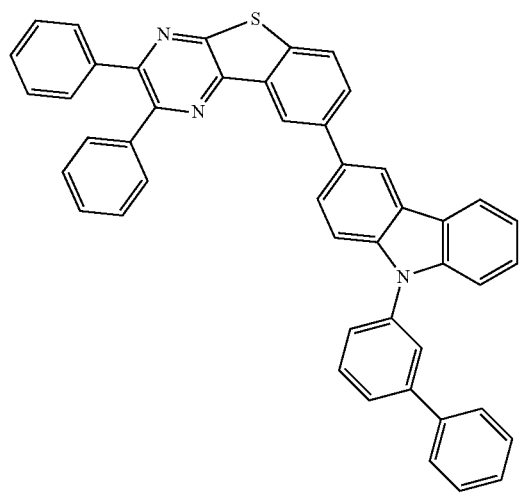
Formula 86
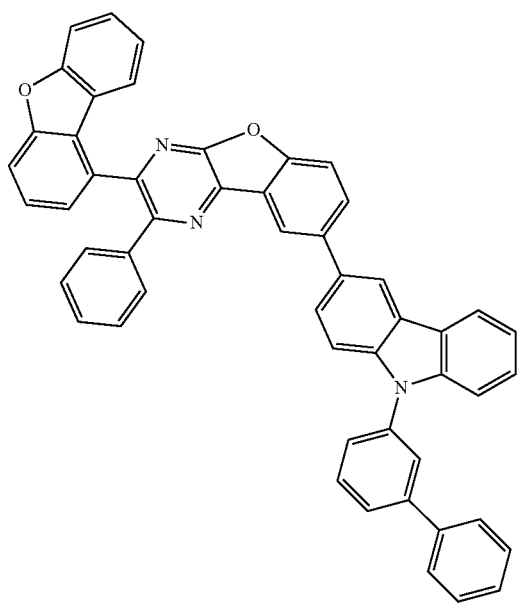
Formula 87
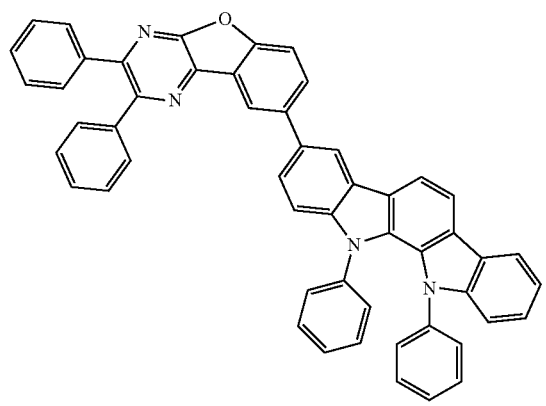
Formula 88
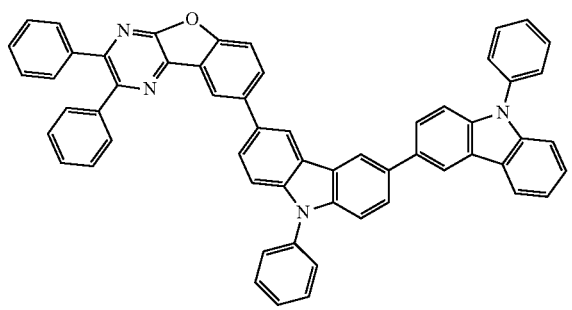

-continued
Formula 89
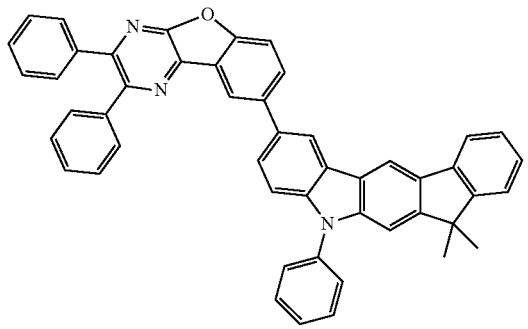
Formula 90
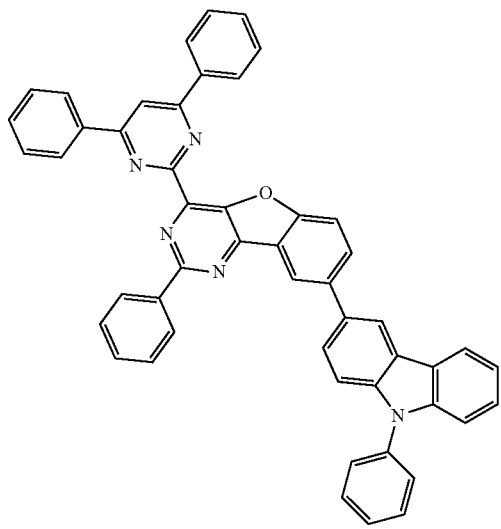
Formula 91
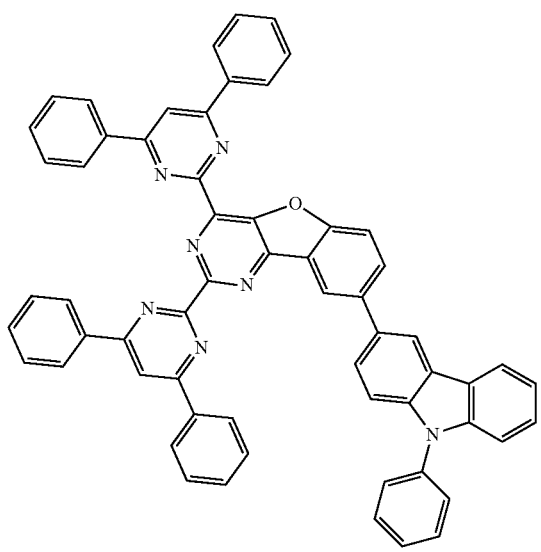
Formula 92
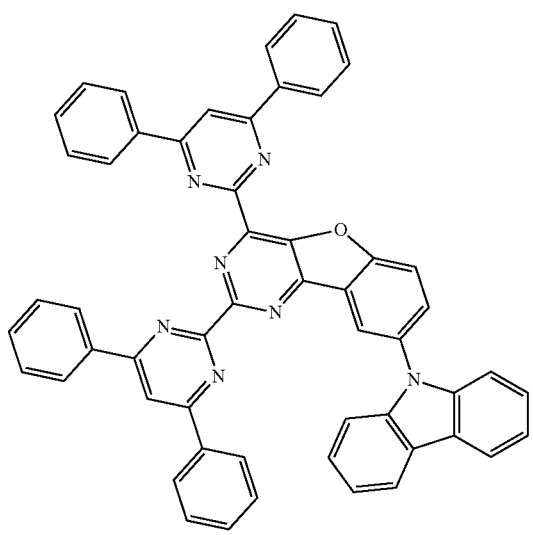

-continued
Formula 93
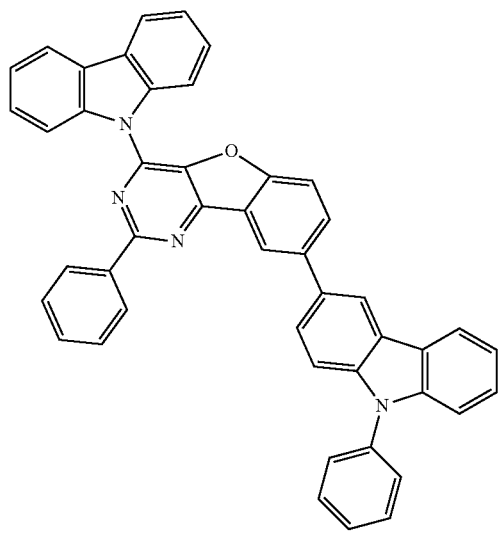
Formula 94
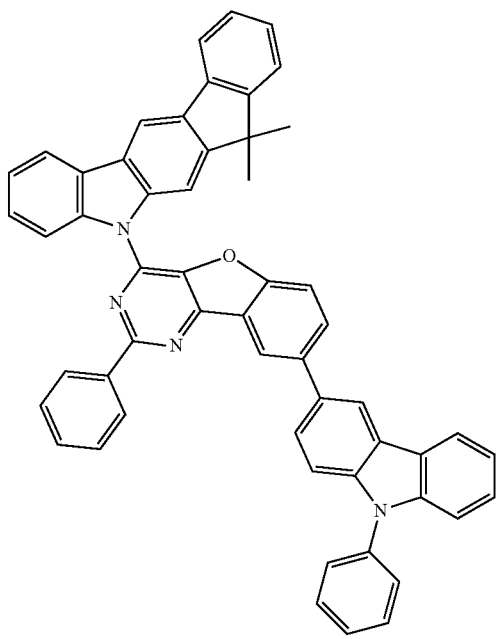
Formula 95
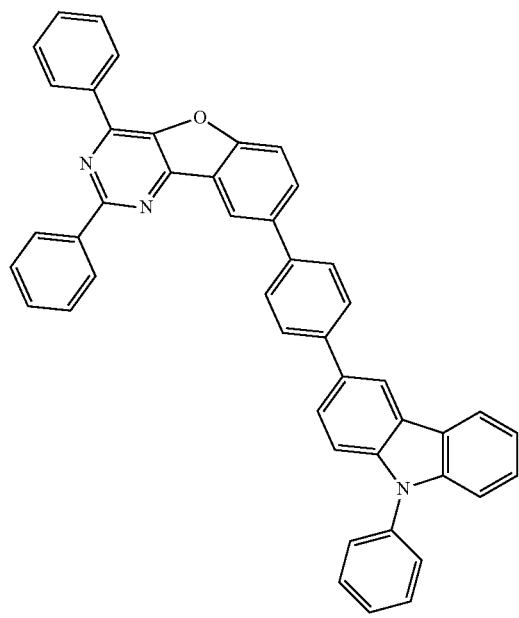
Formula 96
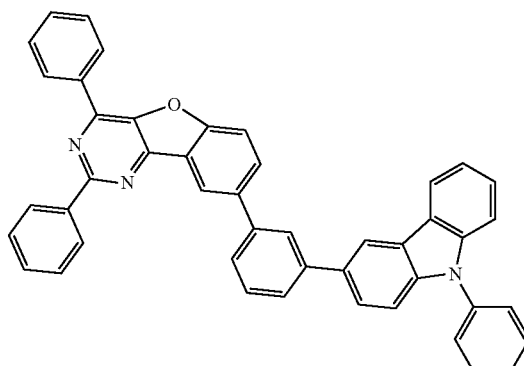

-continued
Formula 97
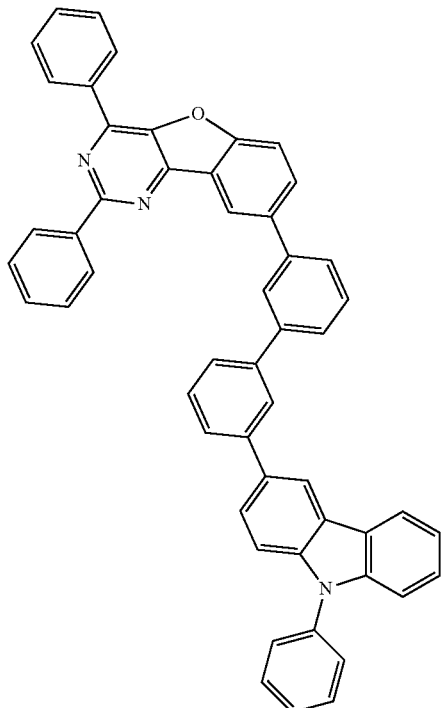
Formula 98
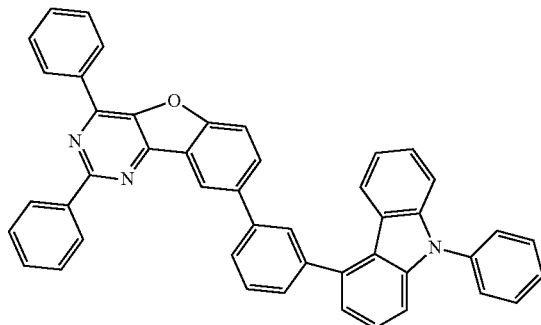
Formula 99
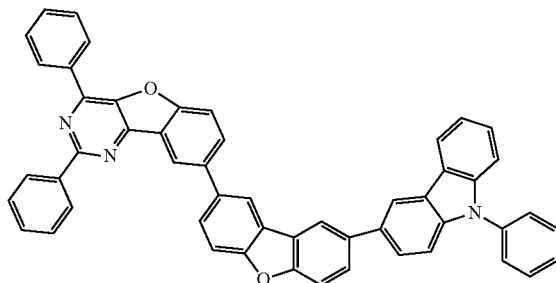
Formula 100
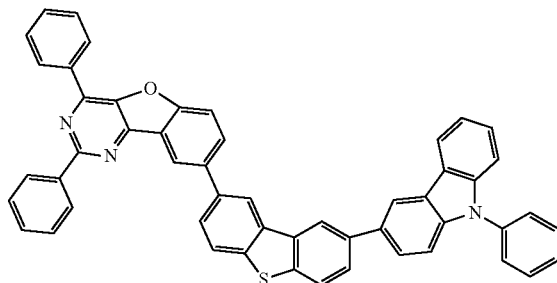
Formula 101
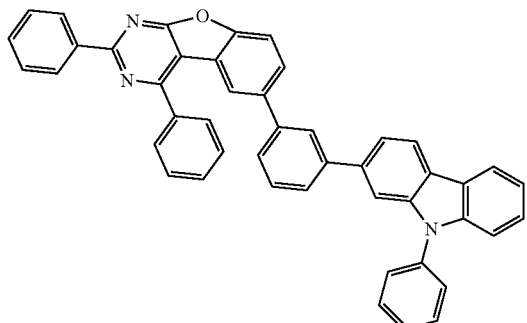
Formula 102
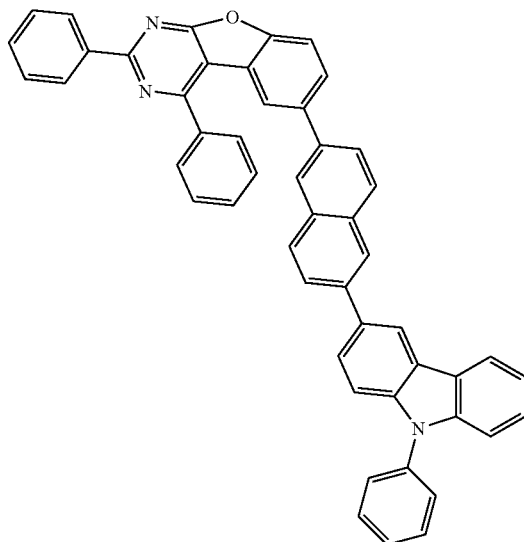

-continued
Formula 103
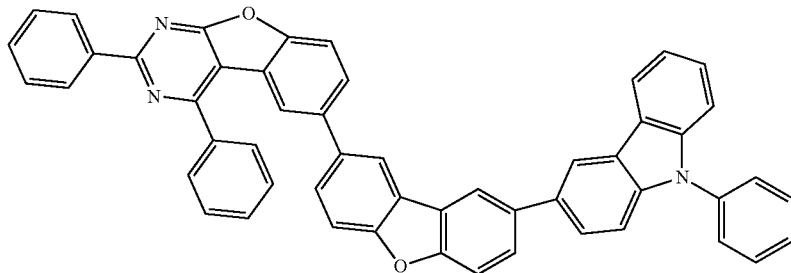
Formula 104
Formula 105
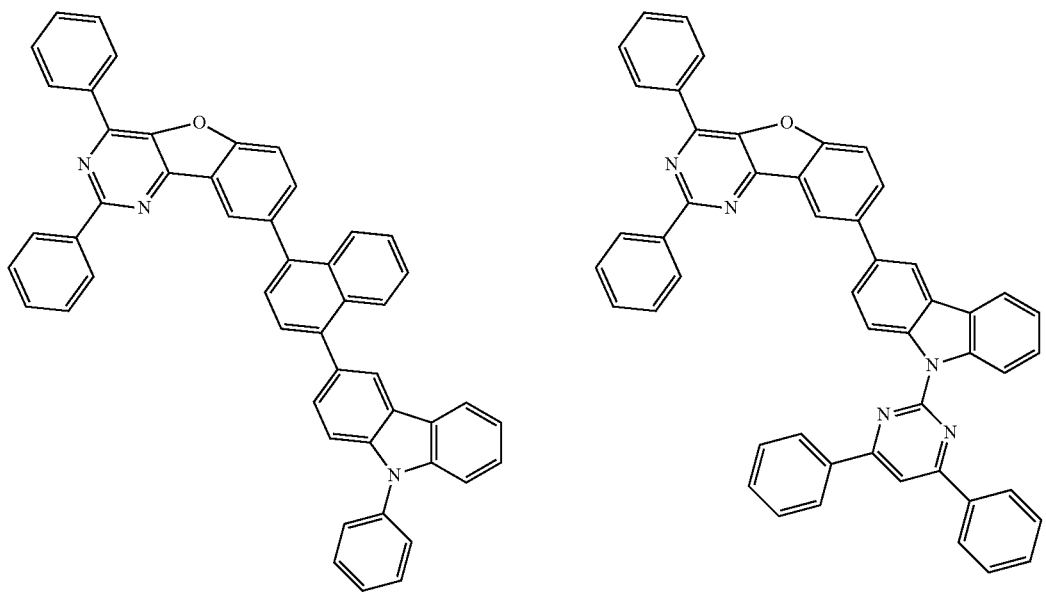
Formula 106
Formula 107
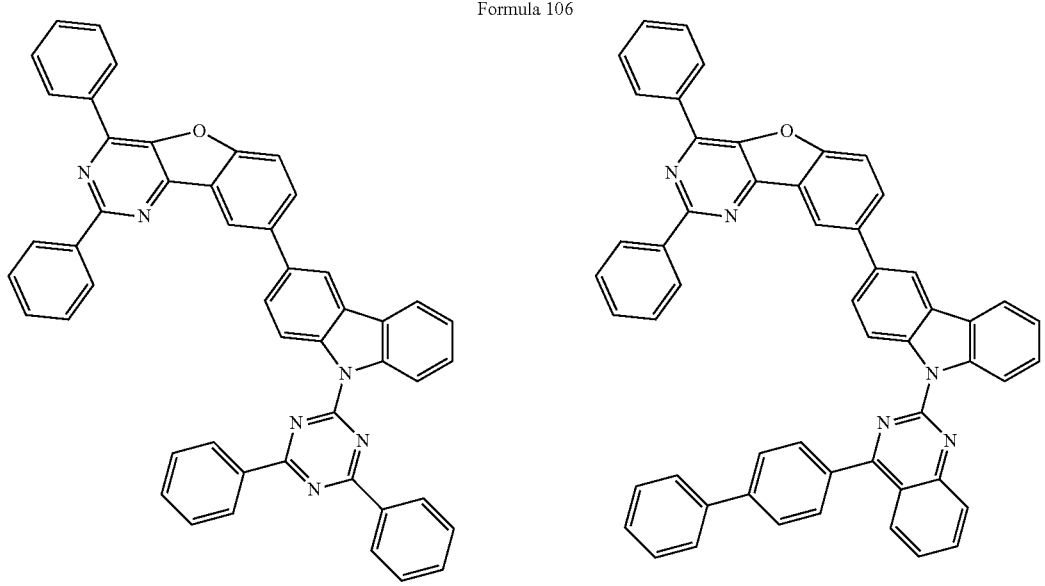

-continued
Formula 108
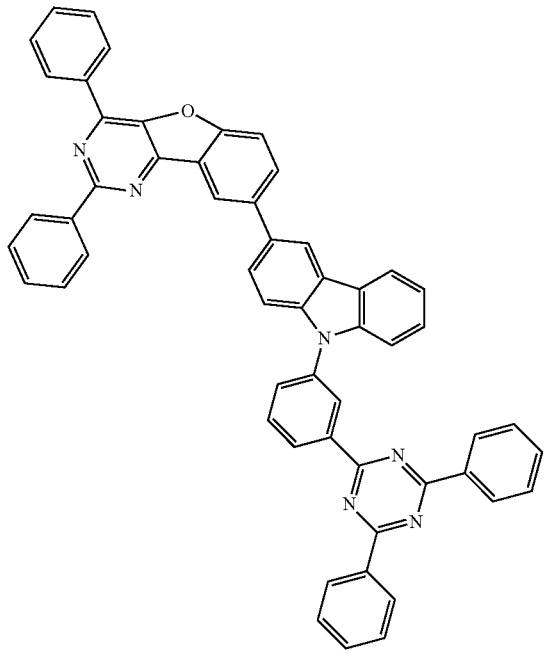
Formula 109
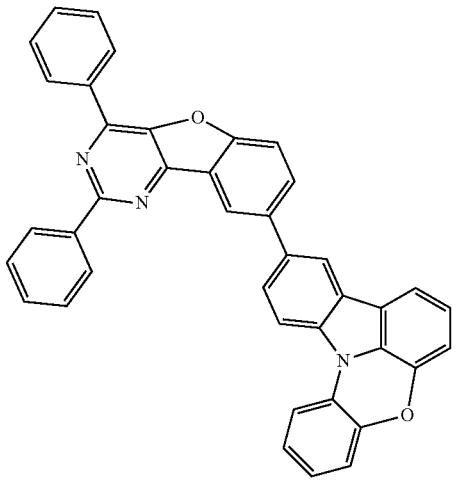
Formula 110
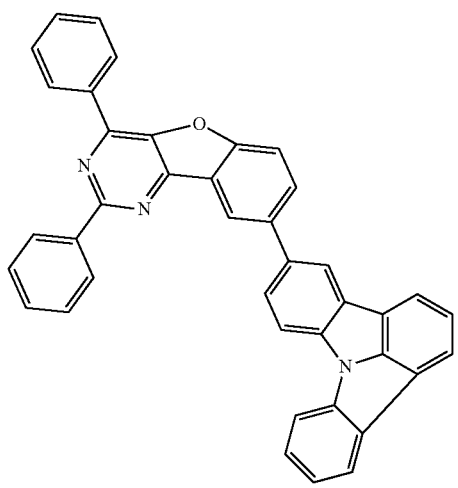
Formula 111
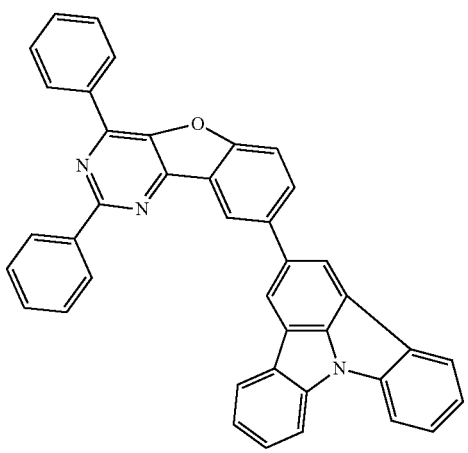

-continued
Formula 112
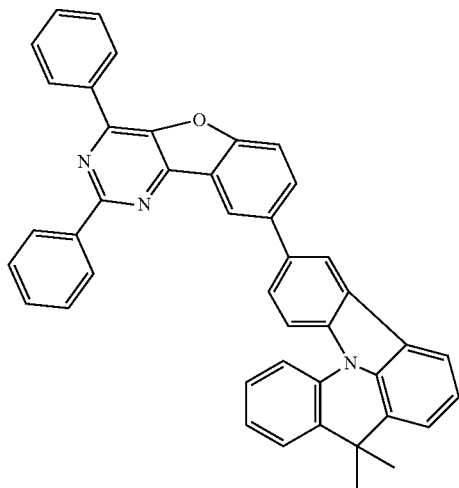
Formula 113
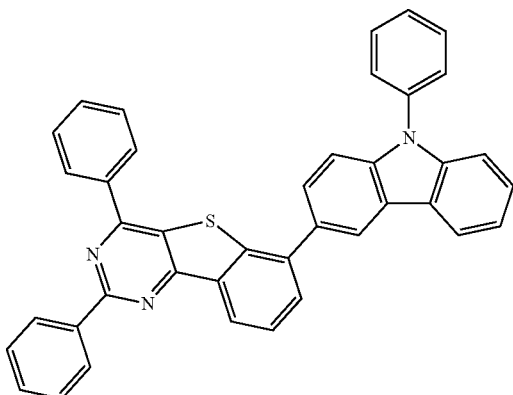
Formula 114
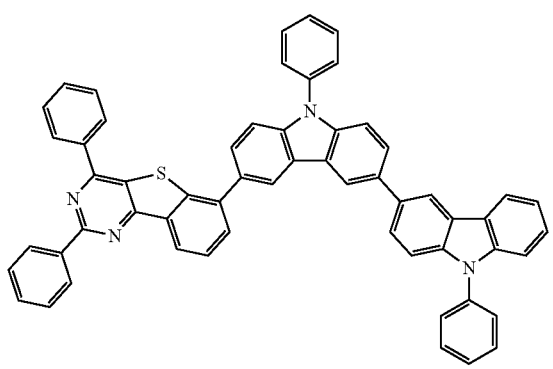
Formula 115
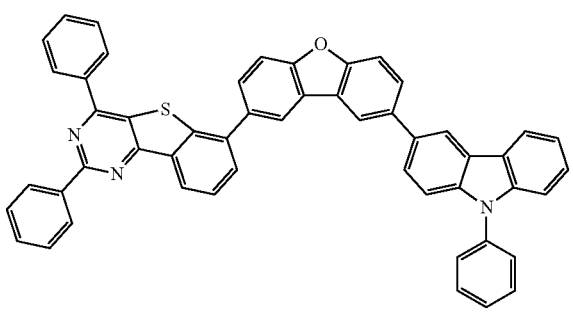
Formula 116
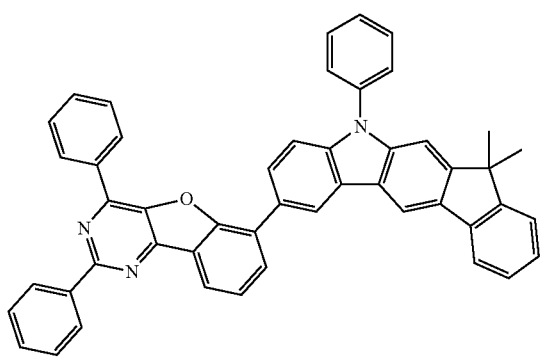
Formula 117
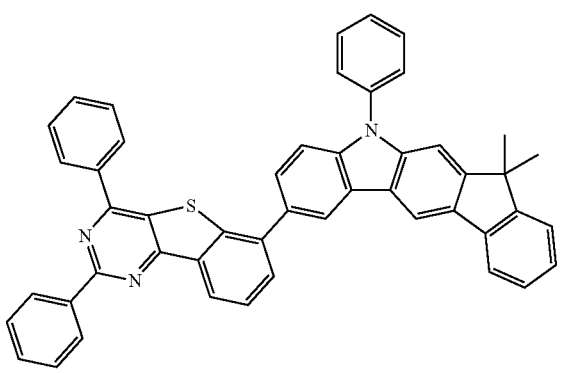

-continued
Formula 118
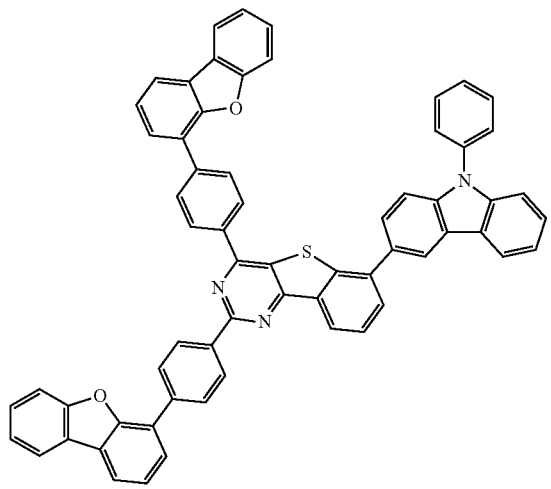
Formula 119
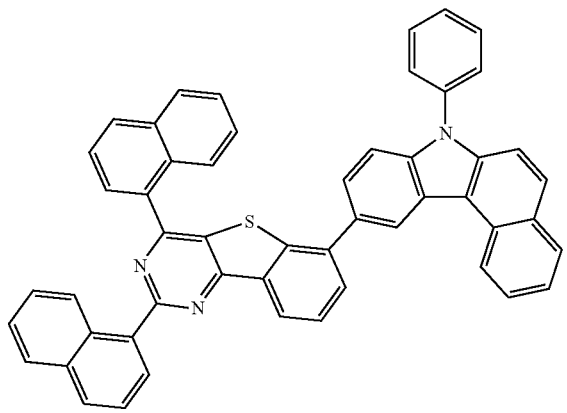
Formula 120
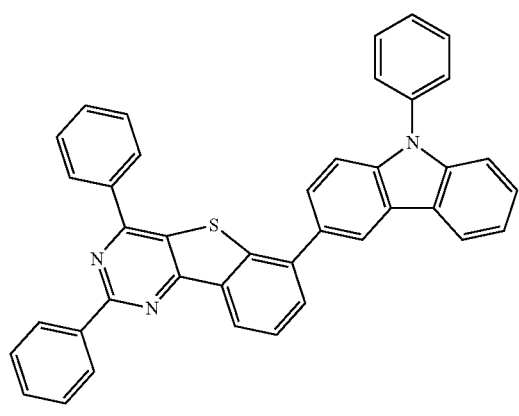
Formula 121
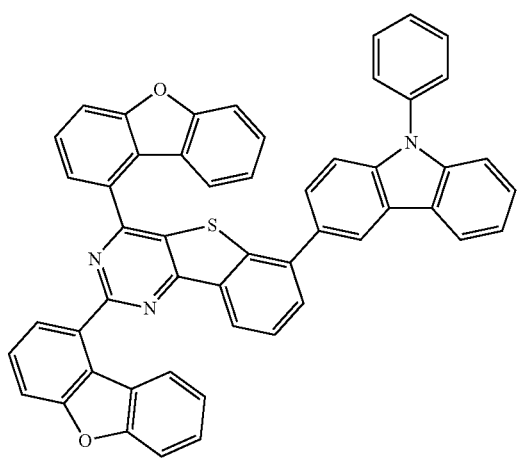
Formula 122
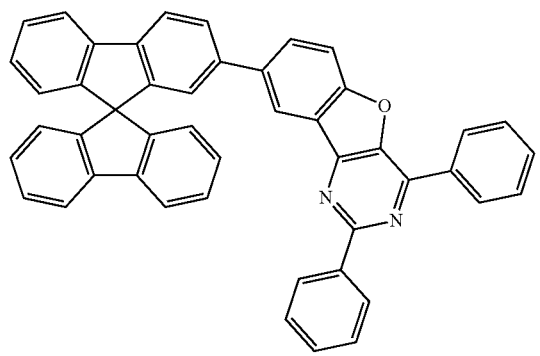
Formula 123
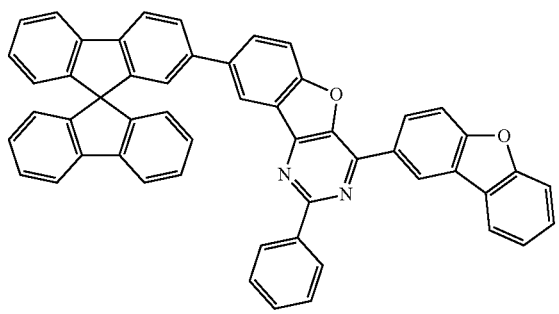

-continued
Formula 124
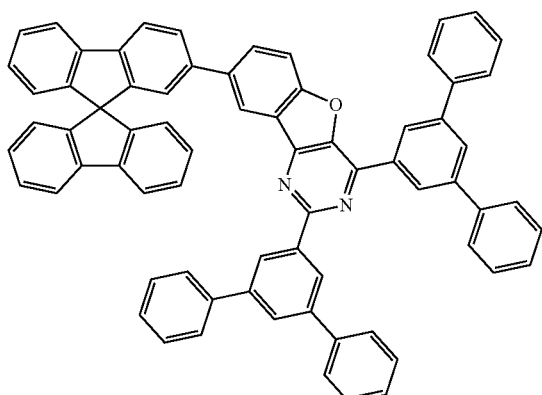
Formula 125
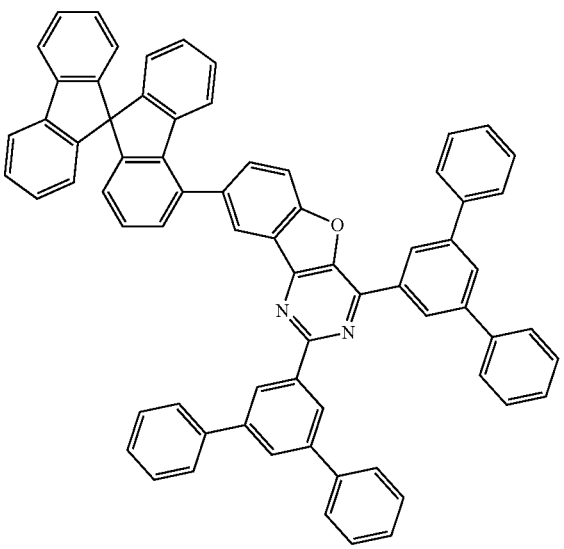
Formula 126
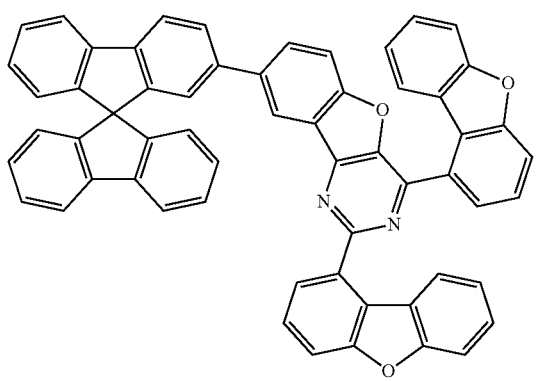
Formula 127
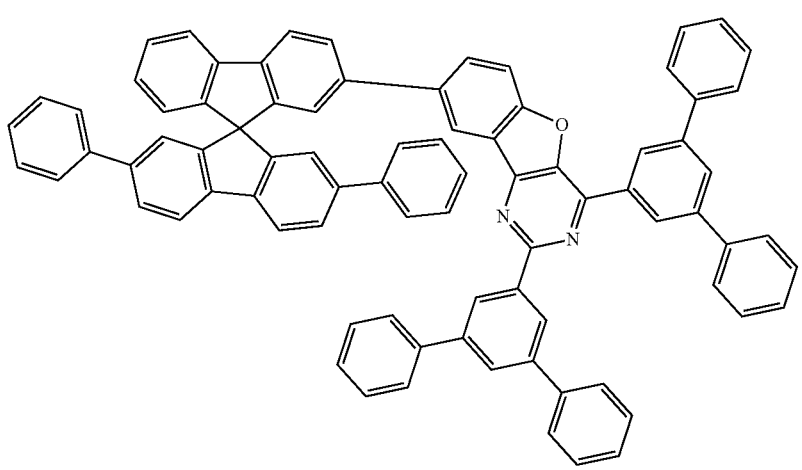

-continued
Formula 128
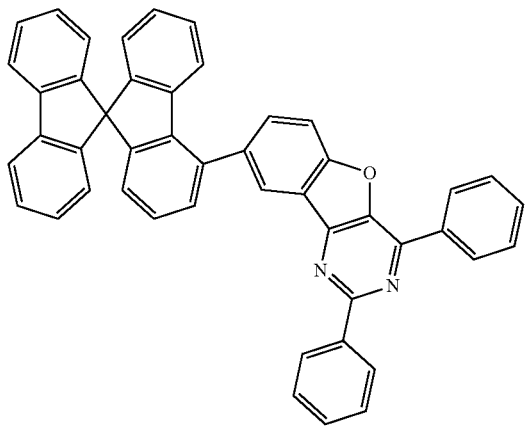
Formual 129
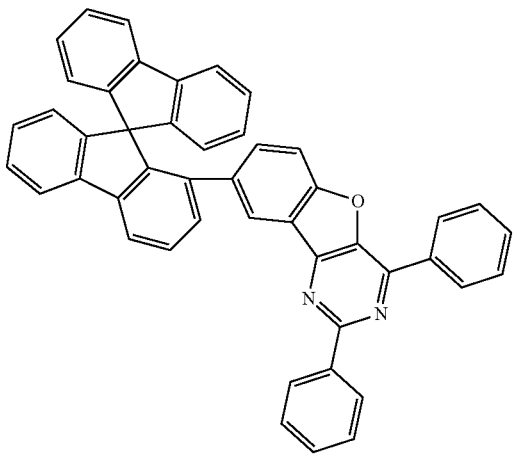
Formula 130
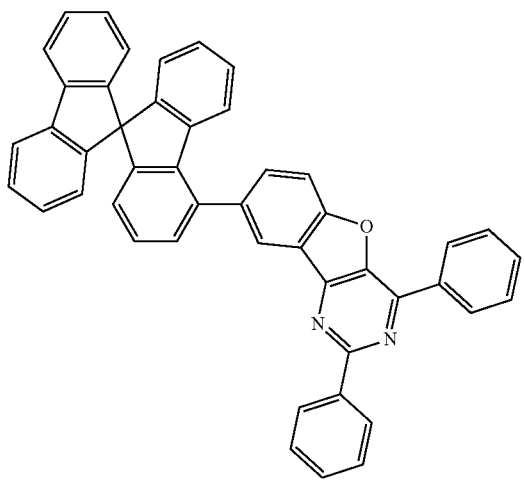
Formula 131
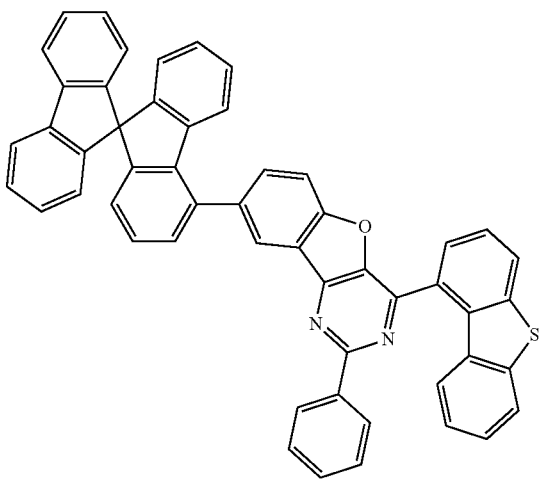
Formula 132
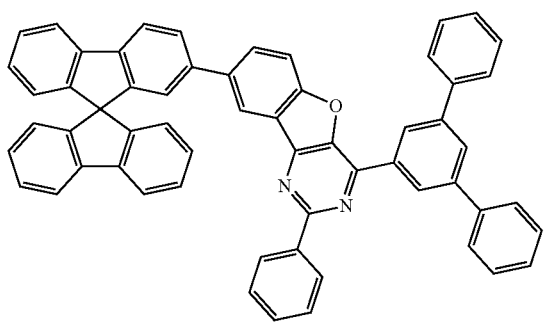
Formula 133
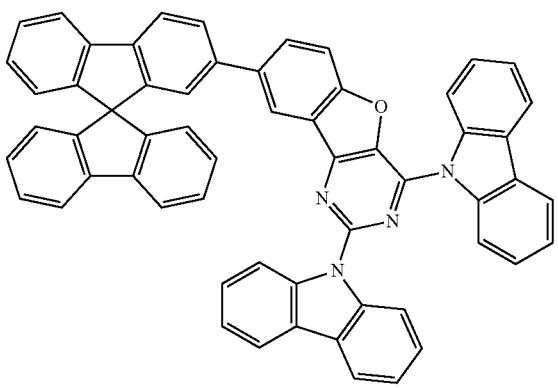

-continued
Formula 134
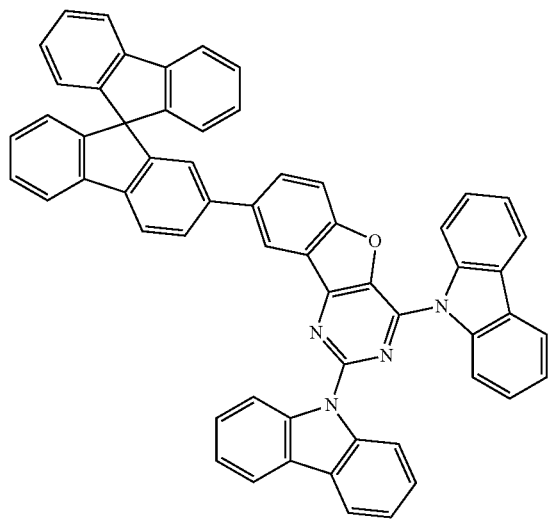
Formula 135
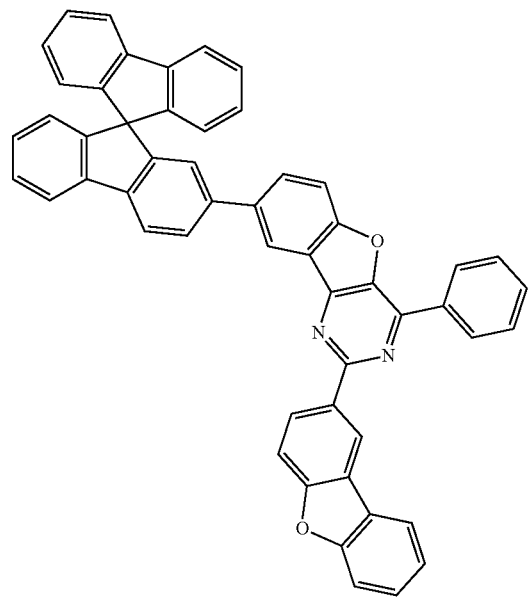
Formula 136
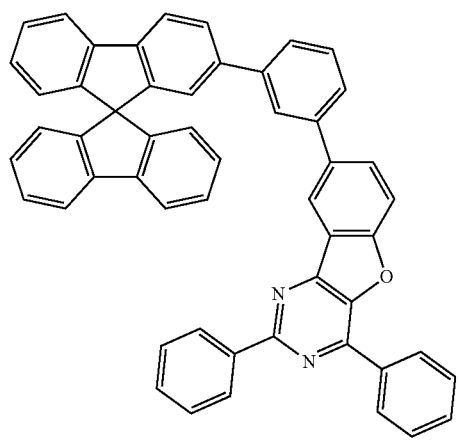
Formula 137
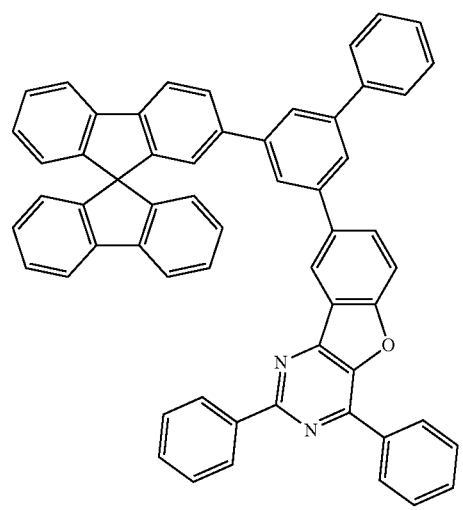
Formula 138
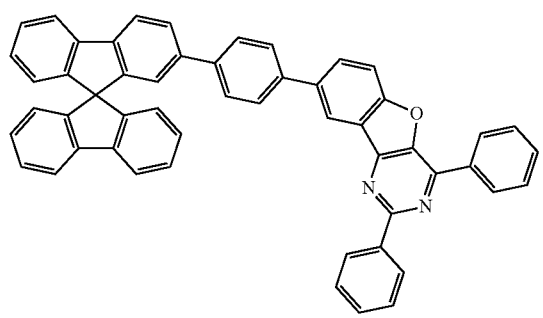
Formula 139
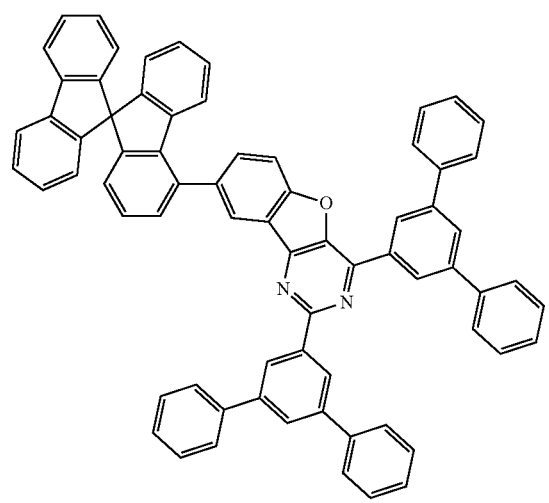

-continued
Formula 140
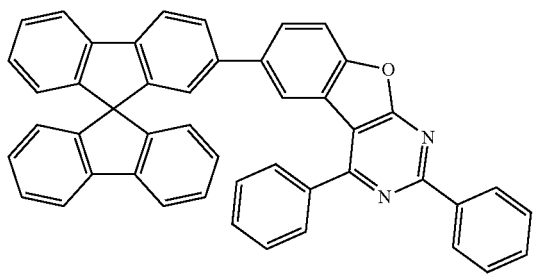
Formula 141
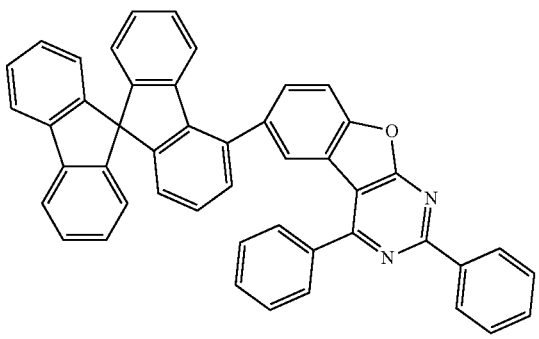
Formula 142
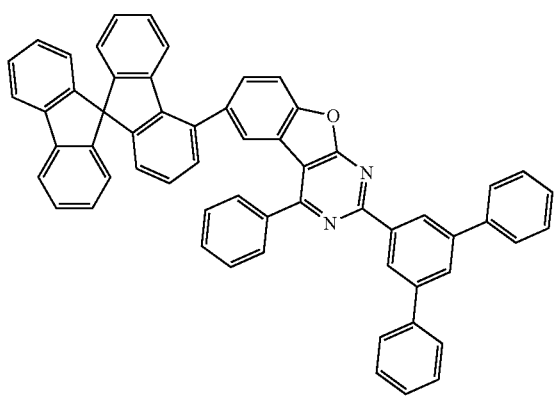
Formula 143
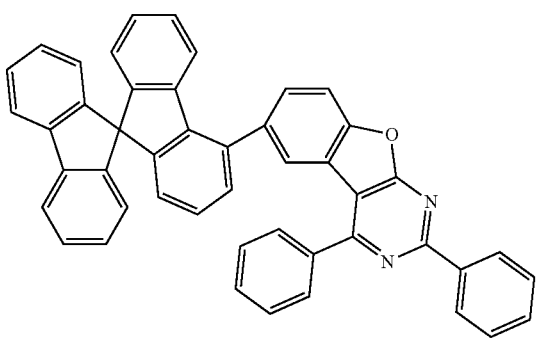
Formula 144
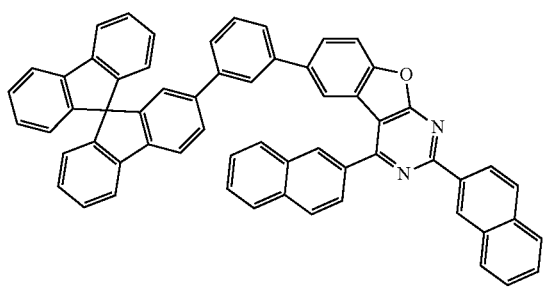
Formula 145
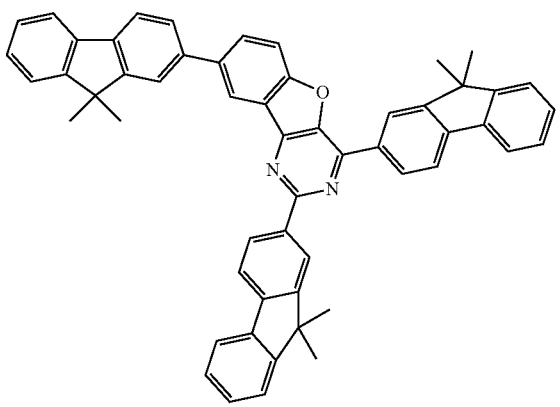
Formula 146
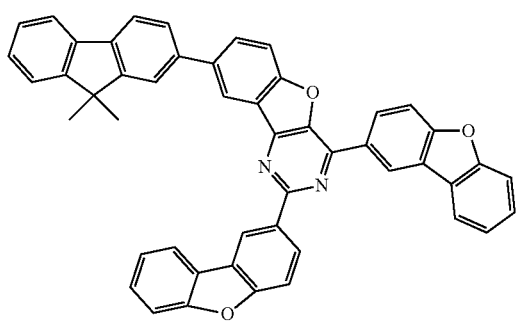
Formula 147
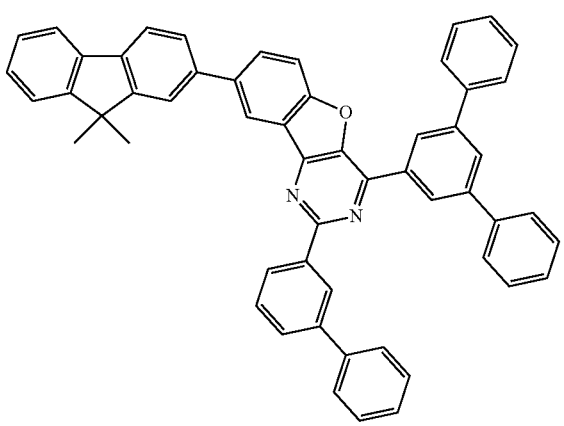

-continued
Formula 148
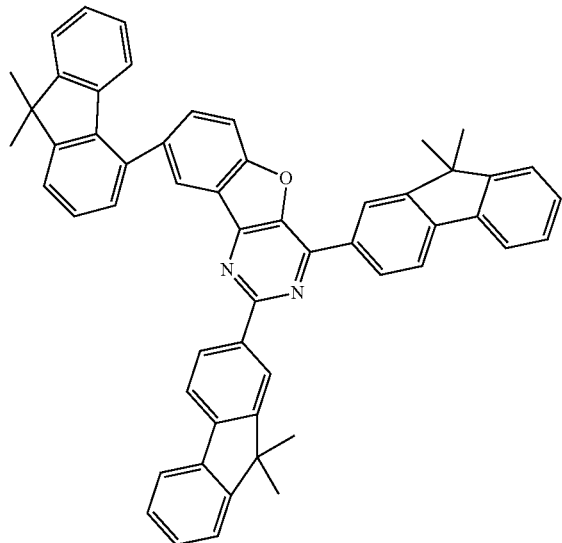
Formula 149
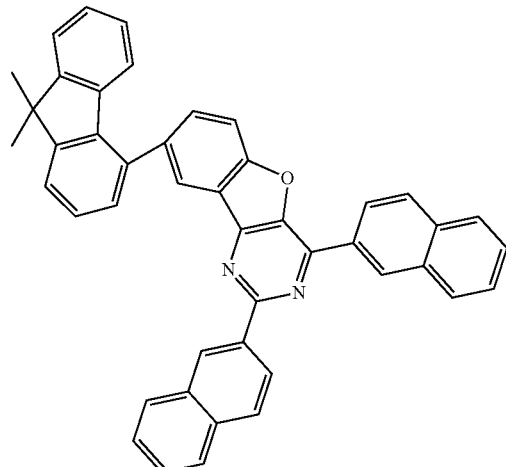
Formula 150
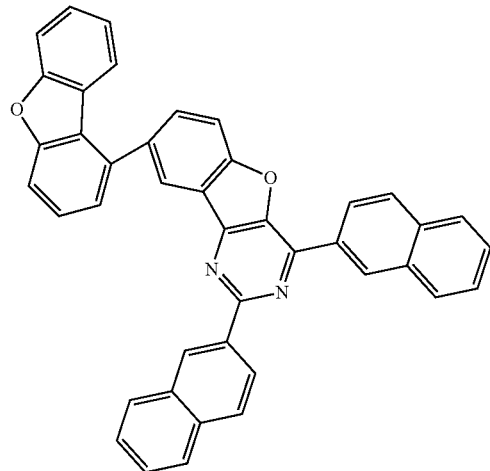
Formula 151
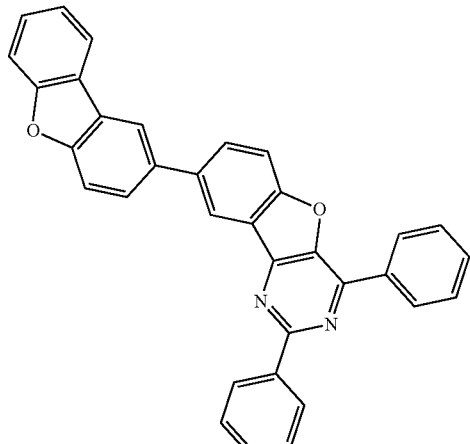
Formula 152
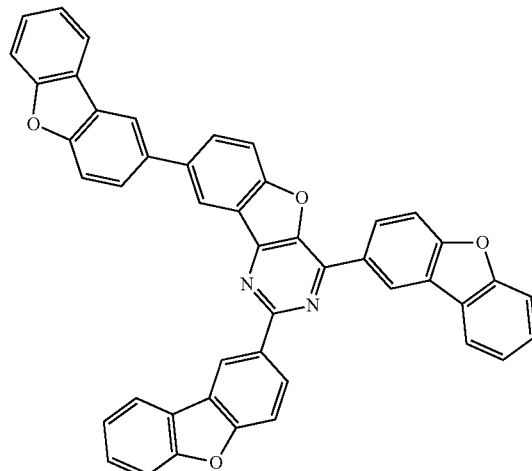
Formula 153
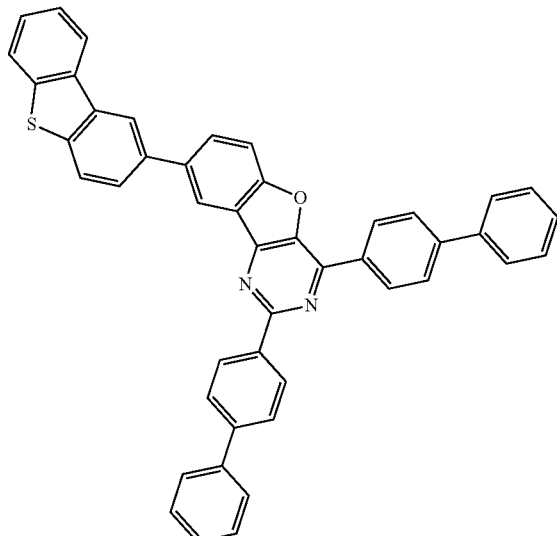

-continued
Formula 154
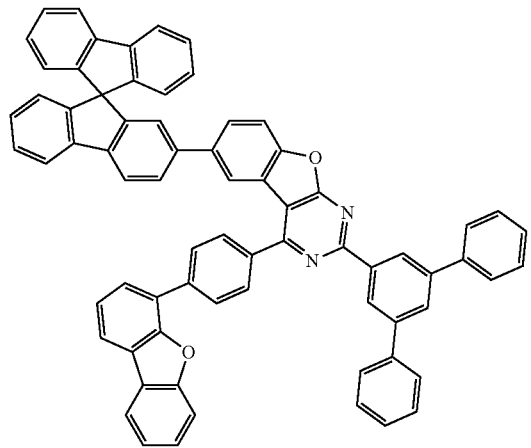
Formula 155
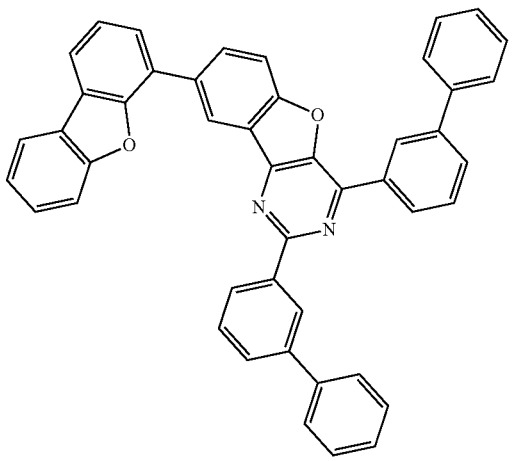
Formula 156
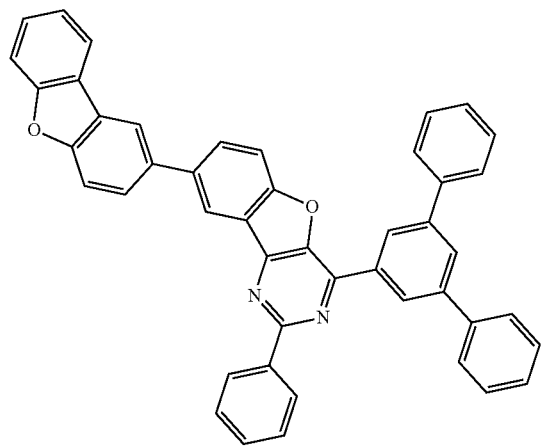
Formula 157
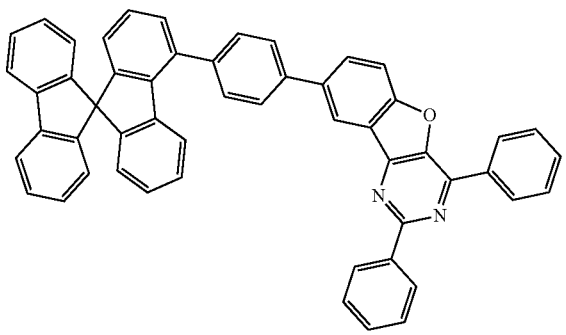
Formula 158
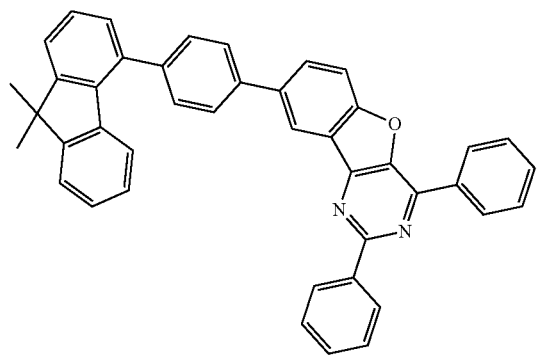
Formula 159
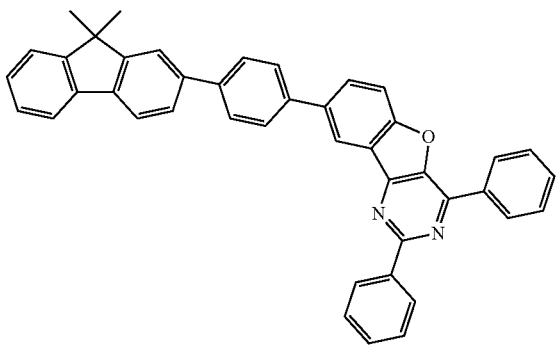

-continued
Formula 160
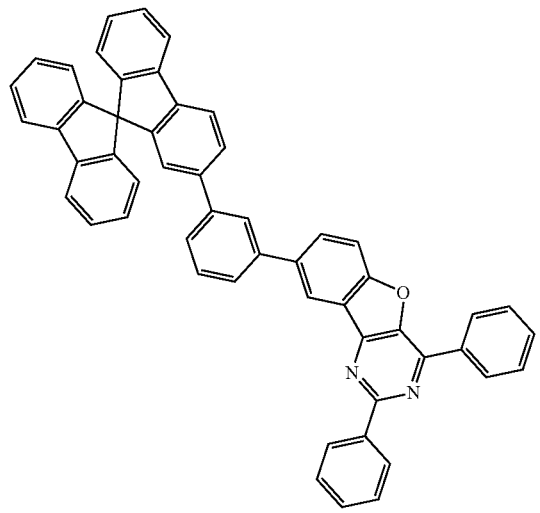
Formula 161
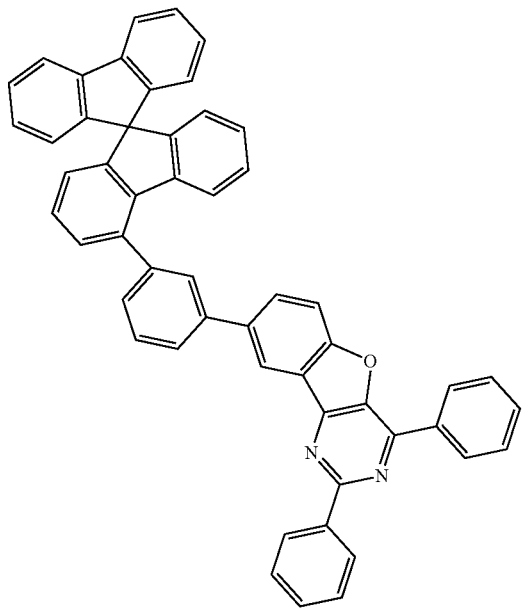
Formula 162
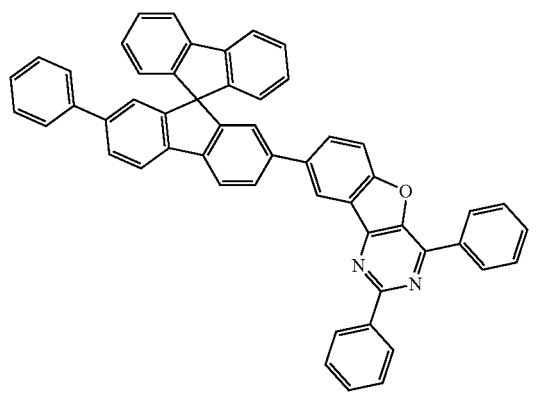
Formula 163
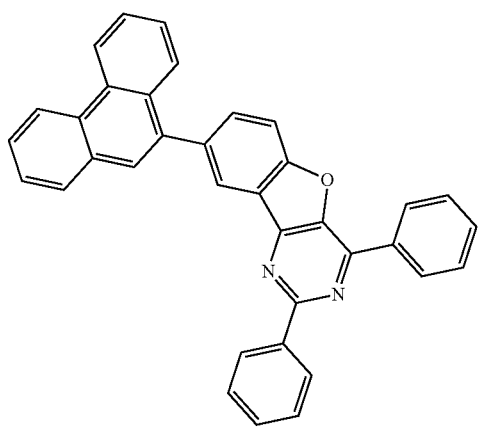
Formula 164
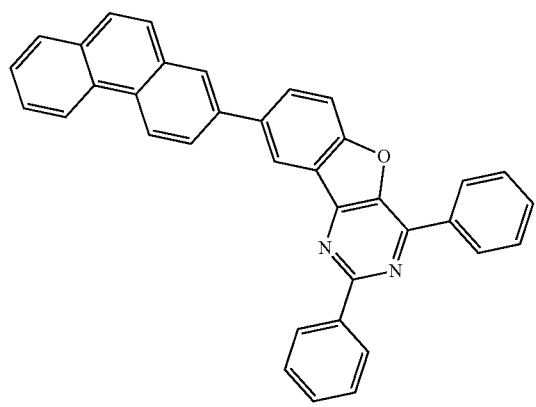
Formula 165
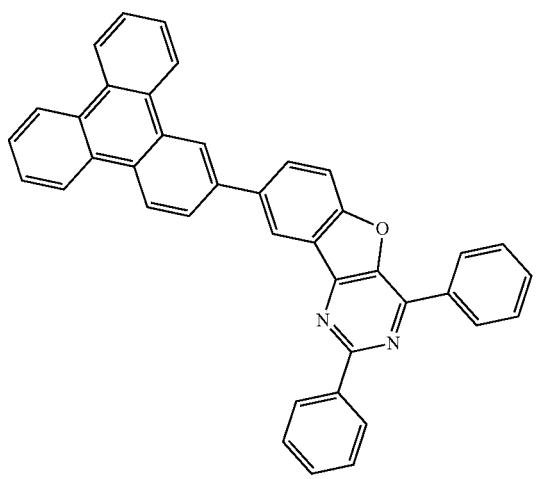

-continued
Formula 166
Formula 167
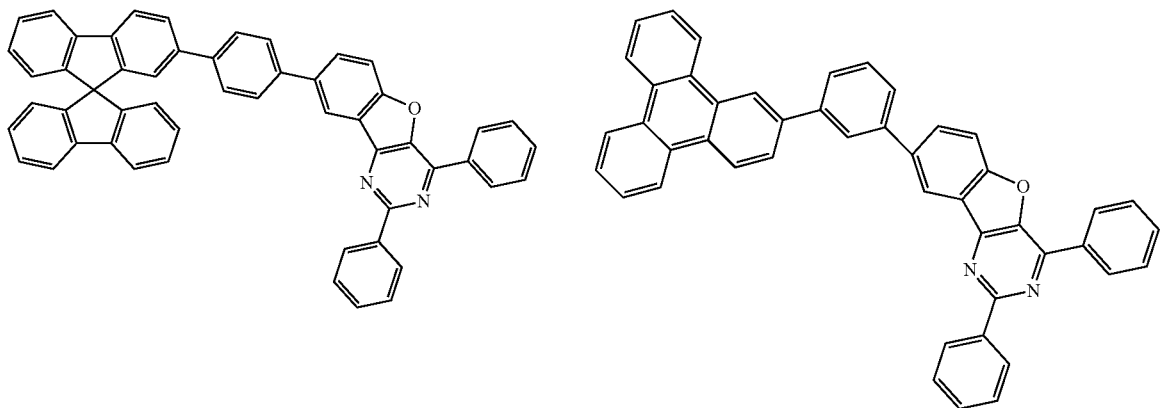
Formula 168
Formula 169
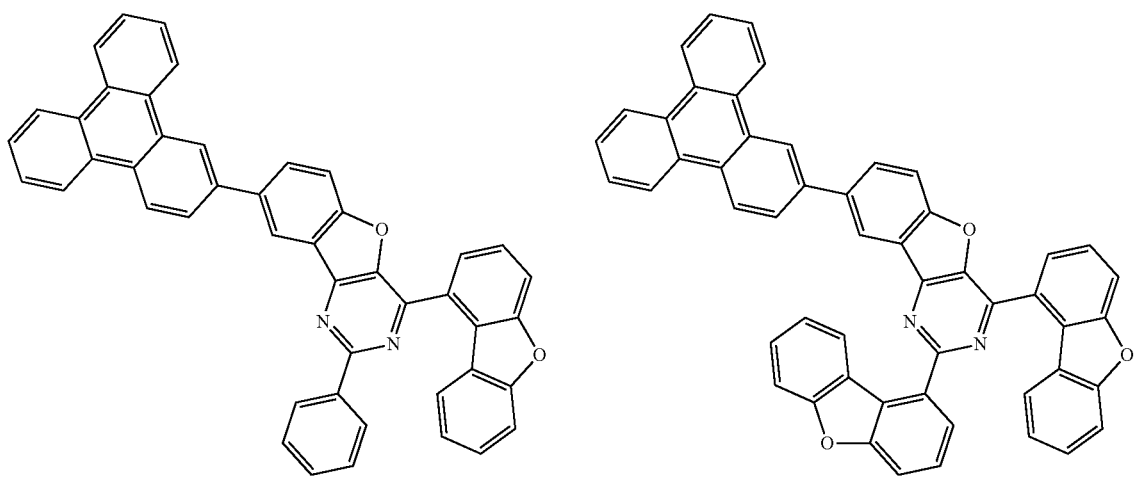
Formula 170
Formula 171
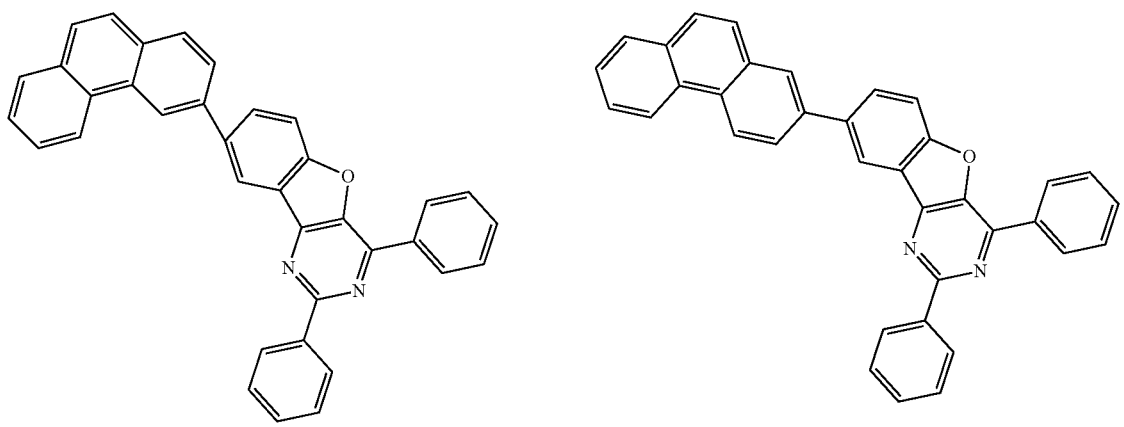

-continued
Formula 172
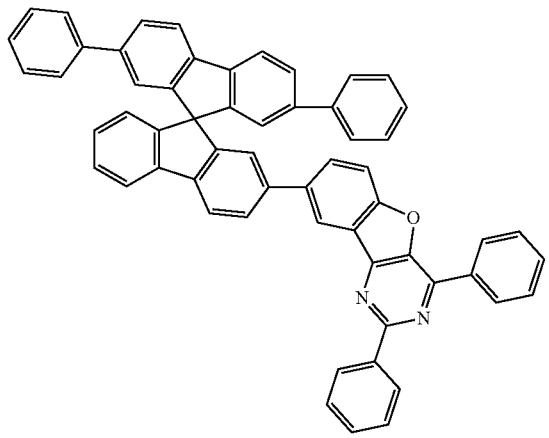
Formula 173
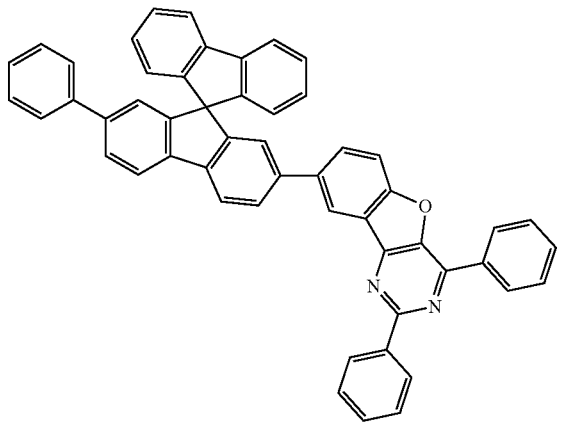
Formula 174
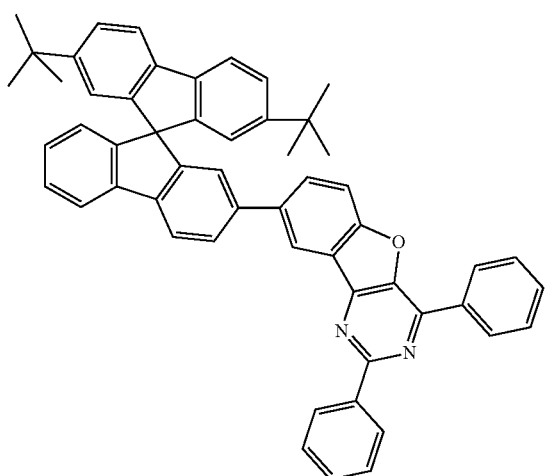
Formula 175
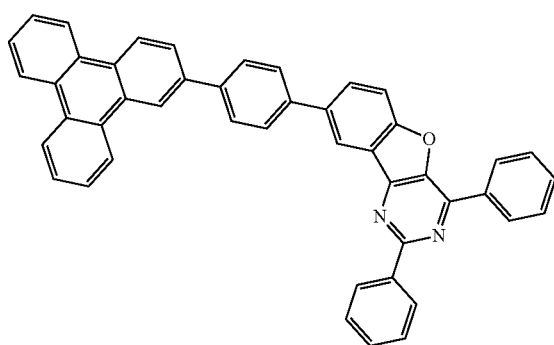
Formula 176
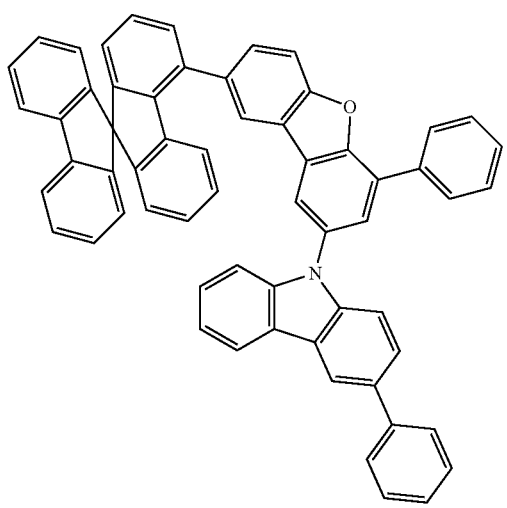
Formula 177
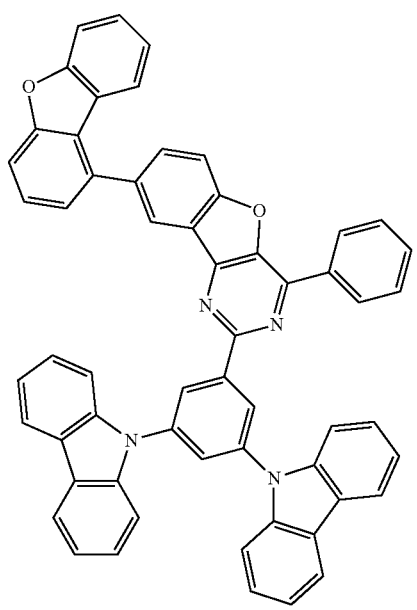

Formula 178
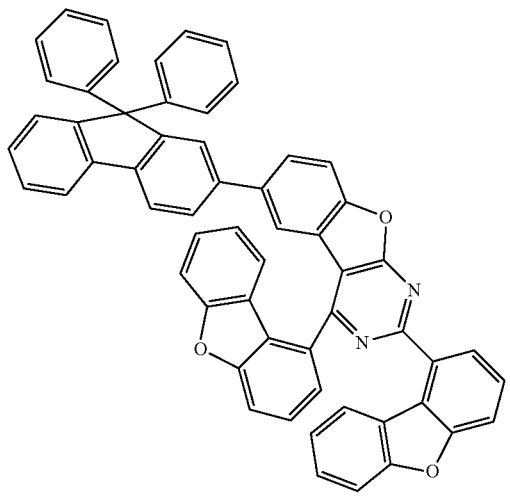
Formula 179
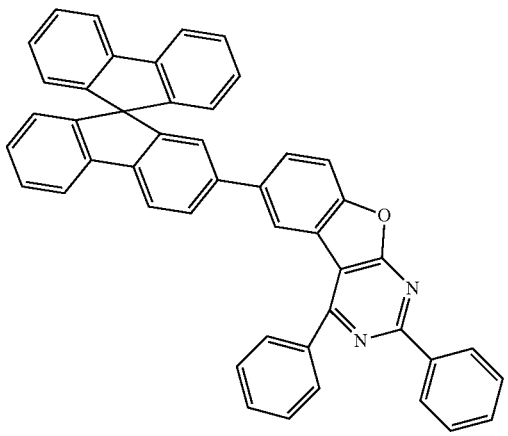
Formula 180
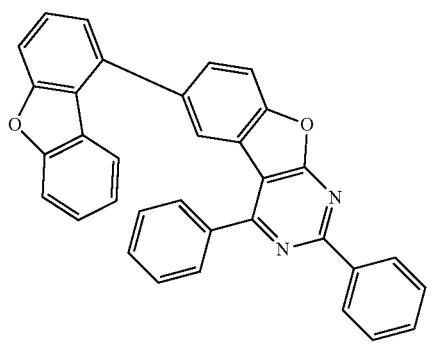
Formula 181
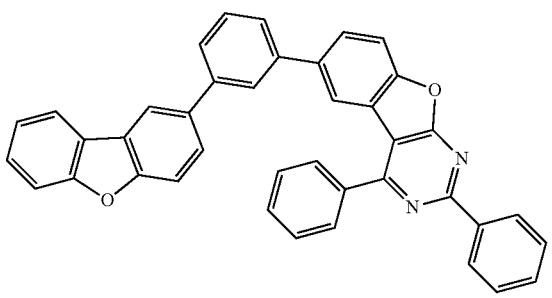
Formula 182
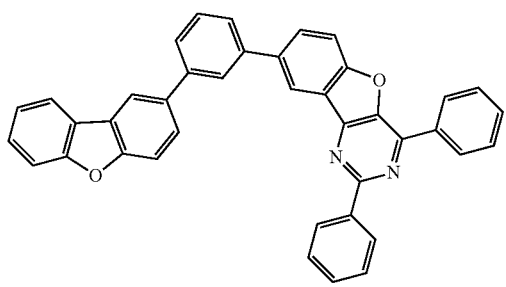
Formula 183
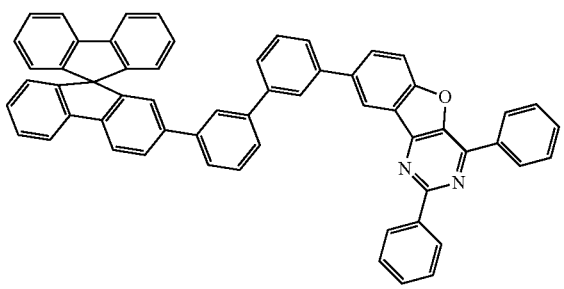

-continued
Formula 184
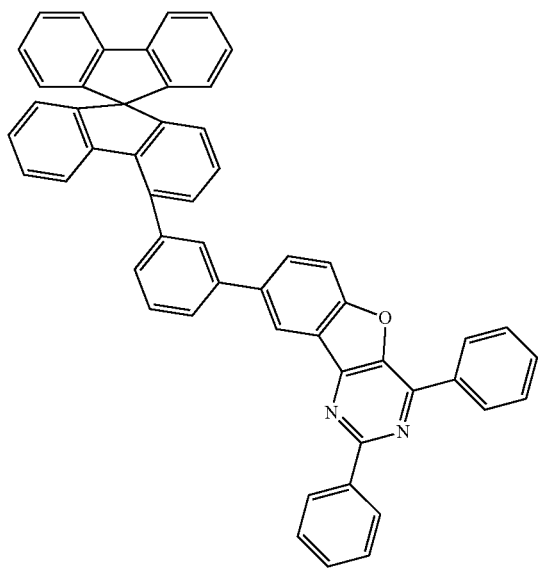
Formula 185
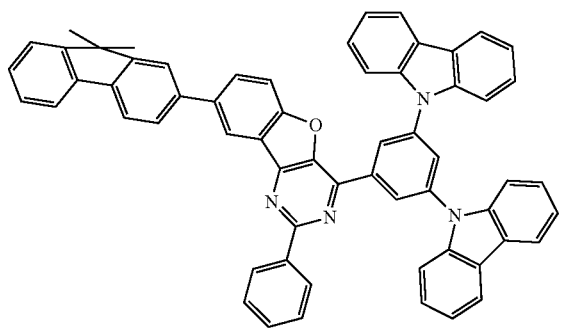
Formula 186
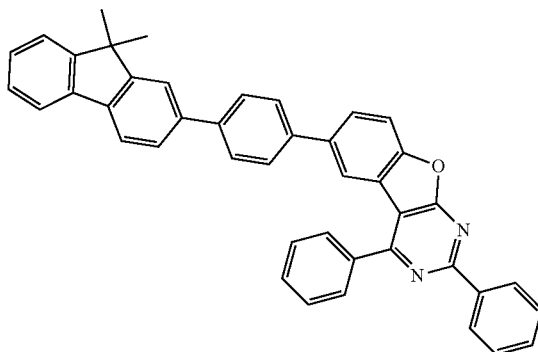
Formula 187
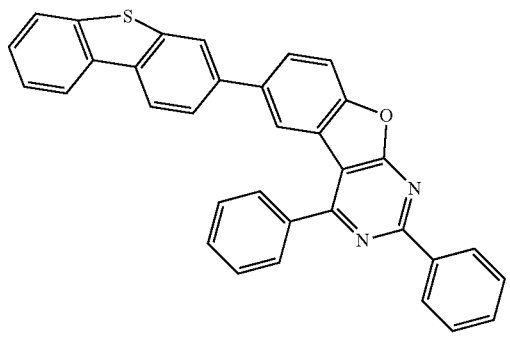
Formula 188
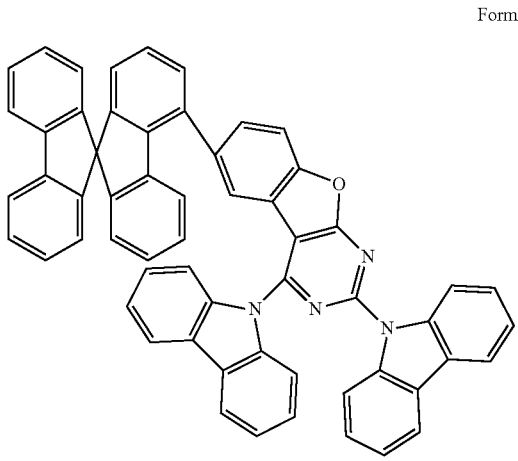
Formula 189
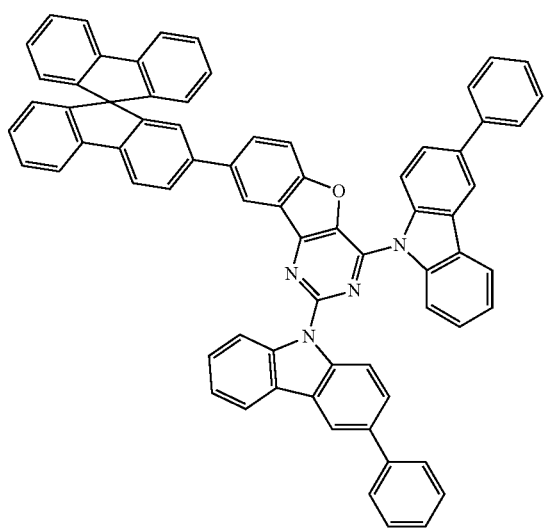

-continued
Formula 190
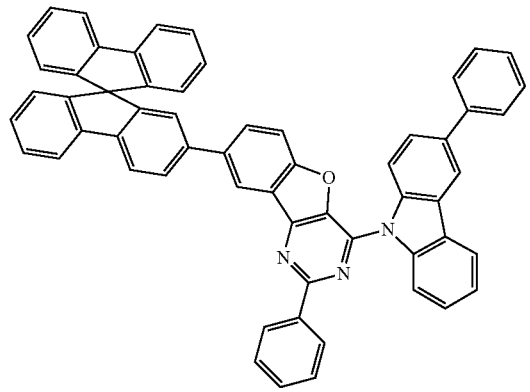
Formula 191
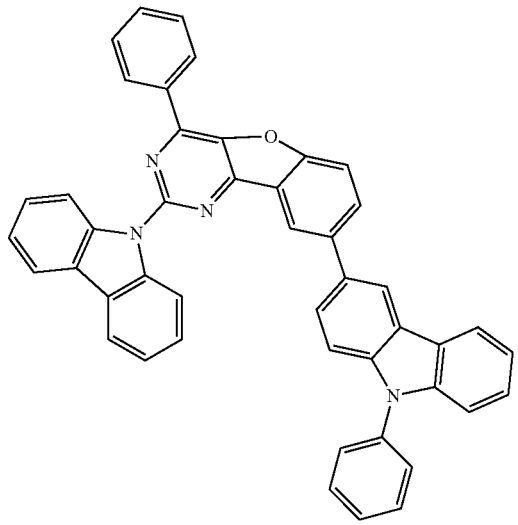
Formula 192
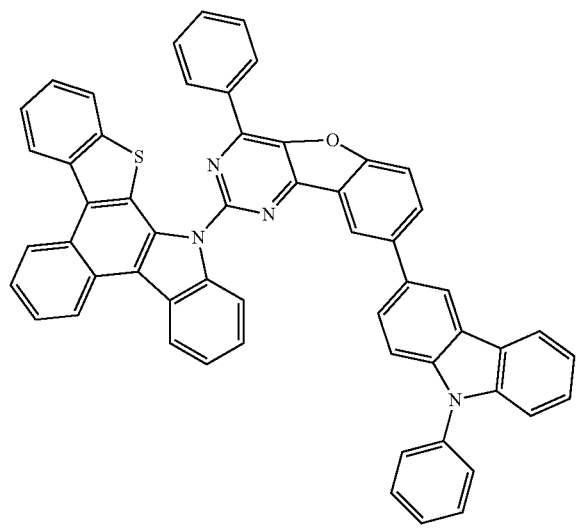
Formula 193
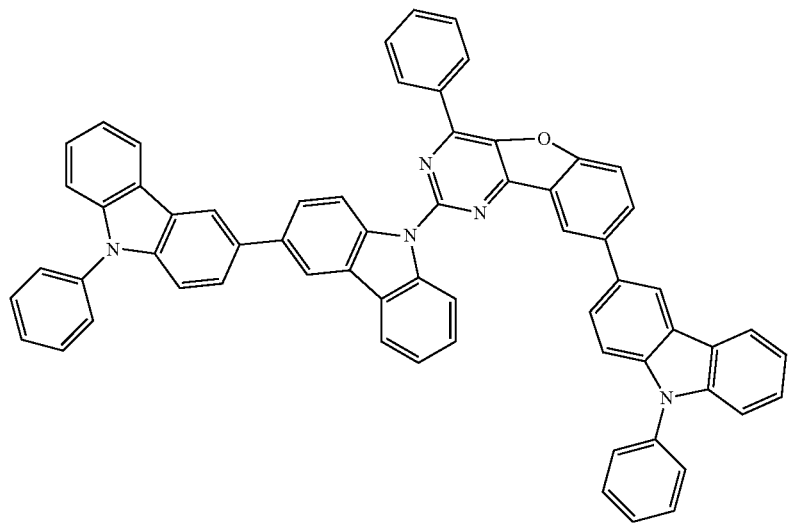

Formula 194
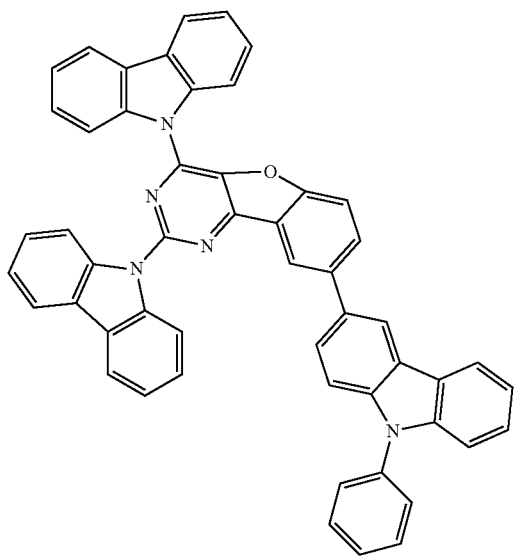
Formula 195
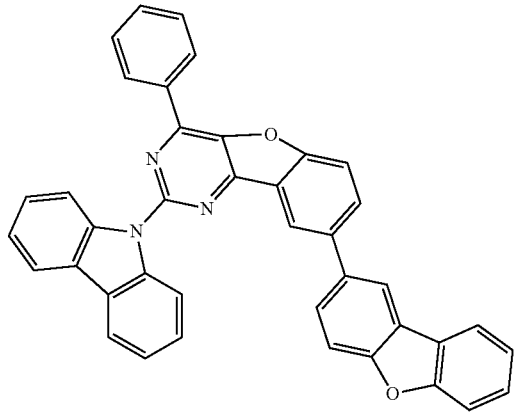
Formula 196
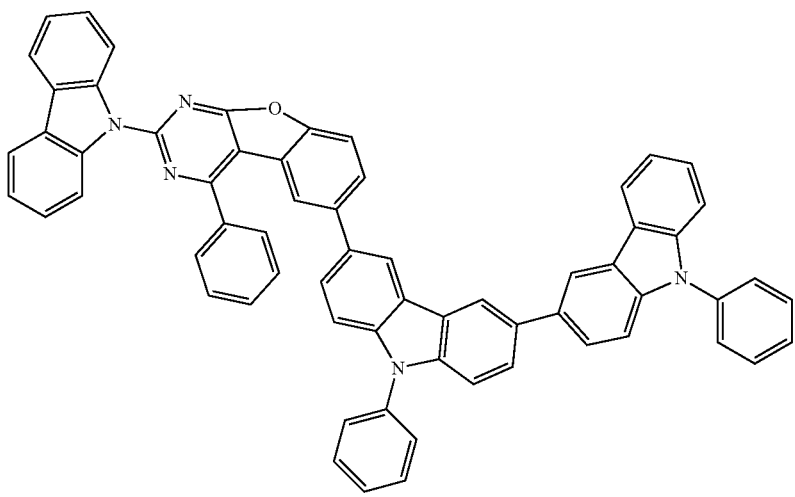
Formula 197
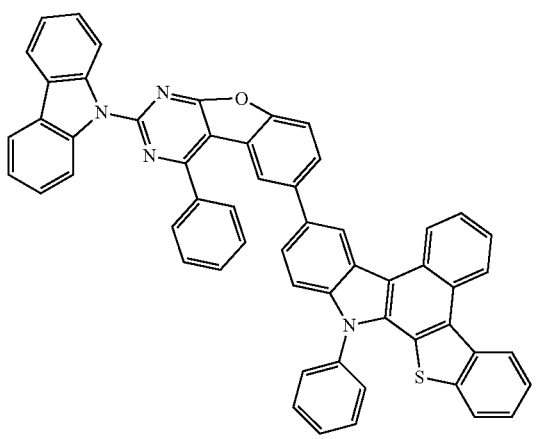
Formula 198
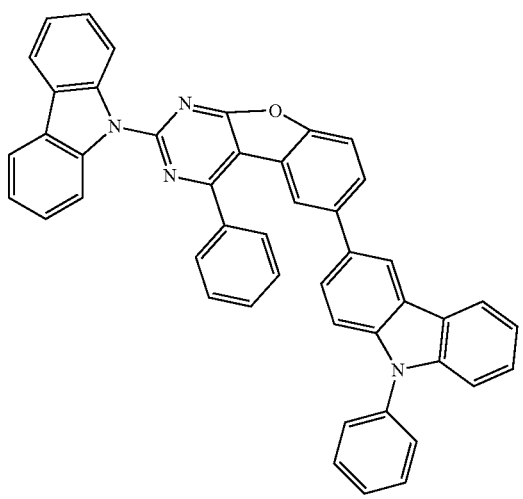

-continued
Formula 199
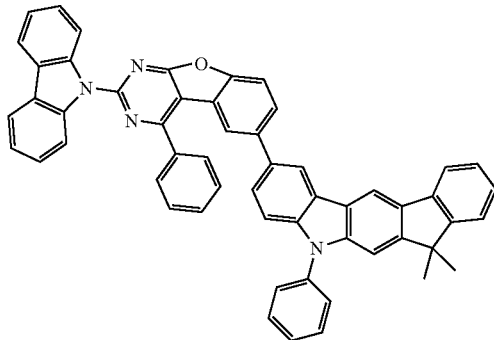
Formula 200
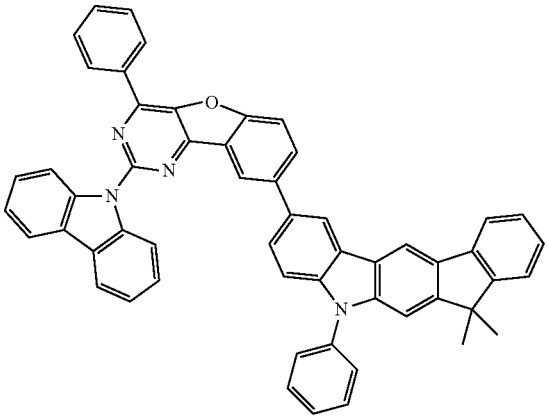
Formula 201
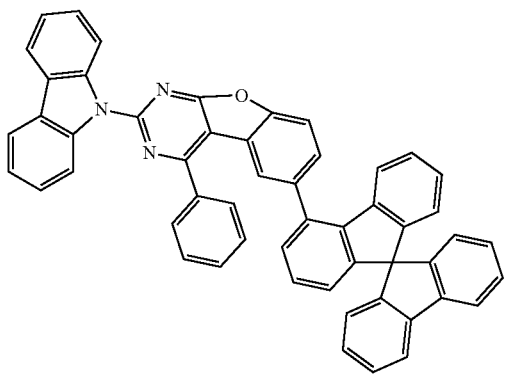
Formula 202
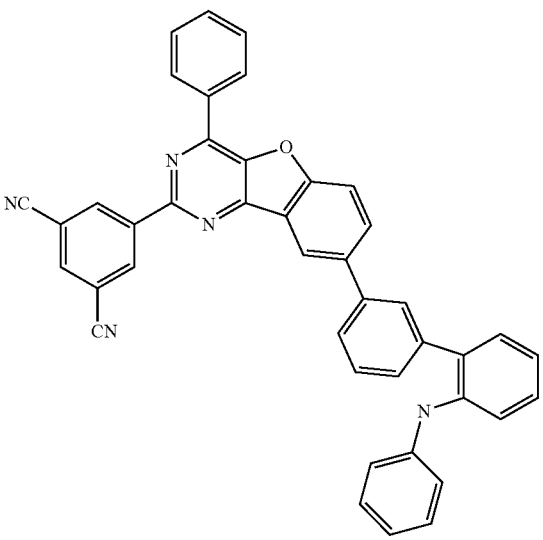
Formula 203
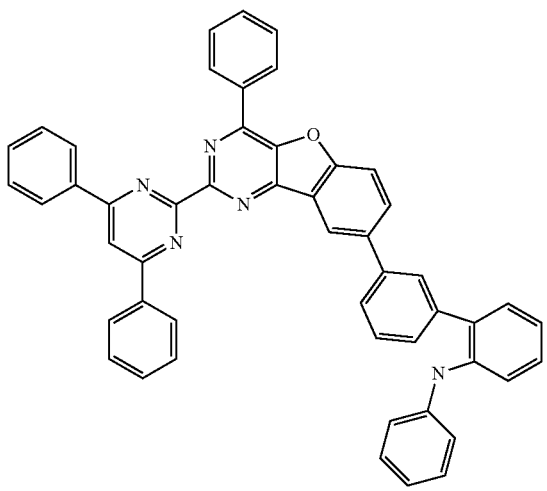
Formula 204
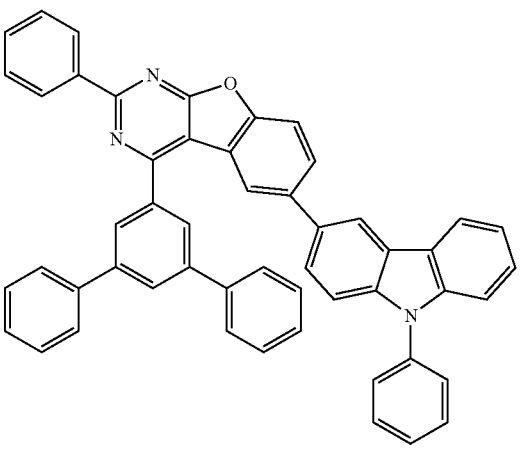

-continued
Formula 205
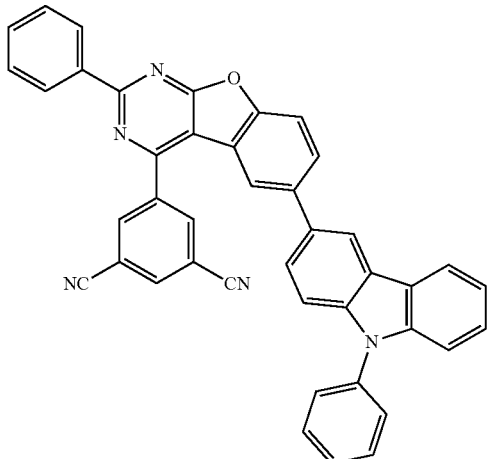
Formula 206
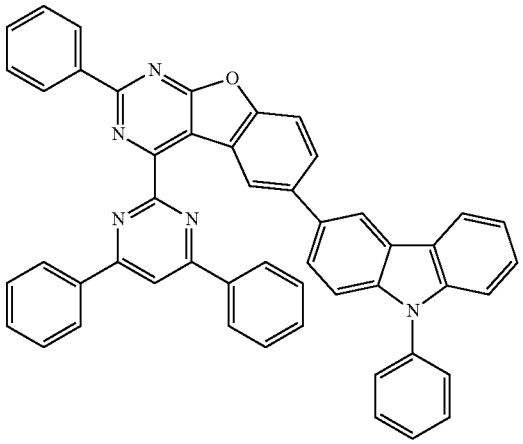
Formula 207
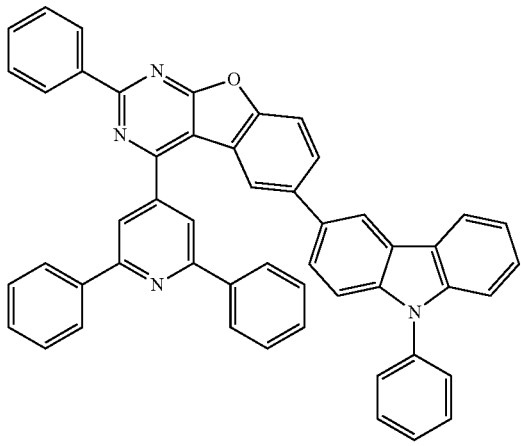
Formula 208
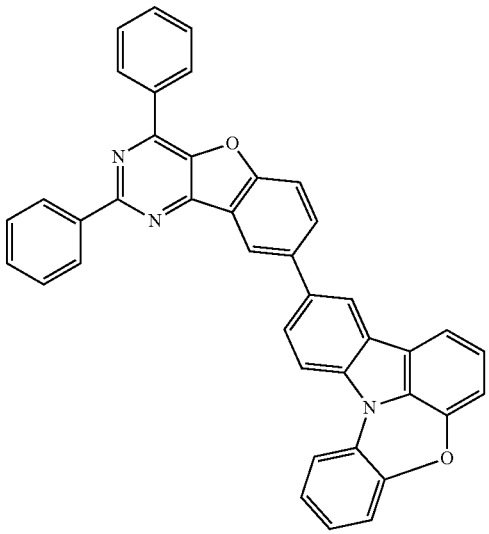
Formula 209
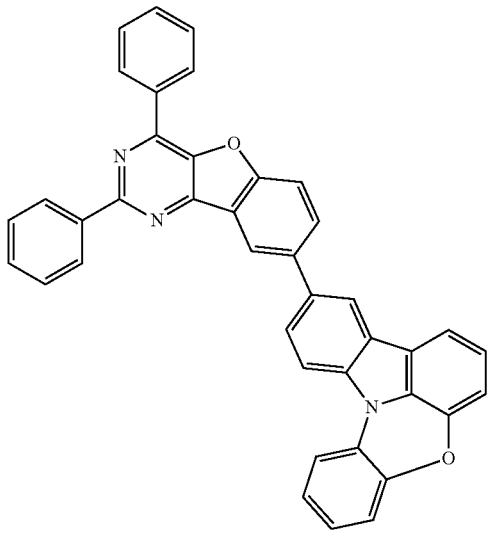
Formula 210
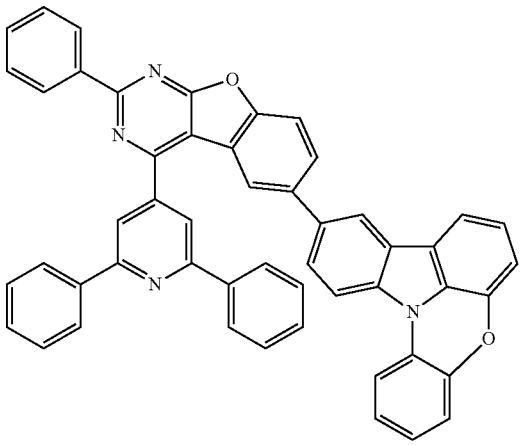

-continued
Formula 211
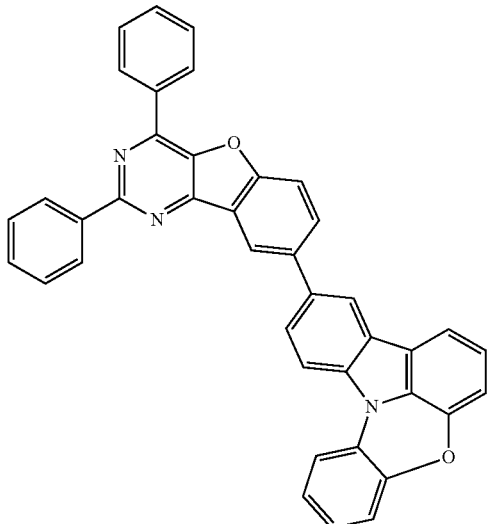
Formula 212
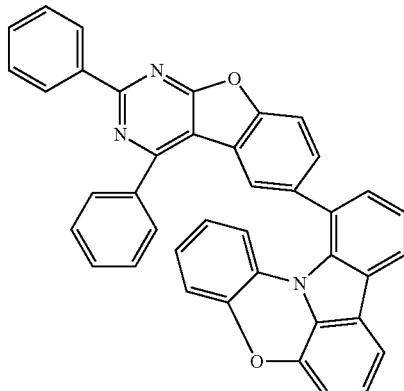
Formula 213
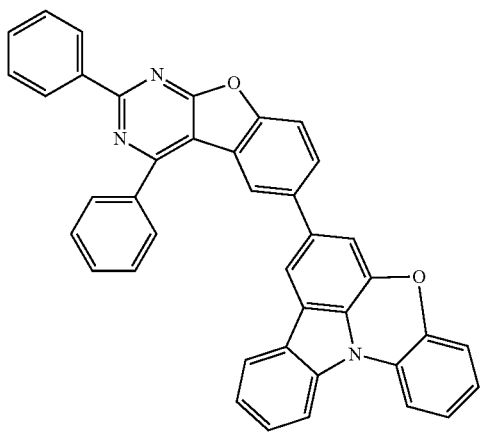
Formula 214
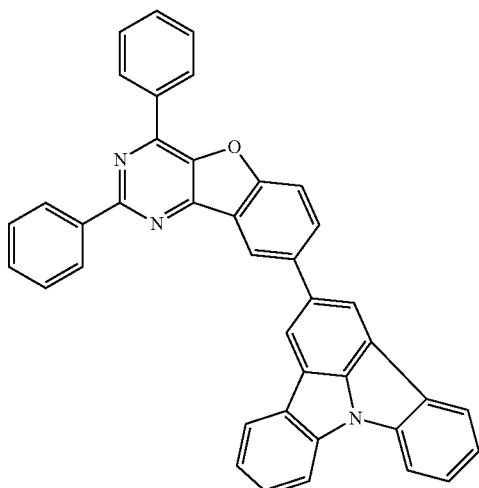
Formula 215
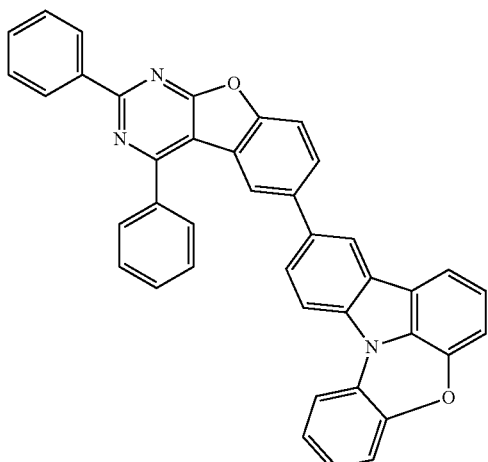
Formula 216
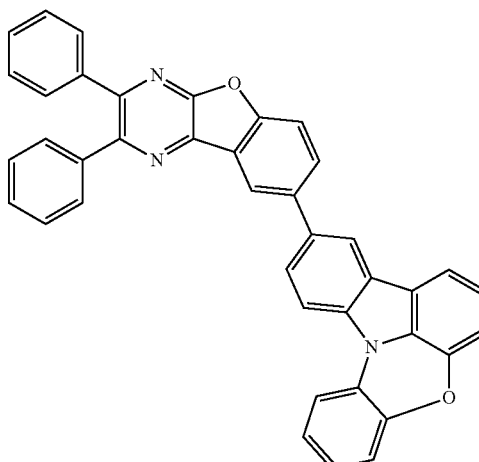

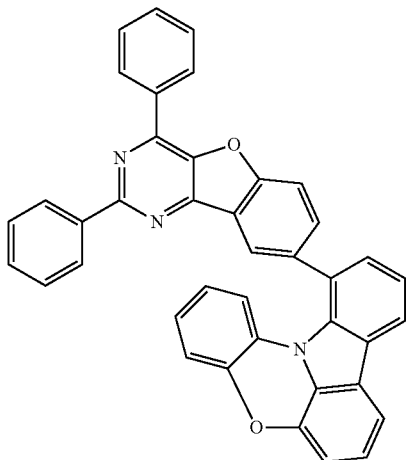

Formula 217

Preferred embodiments of compounds of the invention are recited specifically in the examples, these compounds being usable alone or in combination with further compounds for all purposes of the invention.

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising structures of formula (A) in which, in a coupling reaction, a compound comprising at least one diazadibenzofuran or diazadibenzothiophene group is joined to a group comprising at least one carbazole, fluorene, phenanthrene, benzofuran and/or benzothiophene radical.

Suitable compounds having a diazadibenzofuran or diazadibenzothiophene group are in many cases commercially available, and the starting compounds detailed in the examples are obtainable by known processes, and so reference is made thereto.

These compounds can be reacted with further aryl compounds by known coupling reactions, the necessary conditions for this purpose being known to the person skilled in the art, and detailed specifications in the examples give support to the person skilled in the art in conducting these reactions.

Particularly suitable and preferred coupling reactions which all lead to C—C bond formation and/or C—N bond formation are those according to BUCHWALD, SUZUKI, YAMAMOTO, STILLE, HECK, NEGISHI, SONOGASHIRA and HIYAMA. These reactions are widely known, and the examples will provide the person skilled in the art with further pointers.

In all the synthesis schemes which follow, the compounds are shown with a small number of substituents to simplify the structures. This does not rule out the presence of any desired further substituents in the processes.

An illustrative implementation is given by the schemes which follow, without any intention that these should impose a restriction. The component steps of the individual schemes may be combined with one another as desired.

Synthesis scheme 1

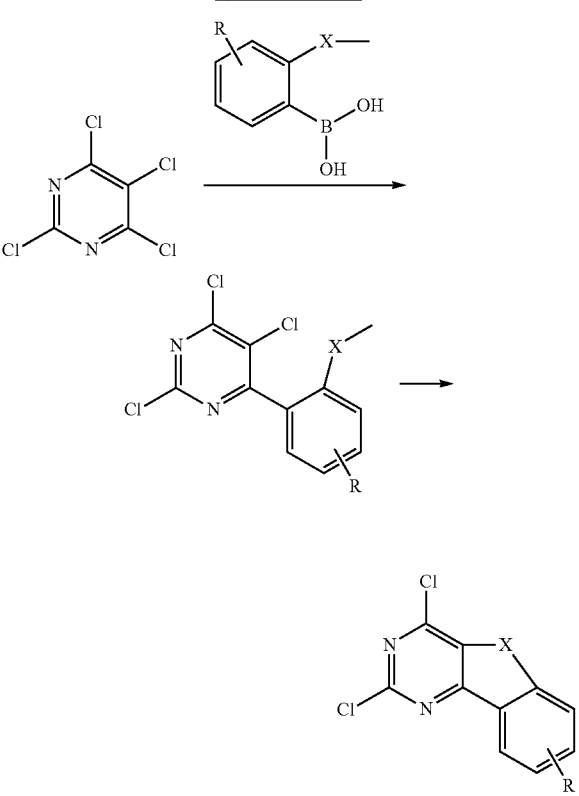

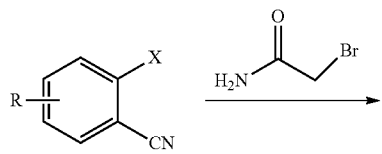

131
-continued
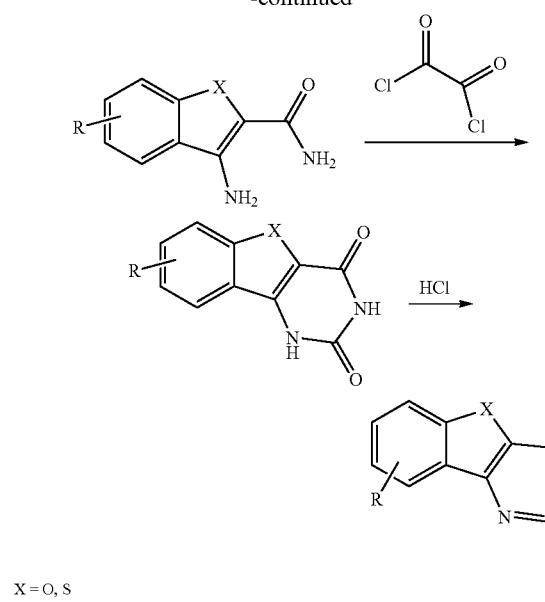
X = O, S
Synthesis scheme 2
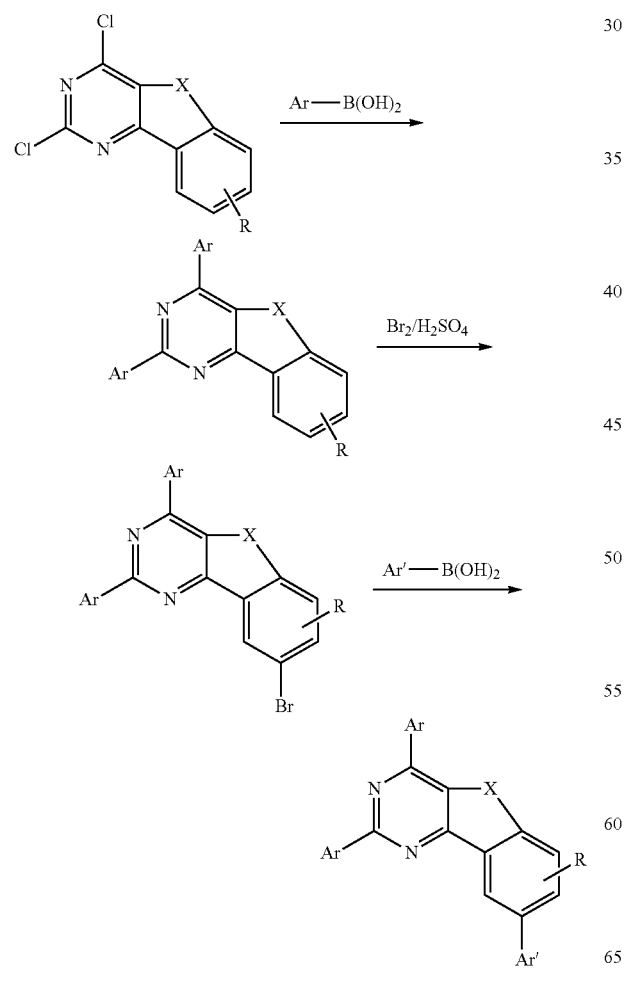
132
Synthesis scheme 3
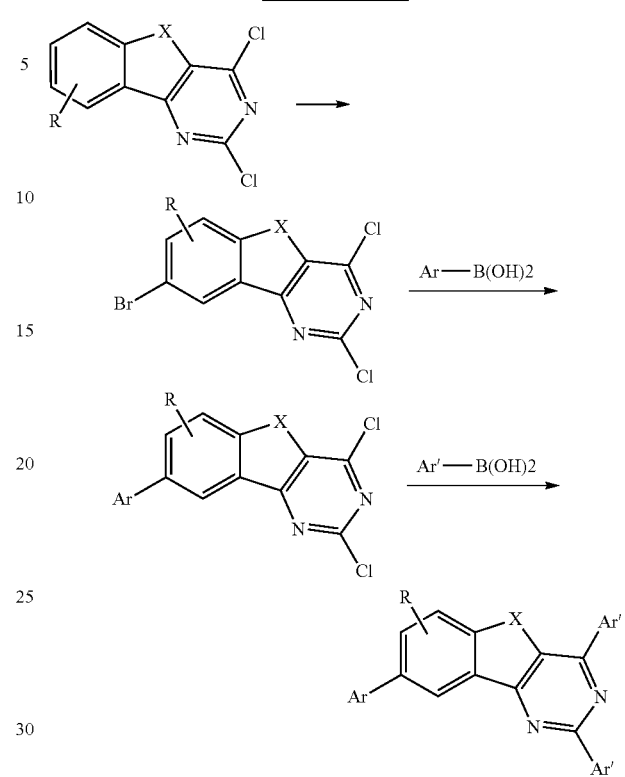
Synthesis scheme 4
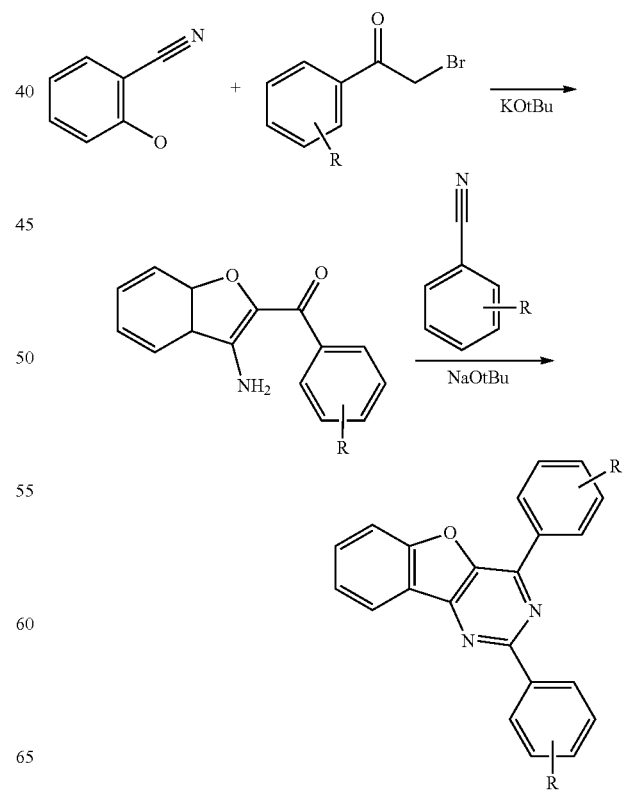

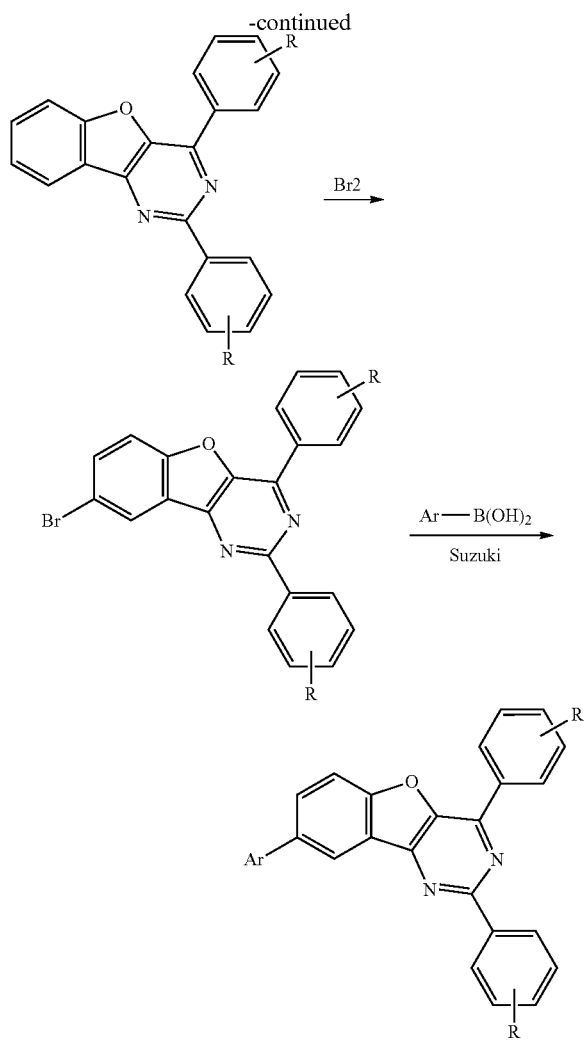

The processes shown for synthesis of the compounds of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formula (A) in high purity, preferably more than 99% (determined by means of $^1$H NMR and/or HPLC).

The compounds of the invention may also have suitable substituents, for example relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration, in order to be able to process the compounds from solution. These soluble compounds are of particularly good suitability for processing from solution, for example by printing methods. In addition, it should be emphasized that the compounds of the invention comprising at least one structure of the formula (A) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds and polymers of the invention may be used in the form of a crosslinked or uncrosslinked layer.

The invention therefore further provides oligomers, polymers or dendrimers containing one or more of the above-detailed structures of the formula (A) or compounds of the invention, wherein one or more bonds of the compounds of the invention or of the structures of the formula (A) to the polymer, oligomer or dendrimer are present. According to the linkage of the structures of the formula (A) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (A) or the preferred embodiments recited above and hereinafter are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

Additionally of particular interest are compounds of the invention which feature a high glass transition temperature. In this connection, preference is given especially to compounds of the invention comprising structures of the general formula (A) or the preferred embodiments recited above and hereinafter which have a glass transition temperature of at least 70° C., more preferably of at least 110° C., even more preferably of at least 125° C. and especially preferably of at least 150° C., determined in accordance with DIN 51005 (2005-08 version).

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (—)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, especially a phosphorescent dopant, and/or a further matrix material. This further compound may also be polymeric.

The present invention therefore still further provides a composition comprising a compound of the invention and at least one further organically functional material. Functional materials are generally the organic or inorganic materials introduced between the anode and cathode. Preferably, the organically functional material is selected from the group consisting of fluorescent emitters, phosphorescent emitters, host materials, matrix materials, electron transport materials, electron injection materials, hole conductor materials, hole injection materials, electron blocker materials, hole blocker materials, wide band gap materials and n-dopants.

The present invention therefore also relates to a composition comprising at least one compound comprising structures of formula (A) or the preferred embodiments recited above and hereinafter and at least one further matrix material. According to a particular aspect of the present invention, the further matrix material has hole-transporting properties.

The present invention further provides a composition comprising at least one compound comprising at least one structure of formula (A) or the preferred embodiments recited above and hereinafter and at least one wide band gap material, a wide band gap material being understood to mean a material in the sense of the disclosure of U.S. Pat. No. 7,294,849. These systems exhibit exceptional advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state Ti and that of the lowest excited singlet state Si of the materials are determined via quantum-chemicalcalculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

$$HOMO(eV) = ((HEh*27.212) - 0.9899)/1.1206$$

$$LUMO(eV) = ((LEh*27.212) - 2.0041)/1.385$$

These values are to be regarded as HOMO and LUMO energy levels of the materials in the context of this application.

The lowest triplet state Ti is defined as the energy of the triplet state having the lowest energy, which is apparent from the quantum-chemical calculation described.

The lowest excited singlet state Si is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The present invention also relates to a composition comprising at least one compound comprising structures of formula (A) or the preferred embodiments recited above and hereinafter and at least one phosphorescent emitter, the term "phosphorescent emitters" also being understood to mean phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in matrix systems, preferably mixed matrix systems, are the preferred phosphorescent dopants specified hereinafter.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960 and the as yet unpublished applications EP 13004411.8, EP 14000345.0, EP 14000417.7 and EP 14002623.8. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Explicit examples of phosphorescent dopants are adduced in the following table:

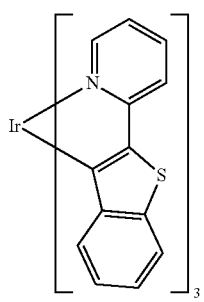

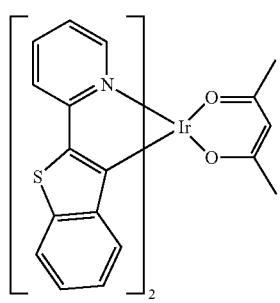

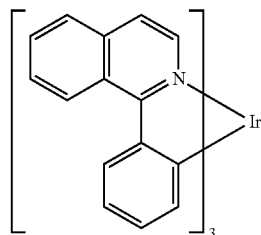

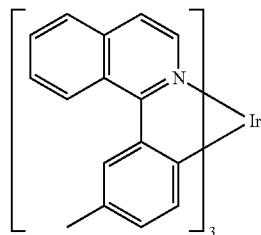

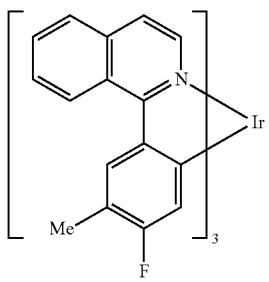

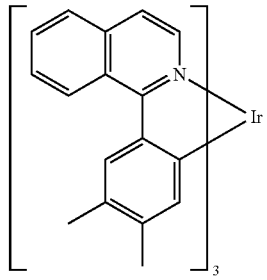

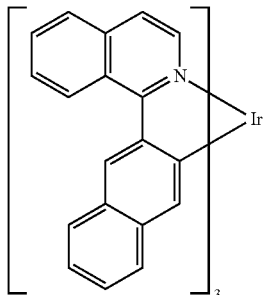

-continued
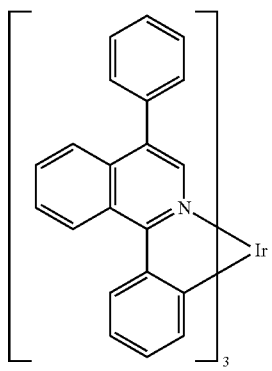
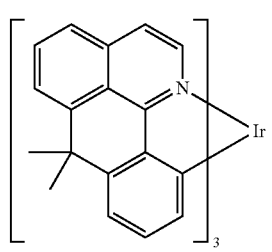
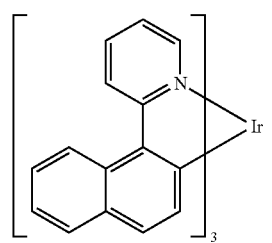
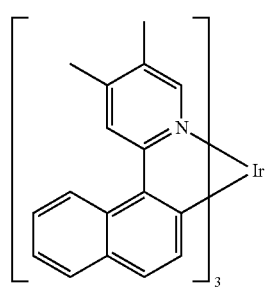
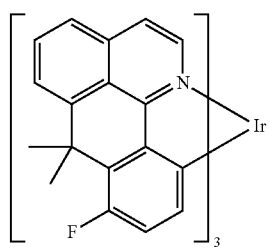
-continued
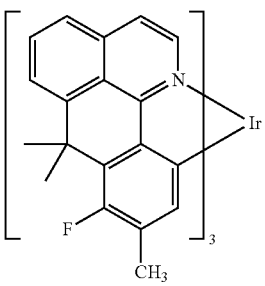
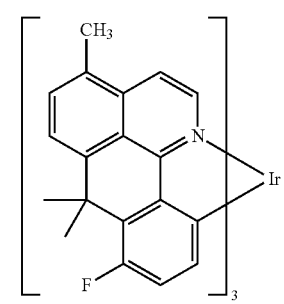
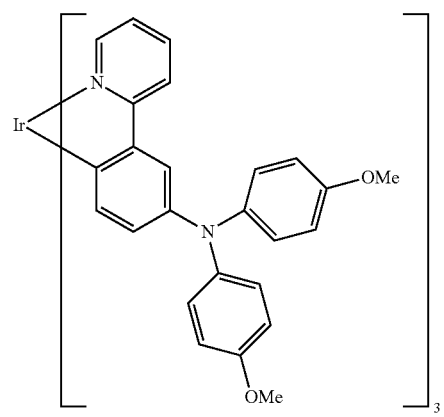
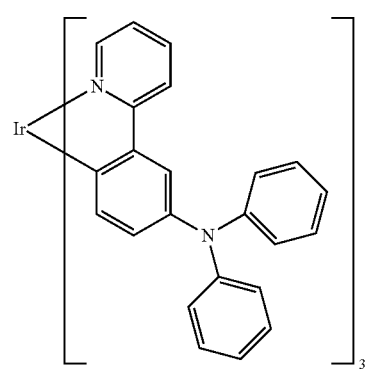

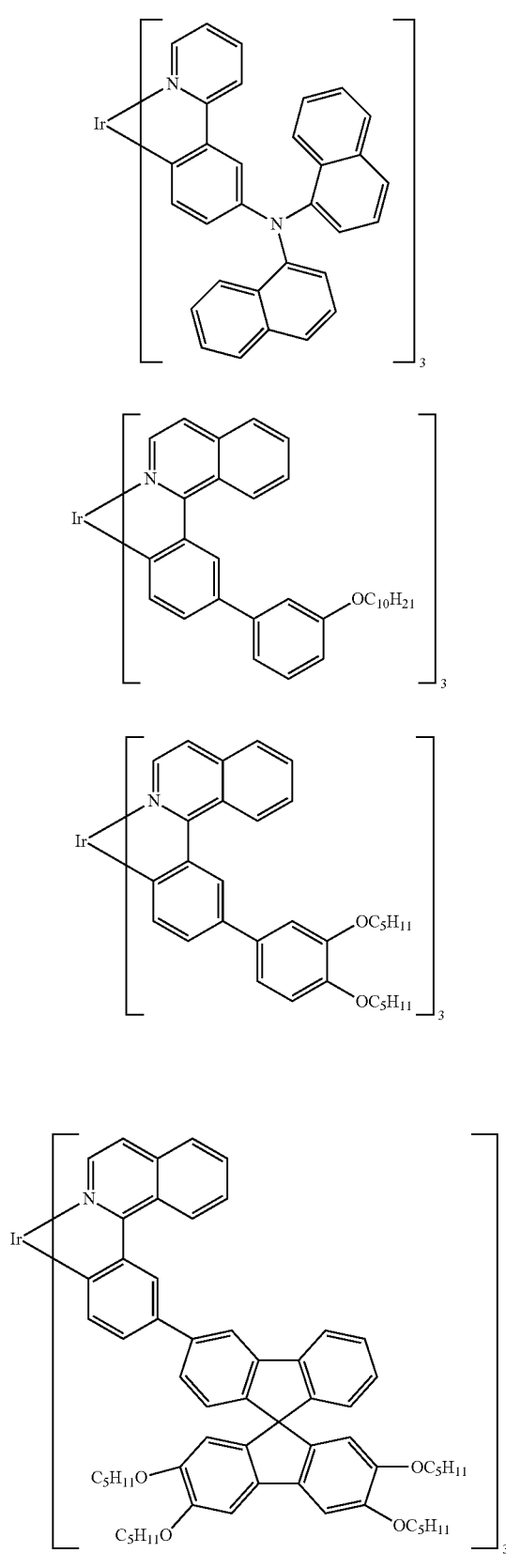
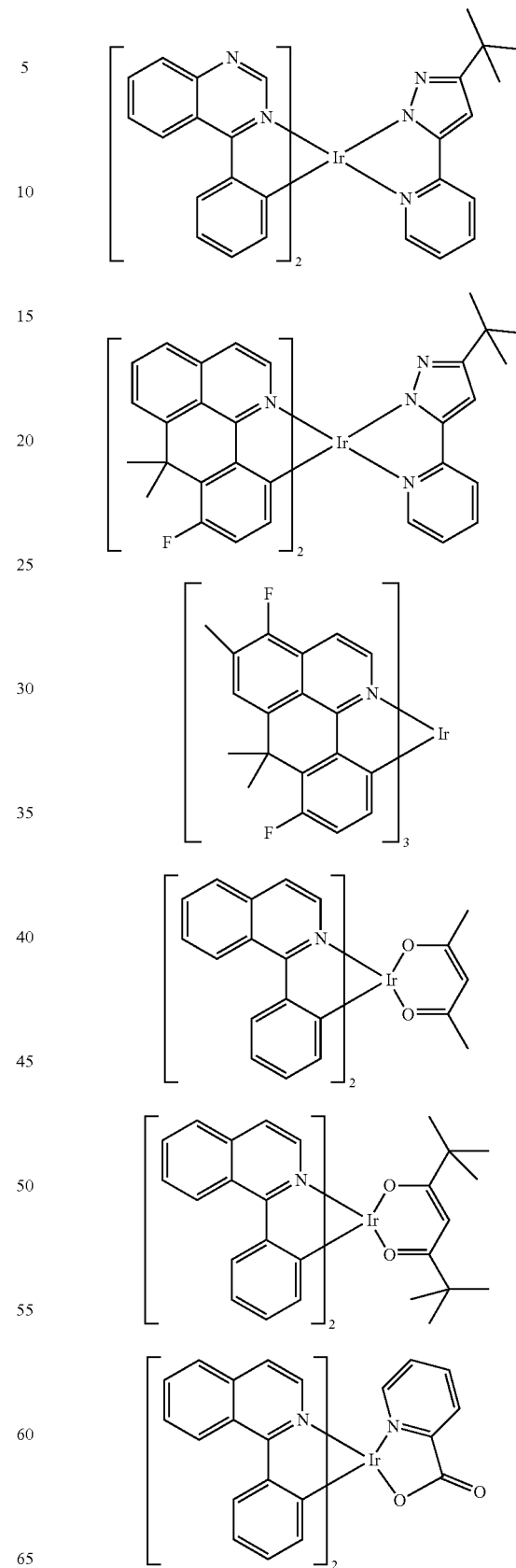

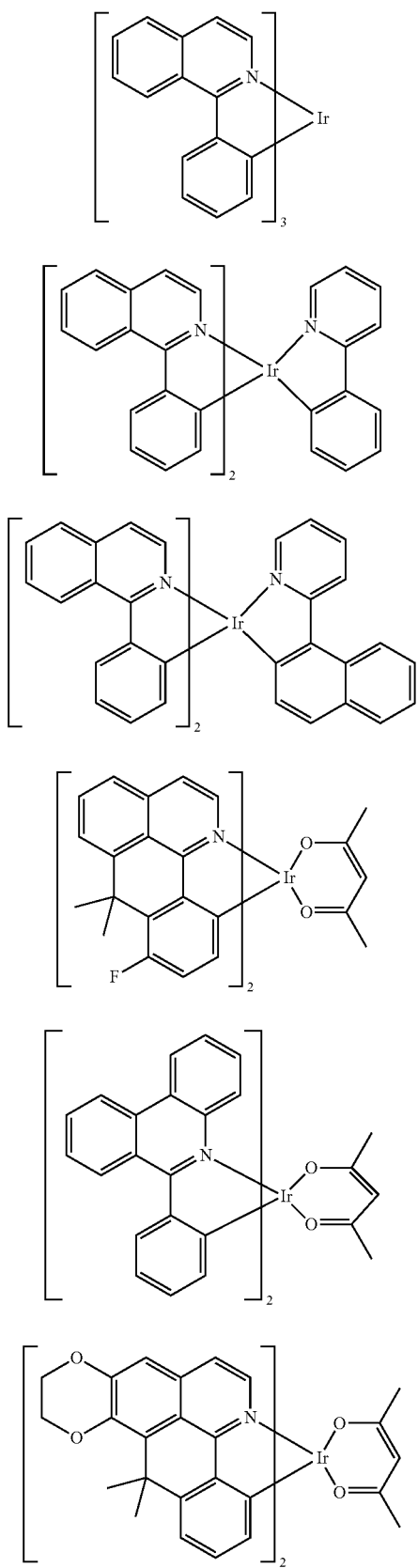
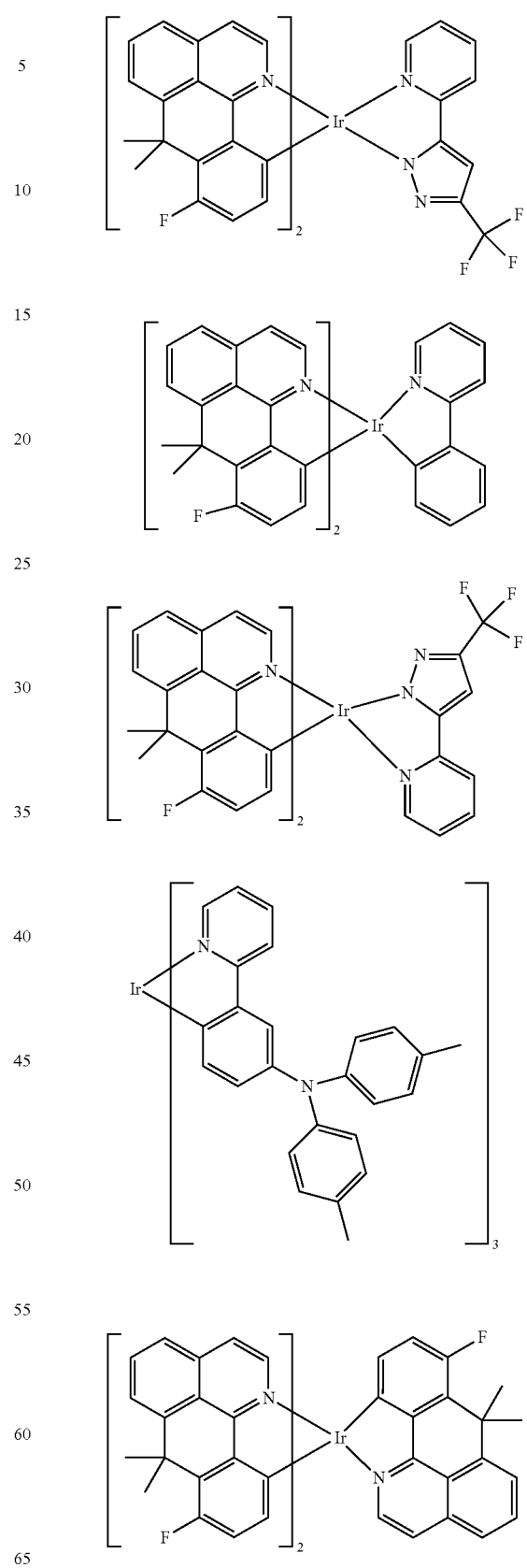

-continued
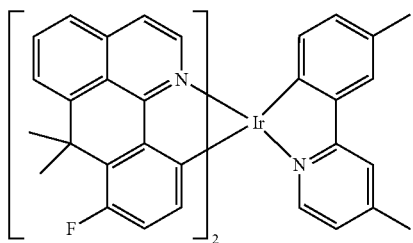
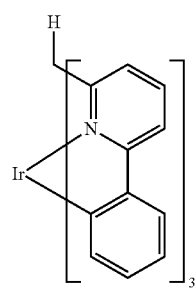
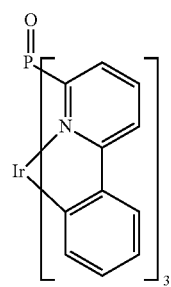
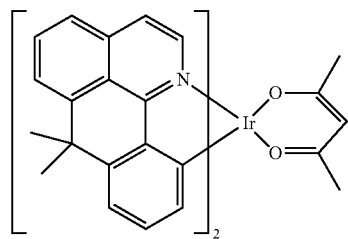
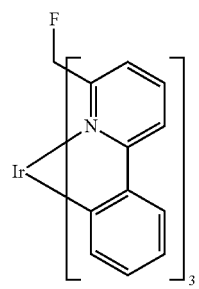
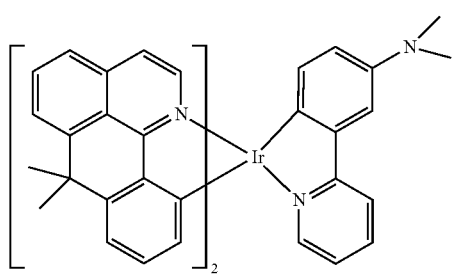
-continued
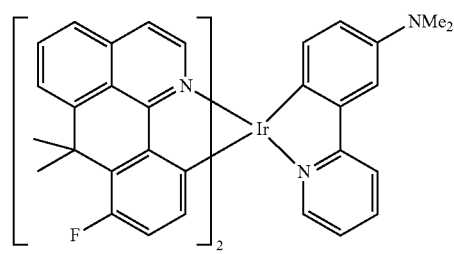
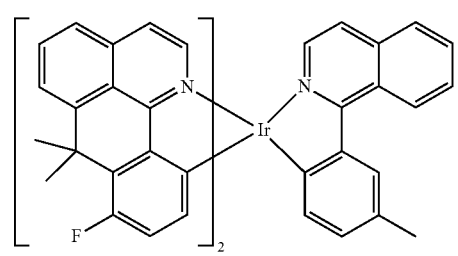
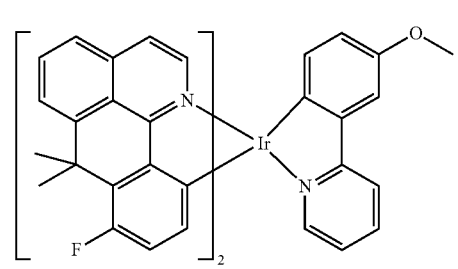
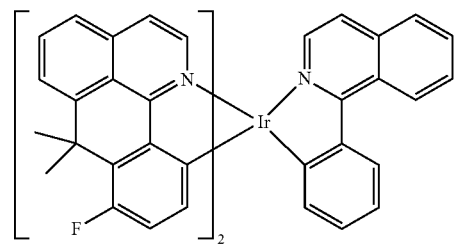
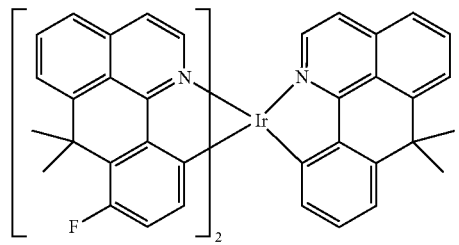

147
-continued
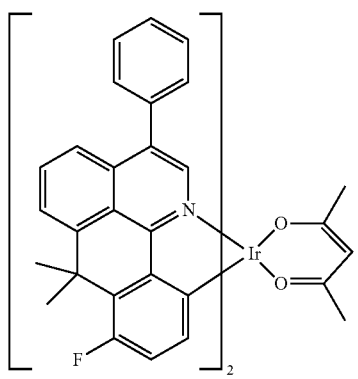
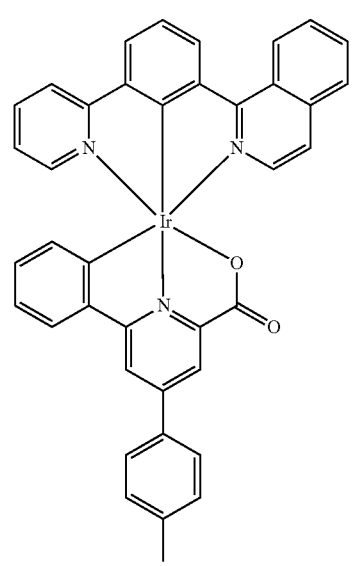
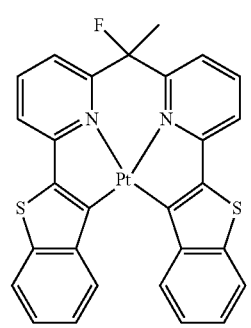
148
-continued
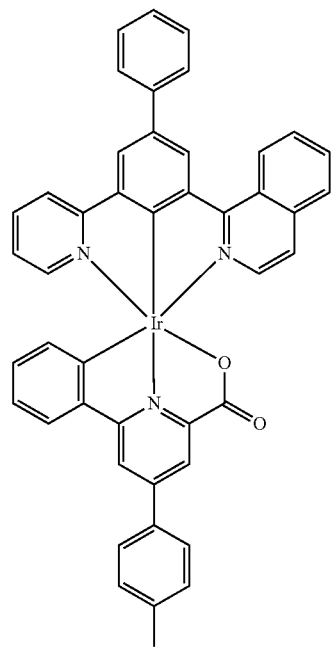
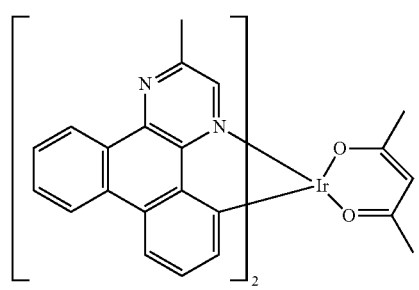
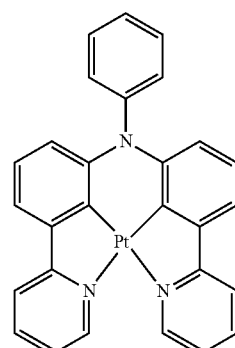
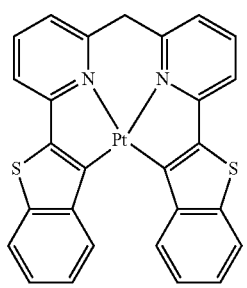

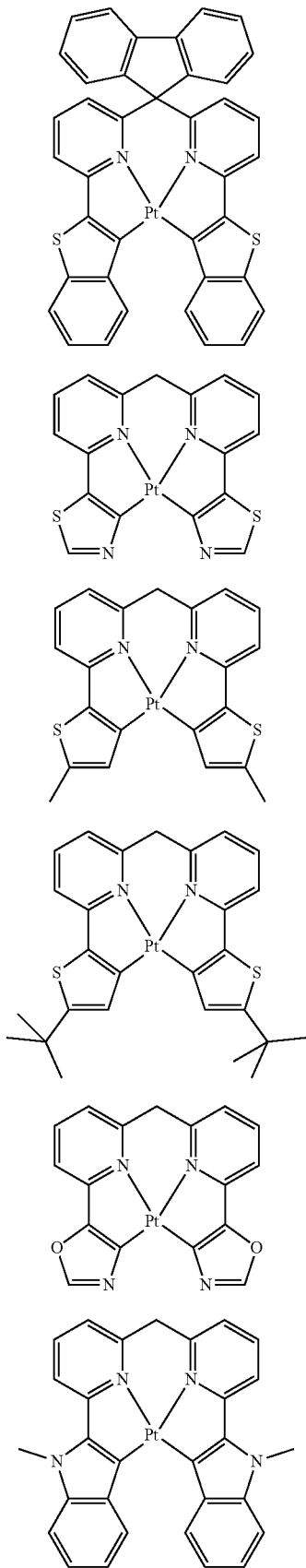
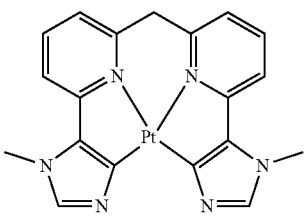
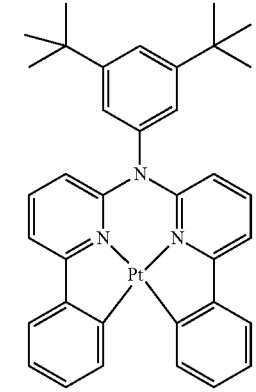
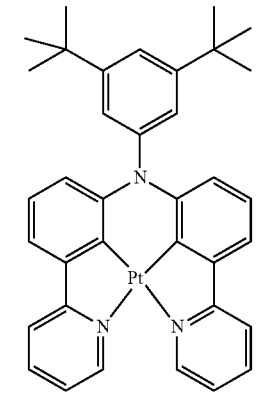
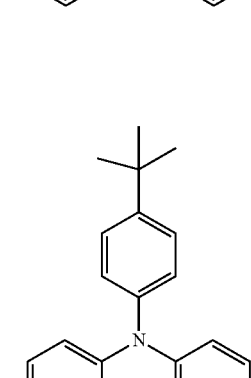
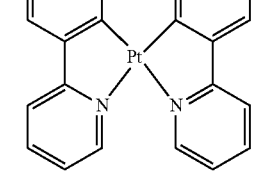

| 151 -continued | 152 -continued |
|---|---|
| 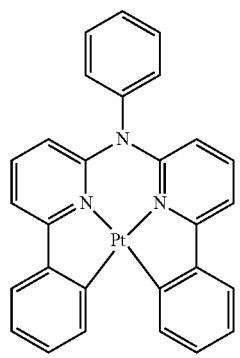 | 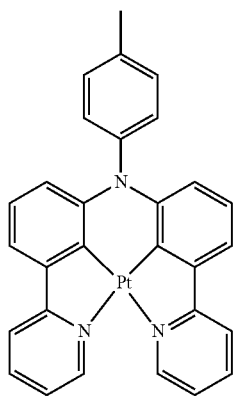 |
| 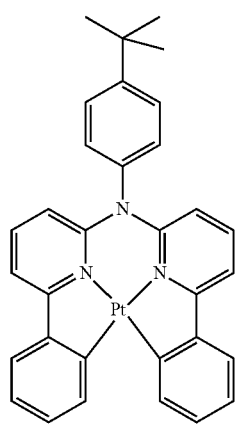 | 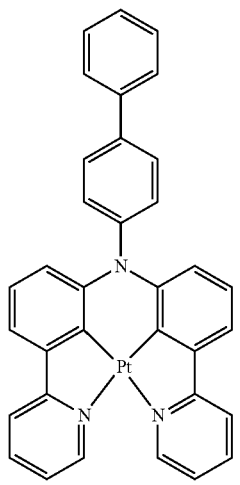 |
| 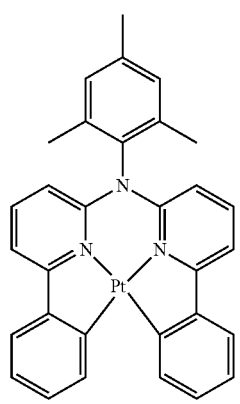 | |
| 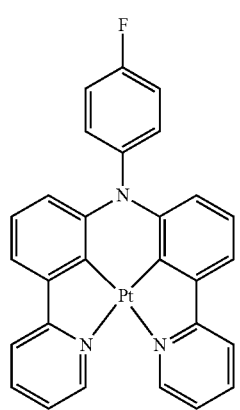 | 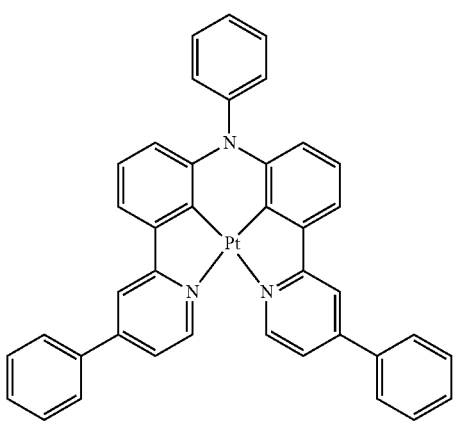 |

153
-continued
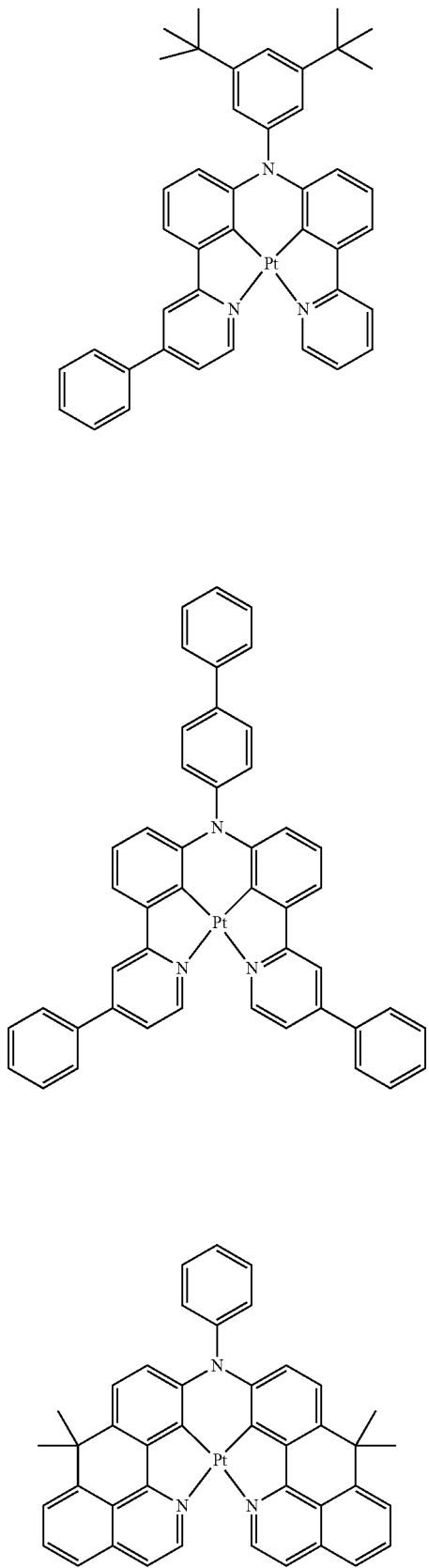
154
-continued
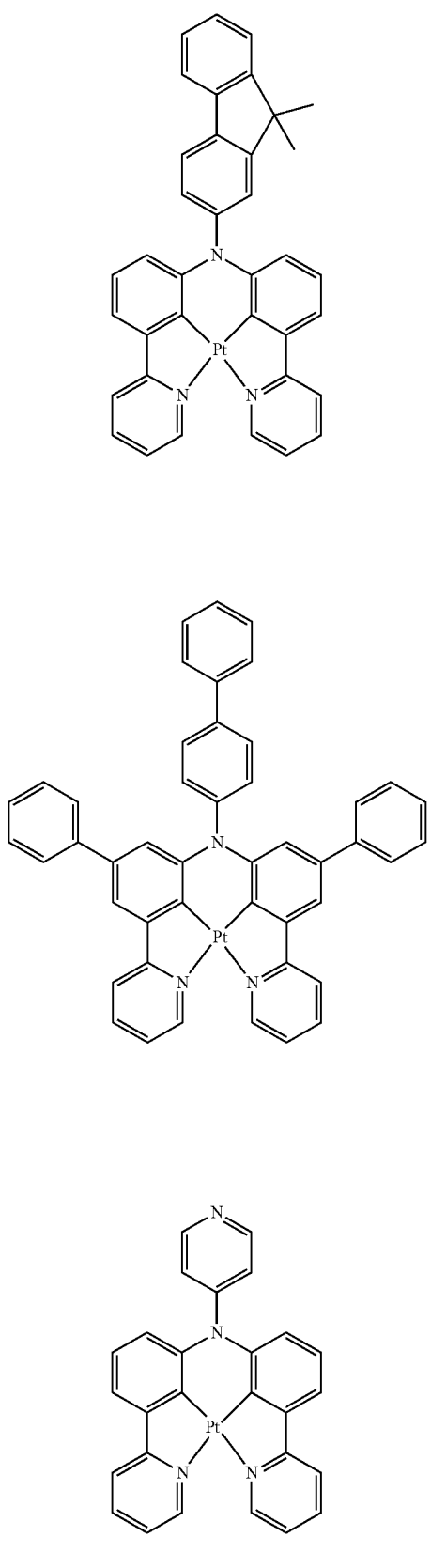

155
-continued
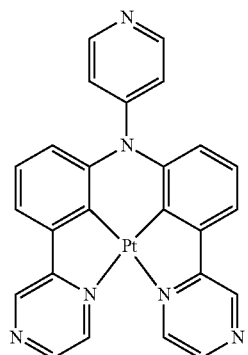
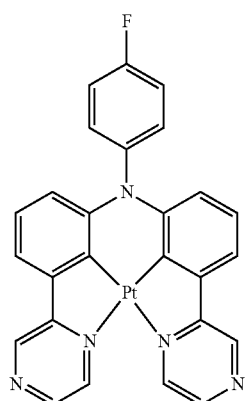
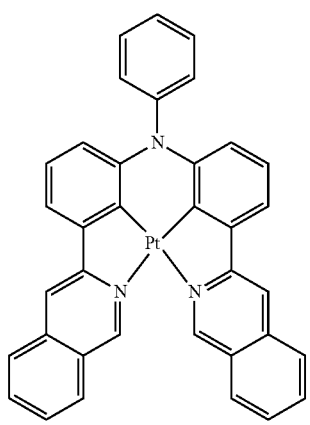
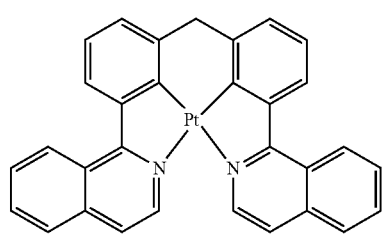
156
-continued
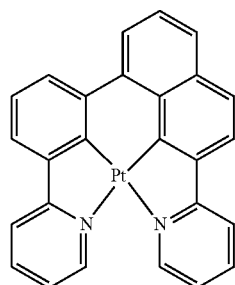
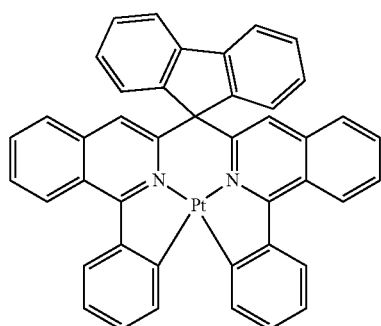
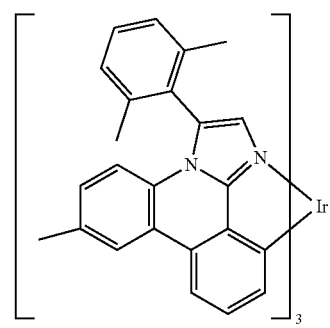
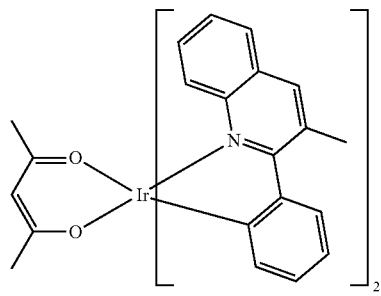
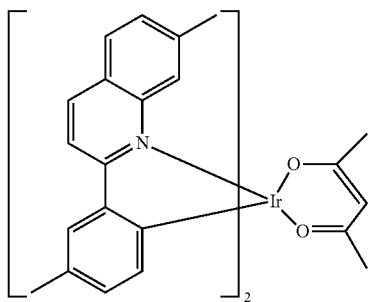

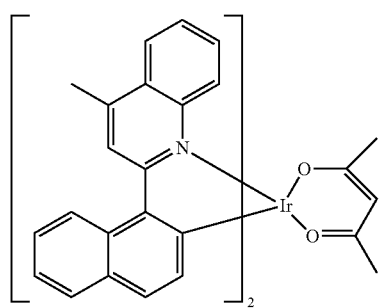
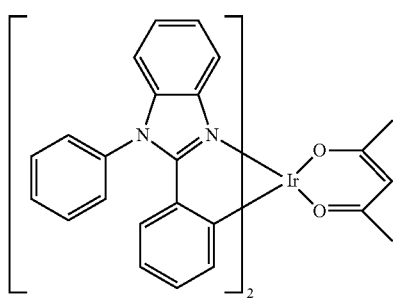
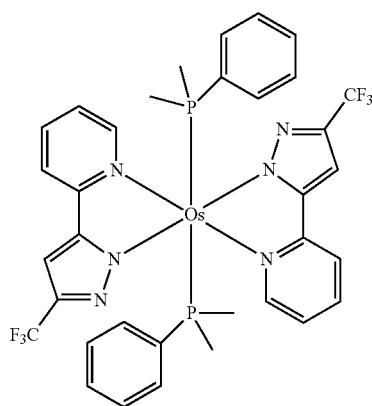
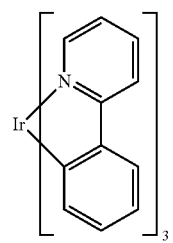
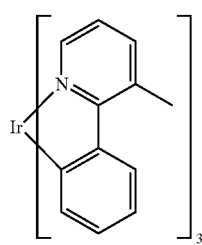
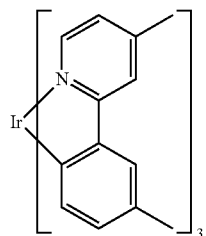
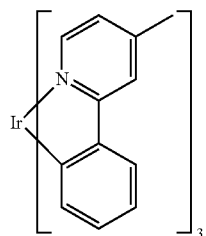
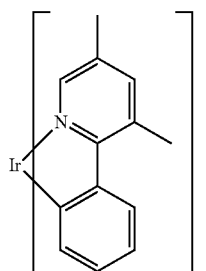
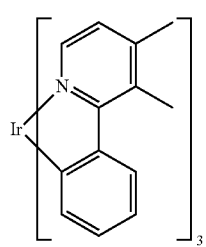
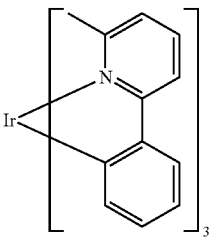
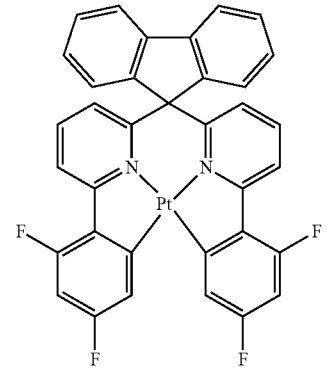

159
-continued
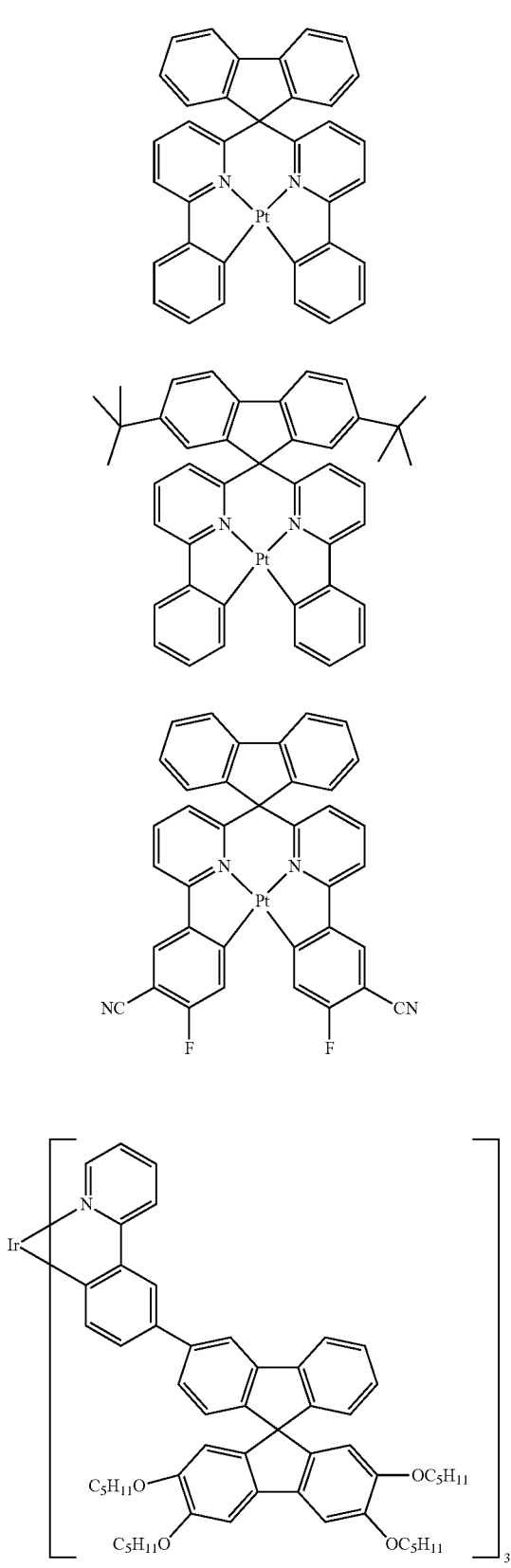
160
-continued
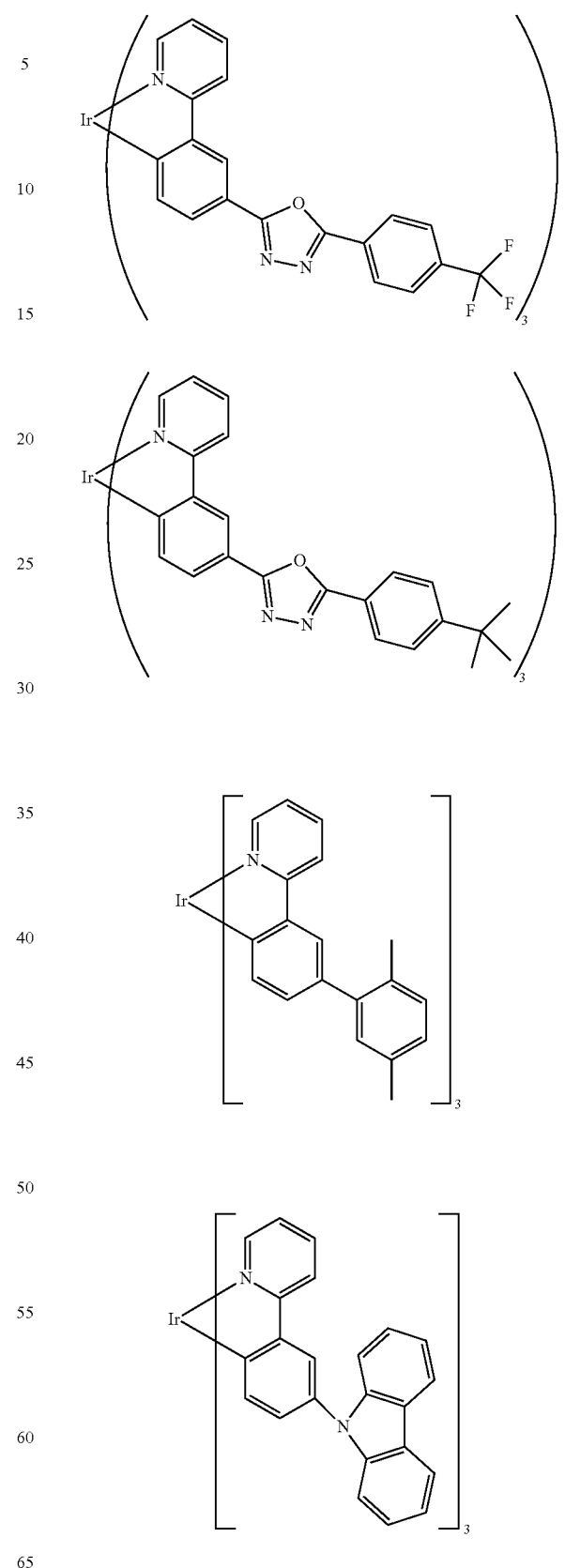

161
-continued
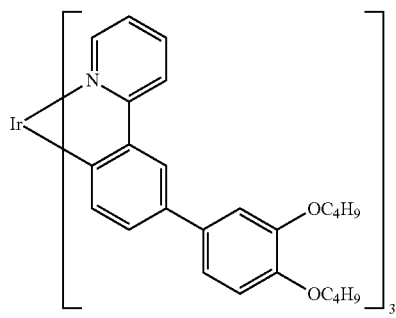
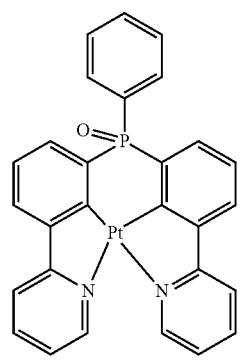
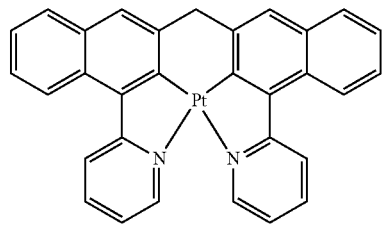
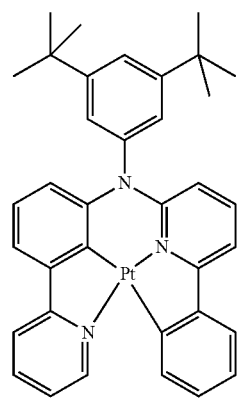
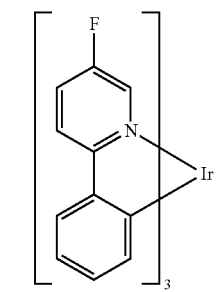
162
-continued
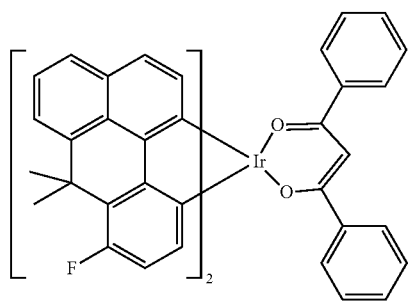
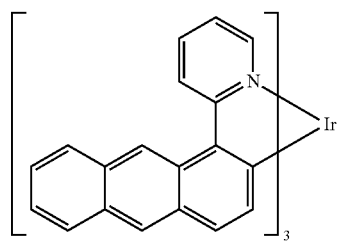
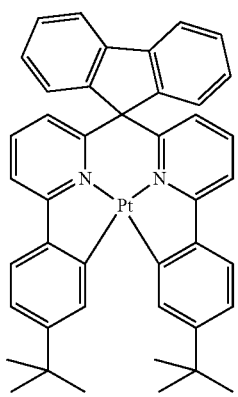
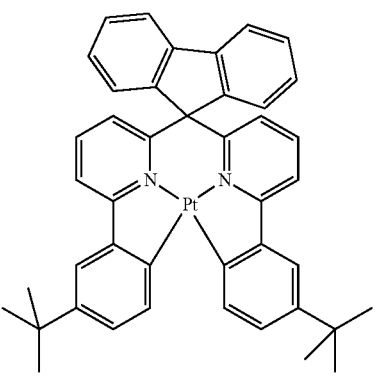

163
-continued
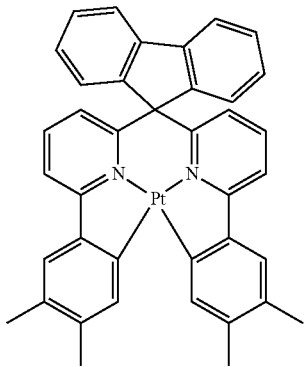
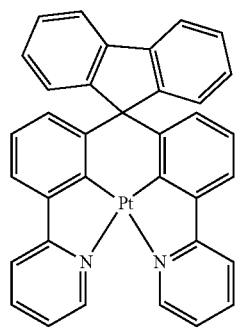
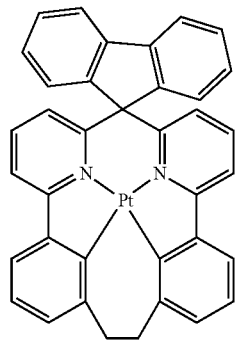
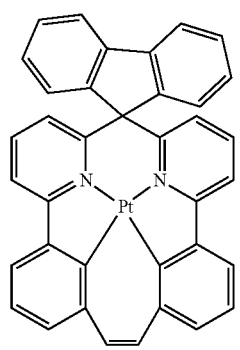
164
-continued
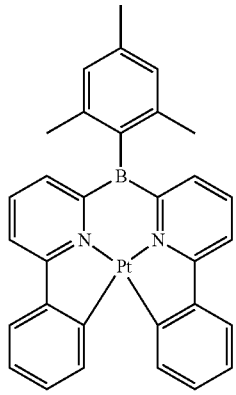
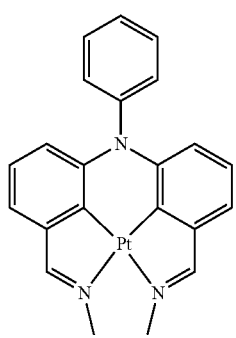
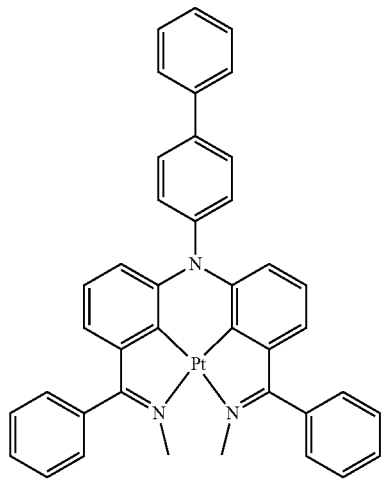
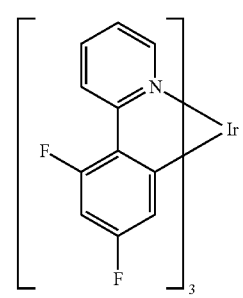

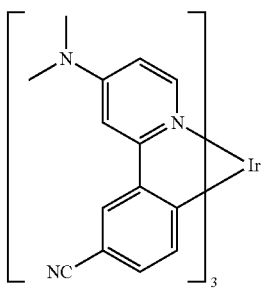
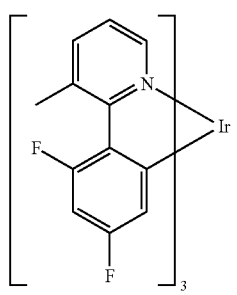
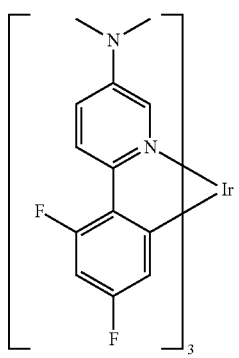
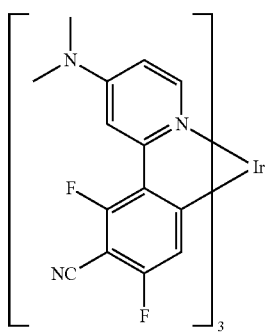
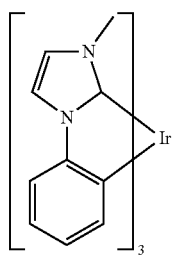
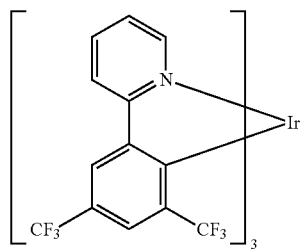
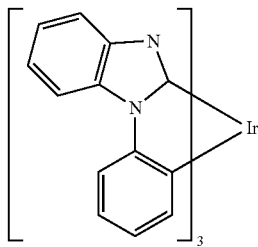
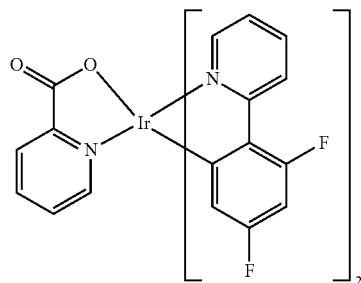
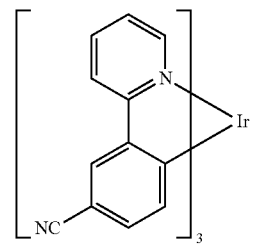
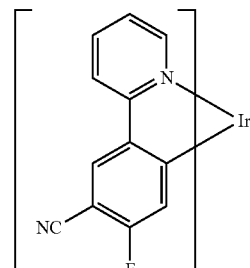

167
-continued
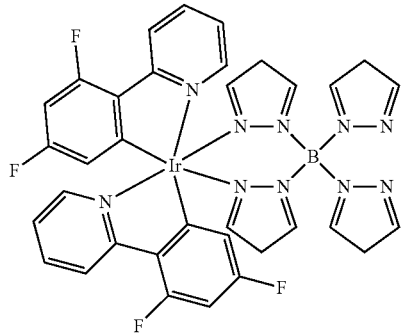
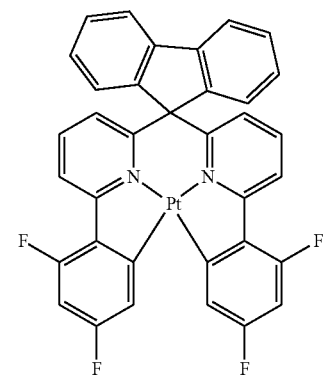
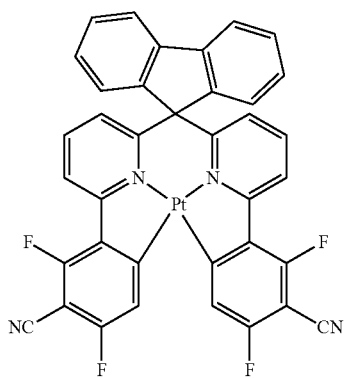
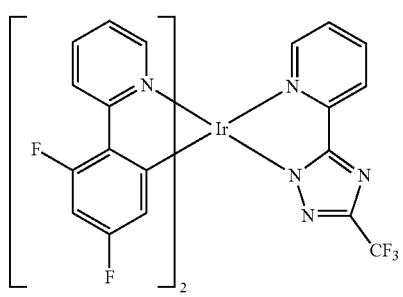
168
-continued
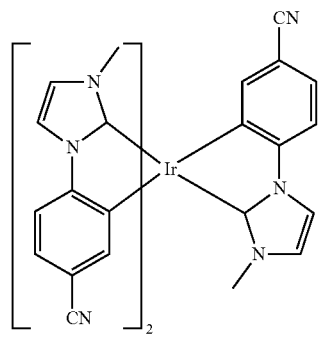
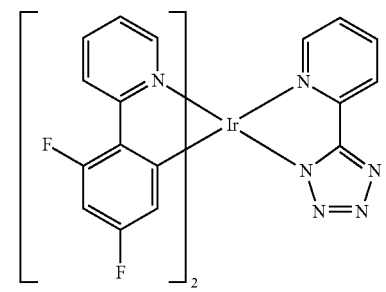
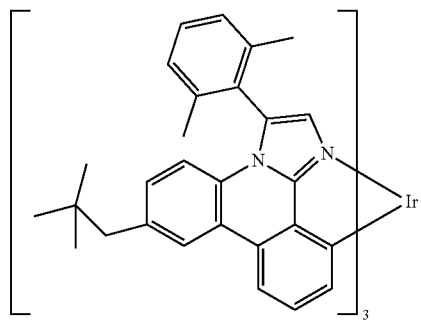
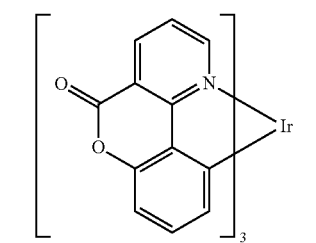
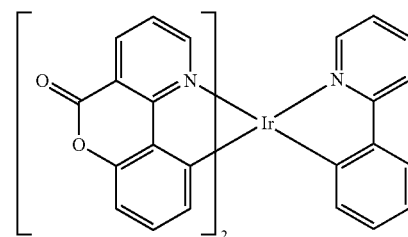

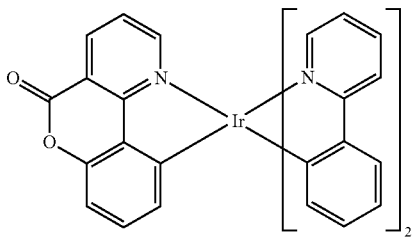

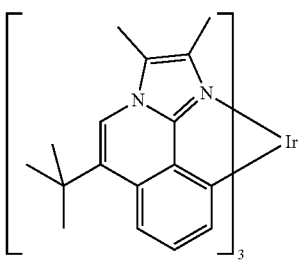

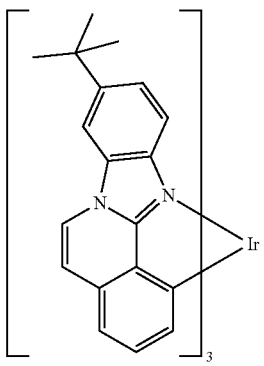

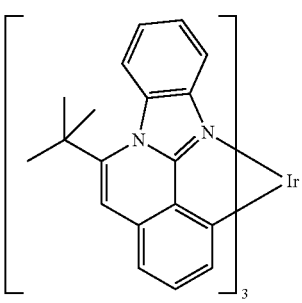

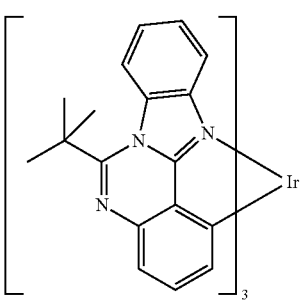

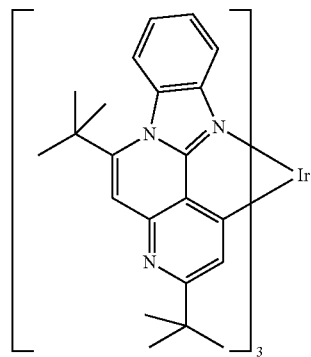

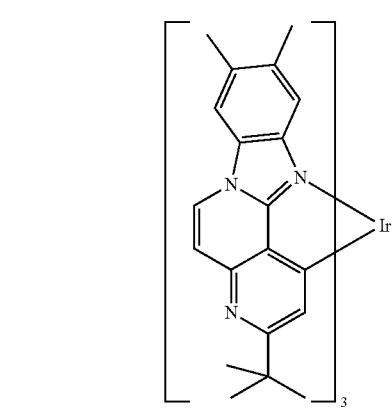

The above-described compound comprising structures of the formula (A) or the above-detailed preferred embodiments can preferably be used as active component in an electronic device. An electronic device is understood to mean any device comprising anode, cathode and at least one layer between anode and cathode, said layer comprising at least one organic or organometallic compound. The electronic device of the invention thus comprises anode, cathode and at least one intervening layer containing at least one compound comprising structures of the formula (A). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., Nature Photonics 2008, 1-4), preferably organic electroluminescent devices (OLEDs, PLEDs), especially phosphorescent OLEDs, containing at least one compound comprising structures of the formula (A) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise still further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (A) or the above-detailed preferred embodiments as matrix material, preferably as electron-conducting matrix material, in one or more emitting layers, preferably in combination with a further matrix material, preferably a hole-conducting matrix material. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer. An emitting layer comprises at least one emitting compound.

Suitable matrix materials which can be used in combination with the compounds of formula (A) or according to the preferred embodiments are aromatic ketones, aromatic phosphine oxides or aromatic sulphoxides or sulphones, for example according to WO 2004/013080, WO 2004/093207, WO 2006/005627 or WO 2010/006680, triarylamines, especially monoamines, for example according to WO 2014/015935, carbazole derivatives, e.g. CBP (N,N-biscarbazolyl-biphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, or 4-spirocarbazole derivatives, for example according to WO 2014/094963 or the as yet unpublished application EP 14002104.9. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

Preferred triarylamine derivatives which are used as co-host materials together with the compounds of the invention are selected from the compounds of the following formula (TA-1):

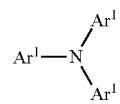

Formula (TA-1)

where $Ar^1$ is the same or different at each instance and is an aromatic or heteroaromatic ring system which has 5 to 60 aromatic ring atoms and may be substituted in each case by one or more $R^2$ radicals, an aryloxy group which has 5 to 60 aromatic ring atoms and may be substituted by one or more $R^2$ radicals, or an aralkyl group which has 5 to 60 aromatic ring atoms and may be substituted in each case by one or more $R^2$ radicals, where two or more adjacent $R^2$ substituents may optionally form a mono- or polycyclic aliphatic ring system which may be substituted by one or more $R^3$ radicals, where the symbol $R^2$ has the definition given above, especially for formula (A). Preferably, $Ar^1$ is the same or different at each instance and is an aryl or heteroaryl group which has 5 to 24 and preferably 5 to 12 aromatic ring atoms, and which may be substituted in each case by one or more $R^2$ radicals, but is preferably unsubstituted.

Examples of suitable $Ar^1$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^2$ radicals, but are preferably unsubstituted.

Preferably, the $Ar^1$ groups are the same or different at each instance and are selected from the abovementioned groups ($R^1$-1) to ($R^1$-87), preferably ($R^1$-1) to ($R^1$-54), particularly preferably ($R^1$-1) to ($R^1$-51), especially preferably ($R^1$-1) to ($R^1$-37), very particular preference being given to radicals according to ($R^1$-1). In this context, the preferences detailed above for the groups of the formulae ($R^1$-1) to ($R^1$-87) with regard to the sum total of the indices and the $R^2$ radicals bonded to these groups are applicable.

In a preferred embodiment of the compounds of the formula (TA-1), at least one $Ar^1$ group is selected from a biphenyl group, which may be an ortho-, meta- or para-biphenyl group. In a further preferred embodiment of the compounds of the formula (TA-1), at least one $Ar^1$ group is selected from a fluorene group or spirobifluorene group, where these groups may each be bonded to the nitrogen atom in the 1, 2, 3 or 4 position. In yet a further preferred embodiment of the compounds of the formula (TA-1), at least one Ar¹ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), one Ar¹ group is selected from a fluorene or spirobifluorene group, especially a 4-fluorene or 4-spirobifluorene group, and one Ar¹ group is selected from a biphenyl group, especially a para-biphenyl group, or a fluorene group, especially a 2-fluorene group, and the third Ar¹ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

Formula (TA-2)

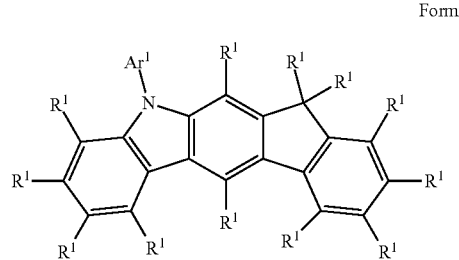

where Ar¹ and R¹ have the definitions listed above, especially for formulae (A) and/or (TA-1). Preferred embodiments of the Ar¹ group are the above-listed structures R¹-1 to R¹-87, more preferably R¹-1 to R¹-51.

A preferred embodiment of the compounds of the formula (TA-2) is the compounds of the following formula (TA-2a):

Formula (TA-2a)

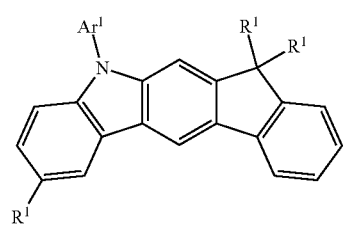

where Ar¹ and R¹ have the definitions listed above, especially for formulae (A) and/or (TA-1). The two R¹ groups bonded to the indeno carbon atom here are preferably the same or different and are an alkyl group having 1 to 4 carbon atoms, especially methyl groups, or an aromatic ring system having 6 to 12 carbon atoms, especially phenyl groups. More preferably, the two R¹ groups bonded to the indeno carbon atom are methyl groups. Further preferably, the R¹ substituent bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

Formula (TA-3)

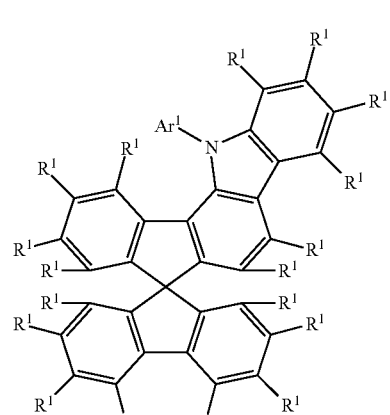

where Ar¹ and R¹ have the definitions listed above, especially for formula (A) and/or (TA-1). Preferred embodiments of the Ar¹ group are the above-listed structures R¹-1 to R¹-87, more preferably R¹-1 to R¹-51.

A preferred embodiment of the compounds of the formula (TA-3) is the compounds of the following formula (TA-3a):

Formula (TA-3a)

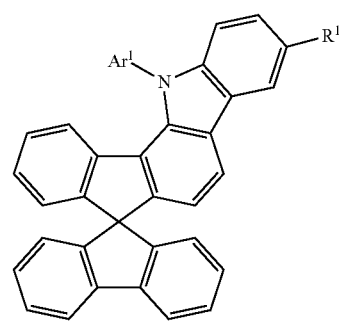

where Ar¹ and R¹ have the definitions listed above, especially for formula (A). Preferred embodiments of the Ar¹ group are the above-listed structures R¹-1 to R¹-87, more preferably R¹-1 to R¹-51.

Preferred lactams which are used as co-host materials together with the compounds of the invention are selected from the compounds of the following formula (LAC-1):

Formula (LAC-1)

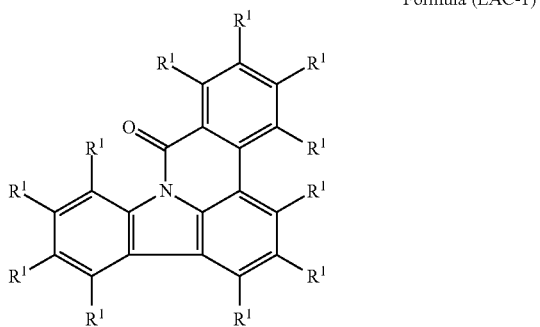

where R¹ has the definition listed above, especially for formula (A).

A preferred embodiment of the compounds of the formula (LAC-1) is the compounds of the following formula (LAC-1a):

Formula (LAC-1a)

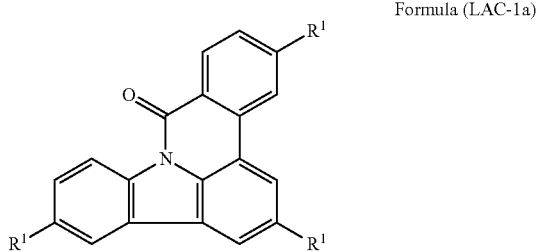

where R¹ has the definition cited above, especially for formula (A). R¹ is preferably the same or different at each instance and is H or an aromatic or heteroaromatic ring system which has 5 to 40 aromatic ring atoms and may be substituted by one or more R² radicals, where R² may have the definition given above, especially for formula (A). Most preferably, the R¹ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic R² radicals, but is preferably unsubstituted. Examples of suitable R¹ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R² radicals, but are preferably unsubstituted. Suitable R¹ structures are the same structures as depicted above for R-1 to R-79, more preferably R¹-1 to R¹-51.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (A), in a preferred embodiment, as matrix material in an emission layer of an organic electronic device, especially in an organic electroluminescent device, for example in an OLED or OLEC. In this case, the matrix material containing compound comprising structures of formula (A) or the preferred embodiments recited above and hereinafter is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (A) or the preferred embodiments recited above and below are used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device, can also be produced as a hybrid system by applying one or more layers from solution and applying one or more other layers by vapour deposition. For example, it is possible to apply an emitting layer comprising a compound of the invention comprising structures of formula (A) and a matrix material from solution, and to apply a hole blocker layer and/or an electron transport layer thereto by vapour deposition under reduced pressure.

These methods are known in general terms to those skilled in the art and can be applied without difficulty to electronic devices, especially organic electroluminescent devices comprising compounds of the invention comprising structures of formula (A) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (A) or the preferred embodiments recited above and hereinafter, especially as electron-conducting materials and/or matrix materials, have a very good lifetime.
2. Electronic devices, especially organic electroluminescent devices, comprising compounds, oligomers, polymers or dendrimers having structures of formula (A) or the preferred embodiments recited above and hereinafter, as electron-conducting materials, electron injection materials and/or matrix materials, have excellent efficiency. More particularly, efficiency is much higher compared to analogous compounds containing no structural unit of formula (A).
3. The compounds, oligomers, polymers or dendrimers of the invention having structures of formula (A) or the preferred embodiments recited above and hereinafter exhibit very high stability and lead to compounds having a very long lifetime.
4. With compounds, oligomers, polymers or dendrimers having structures of formula (A) or the preferred embodiments recited above and hereinafter, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (A) or the preferred embodiments recited above and hereinafter in layers of electronic devices, especially organic electroluminescent devices, leads to high mobility of the electron conductor structures.
6. Compounds, oligomers, polymers or dendrimers having structures of formula (A) or the preferred embodiments recited above and below feature excellent thermal stability, and compounds having a molar mass of less than about 1200 g/mol have good sublimability.

7. Compounds, oligomers, polymers or dendrimers having structures of formula (A) or the preferred embodiments recited above and hereinafter have excellent glass film formation.
8. Compounds, oligomers, polymers or dendrimers having structures of formula (A) or the preferred embodiments recited above and hereinafter form very good films from solutions.
9. The compounds, oligomers, polymers or dendrimers comprising structures of formula (A) or the preferred embodiments recited above and hereinafter have a surprisingly high triplet level Ti, this being particularly true of compounds which are used as electron-conducting materials.

These abovementioned advantages are not accompanied by a deterioration in the further electronic properties.

The compounds and mixtures of the invention are suitable for use in an electronic device. An electronic device is understood to mean a device containing at least one layer containing at least one organic compound.

The component may also comprise inorganic materials or else layers formed entirely from inorganic materials.

The present invention therefore further provides for the use of the compounds or mixtures of the invention in an electronic device, especially in an organic electroluminescent device.

The present invention still further provides for the use of a compound of the invention and/or of an oligomer, polymer or dendrimer of the invention in an electronic device as host material, matrix material, electron transport material, electron injection material and/or hole blocker material.

The present invention still further provides an electronic device comprising at least one of the above-detailed compounds or mixtures of the invention. In this case, the preferences detailed above for the compound also apply to the electronic devices. More preferably, the electronic device is selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs), organic laser diodes (O-lasers) and organic plasmon emitting devices (D. M. Koller et al., Nature Photonics 2008, 1-4), preferably organic electroluminescent devices (OLEDs, PLEDs), especially phosphorescent OLEDs.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In addition, it is possible to use the compounds of the invention in a hole blocker or electron transport layer. This is especially true of compounds of the invention which do not have a carbazole structure. These may preferably also be substituted by one or more further electron-transporting groups, for example benzimidazole groups.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (A) or according to the preferred embodiments.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, should themselves be regarded as inventive and not merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The compounds of the invention can be prepared by means of synthesis methods known to those skilled in the art.

Synthesis Examples a) 2,4-Diphenylbenzo[4,5]furo[3,2-cl]pyrimidine

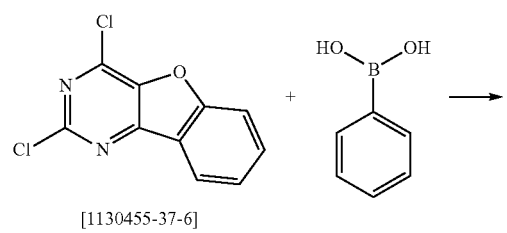

[1130455-37-6]

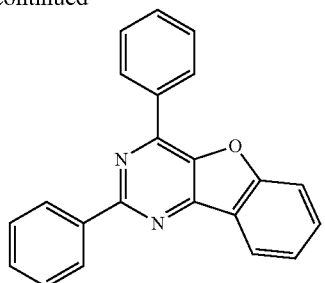

13 g (110.0 mmol) of phenylboronic acid, 13 g (55 mmol) of 2,4-dichlorobenzo[4,5]furo[3,2-d]pyrimidine and 21 g (210.0 mmol) of sodium carbonate are suspended in 500 ml of ethylene glycol diamine ether and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel and then concentrated to dryness. The residue is recrystallized from toluene and from dichloromethane/heptane. Yield: 15 g (47 mmol), 87% of theory.

The following compounds are prepared in an analogous manner:

-continued
6a 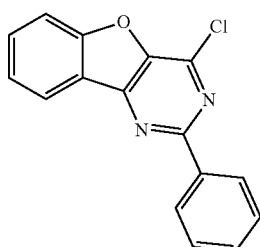
[134221-88-8]
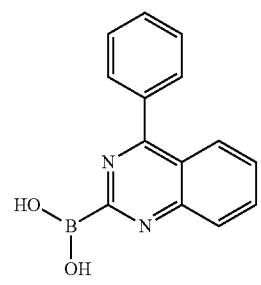
[1629973-75-6]
7a 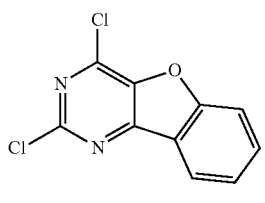
[1130455-37-6]
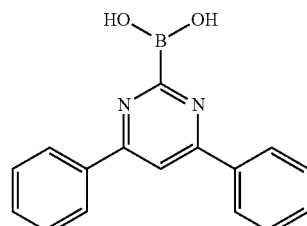
[1350818-50-6]
8a 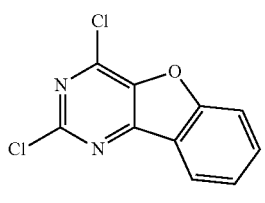
[1130455-37-6]
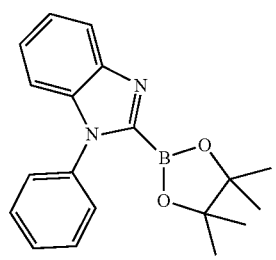
[1316275-47-4]
9a 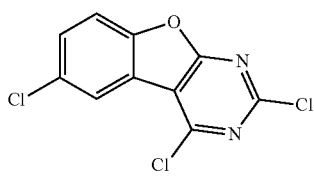
[1130455-37-6]
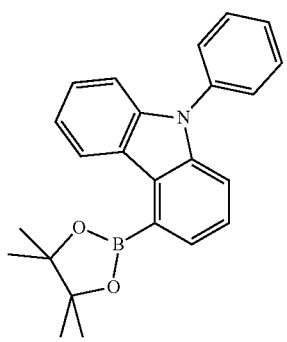
[1547492-13-6]
10a 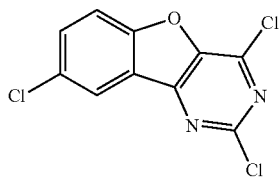
[160199-00-8]
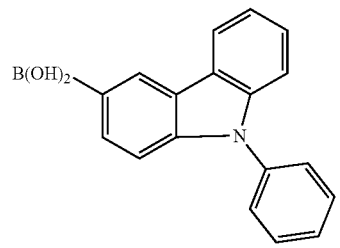
854952-58-2

-continued
| | | | |
|---|---|---|---|
| 11a | 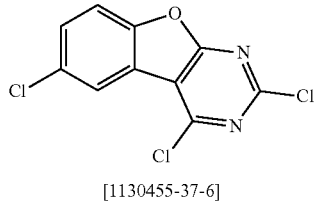 [SMILES: Clc1ccc2oc3nc(Cl)nc(Cl)c3c2c1] [1130455-37-6] | | 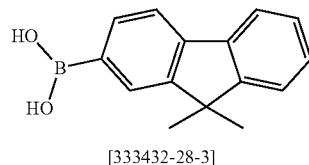 [333432-28-3] |
| 12a | 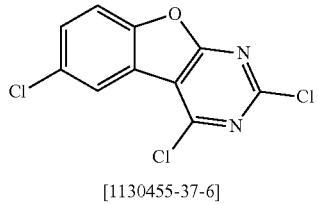 [SMILES: Clc1ccc2oc3nc(Cl)nc(Cl)c3c2c1] [1130455-37-6] | | 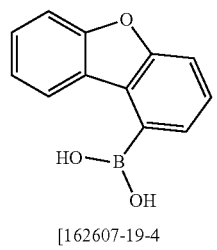 [SMILES: OB(O)c1cccc2oc3ccccc3c12] [162607-19-4] |
| 13a | 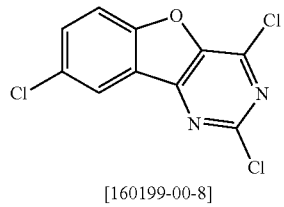 [SMILES: Clc1ccc2oc3c(Cl)nc(Cl)nc3c2c1] [160199-00-8] | | 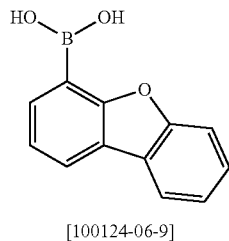 [SMILES: OB(O)c1cccc2c1oc1ccccc12] [100124-06-9] |
| 14a | 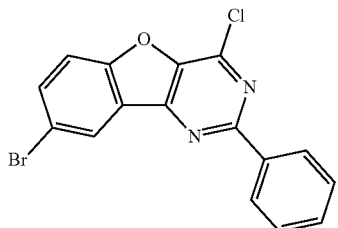 13b | | 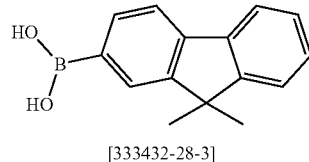 [333432-28-3] |
| 15a | 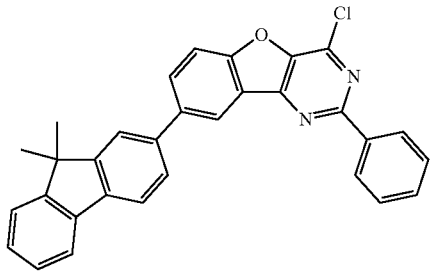 [SMILES: CC1(C)c2ccccc2-c2ccc(-c3ccc4oc5c(Cl)nc(-c6ccccc6)nc5c4c3)cc21] | | 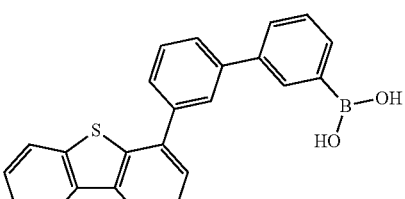 [1346010-12-5] |
| 16a | 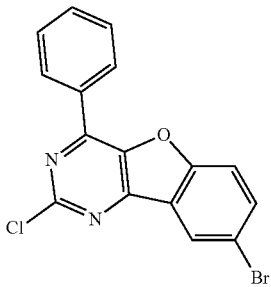 [SMILES: Clc1nc(-c2ccccc2)c2oc3ccc(Br)cc3c2n1] | | 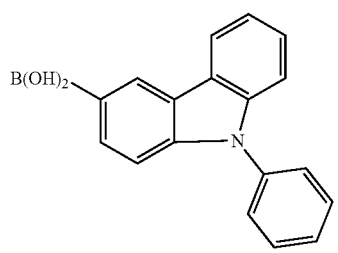 854952-58-2 |

-continued

| | Product | Yield |
|---|---|---|
| 2a | | 89% |
| 3a | | 70% |
| 4a | | 77% |
| 5a | | 76% |

| | | |
|---|---|---|
| 6a | 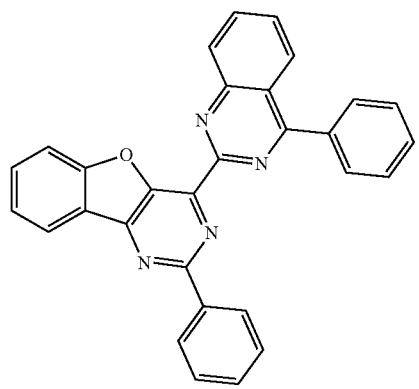 [SMILES: c1ccc(-c2nc(-c3nc(-c4ccccc4)c4ccccc4n3)c3oc4ccccc4c3n2)cc1] | 77% |
| 7a | 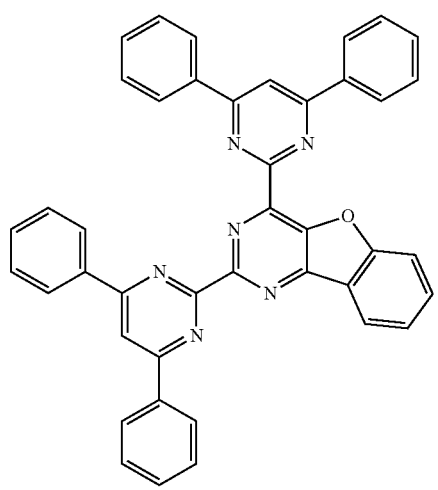 [SMILES: c1ccc(-c2cc(-c3ccccc3)nc(-c3nc(-c4nc(-c5ccccc5)cc(-c5ccccc5)n4)c4oc5ccccc5c4n3)n2)cc1] | 74% |
| 8a | 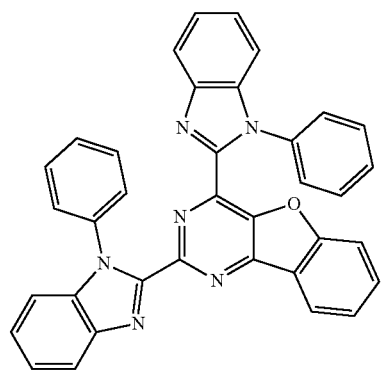 [SMILES: c1ccc(-n2c(-c3nc(-c4nc5ccccc5n4-c4ccccc4)c4oc5ccccc5c4n3)nc3ccccc32)cc1] | 76% |

9a 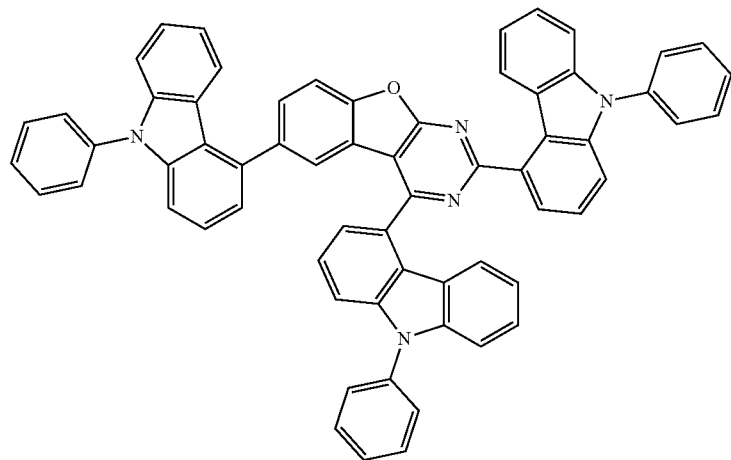 [SMILES: c1ccc(-n2c3ccccc3c3c(-c4ccc5oc6nc(-c7cccc8c7c7ccccc7n8-c7ccccc7)nc(-c7cccc8c7c7ccccc7n8-c7ccccc7)c6c5c4)cccc32)cc1] 69%
10a 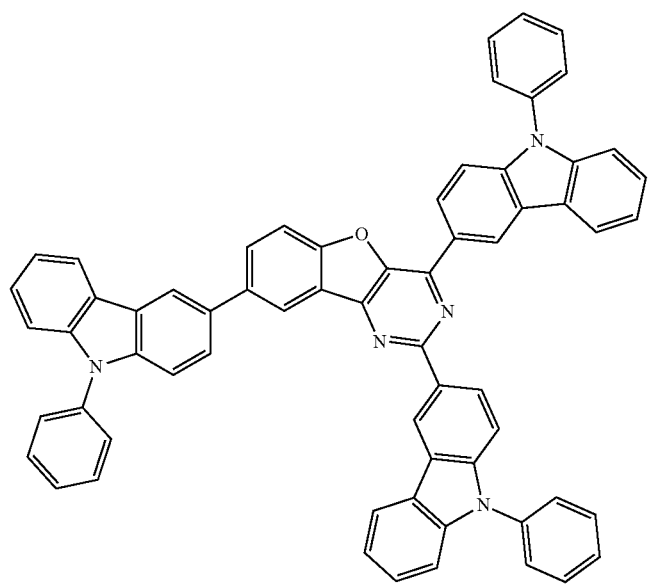 [SMILES: c1ccc(-n2c3ccccc3c3cc(-c4ccc5oc6c(-c7ccc8c(c7)c7ccccc7n8-c7ccccc7)nc(-c7ccc8c(c7)c7ccccc7n8-c7ccccc7)nc6c5c4)ccc32)cc1] 75%
11a 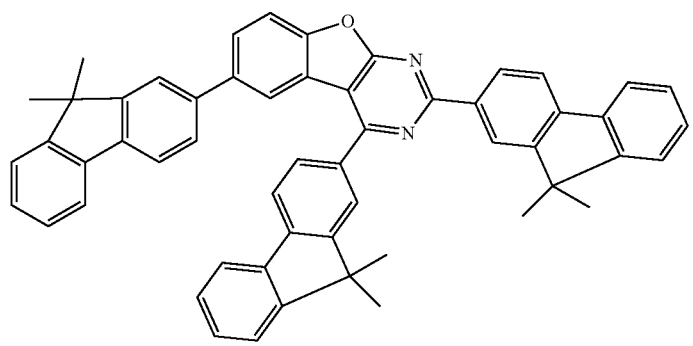 [SMILES: CC1(C)c2ccccc2-c2ccc(-c3ccc4oc5nc(-c6ccc7c(c6)C(C)(C)c6ccccc6-7)nc(-c6ccc7c(c6)C(C)(C)c6ccccc6-7)c5c4c3)cc21] 73%

| | | |
|---|---|---|
| 12a | 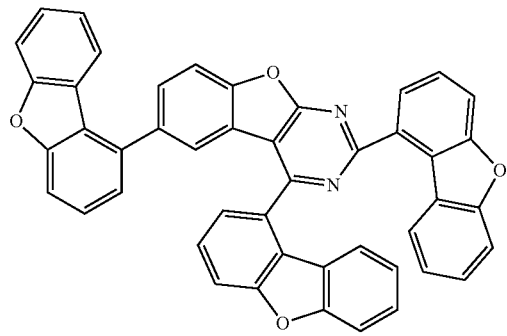 [SMILES: c1ccc2c(c1)oc1cccc(-c3ccc4oc5nc(-c6cccc7oc8ccccc8c67)nc(-c6cccc7oc8ccccc8c67)c5c4c3)c12] | 75% |
| 13a | 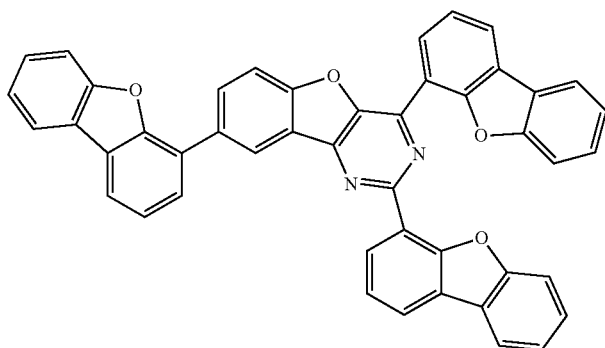 [SMILES: c1ccc2c(c1)oc1c(-c3ccc4oc5c(-c6cccc7c6oc6ccccc67)nc(-c6cccc7c6oc6ccccc67)nc5c4c3)cccc12] | 76% |
| 14a | 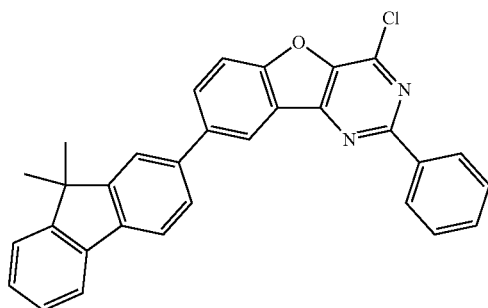 | 68% |
| 15a | 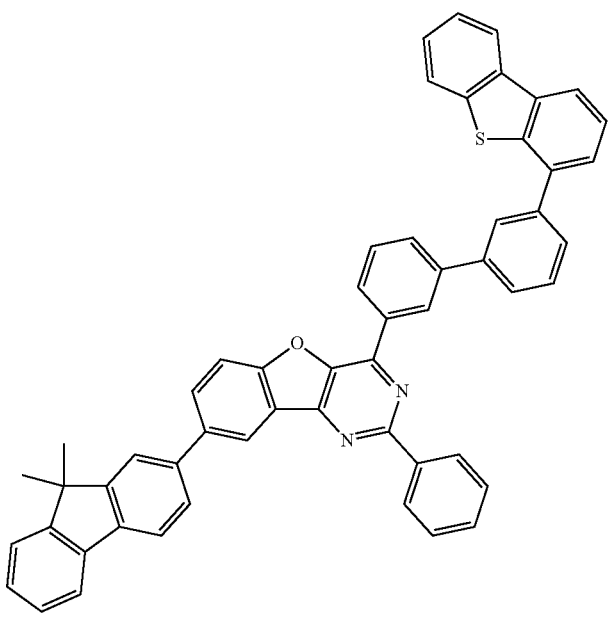 [SMILES: CC1(C)c2ccccc2-c2ccc(-c3ccc4oc5c(-c6cccc(-c7cccc(-c8cccc9c8sc8ccccc89)c7)c6)nc(-c6ccccc6)nc5c4c3)cc21] | 71% |

| | | |
|---|---|---|
| 16a | 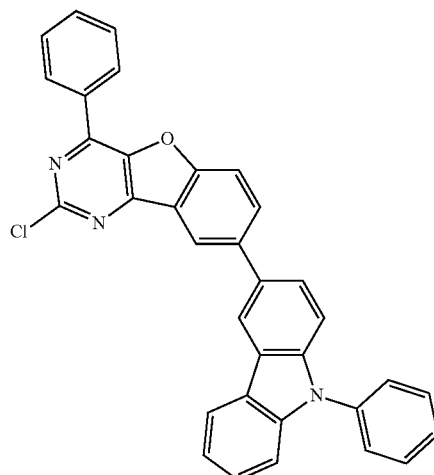 | 73% |

The product 9a and 13a is purified via column chromatography on silica gel with toluene/heptane (1:2) and finally sublimed under high vacuum (p=5×10⁻⁷ mbar) (99.9% purity).

b) 8-Bromo-2,4-diphenylbenzo[4,5]furo[3,2-d]pyrimidine

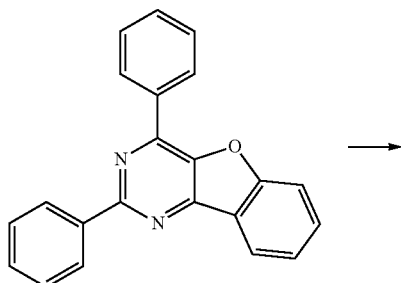 →  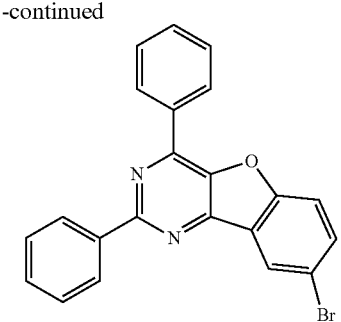

61 g (190.0 mmol) of 2,4-diphenylbenzo[4,5]furo[3,2-d]pyrimidine are suspended in 2000 ml of acetic acid (100%) and 2000 ml of sulphuric acid (95-98%). 34 g (190 mmol) of NBS are added to this suspension in portions and the mixture is stirred in the dark for 2 hours. Thereafter, water/ice is added and solids are removed and washed with ethanol. The residue is recrystallized in toluene. The yield is 65 g (163 mmol), corresponding to 86% of theory.

The following compounds are prepared in an analogous manner:

| | Reactant 1 | Product | Yield |
|---|---|---|---|
| 2b | 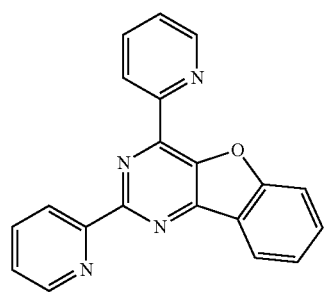 [SMILES: c1ccc(-c2nc(-c3ccccn3)c3oc4ccccc4c3n2)nc1] | 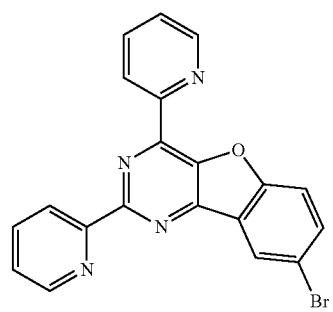 [SMILES: Brc1ccc2oc3c(-c4ccccn4)nc(-c4ccccn4)nc3c2c1] | 85% |

-continued

| | Reactant 1 | Product | Yield |
|---|---|---|---|
| 3b | | | 84% |
| 4b | | | 85% |
| 5b | | | 79% |
| 6b | | | 70% |

| | Reactant 1 | Product | Yield |
|---|---|---|---|
| 7b | | | 73% |
| 8b | [101537-71-7] | | 80% |
| 9b | [129190-79-0] | | 85% |
| 10b | [1130455-37-6] | | 69% |
| 11b | [76872-40-7] | | 71% |

-continued
| Reactant 1 | Product | Yield |
|---|---|---|
| 12b 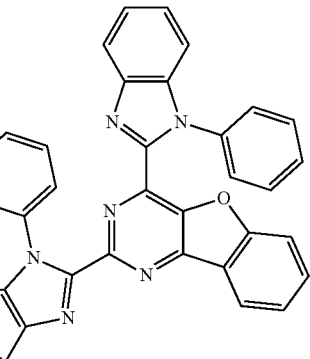 | 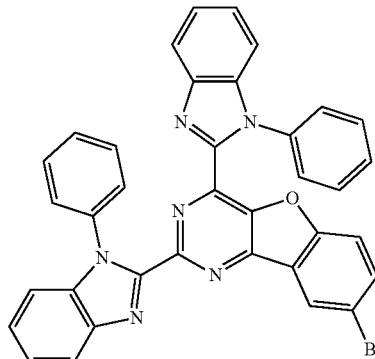 | 74% |
| 13b 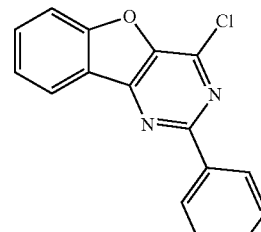 [134221-88-8] | 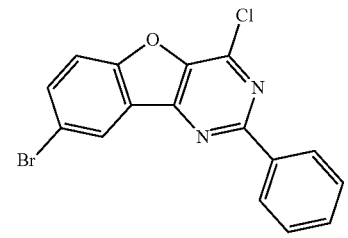 [SMILES: Clc1nc(-c2ccccc2)nc2c1oc1ccc(Br)cc12] | 67% |
| 14b 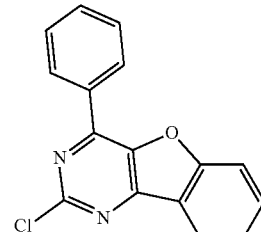 [1801233-17-9] | 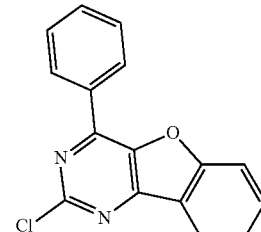 | 56% |
c) 2,4-Diphenyl-8-(9-phenyl-9H-carbazol-3-yl)-benzo[4,5]furo[3,2-d]pyrimidine
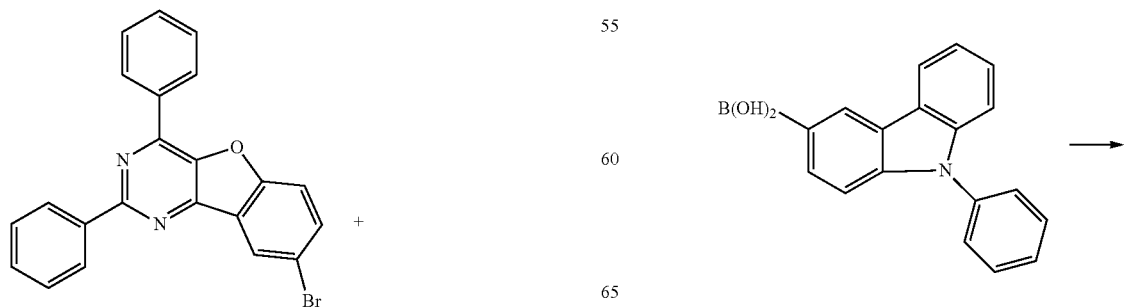

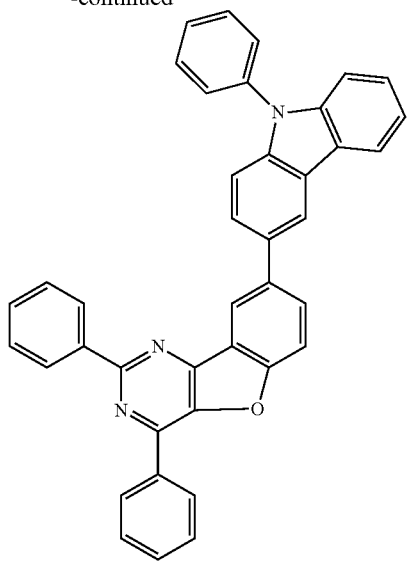

62 g (156 mmol) of 8-bromo-2,4-diphenylbenzo[4,5]furo[3,2-d]pyrimidine, 50 g (172 mmol) of N-phenylcarbazole-3-boronic acid and 36 g (340 mmol) of sodium carbonate are suspended in 1000 ml of ethylene glycol diamine ether and 280 ml of water. To this suspension are added 1.8 g (1.5 mmol) of tetrakis(triphenylphosphine)palladium(0), and the reaction mixture is heated under reflux for 16 h. After cooling, the organic phase is removed, filtered through silica gel and then concentrated to dryness. The product is purified via column chromatography on silica gel with toluene/heptane (1:2) and finally sublimed under high vacuum (p=$5\times10^{-7}$ mbar) (purity 99.9%). The yield is 60 g (106 mmol), corresponding to 69% of theory.

In an analogous manner, the following compounds are prepared:

| | Reactant 1 | Reactant 2 |
|---|---|---|
| 1c | 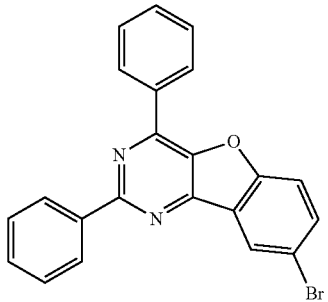 [SMILES: Brc1ccc2oc3c(-c4ccccc4)nc(-c4ccccc4)nc3c2c1] | 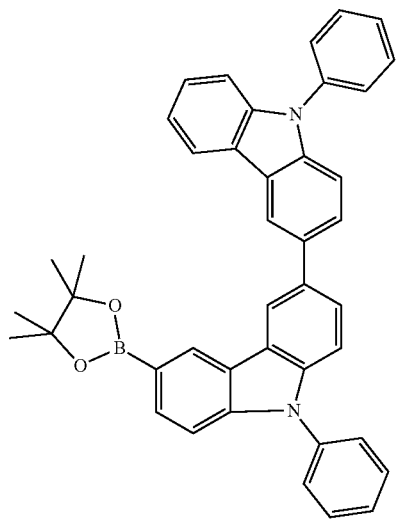<br>[1572537-61-1] |
| 2c | 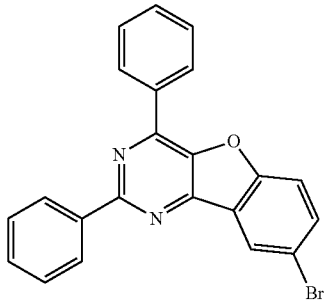 [SMILES: Brc1ccc2oc3c(-c4ccccc4)nc(-c4ccccc4)nc3c2c1] | 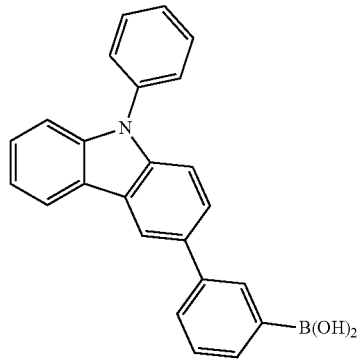 [SMILES: OB(O)c1cccc(-c2ccc3c(c2)c2ccccc2n3-c2ccccc2)c1] |

-continued
3c
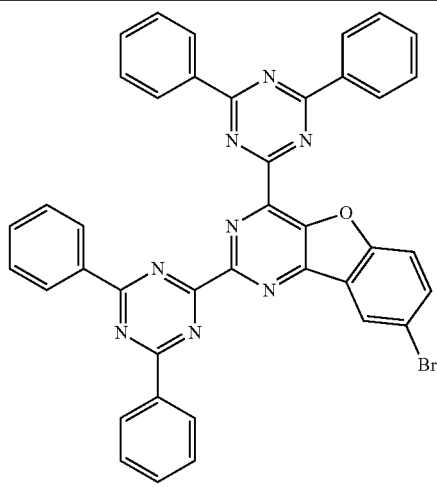
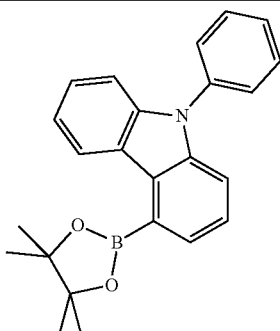
[1547492-13-6]
4c
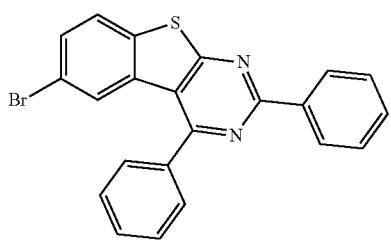 [SMILES: Brc1ccc2sc3nc(-c4ccccc4)nc(-c4ccccc4)c3c2c1]
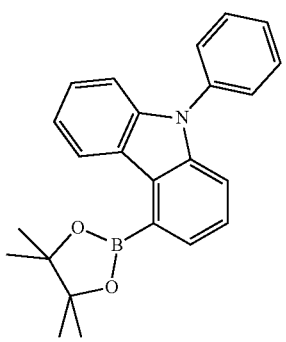
[1547492-13-6]
5c
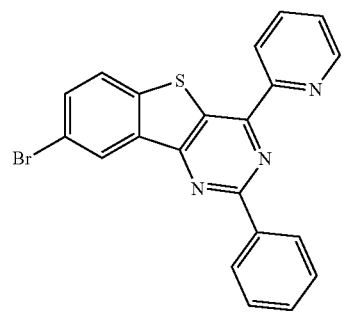 [SMILES: Brc1ccc2sc3c(-c4ccccn4)nc(-c4ccccc4)nc3c2c1]
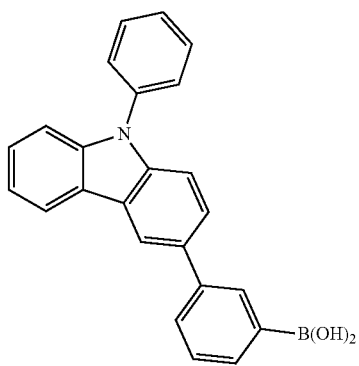
854952-60-6
6c
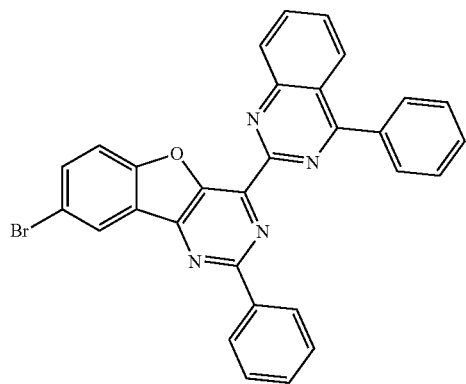 [SMILES: Brc1ccc2oc3c(-c4nc(-c5ccccc5)c5ccccc5n4)nc(-c4ccccc4)nc3c2c1]
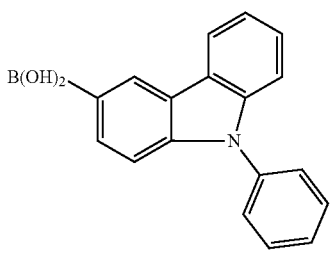
854952-58-2

7c 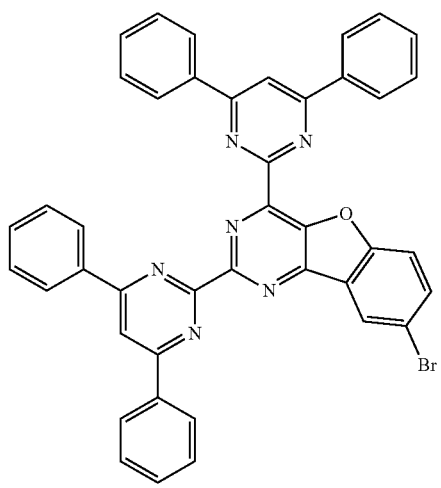 [SMILES: Brc1ccc2oc3c(-c4nc(-c5ccccc5)cc(-c5ccccc5)n4)nc(-c4nc(-c5ccccc5)cc(-c5ccccc5)n4)nc3c2c1] 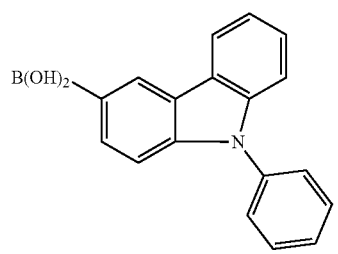
854952-58-2
8c 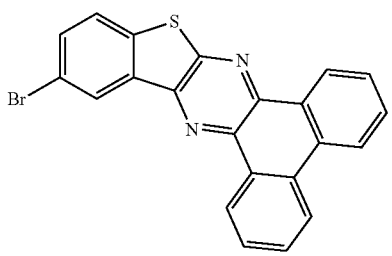 [SMILES: Brc1ccc2sc3nc4c5ccccc5c5ccccc5c4nc3c2c1] 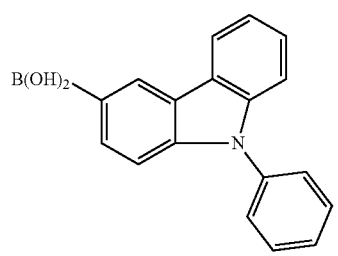
854952-58-2
9c 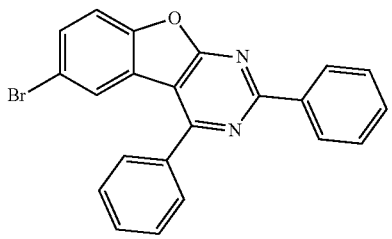 [SMILES: Brc1ccc2oc3nc(-c4ccccc4)nc(-c4ccccc4)c3c2c1] 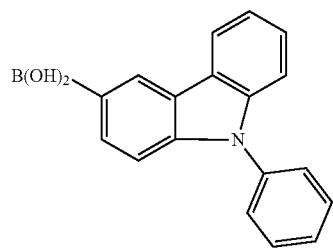
854952-58-2
10c 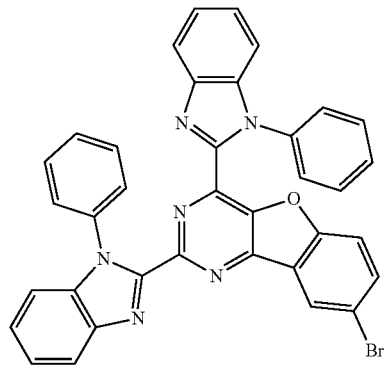 [SMILES: Brc1ccc2oc3c(-c4nc5ccccc5n4-c4ccccc4)nc(-c4nc5ccccc5n4-c4ccccc4)nc3c2c1] 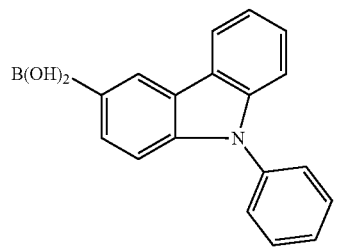
854952-58-2

-continued
11c 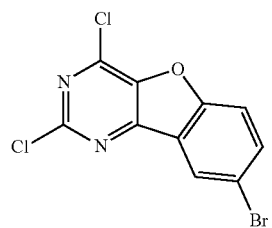 [SMILES: Clc1nc(Cl)c2oc3ccc(Br)cc3c2n1] 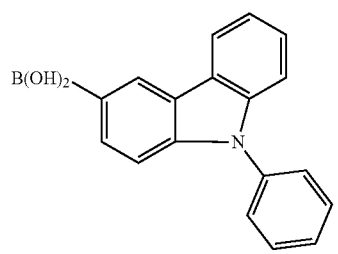
854952-58-2
12c 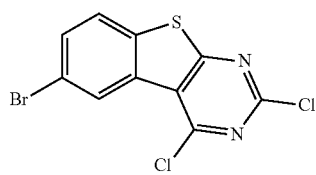 [SMILES: Clc1nc(Cl)c2c(n1)sc1ccc(Br)cc12] 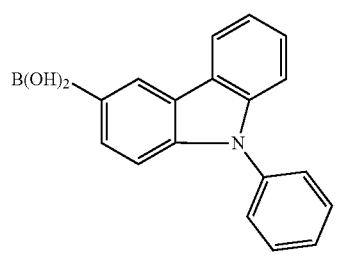
854952-58-2
13c 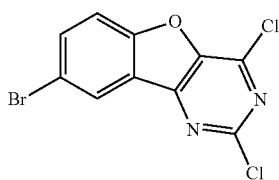 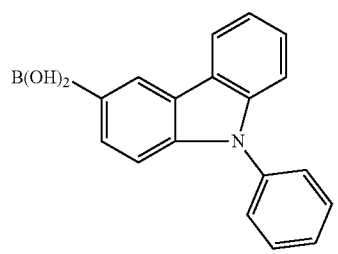
[1169560-03-5]
854952-58-2
14c 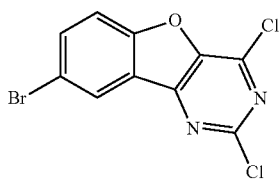 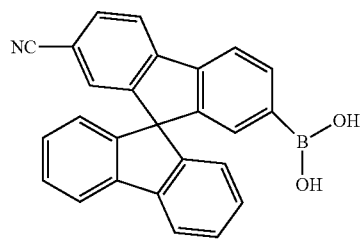
[1169560-03-5]
[1838683-74-1]
15c 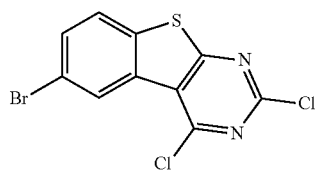 [SMILES: Clc1nc(Cl)c2c(n1)sc1ccc(Br)cc12] 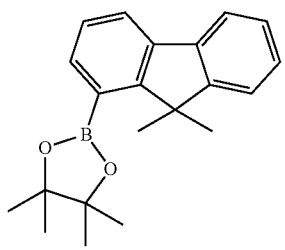
[1792218-53-1]

-continued
| 16c | 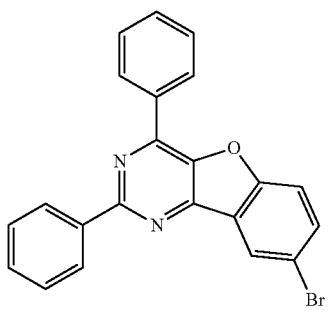 [SMILES: Brc1ccc2oc3c(-c4ccccc4)nc(-c4ccccc4)nc3c2c1] | 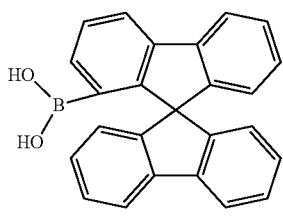
[1561044-65-2] |
| 17c | 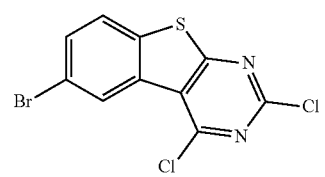 | 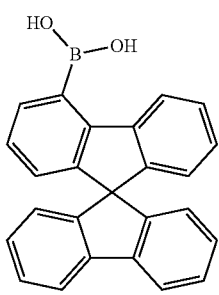
[1421789-05-0] |
| 18c | 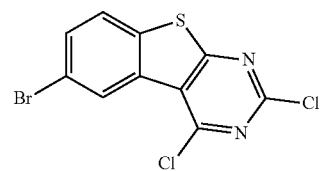 [SMILES: Clc1nc(Cl)c2c(n1)sc1ccc(Br)cc12] | 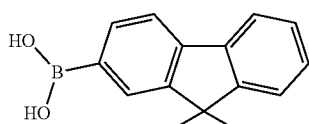
[333432-28-3] |
| 19c | 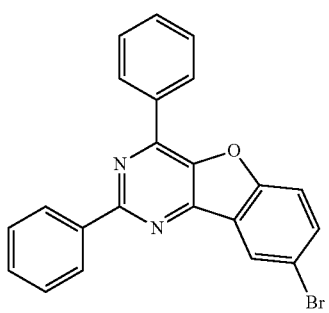 [SMILES: Brc1ccc2oc3c(-c4ccccc4)nc(-c4ccccc4)nc3c2c1] | 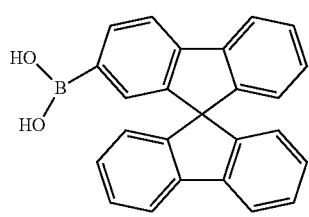
[236389-21-2] |
| 20c | 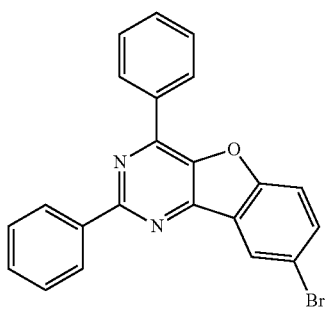 [SMILES: Brc1ccc2oc3c(-c4ccccc4)nc(-c4ccccc4)nc3c2c1] | 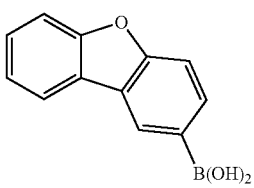
[402936-15-6] |

-continued
| | | |
|---|---|---|
| 21c | 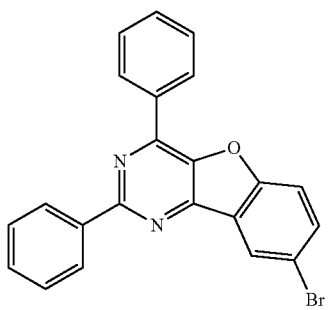 [SMILES: Brc1ccc2oc3c(-c4ccccc4)nc(-c4ccccc4)nc3c2c1] | 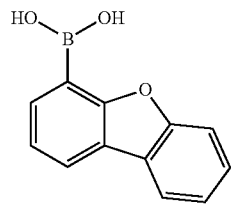
[100124-06-9] |
| 22c | 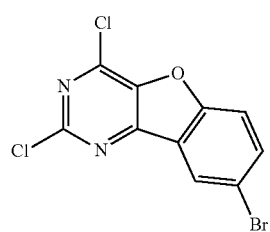 [SMILES: Clc1nc(Cl)c2oc3ccc(Br)cc3c2n1] | 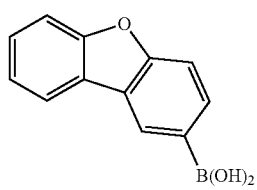
[402936-15-6] |
| 23c | 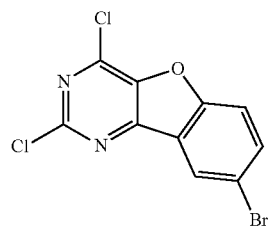 [SMILES: Clc1nc(Cl)c2oc3ccc(Br)cc3c2n1] | 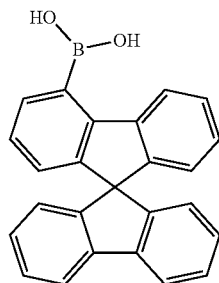
[1421789-05-0] |
| 24c | 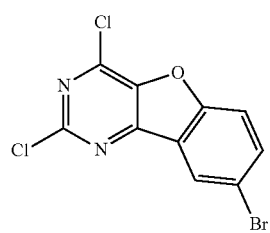 [SMILES: Clc1nc(Cl)c2oc3ccc(Br)cc3c2n1] | 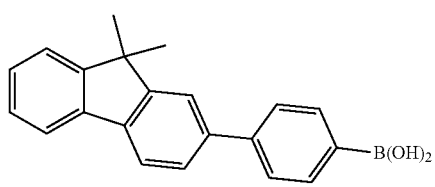
[736928-21-5] |

-continued

| Product | Yield |
|---|---|
| 1c | 65% |
| 2c | 68% |
| 3c | 65% |

| | | |
|---|---|---|
| 4c | 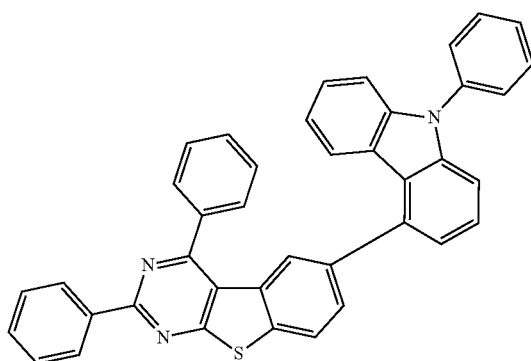 | 65% |
| 5c | 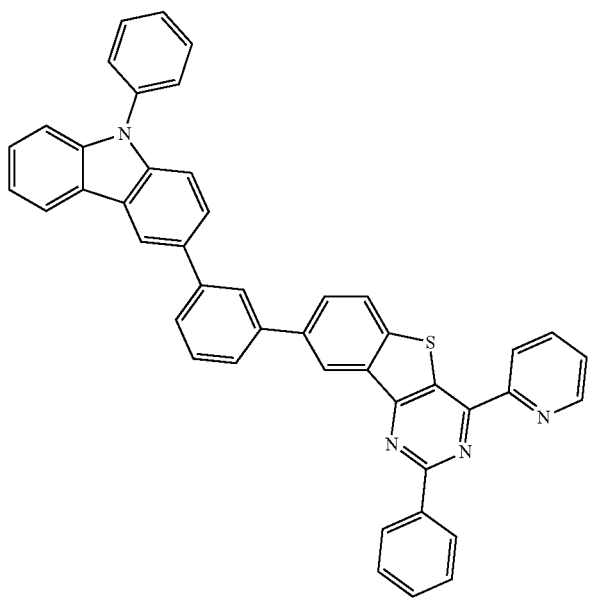 [SMILES: c1ccc(-c2nc(-c3ccccn3)c3sc4ccc(-c5cccc(-c6ccc7c(c6)c6ccccc6n7-c6ccccc6)c5)cc4c3n2)cc1] | 71% |
| 6c | 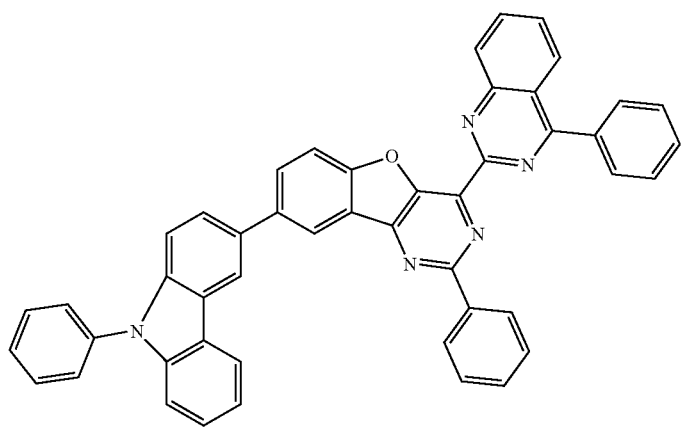 [SMILES: c1ccc(-c2nc(-c3nc(-c4ccccc4)c4ccccc4n3)c3oc4ccc(-c5ccc6c(c5)c5ccccc5n6-c5ccccc5)cc4c3n2)cc1] | 76% |

| | | |
|---|---|---|
| 7c | 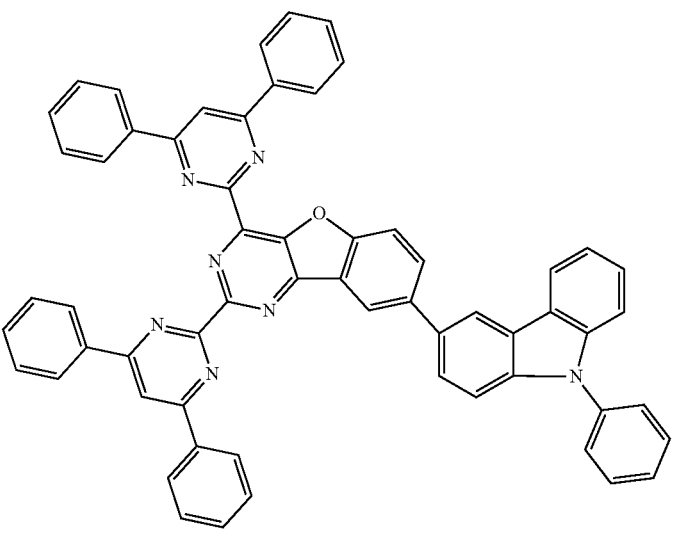 [SMILES: c1ccc(-c2cc(-c3ccccc3)nc(-c3nc(-c4nc(-c5ccccc5)cc(-c5ccccc5)n4)c4oc5ccc(-c6ccc7c(c6)c6ccccc6n7-c6ccccc6)cc5c4n3)n2)cc1] | 74% |
| 8c | 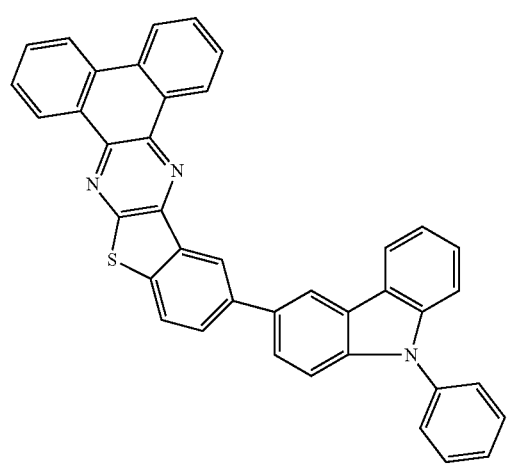 [SMILES: c1ccc(-n2c3ccccc3c3cc(-c4ccc5sc6nc7c8ccccc8c8ccccc8c7nc6c5c4)ccc32)cc1] | 71% |
| 9c | 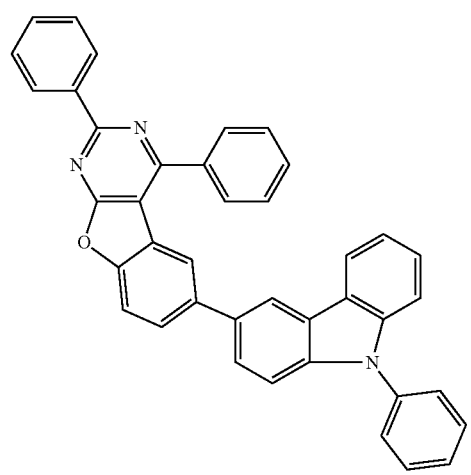 [SMILES: c1ccc(-c2nc(-c3ccccc3)c3c(n2)oc2ccc(-c4ccc5c(c4)c4ccccc4n5-c4ccccc4)cc23)cc1] | 69% |

| | | |
|---|---|---|
| 10c | 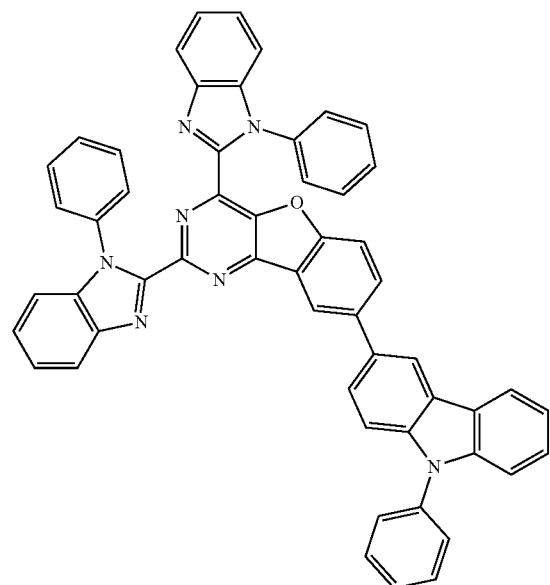 [SMILES: c1ccc(-n2c(-c3nc(-c4nc5ccccc5n4-c4ccccc4)c4oc5ccc(-c6ccc7c(c6)c6ccccc6n7-c6ccccc6)cc5c4n3)nc3ccccc32)cc1] | 70% |
| 11c | 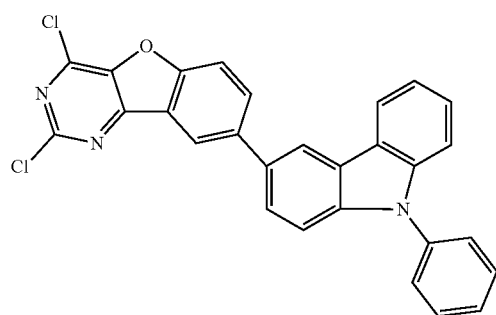 | 77% |
| 12c | 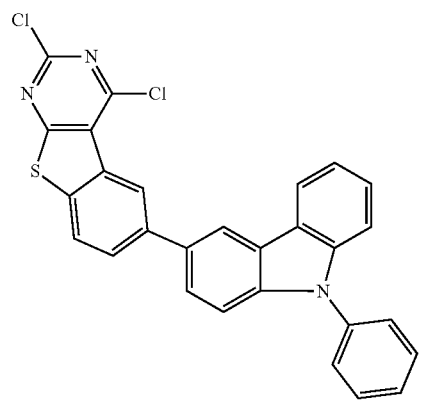 [SMILES: Clc1nc(Cl)c2c(n1)sc1ccc(-c3ccc4c(c3)c3ccccc3n4-c3ccccc3)cc12] | 60% |
| 13c | 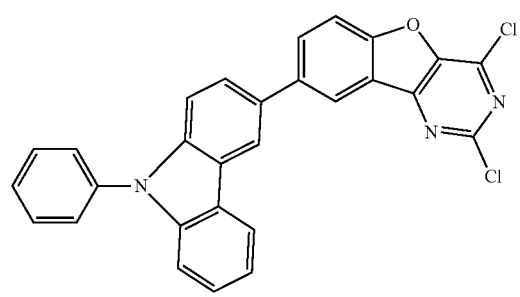 [SMILES: Clc1nc(Cl)c2oc3ccc(-c4ccc5c(c4)c4ccccc4n5-c4ccccc4)cc3c2n1] | 56% |

-continued
| | | |
|---|---|---|
| 14c | 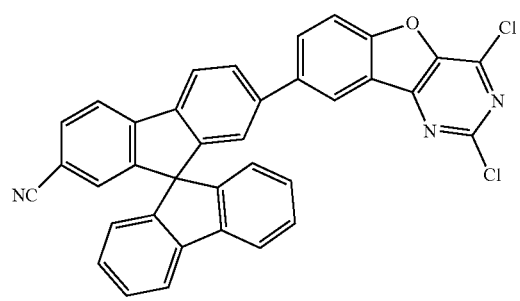 [SMILES: N#Cc1ccc2c(c1)C1(c3ccccc3-c3ccccc31)c1cc(-c3ccc4oc5c(Cl)nc(Cl)nc5c4c3)ccc1-2] | 64% |
| 15c | 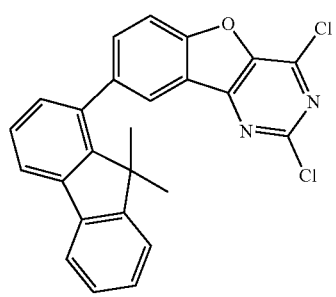 [SMILES: CC1(C)c2ccccc2-c2cccc(-c3ccc4oc5c(Cl)nc(Cl)nc5c4c3)c21] | 65% |
| 16c | 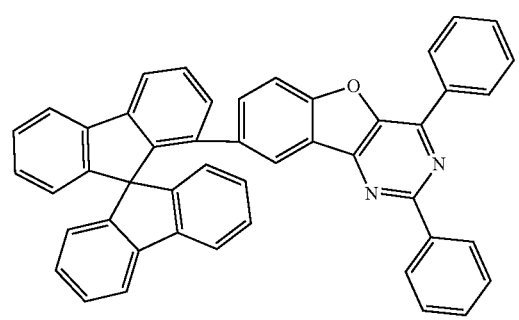 [SMILES: c1ccc(-c2nc(-c3ccccc3)c3oc4ccc(-c5cccc6c5C5(c7ccccc7-c7ccccc75)c5ccccc5-6)cc4c3n2)cc1] | 67% |
| 17c | 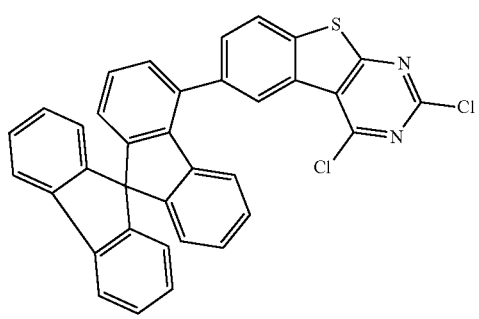 [SMILES: Clc1nc(Cl)c2c(n1)sc1ccc(-c3cccc4c3-c3ccccc3C43c4ccccc4-c4ccccc43)cc12] | 68% |
| 18c | 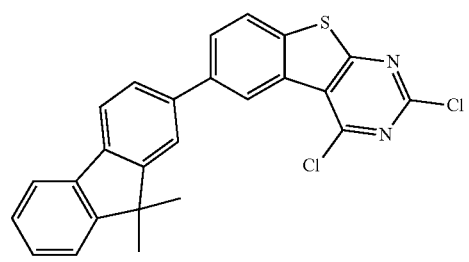 [SMILES: CC1(C)c2ccccc2-c2ccc(-c3ccc4sc5nc(Cl)nc(Cl)c5c4c3)cc21] | 66% |

| | | |
|---|---|---|
| 19c | 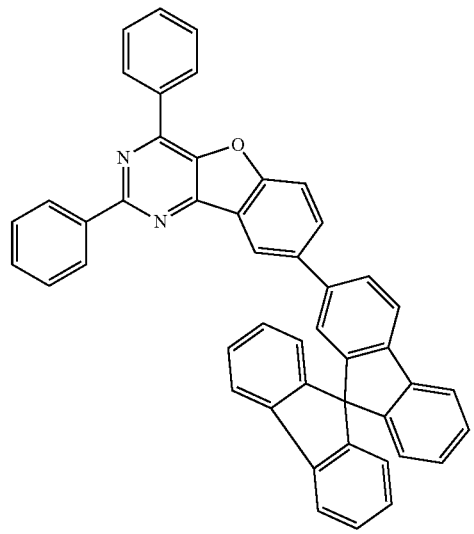 [SMILES: c1ccc(-c2nc(-c3ccccc3)c3oc4ccc(-c5ccc6c(c5)C5(c7ccccc7-c7ccccc75)c5ccccc5-6)cc4c3n2)cc1] | 77% |
| 20c | 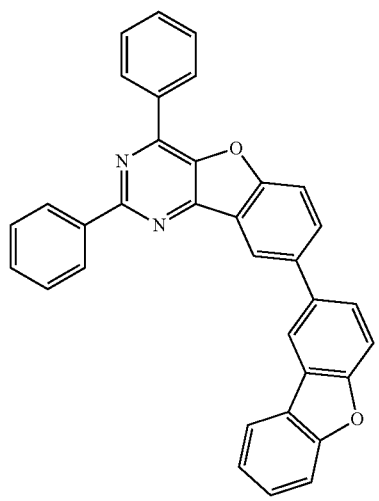 [SMILES: c1ccc(-c2nc(-c3ccccc3)c3oc4ccc(-c5ccc6oc7ccccc7c6c5)cc4c3n2)cc1] | 75% |
| 21c | 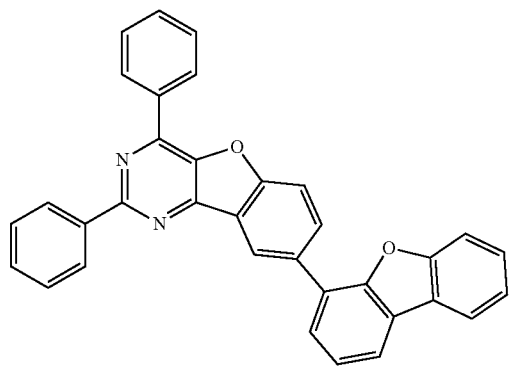 [SMILES: c1ccc(-c2nc(-c3ccccc3)c3oc4ccc(-c5cccc6c5oc5ccccc56)cc4c3n2)cc1] | 80% |

| | | |
|---|---|---|
| 22c | 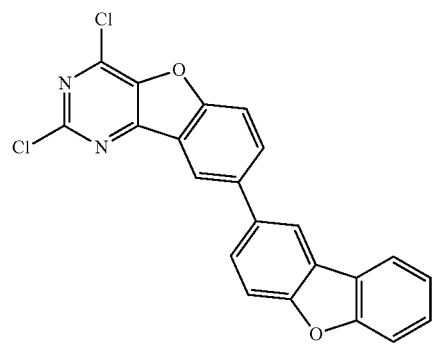 [SMILES: Clc1nc(Cl)c2oc3ccc(-c4ccc5oc6ccccc6c5c4)cc3c2n1] | 64% |
| 23c | 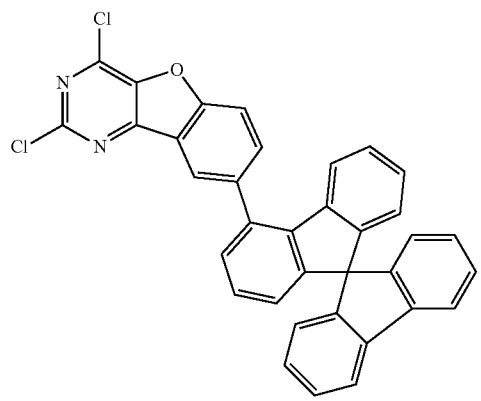 [SMILES: Clc1nc(Cl)c2oc3ccc(-c4cccc5c4-c4ccccc4C54c5ccccc5-c5ccccc54)cc3c2n1] | 61% |
| 24c | 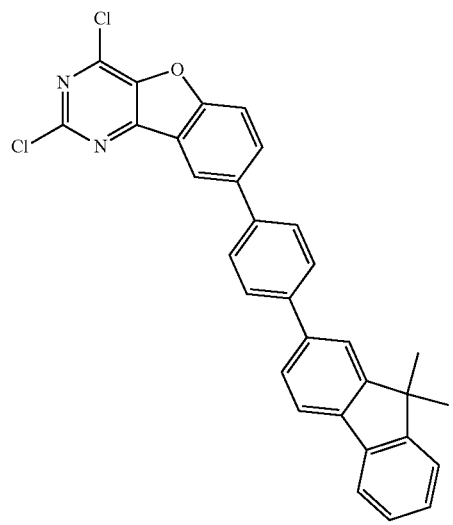 [SMILES: CC1(C)c2ccccc2-c2ccc(-c3ccc(-c4ccc5oc6c(Cl)nc(Cl)nc6c5c4)cc3)cc21] | 62% |

In an analogous manner, 11c-17c and also 12c-18c and 22c-24c are used to prepare the following compounds:
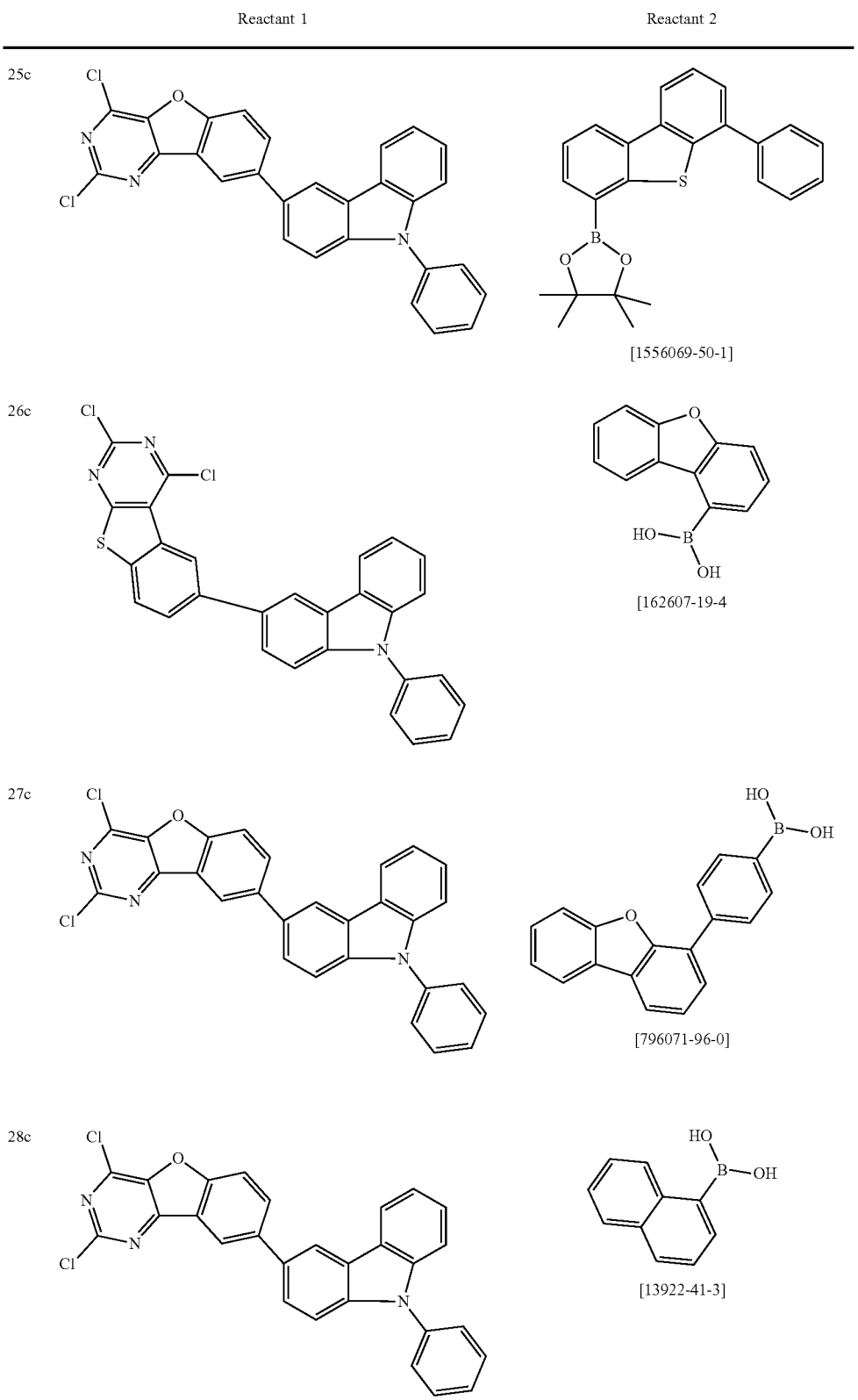

29c 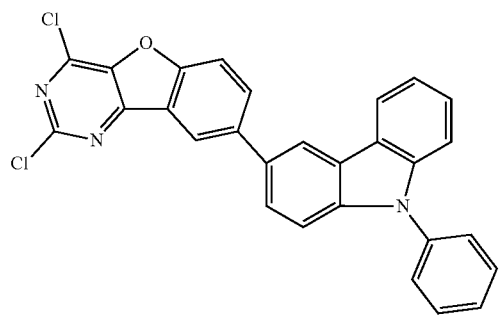 [SMILES: Clc1nc(Cl)c2oc3ccc(-c4ccc5c(c4)c4ccccc4n5-c4ccccc4)cc3c2n1] 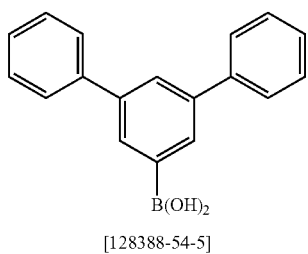 [SMILES: OB(O)c1cc(-c2ccccc2)cc(-c2ccccc2)c1]
[128388-54-5]
30c 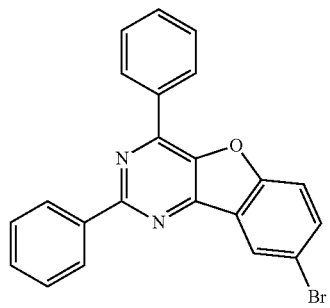 [SMILES: Brc1ccc2oc3c(-c4ccccc4)nc(-c4ccccc4)nc3c2c1] 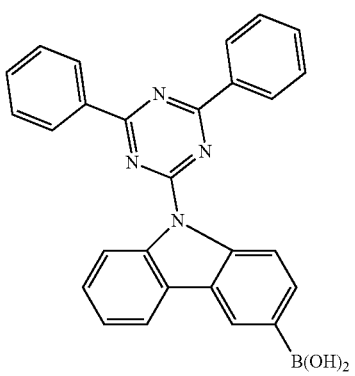
[1266389-18-7]
31c 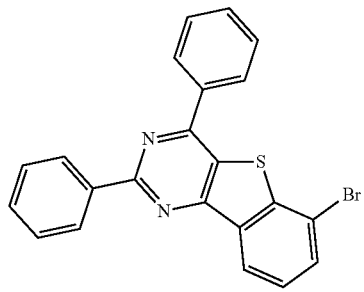
[1801233-18-0]
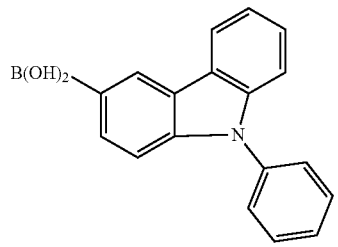
854952-58-2
32c 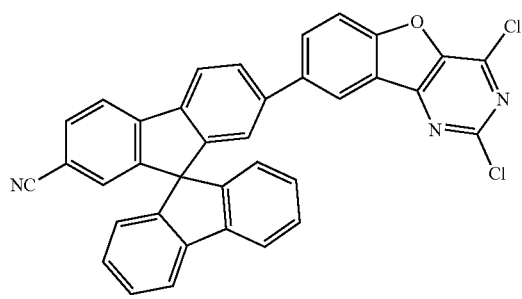 [SMILES: N#Cc1ccc2c(c1)C1(c3ccccc3-c3ccccc31)c1cc(-c3ccc4oc5c(Cl)nc(Cl)nc5c4c3)ccc1-2] 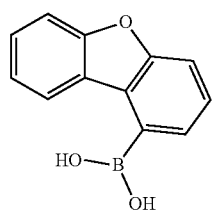
[162607-19-4]

-continued
33c 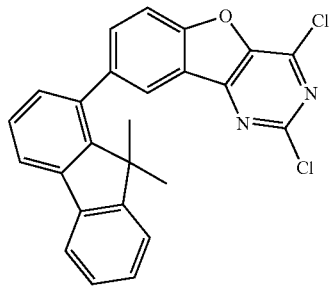 [SMILES: CC1(C)c2ccccc2-c2cccc(-c3ccc4oc5c(Cl)nc(Cl)nc5c4c3)c21] 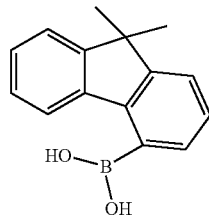
[1246022-50-3]
34c 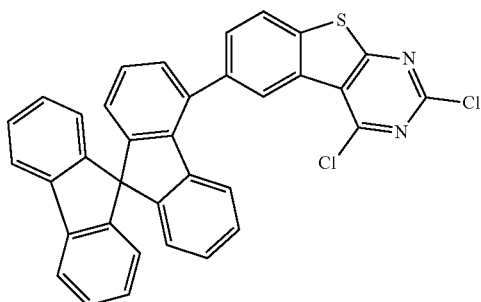 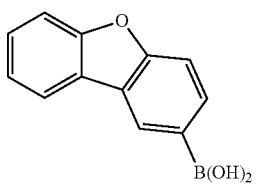
[402936-15-6]
35c 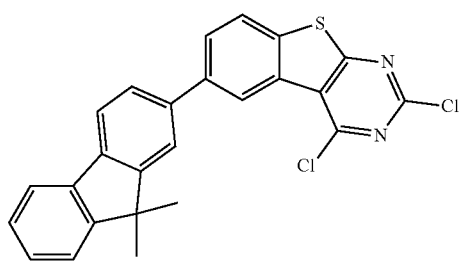 [SMILES: CC1(C)c2ccccc2-c2ccc(-c3ccc4sc5nc(Cl)nc(Cl)c5c4c3)cc21] 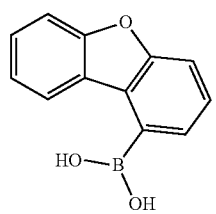
[162607-19-4]
36c 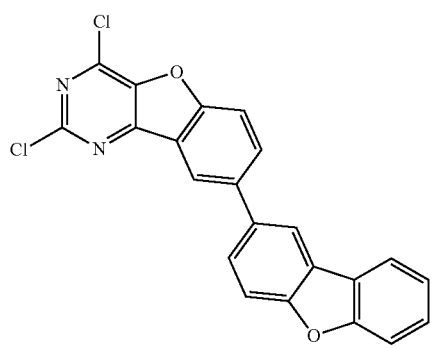 [SMILES: Clc1nc(Cl)c2oc3ccc(-c4ccc5oc6ccccc6c5c4)cc3c2n1] 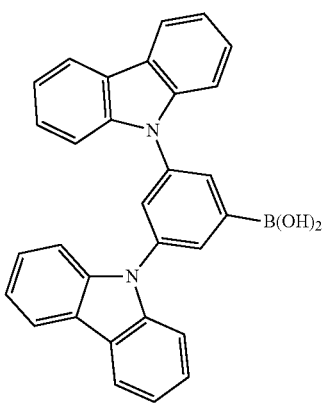
[854952-51-5]
37c 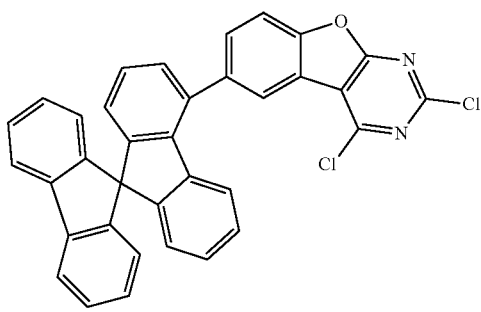 [SMILES: Clc1nc(Cl)c2c(n1)oc1ccc(-c3cccc4c3-c3ccccc3C43c4ccccc4-c4ccccc43)cc12] 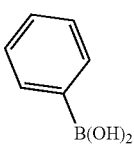

-continued
| 38c | 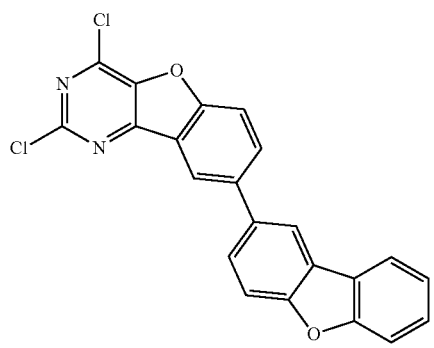 [SMILES: Clc1nc(Cl)c2oc3ccc(-c4ccc5oc6ccccc6c5c4)cc3c2n1] | 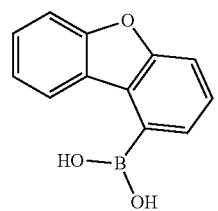 [162607-19-4] |
|---|---|---|
| 39c | 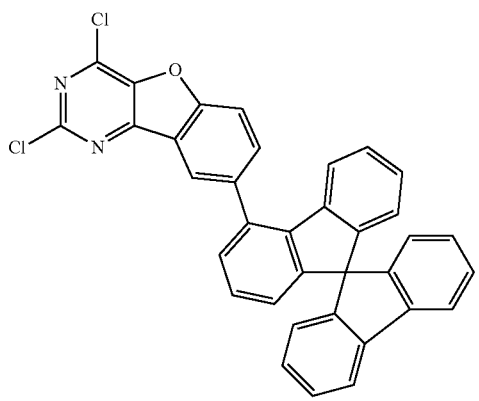 [SMILES: Clc1nc(Cl)c2oc3ccc(-c4cccc5c4-c4ccccc4C54c5ccccc5-c5ccccc54)cc3c2n1] | 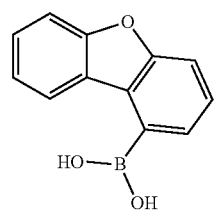 [162607-19-4] |
| 40c | 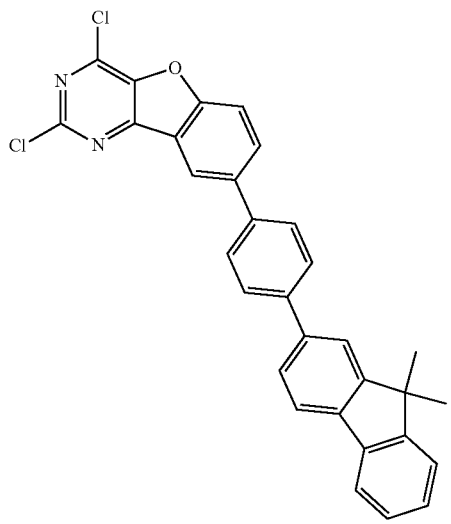 [SMILES: CC1(C)c2ccccc2-c2ccc(-c3ccc(-c4ccc5oc6c(Cl)nc(Cl)nc6c5c4)cc3)cc21] | 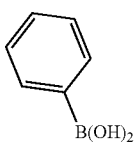 |

| Product | Yield |
|---|---|
| 25c 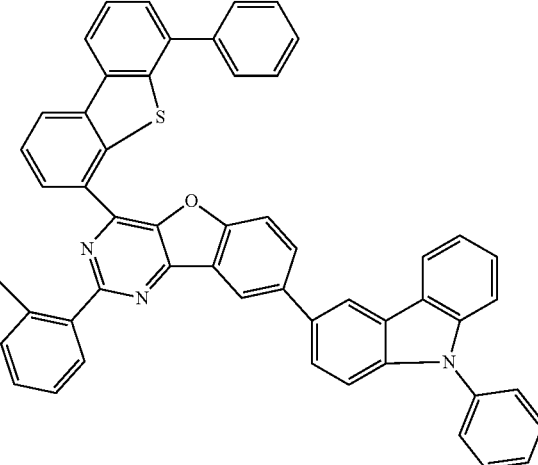 | 72% |
| 26c 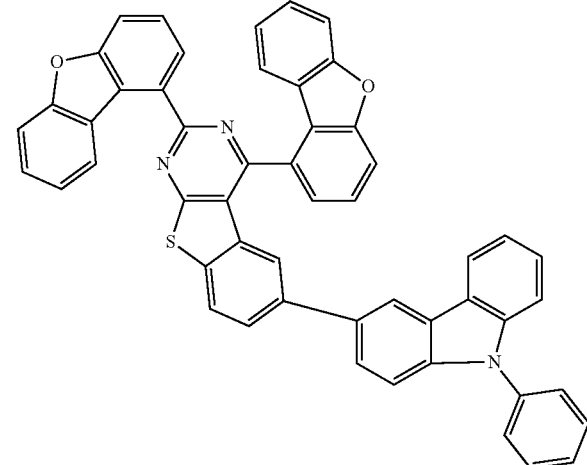 [SMILES: c1ccc(-n2c3ccccc3c3cc(-c4ccc5sc6nc(-c7cccc8oc9ccccc9c78)nc(-c7cccc8oc9ccccc9c78)c6c5c4)ccc32)cc1] | 74% |
| 27c 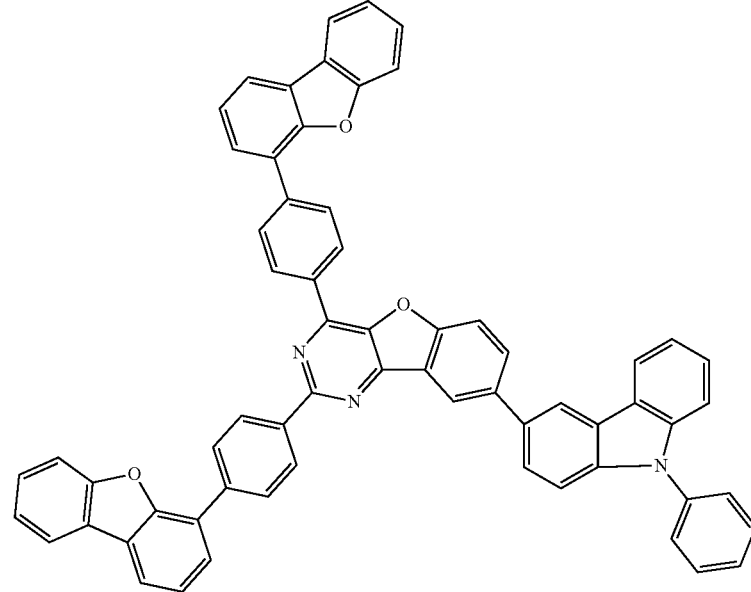 [SMILES: c1ccc(-n2c3ccccc3c3cc(-c4ccc5oc6c(-c7ccc(-c8cccc9c8oc8ccccc89)cc7)nc(-c7ccc(-c8cccc9c8oc8ccccc89)cc7)nc6c5c4)ccc32)cc1] | 68% |

-continued
28c 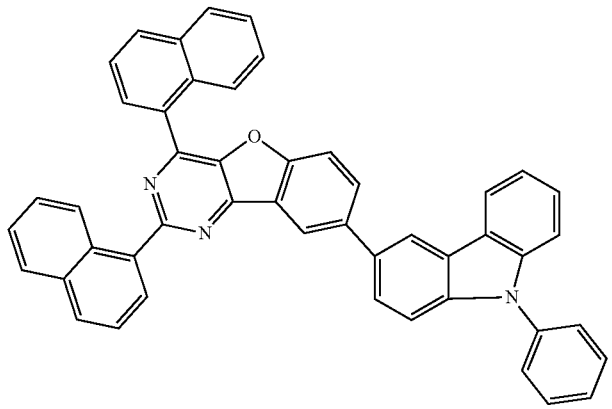 [SMILES: c1ccc(-n2c3ccccc3c3cc(-c4ccc5oc6c(-c7cccc8ccccc78)nc(-c7cccc8ccccc78)nc6c5c4)ccc32)cc1] 66%
29c 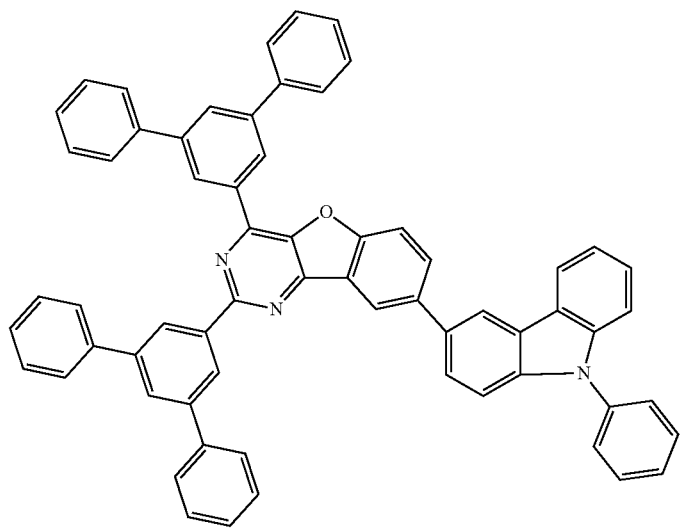 [SMILES: c1ccc(-c2cc(-c3ccccc3)cc(-c3nc(-c4cc(-c5ccccc5)cc(-c5ccccc5)c4)c4oc5ccc(-c6ccc7c(c6)c6ccccc6n7-c6ccccc6)cc5c4n3)c2)cc1] 64%
30c 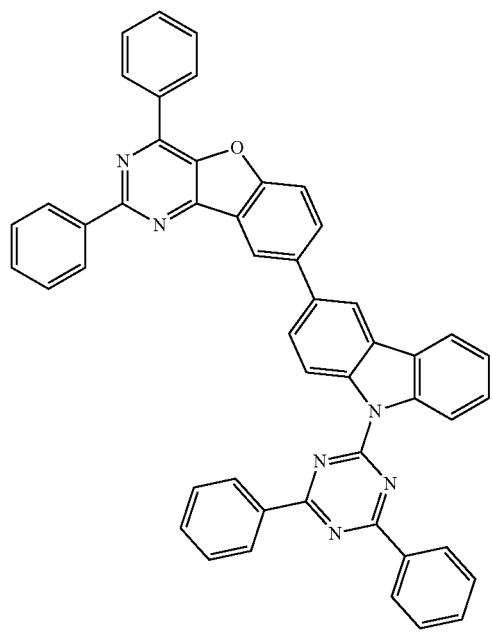 [SMILES: c1ccc(-c2nc(-c3ccccc3)nc(-n3c4ccccc4c4cc(-c5ccc6oc7c(-c8ccccc8)nc(-c8ccccc8)nc7c6c5)ccc43)n2)cc1] 72%

-continued
31c 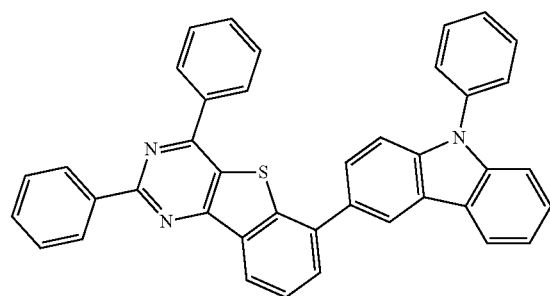 [SMILES: c1ccc(-c2nc(-c3ccccc3)c3sc4c(-c5ccc6c(c5)c5ccccc5n6-c5ccccc5)cccc4c3n2)cc1] 73%
32c 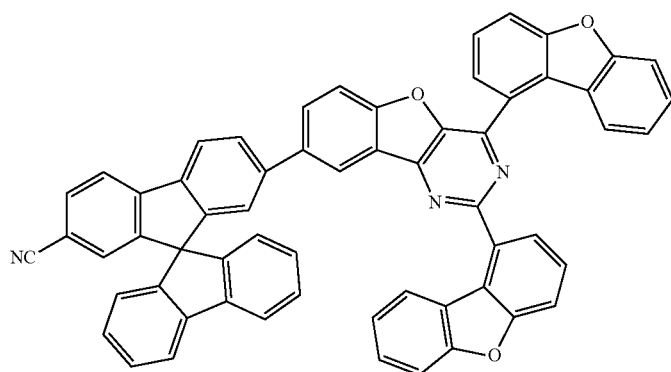 [SMILES: N#Cc1ccc2c(c1)C1(c3ccccc3-c3ccccc31)c1cc(-c3ccc4oc5c(-c6cccc7oc8ccccc8c67)nc(-c6cccc7oc8ccccc8c67)nc5c4c3)ccc1-2] 71%
33c 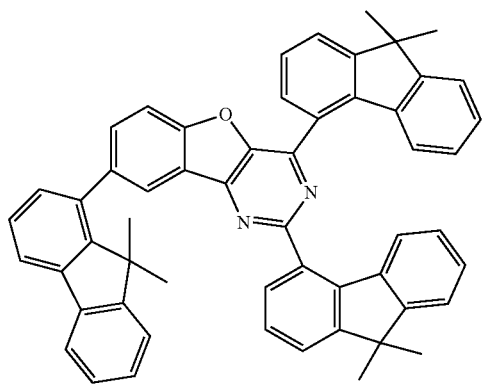 [SMILES: CC1(C)c2ccccc2-c2c(-c3nc(-c4cccc5c4-c4ccccc4C5(C)C)c4oc5ccc(-c6cccc7c6C(C)(C)c6ccccc6-7)cc5c4n3)cccc21] 75%
34c 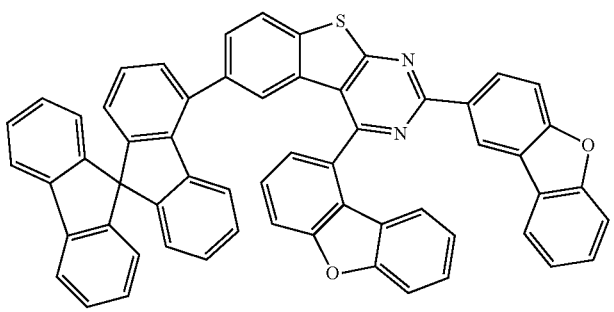 [SMILES: c1ccc2c(c1)-c1ccccc1C21c2ccccc2-c2c(-c3ccc4sc5nc(-c6ccc7oc8ccccc8c7c6)nc(-c6cccc7oc8ccccc8c67)c5c4c3)cccc21] 75%

-continued
| | | |
|---|---|---|
| 35c | 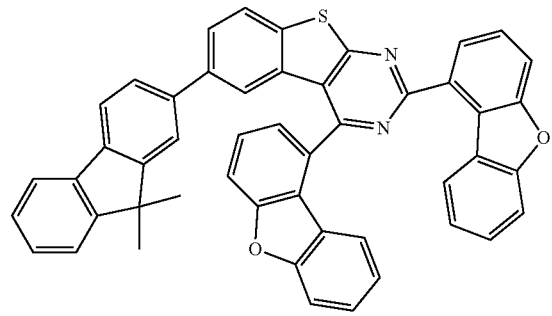 [SMILES: CC1(C)c2ccccc2-c2ccc(-c3ccc4sc5nc(-c6cccc7oc8ccccc8c67)nc(-c6cccc7oc8ccccc8c67)c5c4c3)cc21] | 76% |
| 36c | 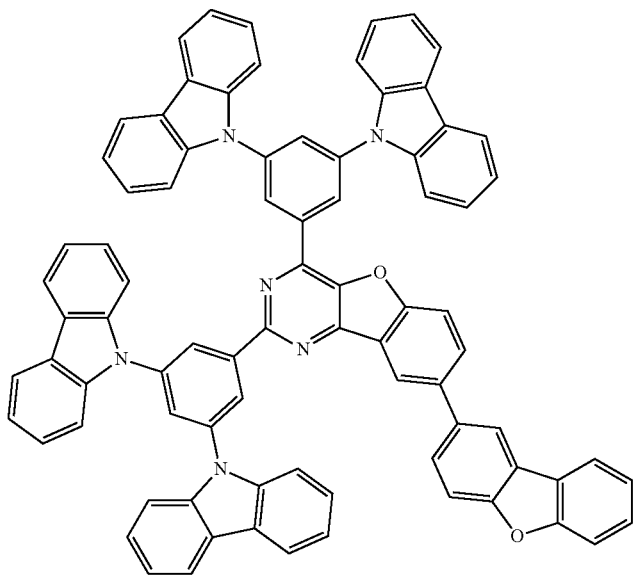 [SMILES: c1ccc2c(c1)oc1ccc(-c3ccc4oc5c(-c6cc(-n7c8ccccc8c8ccccc87)cc(-n7c8ccccc8c8ccccc87)c6)nc(-c6cc(-n7c8ccccc8c8ccccc87)cc(-n7c8ccccc8c8ccccc87)c6)nc5c4c3)cc12] | 63% |
| 37c | 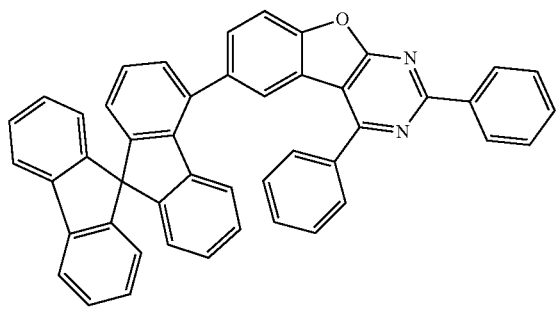 [SMILES: c1ccc(-c2nc(-c3ccccc3)c3c(n2)oc2ccc(-c4cccc5c4-c4ccccc4C54c5ccccc5-c5ccccc54)cc23)cc1] | 75% |
| 38c | 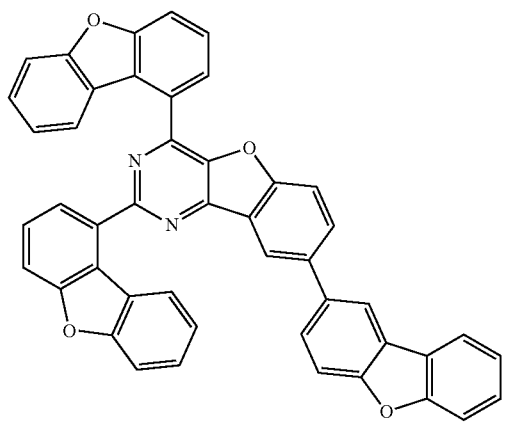 [SMILES: c1ccc2c(c1)oc1ccc(-c3ccc4oc5c(-c6cccc7oc8ccccc8c67)nc(-c6cccc7oc8ccccc8c67)nc5c4c3)cc12] | 73% |

| | |
|---|---|
| 39c 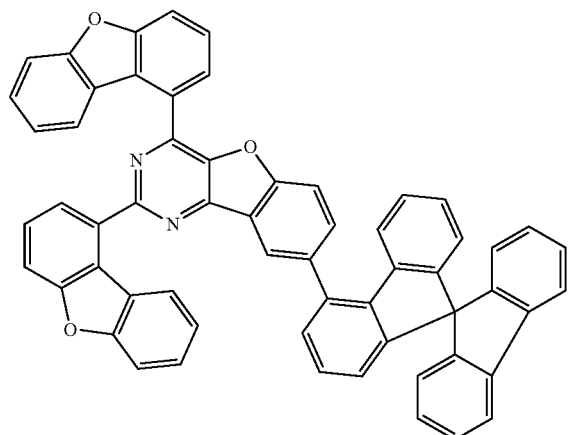 | 76% |
| 40c 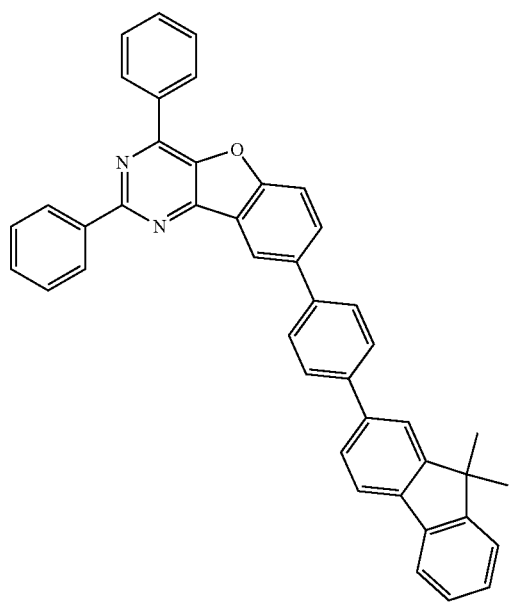 [SMILES: CC1(C)c2ccccc2-c2ccc(-c3ccc(-c4ccc5oc6c(-c7ccccc7)nc(-c7ccccc7)nc6c5c4)cc3)cc21] | 78% |
d) 2,4-Bis(carbazol-9-yl)-8-[2-eth-(Z)-ylidene-3,3-dimethyl-1-prop-2-en-(Z)-ylideneindan-4-yl]benzo[4,5]furo[3,2-d]pyrimidine
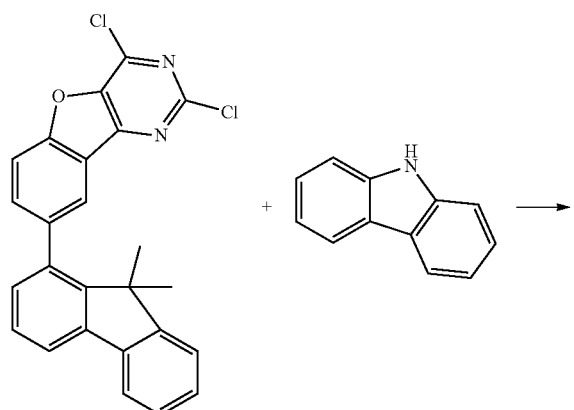
-continued
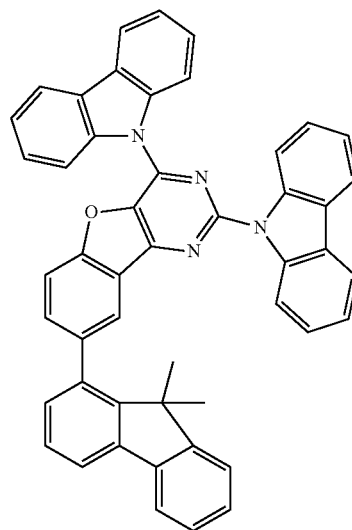

A degassed solution of 53 g (147 mmol) of 2,4-dichloro-8-(9,9-dimethyl-9H-fluoren-1-yl)benzo[4,5]furo[3,2-d]pyrimidine and 24 g (147 mmol) of 9H-carbazole in 600 ml of toluene is saturated with N2 for 1 h. Added to the solution thereafter are first 2.09 ml (8.6 mmol) of P(tBu)₃, then 1.38 g (6.1 mmol) of palladium(II) acetate, and then 17.7 g (185 mmol) of NaOtBu are added in the solid state. The reaction mixture is heated under reflux for 1 h. After cooling to room temperature, 500 ml of water are added cautiously. The aqueous phase is washed with 3×50 ml of toluene, dried over MgSO₄, and the solvent is removed under reduced pressure. Thereafter, the crude product is purified by chromatography using silica gel with heptane/ethyl acetate (20/1). The residue is recrystallized from toluene and finally sublimed under high vacuum (p=5×10⁻⁶ mbar).

The yield is 67 g (95 mmol), corresponding to 78% of theory.

In an analogous manner, it is possible to obtain the following compounds:

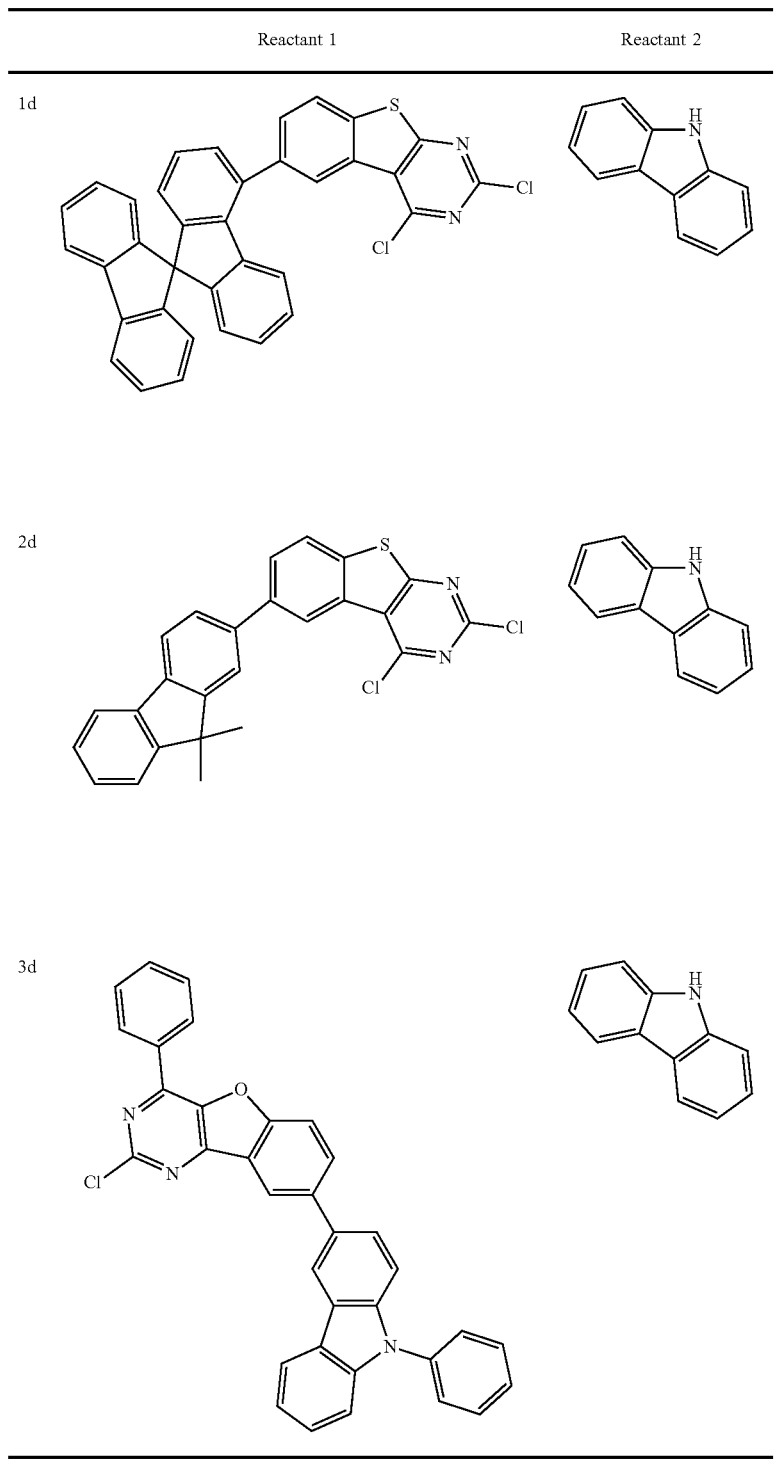

| Product | Yield |
|---|---|
| 1d | 75% |
| 2d | 70% |
| 3d | 73% |
e) 4-Phenyl-2,8-bis-(9-phenyl-9H-carbazol-3-yl)benzo[4,5]thieno[3,2-d]-pyrimidine (Ie)
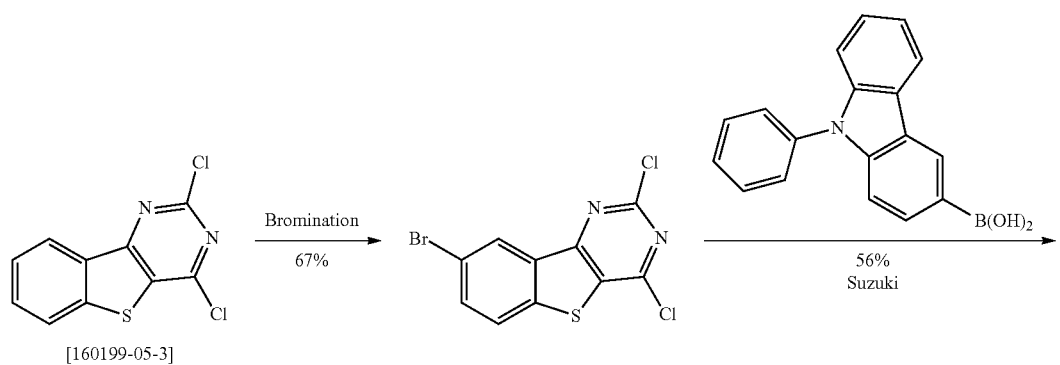

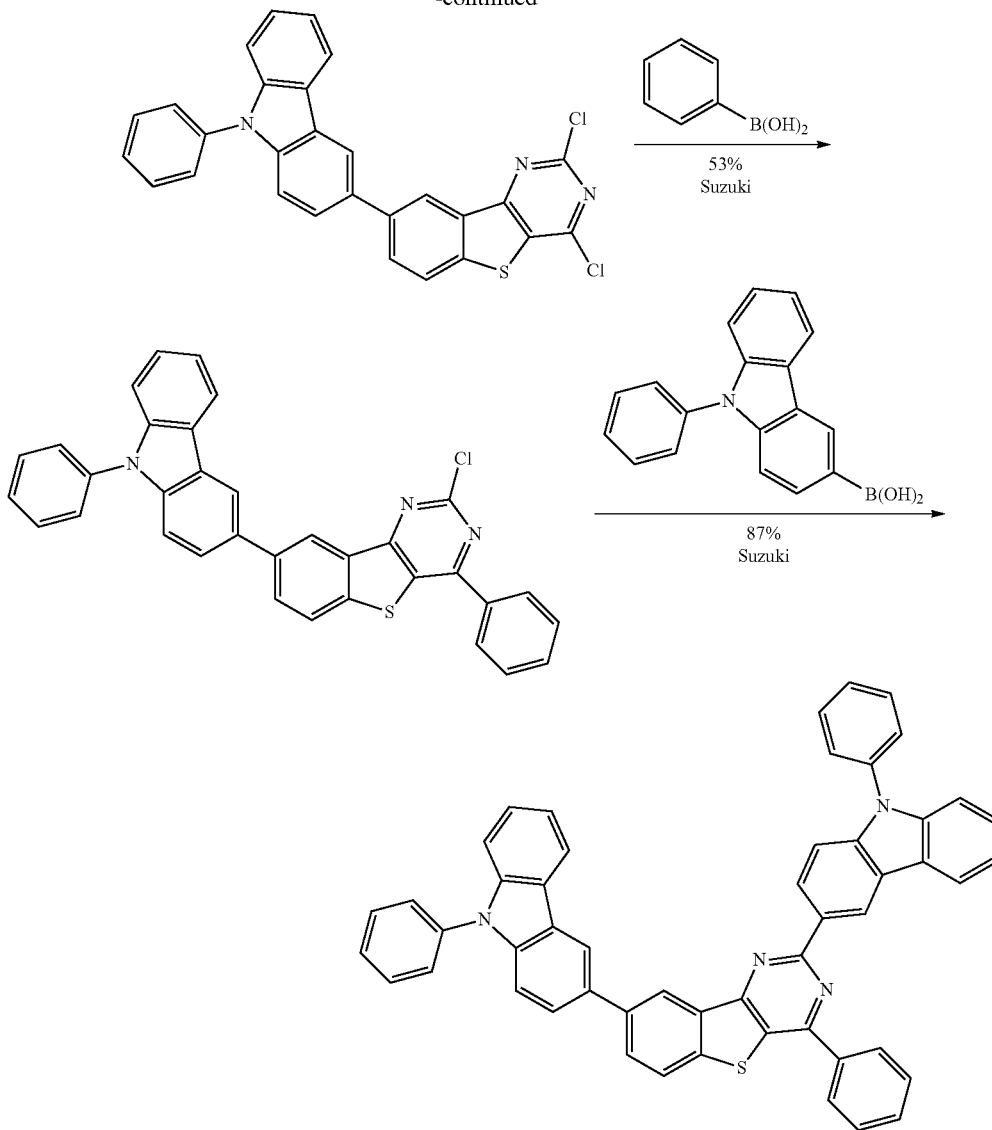

2,4-Dichlorobenzo[4,5]thieno[3,2-d]pyrimidine is brominated analogously to method b, then reacted with phenylcarbazoleboronic acid via Suzuki analogously to method c and then reacted, again analogously to method c, first with phenylboronic acid and finally with phenylcarbazoleboronic acid.

f) 4-(6-Dibenzofuran-4-yl-pyridin-2-yl)-2,8-di(pyridin-2-yl)-benzo[4,5]thieno[3,2-d]pyrimidine (If)

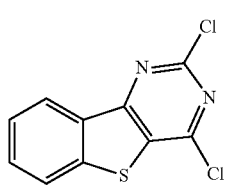

[160199-05-3]

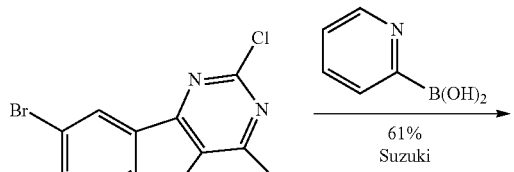

-continued

253
-continued
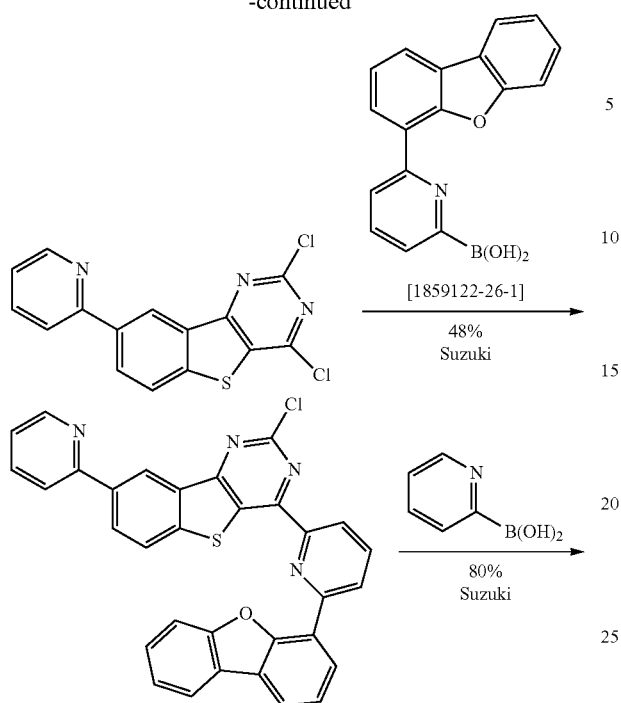
254
-continued
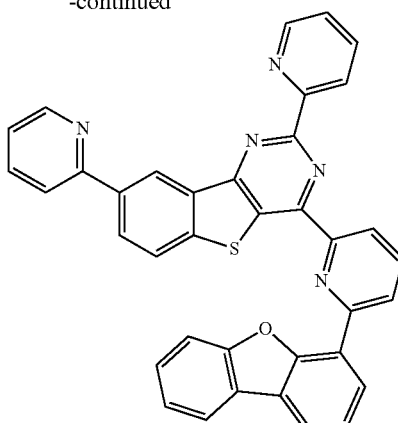
The preparation is effected according to the method detailed above under e).
g) 2,2'-Bis(carbazol-9-yl-4,4'-diphenyl-[8,8]bi[benzo[4,5]thieno[3,2-d]pyrimidinyl])
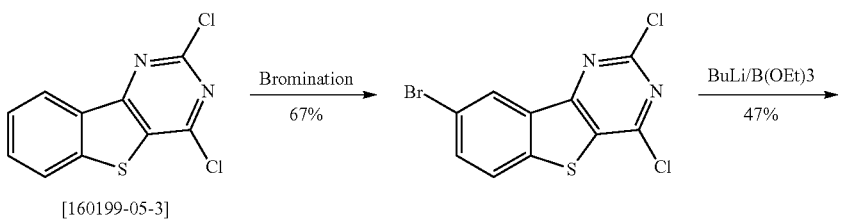
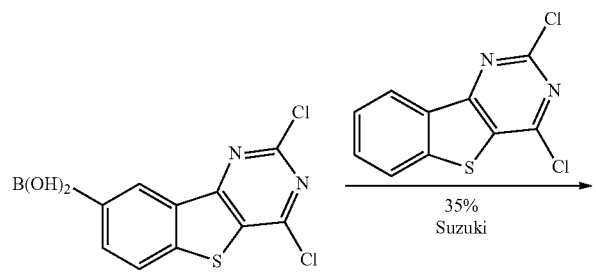
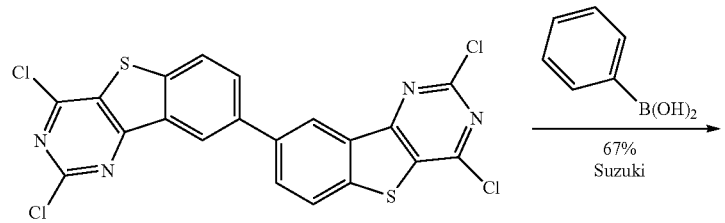

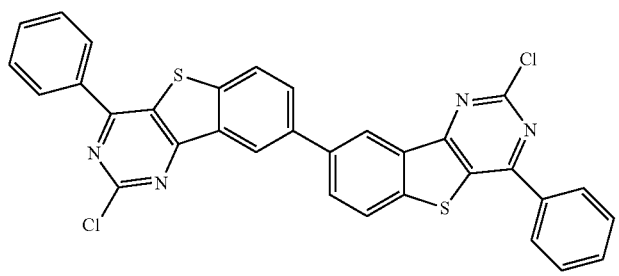
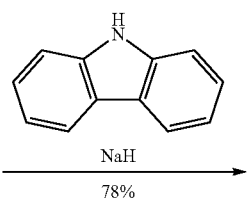

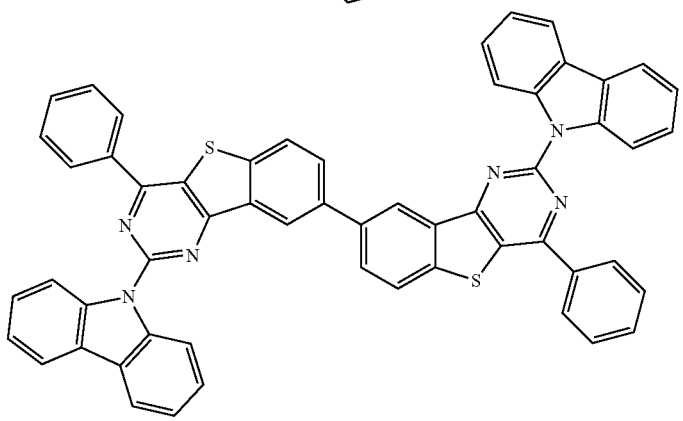

2,4-Dichlorobenzo[4,5]thieno[3,2-d]pyrimidine is brominated analogously to method b, then converted to the corresponding boronic acid with BuLi and triethyl borate. Then the coupling is effected analogously to method c to give the corresponding dimer and then, in turn, first reacted with phenylboronic acid analogously to method c and finally converted to the target molecule by reaction with NaH and carbazole via nucleophilic substitution.

j) 2-Carbazol-9-yl-8-dibenzothiophen-2-yl-4-phenyl-benzo[4,5]thieno[3,2-d]pyrimidine

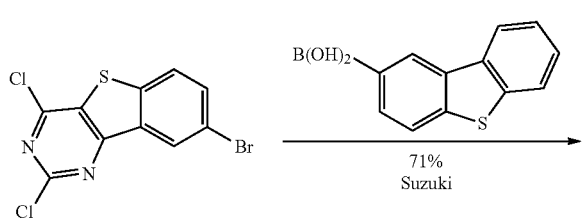
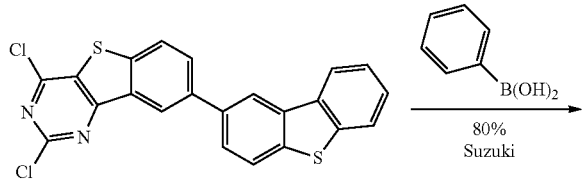
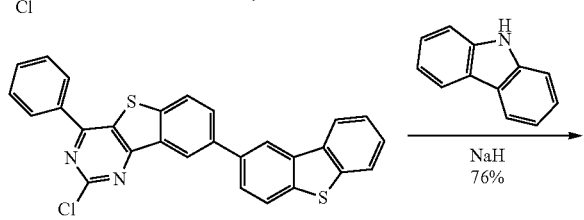
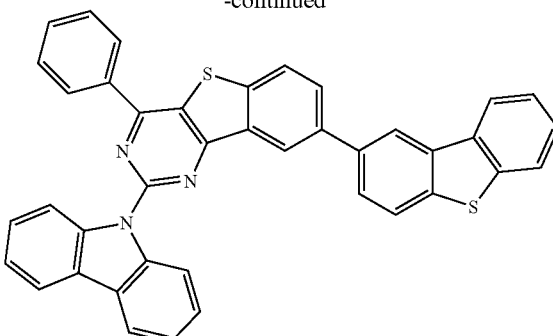

The preparation is conducted according to the procedure set out above under g).

Production of the OLEDs

In examples C1 to I13 which follow (see Tables 1 and 2), the data of various OLEDs are presented.

Pretreatment for Examples C1-I13

Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC5:IC3:TEG2 (55%: 35%:10%) mean here that the material 105 is present in the layer in a proportion by volume of 55%, 103 in a proportion of 35% and TEG2 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined.

The electroluminescence spectra are determined at a luminance of 1000 cd/m$^2$, and the CIE 1931 x and y colour coordinates are calculated therefrom. The parameter U1000 in Table 2 refers to the voltage which is required for a luminance of 1000 cd/m$^2$. Finally, EQE1000 refers to the external quantum efficiency at an operating luminance of 1000 cd/m$^2$. The lifetime LT is defined as the time after which the luminance drops from the starting luminance to a certain proportion L1 in the course of operation with constant current. Figures of L0;j0=4000 cd/m$^2$ and L1=70% in Table 2 mean that the lifetime given in the column LT corresponds to the time after which the starting luminance drops from 4000 cd/m$^2$ to 2800 cd/m$^2$. Analogously, L0;j0=20 mA/cm$^2$ and L1=80% means that the luminance in the course of operation at 20 mA/cm$^2$ drops to 80% of its starting value after the time LT.

The data for the various OLEDs are collated in Table 2. Examples C1-C4 are comparative examples according to the prior art; examples I1-I13 show data of OLEDs of the invention.

Some of the examples are elucidated in detail hereinafter, in order to illustrate the advantages of the OLEDs of the invention.

Use of Materials of the Invention in Phosphorescent OLEDs

The materials of the invention, when used in the emission layer (EML) in OLEDs, give significant improvements over the prior art, particularly with regard to lifetime.

Through use of the inventive compounds 3d,1e,1f and 15a, it is possible to achieve an increase in the lifetime by about 20-30% compared to the prior art (comparison of example I1 with C1; comparison of example I2 with C2; comparison of example I3 with C3; comparison of example I4 with C4).

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| C1 | HATCN 5 nm | SpMA1 125 nm | SpMA3 10 nm | PA1:TER5 (95%:5%) 40 nm | — | ST2:LiQ (50%:50%) 35 nm | — |
| C2 | HATCN 5 nm | SpMA1 125 nm | SpMA3 10 nm | PA2:TER5 (95%:5%) 40 nm | — | ST2:LiQ (50%:50%) 35 nm | — |
| C3 | HATCN 5 nm | SpMA1 125 nm | SpMA3 10 nm | PA3:TER5 (95%:5%) 40 nm | — | ST2:LiQ (50%:50%) 35 nm | — |
| C4 | HATCN 5 nm | SpMA1 125 nm | SpMA3 10 nm | PA4:TER5 (95%:5%) 40 nm | — | ST2:LiQ (50%:50%) 35 nm | — |
| I1 | HATCN 5 nm | SpMA1 125 nm | SpMA3 10 nm | 3d:TER5 (95%:5%) 40 nm | — | ST2:LiQ (50%:50%) 35 nm | — |
| I2 | HATCN 5 nm | SpMA1 125 nm | SpMA3 10 nm | 1e:TER5 (95%:5%) 40 nm | — | ST2:LiQ (50%:50%) 35 nm | — |
| I3 | HATCN 5 nm | SpMA1 125 nm | SpMA3 10 nm | 1f:TER5 (95%:5%) 40 nm | — | ST2:LiQ (50%:50%) 35 nm | — |
| I4 | HATCN 5 nm | SpMA1 125 nm | SpMA3 10 nm | 15a:TER5 (95%:5%) 40 nm | — | ST2:LiQ (50%:50%) 35 nm | — |
| I5 | HATCN 5 nm | SpMA1 125 nm | SpMA3 10 nm | 11a:TER5 (95%:5%) 40 nm | — | ST2:LiQ (50%:50%) 35 nm | — |
| I6 | HATCN 5 nm | SpMA1 125 nm | SpMA3 10 nm | 12a:TER5 (95%:5%) 40 nm | — | ST2:LiQ (50%:50%) 35 nm | — |
| I7 | HATCN 5 nm | SpMA1 125 nm | SpMA3 10 nm | 9c:TER5 (95%:5%) 40 nm | — | ST2:LiQ (50%:50%) 35 nm | — |
| I8 | HATCN 5 nm | SpMA1 125 nm | SpMA3 10 nm | 1c:TER5 (95%:5%) 40 nm | — | ST2:LiQ (50%:50%) 35 nm | — |
| I9 | HATCN 5 nm | SpMA1 125 nm | SpMA3 10 nm | 39c:TER5 (95%:5%) 40 nm | — | ST2:LiQ (50%:50%) 35 nm | — |
| I10 | HATCN 5 nm | SpMA1 125 nm | SpMA3 10 nm | 19c:TER5 (95%:5%) 40 nm | — | ST2:LiQ (50%:50%) 35 nm | — |

TABLE 1-continued

Structure of the OLEDs

| Ex. | HIL thickness | HTL thickness | EBL thickness | EML thickness | HBL thickness | ETL thickness | EIL thickness |
|---|---|---|---|---|---|---|---|
| I11 | HATCN 5 nm | SpMA1 125 nm | SpMA3 10 nm | 27c:TER5 (95%:5%) 40 nm | — | ST2:LiQ (50%:50%) 35 nm | — |
| I12 | HATCN 5 nm | SpMA1 125 nm | SpMA3 10 nm | 30c:TER5 (95%:5%) 40 nm | — | ST2:LiQ (50%:50%) 35 nm | — |
| I13 | HATCN 5 nm | SpMA1 235 nm | SpMA3 20 nm | 9c:IC3:TEG2 (45%:45%:10%) 30 nm | — | ST2:LiQ (50%:50%) 40 nm | — |

TABLE 2

Data of the OLEDs

| Ex. | U1000 (V) | EQE 1000 | CIE x/y at 1000 cd/m² | $L_0; j_0$ | L1 % | LD (h) |
|---|---|---|---|---|---|---|
| C1 | 3.5 | 22.2% | 0.67/0.33 | 50 mA/cm² | 95 | 45 |
| C2 | 3.6 | 21.6% | 0.67/0.33 | 50 mA/cm² | 95 | 40 |
| C3 | 3.7 | 22.2% | 0.67/0.33 | 50 mA/cm² | 95 | 5 |
| C4 | 3.7 | 22.4% | 0.67/0.33 | 50 mA/cm² | 95 | 45 |
| I1 | 3.6 | 21.8% | 0.67/0.33 | 50 mA/cm² | 95 | 60 |
| I2 | 3.7 | 22.4% | 0.67/0.33 | 50 mA/cm² | 95 | 50 |
| I3 | 3.6 | 22.1% | 0.67/0.33 | 50 mA/cm² | 95 | 10 |
| I4 | 3.7 | 22.3% | 0.67/0.33 | 50 mA/cm² | 95 | 55 |
| I5 | 3.7 | 22.2% | 0.67/0.33 | 50 mA/cm² | 95 | 50 |
| I6 | 3.8 | 22.4% | 0.67/0.33 | 50 mA/cm² | 95 | 45 |
| I7 | 3.7 | 22.5% | 0.67/0.33 | 50 mA/cm² | 95 | 50 |
| I8 | 3.6 | 22.2% | 0.67/0.33 | 50 mA/cm² | 95 | 60 |
| I9 | 3.8 | 22.0% | 0.67/0.33 | 50 mA/cm² | 95 | 50 |
| I10 | 3.8 | 22.2% | 0.67/0.33 | 50 mA/cm² | 95 | 55 |
| I11 | 3.8 | 22.4% | 0.67/0.33 | 50 mA/cm² | 95 | 60 |
| I12 | 3.4 | 21.8% | 0.67/0.33 | 50 mA/cm² | 95 | 45 |
| I13 | 3.4 | 20.2% | 0.33/0.63 | 40 mA/cm² | 80 | 120 |

TABLE 3

Structural formulae of the materials for the OLEDs

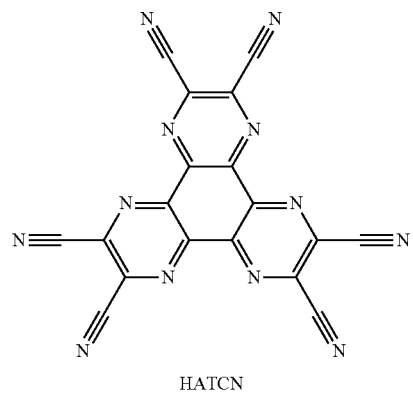

HATCN

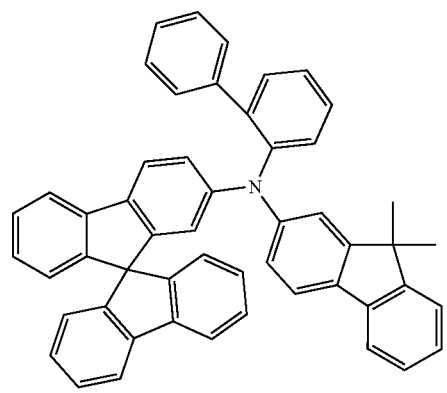

SpMA1

TABLE 3-continued
Structural formulae of the materials for the OLEDs
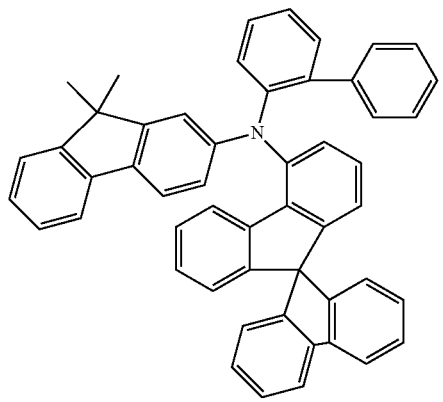
SpMA3
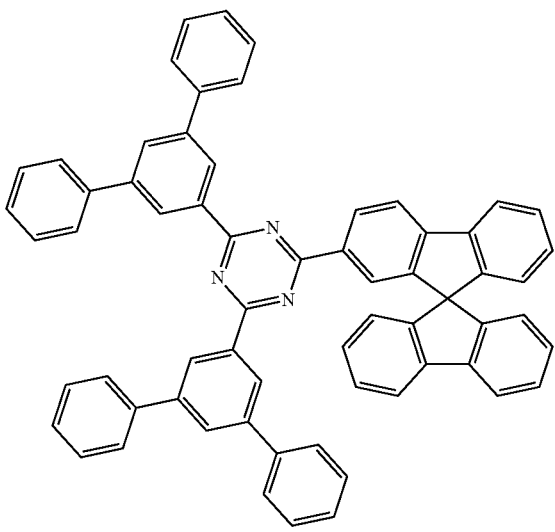
ST2
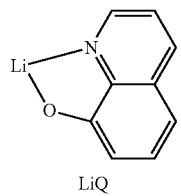
LiQ
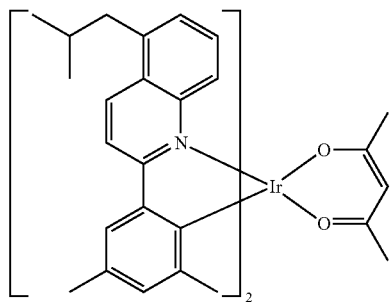
TER5

TABLE 3-continued
Structural formulae of the materials for the OLEDs
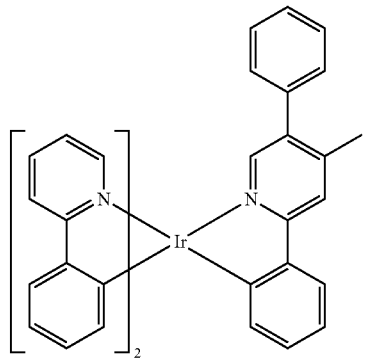
TEG2
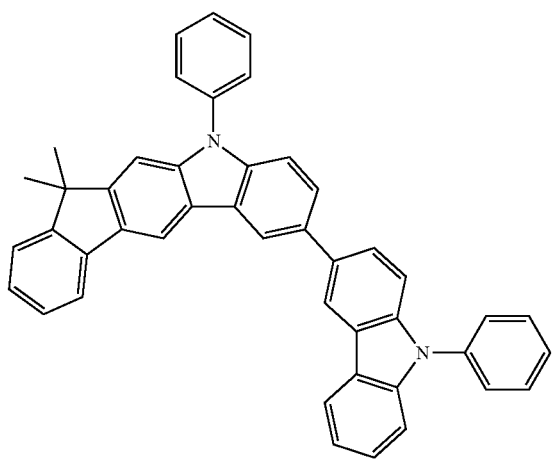
IC3
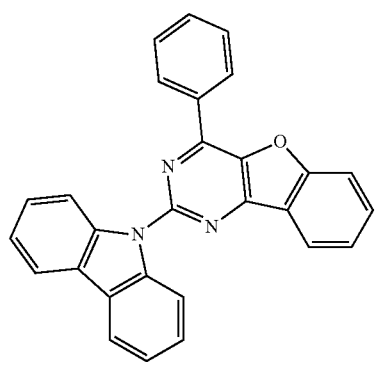
SdT1

TABLE 3-continued
Structural formulae of the materials for the OLEDs
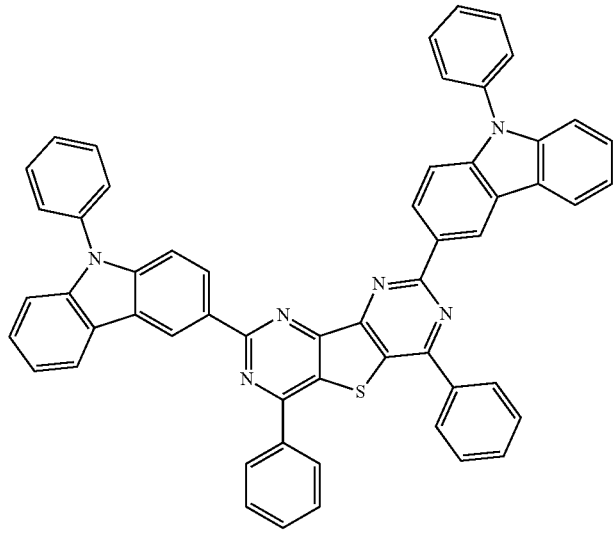
SdT2
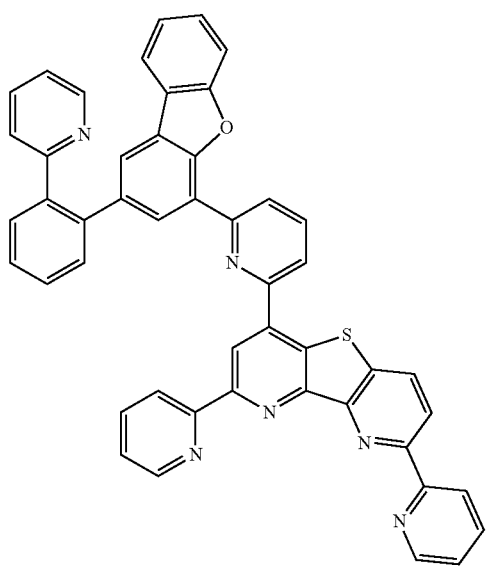
SdT3

TABLE 3-continued
Structural formulae of the materials for the OLEDs
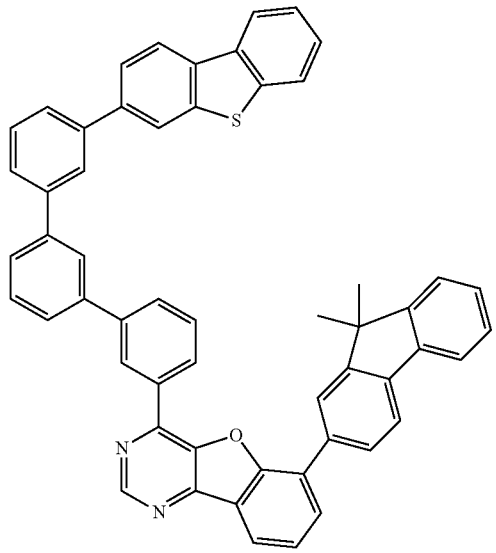
SdT4
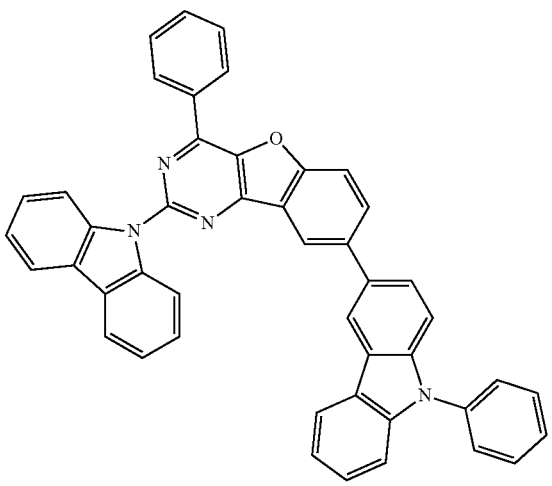 [SMILES: c1ccc(-c2nc(-n3c4ccccc4c4ccccc43)nc3c2oc2ccc(-c4ccc5c(c4)c4ccccc4n5-c4ccccc4)cc23)cc1]
3d
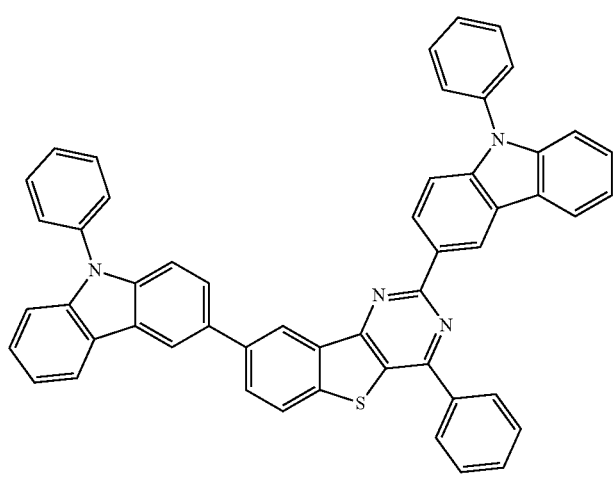 [SMILES: c1ccc(-c2nc(-c3ccc4c(c3)c3ccccc3n4-c3ccccc3)nc3c2sc2ccc(-c4ccc5c(c4)c4ccccc4n5-c4ccccc4)cc23)cc1]
1e TABLE 3-continued
Structural formulae of the materials for the OLEDs
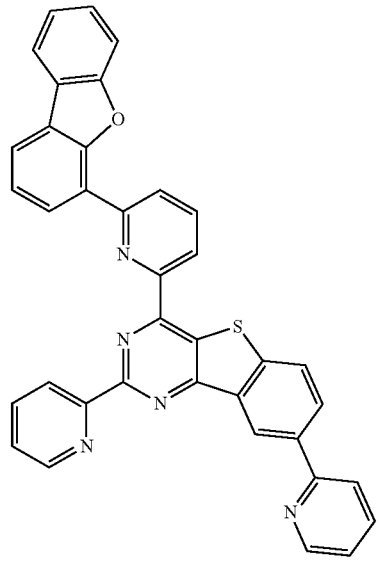 [SMILES: c1ccc(-c2ccc3sc4c(-c5cccc(-c6cccc7c6oc6ccccc67)n5)nc(-c5ccccn5)nc4c3c2)nc1]
1f
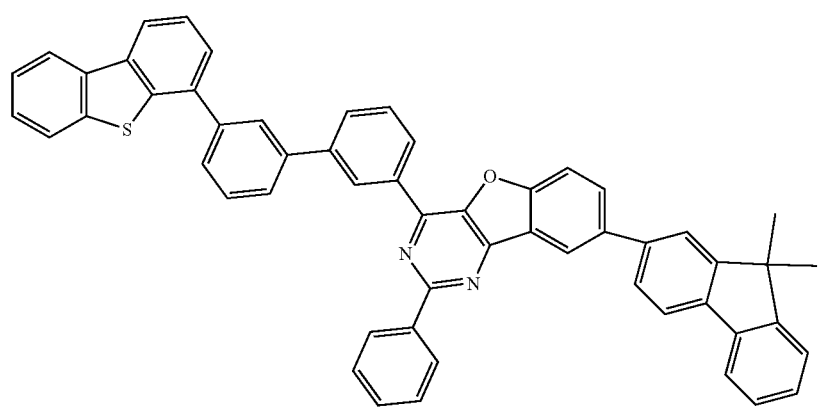 [SMILES: CC1(C)c2ccccc2-c2ccc(-c3ccc4oc5c(-c6cccc(-c7cccc(-c8cccc9c8sc8ccccc89)c7)c6)nc(-c6ccccc6)nc5c4c3)cc21]
15a
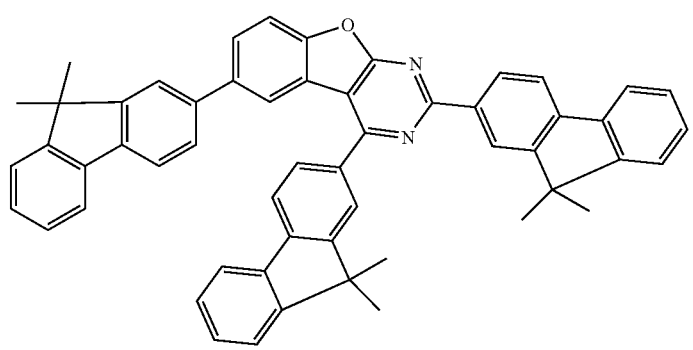 [SMILES: CC1(C)c2ccccc2-c2ccc(-c3ccc4oc5nc(-c6ccc7c(c6)C(C)(C)c6ccccc6-7)nc(-c6ccc7c(c6)C(C)(C)c6ccccc6-7)c5c4c3)cc21]
11a TABLE 3-continued
Structural formulae of the materials for the OLEDs
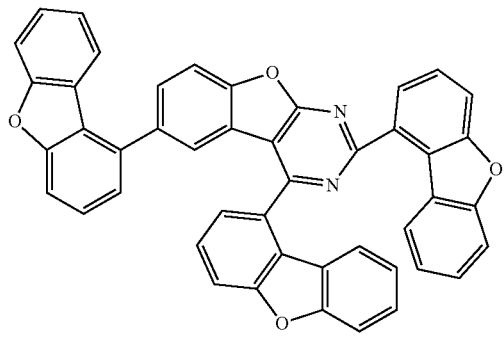 [SMILES: c1ccc2c(c1)oc1cccc(-c3ccc4oc5nc(-c6cccc7oc8ccccc8c67)nc(-c6cccc7oc8ccccc8c67)c5c4c3)c12]
12a
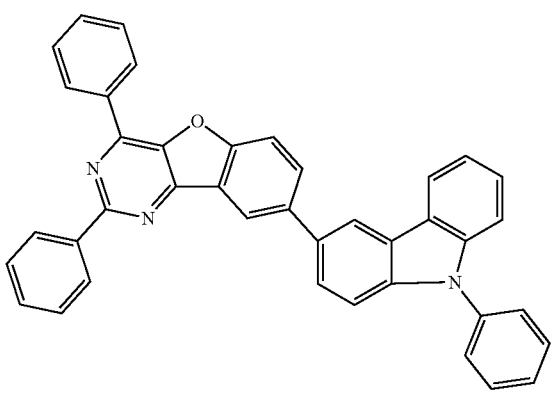 [SMILES: c1ccc(-c2nc(-c3ccccc3)c3oc4ccc(-c5ccc6c(c5)c5ccccc5n6-c5ccccc5)cc4c3n2)cc1]
9c
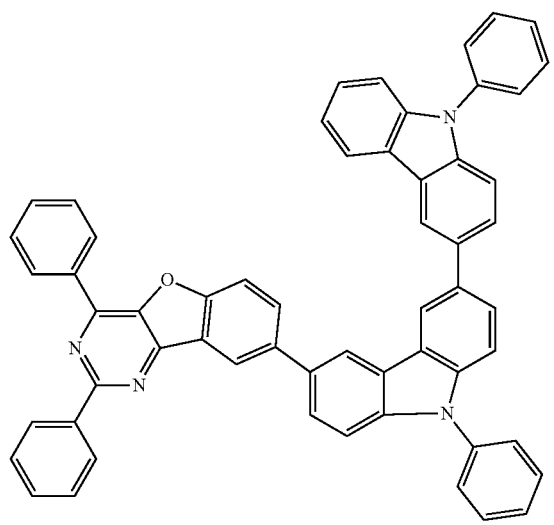 [SMILES: c1ccc(-c2nc(-c3ccccc3)c3oc4ccc(-c5ccc6c(c5)c5cc(-c7ccc8c(c7)c7ccccc7n8-c7ccccc7)ccc5n6-c5ccccc5)cc4c3n2)cc1]
1c TABLE 3-continued
Structural formulae of the materials for the OLEDs
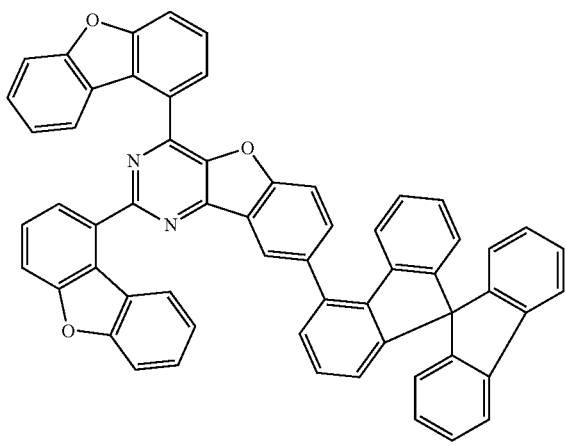 [SMILES: c1ccc2c(c1)-c1ccccc1C21c2ccccc2-c2c(-c3ccc4oc5c(-c6cccc7oc8ccccc8c67)nc(-c6cccc7oc8ccccc8c67)nc5c4c3)cccc21]
39c
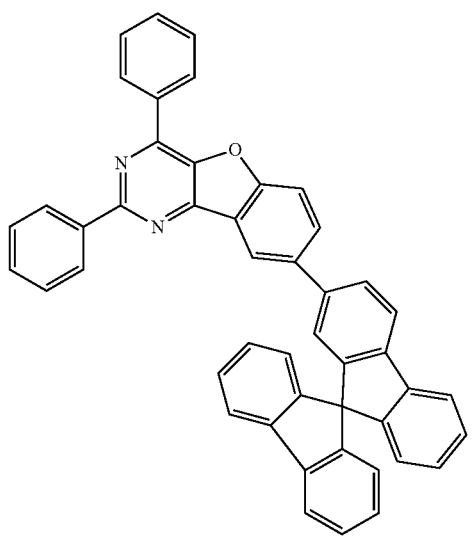 [SMILES: c1ccc(-c2nc(-c3ccccc3)c3oc4ccc(-c5ccc6c(c5)C5(c7ccccc7-c7ccccc75)c5ccccc5-6)cc4c3n2)cc1]
19c
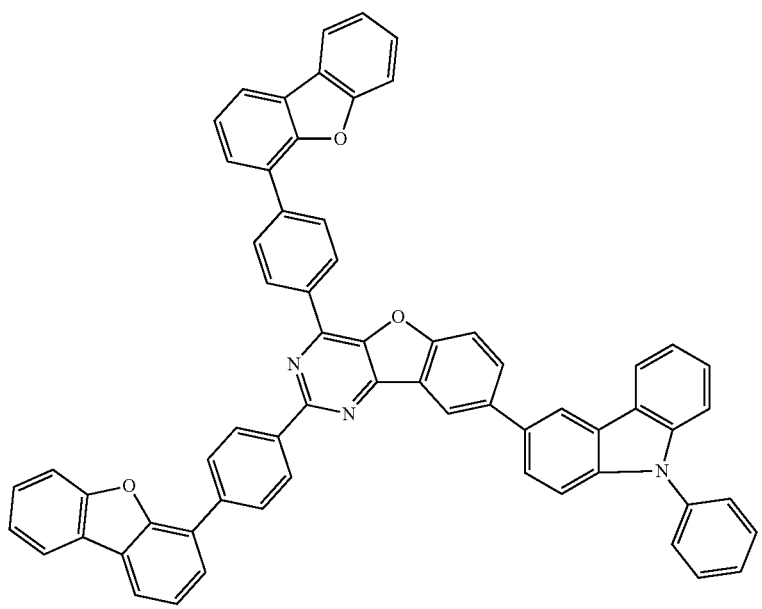 [SMILES: c1ccc(-n2c3ccccc3c3cc(-c4ccc5oc6c(-c7ccc(-c8cccc9c8oc8ccccc89)cc7)nc(-c7ccc(-c8cccc9c8oc8ccccc89)cc7)nc6c5c4)ccc32)cc1]
27c TABLE 3-continued Structural formulae of the materials for the OLEDs

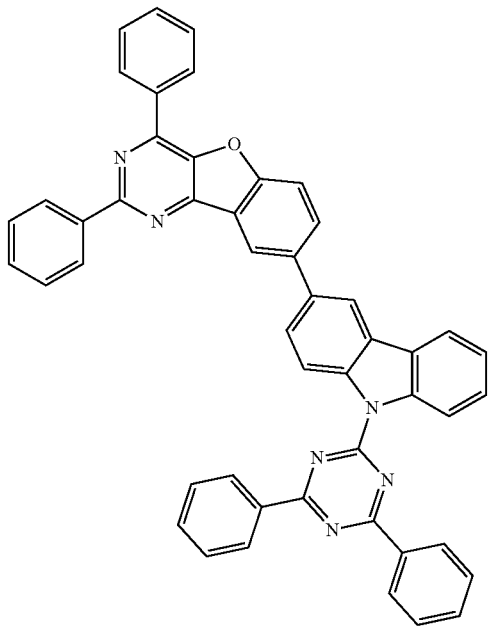 [SMILES: c1ccc(-c2nc(-c3ccccc3)nc(-n3c4ccccc4c4cc(-c5ccc6oc7c(-c8ccccc8)nc(-c8ccccc8)nc7c6c5)ccc43)n2)cc1]

30c

The invention claimed is:

1. A compound of formula (A):

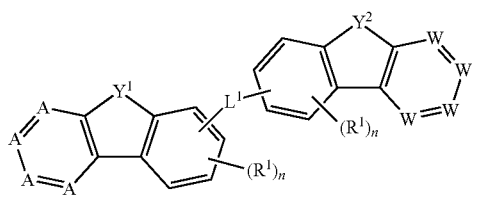

wherein

Y$^1$ is O or S;

Y$^2$ is C(R$^1$)$_2$, or —R$^1$C═CR$^1$—;

W is the same or different in each instance and is N or CR$^1$, with the proviso that not more than two W in one cycle are N, wherein the R$^1$ radicals in the W groups do not form a fused heteroaromatic ring system;

L$^1$ is a bond or an aromatic or heteroaromatic ring system having 5 to 30 aromatic ring atoms and which is optionally substituted by one or more R$^1$ radicals;

A is the same or different in each instance and is N, CAr$^a$, or CAr$^b$, wherein exactly two A are N separated by at least one CAr$^a$ or CAr$^b$ group, with the proviso that A is CAr$^b$ if two N are adjacent to this A;

Ar is the same or different in each instance and is an aromatic or heteroaromatic ring system having 5 to 30 aromatic ring atoms and which is optionally substituted by one or more radicals R$^1$;

Ar$^a$ is the same or different in each instance and is an aromatic or heteroaromatic ring system having 5 to 30 aromatic ring atoms and which is optionally substituted by one or more radicals R';

Ar$^b$ is the same or different in each instance and is an aromatic or heteroaromatic ring system having 5 to 30 aromatic ring atoms and which is optionally substituted by one or more radicals R';

R$^1$ is the same or different in each instance and is H, D, F, Cl, Br, I, CN, NO$_2$, N(Ar$^1$)$_2$, N(R$^2$)$_2$, C(═O)Ar$^1$, C(═O)R$^2$, P(═O)(Ar$^1$)$_2$, P(Ar$^1$)$_2$, B(Ar$^1$)$_2$, Si(Ar$^1$)$_3$, Si(R$^2$)$_3$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R$^2$ radicals, wherein one or more nonadjacent CH$_2$ groups are optionally replaced by —R$^2$C═CR$^2$—, Si(R$^2$)$_2$, C═O, C═S, C═NR$^2$, —C(═O)O—, —C(═O)NR$^2$—, NR$^2$, P(═O)(R$^2$), —O—, —S—, SO, or SO$_2$, and wherein one or more hydrogen atoms are optionally replaced by D, F, Cl, Br, I, CN, or NO$_2$, or an aromatic or heteroaromatic ring system having 5 to 40 aromatic ring atoms, each of which is optionally substituted by one or more R$^2$ radicals, or an aryloxy or heteroaryloxy group having 5 to 40 aromatic ring atoms and which is optionally substituted by one or more R$^2$ radicals, or an aralkyl or heteroaralkyl group having 5 to 40 aromatic ring atoms and which is optionally substituted by one or more R$^2$ radicals, or a combination of these systems; and wherein two or more R$^1$ together optionally define a mono- or polycyclic, aliphatic, or aromatic ring system;

Ar$^1$ is the same or different in each instance and is an aromatic or heteroaromatic ring system having 5 to 30 aromatic ring atoms and which is optionally substituted by one or more nonaromatic R$^2$ radicals; and wherein two Ar$^1$ bonded to the same silicon atom, nitrogen atom, phosphorus atom, or baron atom are optionally also joined together via a single bond or a bridge selected from the group consisting of B(R$^2$), C(R$^2$)$_2$, Si(R$^2$)$_2$, C═O, C═NR$^2$, C═C(R$^2$)$_2$, O, S, S═O, SO$_2$, N(R$^2$), P(R$^2$), and P(═O)R$^2$;

R² is the same or different in each instance and is H, D, F, Cl, Br, I, CN, B(OR³)₂, CHO, C(=O)R³, CR³=C(R³)₂, C(=O)OR³, C(=O)N(R³)₂, Si(R³)₃, P(R³)₂, B(R¹³)₂, N(R³)₂, NO₂, P(=O)(R³)₂, OSO₂R³, OR³, S(=O)R³, S(=O)₂R³, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more R³ radicals, wherein one or more nonadjacent CH₂ groups are optionally replaced by —R³C=CR³—, Si(R³)₂, C=O, C=S, C=NR³, —C(=O)O—, —C(=O)NR³—, NR³, P(=O)(R³), —O—, —S—, SO, or SO₂ and wherein one or more hydrogen atoms are optionally replaced by D, F, Cl, Br, I, CN, or NO₂, or an aromatic or heteroaromatic ring system having 5 to 40 aromatic ring atoms and which is optionally substituted in each case by one or more R³ radicals, or an aryloxy or heteroaryloxy group having 5 to 40 aromatic ring atoms and which is optionally substituted by one or more R³ R³ radicals, or a combination of these systems; and wherein two or more adjacent R² together optionally define a mono- or polycyclic, aliphatic, or aromatic ring system;

R³ is the same or different in each instance and is H, D, F, or an aliphatic, aromatic, and/or heteroaromatic hydrocarbyl radical having 1 to 20 carbon atoms, wherein hydrogen atoms are also optionally replaced by F; and wherein two or more adjacent R³ together optionally define a mono- or polycyclic, aliphatic, or aromatic ring system;

n is 0, 1, 2, or 3.

2. The compound of claim 1, wherein the compound comprises a compound of formula (I), (II), or (III):

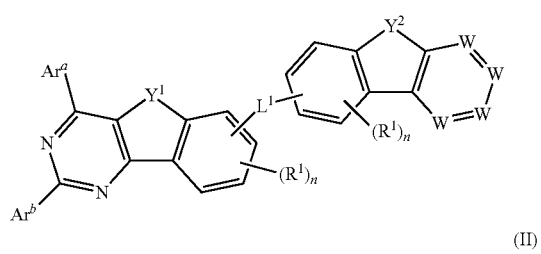

(I)

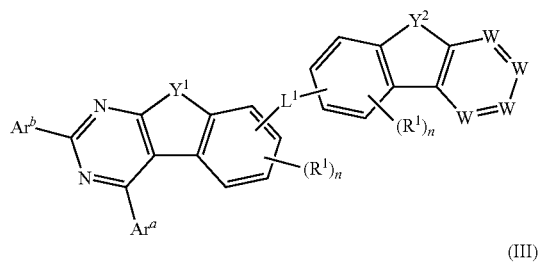

(II)

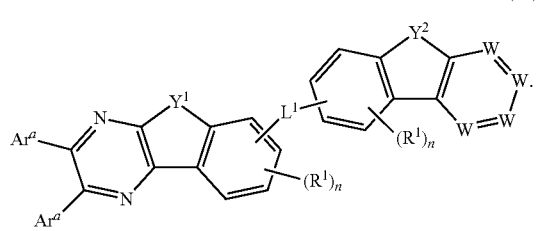

(III)

3. The compound of claim 1, wherein the compound is a compound of formulae (Ia), (IIa), or (IIIa):

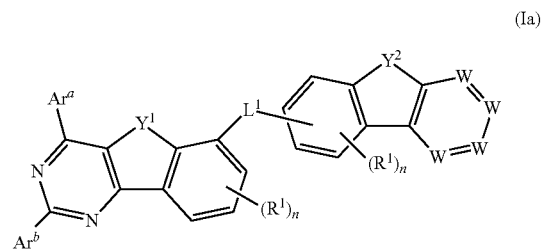

(Ia)

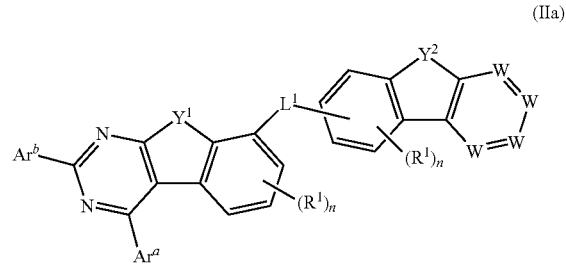

(IIa)

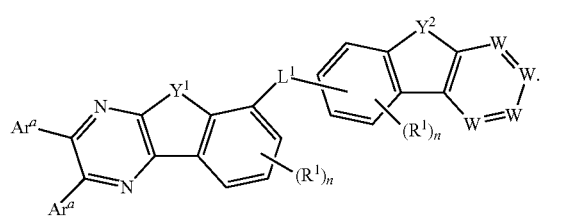

(IIIa)

4. The compound of claim 1, wherein the compound is a compound of formulae (Ib), (IIb), or (IIIb):

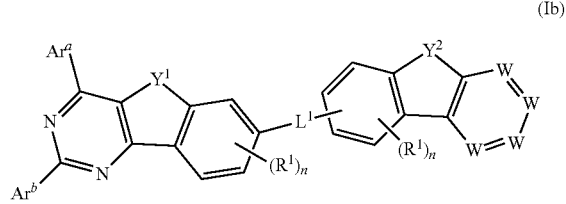

(Ib)

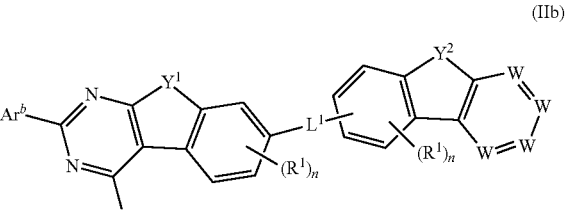

(IIb)

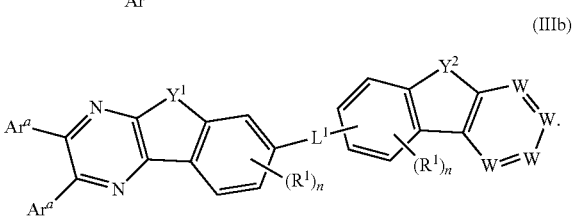

(IIIb)

5. The compound of claim 1, wherein the compound is a compound of formulae (Ic), (IIc), or (IIc):

(Ic)
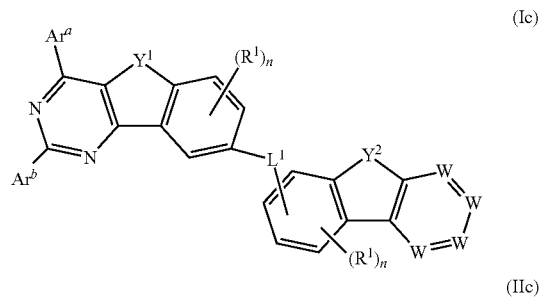

(IIc)
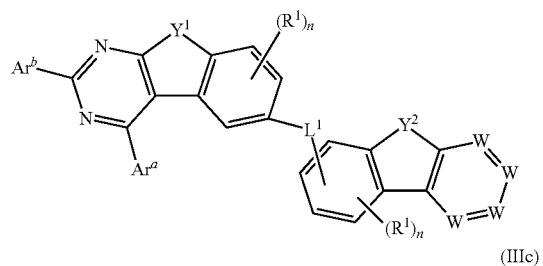

(IIIc)
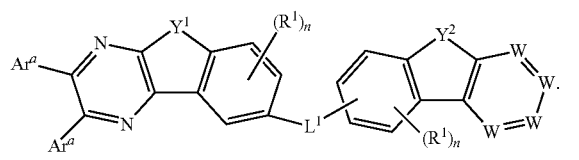

6. The compound of claim 1, wherein the compound is a compound of formulae (Id), (IId), or (IIId):

(Id)
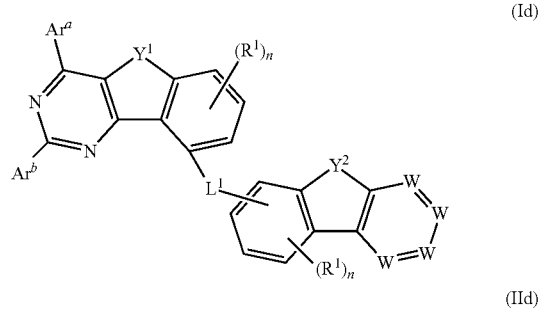

(IId)
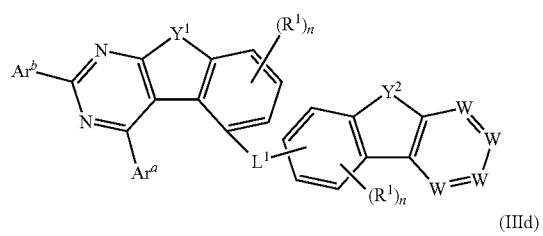

(IIId)
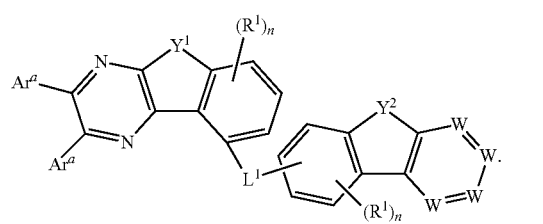

7. The compound of claim 1, wherein the compound is a compound of formulae (Ie), (IIe), or (IIIe):

(Ie)
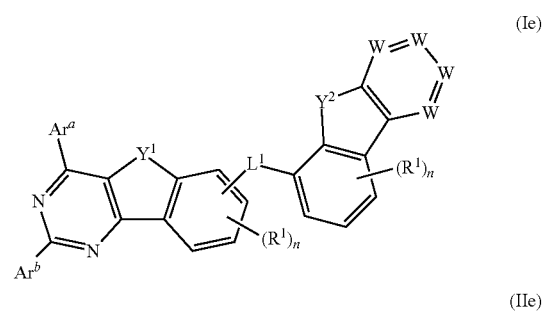

(IIe)
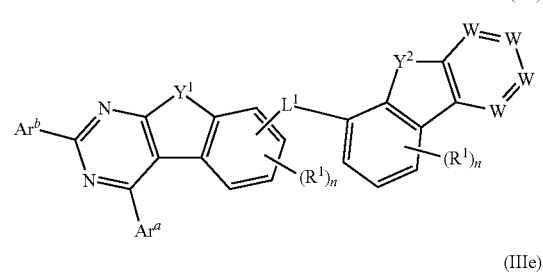

(IIIe)
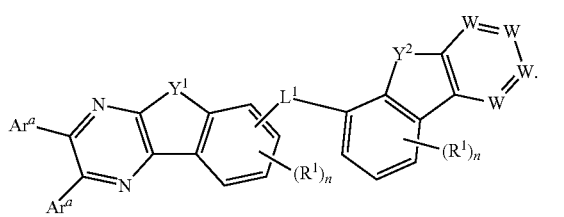

8. The compound of claim 1, wherein the compound is a compound of formulae (If), (IIf), or (IIIf):

(If)
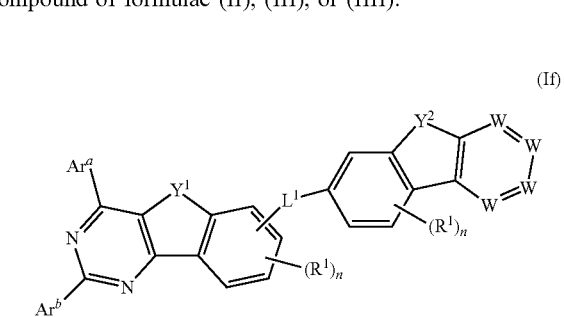

(IIf)
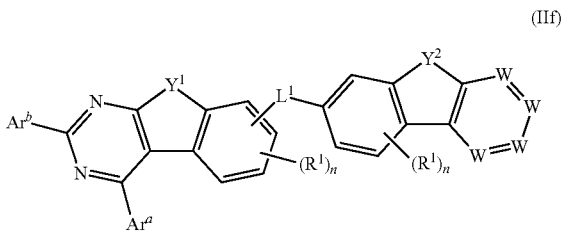

(IIIf)
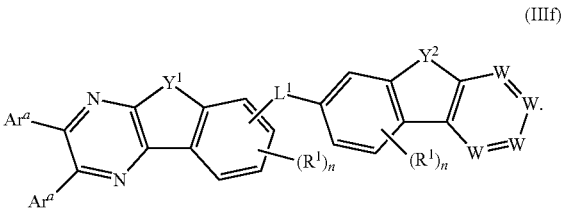

9. The compound of claim 1, wherein the compound is a compound of formulae (Ig), (IIg), or (IIIg):

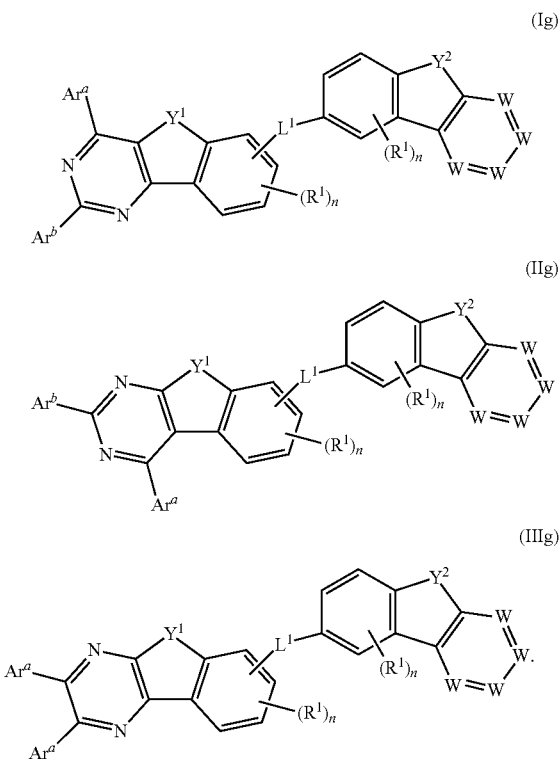

10. The compound of claim 1, wherein the compound is a compound of formulae (Ih), (IIh), or (IIIh):

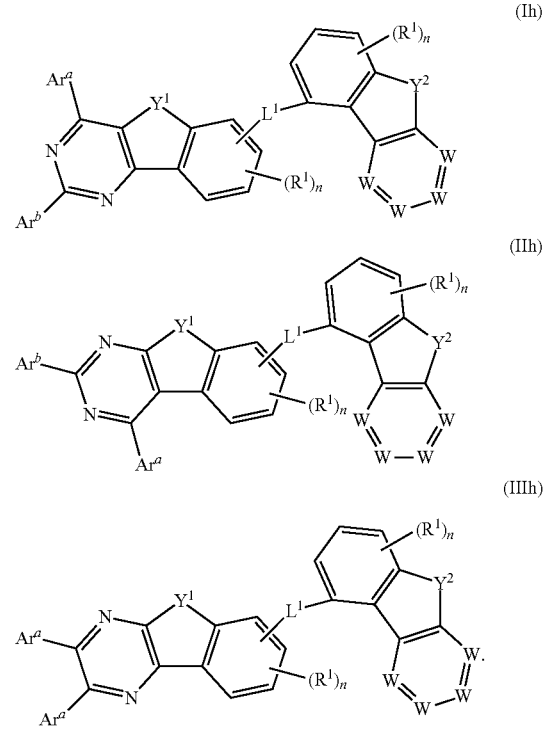

11. The compound of claim 1, wherein Y² is C(R¹)₂ and R¹ is the same or different in each instance and is an aromatic or heteroaromatic ring system having 5 to 40 aromatic ring atoms and which are optionally substituted in each case by one or more R² radicals.

12. The compound of claim 1, wherein Y² is a group of formula (Y²-2):

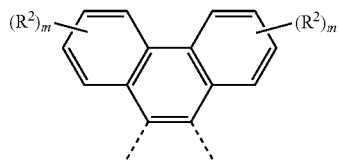

wherein the dotted lines denote the bonds to the adjacent atoms and m is 0, 1, 2, 3, or 4.

13. The compound of claim 1, wherein Ar^b is a group of formula (Ar^b-1):

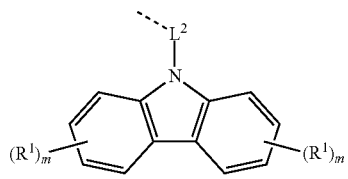

wherein
L² is a bond or an aromatic or heteroaromatic ring system having 5 to 30 aromatic ring atoms and which is optionally substituted by one or more R¹ radicals;
m is 0, 1, 2, 3, or 4; and
the dotted line denotes the bond.

14. An oligomer, polymer, or dendrimer comprising one or more compounds according to claim 1, wherein one or more bonds of the compound to the polymer, oligomer, or dendrimer are present.

15. A composition comprising at least one compound of claim 1 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

16. A composition comprising at least one oligomer, polymer, or dendrimer of claim 14 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

17. A formulation comprising at least one compound of claim 1 and at least one solvent.

18. A formulation comprising at least one oligomer, polymer, or dendrimer of claim 14 and at least one solvent.

19. A formulation comprising at least one composition of claim 15 and at least one solvent.

20. A formulation comprising at least one composition of claim 16 and at least one solvent.

21. A process for preparing the compound of claim 1, comprising joining a compound comprising at least one diazadibenzofuran or diazadibenzothiophene group to a group comprising at least one, fluorene, and/or phenanthrene radical in a coupling reaction.

22. A process for preparing an oligomer, polymer, or dendrimer of claim 14, comprising joining a compound comprising at least one diazadibenzofuran or diazadibenzothiophene group to a group comprising at least one and/or phenanthren radical in a coupling reaction.

23. An electronic device comprising at least one compound of claim 1.

24. An electronic device comprising at least one oligomer, polymer, or dendrimer of claim 14.

25. The electronic device of claim 23, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

26. The electronic device of claim 24, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

27. A compound of formula (A):

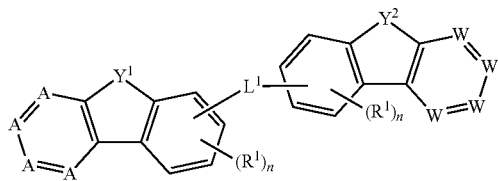

wherein
$Y^1$ is O or S;
$Y^2$ is N(Ar), O, $C(R^1)_2$, or $-R^1C=CR^1-$;
W is the same or different in each instance and is N or $CR^1$, with the proviso that not more than two W in one cycle are N, wherein the $R^1$ radicals in the W groups do not form a fused heteroaromatic ring system;
$L^1$ is a bond or an aromatic or heteroaromatic ring system having 5 to 30 aromatic ring atoms and which is optionally substituted by one or more $R^1$ radicals;
A is the same or different in each instance and is N, $CAr^a$, or $CAr^b$, wherein exactly two A are N separated by at least one $CAr^a$ or $CAr^b$ group, with the proviso that A is $CAr^b$ if two N are adjacent to this A;
Ar is the same or different in each instance and is an aromatic or heteroaromatic ring system having 5 to 30 aromatic ring atoms and which is optionally substituted by one or more radicals $R^1$;
$Ar^a$ is the same or different in each instance and is an aromatic or heteroaromatic ring system having 5 to 30 aromatic ring atoms and which is optionally substituted by one or more radicals R';
$Ar^b$ is a group of formula ($Ar^b$-1):

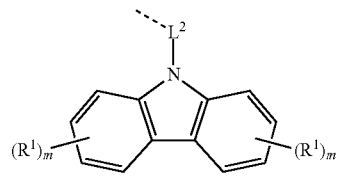

wherein
$L^2$ is a bond or an aromatic or heteroaromatic ring system having 5 to 30 aromatic ring atoms and which is optionally substituted by one or more $R^1$ radicals;
m is 0, 1, 2, 3, or 4; and
the dotted line denotes the bond,
$R^1$ is the same or different in each instance and is H, D, F, Cl, Br, I, CN, $NO_2$, $N(Ar^1)_2$, $N(R^2)_2$, $C(=O)Ar^1$, $C(=O)R^2$, $P(=O)(Ar^1)_2$, $P(Ar^1)_2$, $B(Ar^1)_2$, $Si(Ar^1)_3$, $Si(R^2)_3$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more $R^2$ radicals, wherein one or more nonadjacent $CH_2$ groups are optionally replaced by $-R^2C=CR^2-$, $Si(R^2)_2$, C=O, C=S, $C=NR^2$, $-C(=O)O-$, $-C(=O)NR^2-$, $NR^2$, $P(=O)(R^2)$, $-O-$, $-S-$, SO, or $SO_2$, and wherein one or more hydrogen atoms are optionally replaced by D, F, Cl, Br, I, CN, or $NO_2$, or an aromatic or heteroaromatic ring system having 5 to 40 aromatic ring atoms, each of which is optionally substituted by one or more $R^2$ radicals, or an aryloxy or heteroaryloxy group having 5 to 40 aromatic ring atoms and which is optionally substituted by one or more $R^2$ radicals, or an aralkyl or heteroaralkyl group having 5 to 40 aromatic ring atoms and which is optionally substituted by one or more $R^2$ radicals, or a combination of these systems; and wherein two or more $R^1$ together optionally define a mono- or polycyclic, aliphatic, or aromatic ring system;
$Ar^1$ is the same or different in each instance and is an aromatic or heteroaromatic ring system having 5 to 30 aromatic ring atoms and which is optionally substituted by one or more nonaromatic $R^2$ radicals; and wherein two $Ar^1$ bonded to the same silicon atom, nitrogen atom, phosphorus atom, or baron atom are optionally also joined together via a single bond or a bridge selected from the group consisting of $B(R^2)$, $C(R^2)_2$, $Si(R^2)_2$, C=O, $C=NR^2$, $C=C(R^2)_2$, O, S, S=O, $SO_2$, $N(R^2)$, $P(R^2)$, and $P(=O)R^2$;
$R^2$ is the same or different in each instance and is H, D, F, Cl, Br, I, CN, $B(OR^3)_2$, $-CHO$, $C(=O)R^3$, $CR^3=C(R^3)_2$, $C(=O)OR^3$, $C(=O)N(R^3)_2$, $Si(R^3)_3$, $P(R^3)_2$, $B(R^{13})_2$, $N(R^3)_2$, $NO_2$, $P(=O)(R^3)_2$, $OSO_2R^3$, $OR^3$, $S(=O)R^3$, $S(=O)_2R^3$, a straight-chain alkyl, alkoxy, or thioalkoxy group having 1 to 40 carbon atoms or a branched or cyclic alkyl, alkoxy, or thioalkoxy group having 3 to 40 carbon atoms, each of which is optionally substituted by one or more $R^3$ radicals, wherein one or more nonadjacent $CH_2$ groups are optionally replaced by $-R^3C=CR^3-$, $Si(R^3)_2$, C=O, C=S, $C=NR^3$, $-C(=O)O-$, $-C(=O)NR^3-$, $NR^3$, $P(=O)(R^3)$, $-O-$, $-S-$, SO, or $SO_2$ and wherein one or more hydrogen atoms are optionally replaced by D, F, Cl, Br, I, CN, or $NO_2$, or an aromatic or heteroaromatic ring system having 5 to 40 aromatic ring atoms and which is optionally substituted in each case by one or more $R^3$ radicals, or an aryloxy or heteroaryloxy group having 5 to 40 aromatic ring atoms and which is optionally substituted by one or more $R^3$ radicals, or a combination of these systems; and wherein two or more adjacent $R^2$ together optionally define a mono- or polycyclic, aliphatic, or aromatic ring system;
$R^3$ is the same or different in each instance and is H, D, F, or an aliphatic, aromatic, and/or heteroaromatic hydrocarbyl radical having 1 to 20 carbon atoms, wherein hydrogen atoms are also optionally replaced by F; and wherein two or more adjacent $R^3$ together optionally define a mono- or polycyclic, aliphatic, or aromatic ring system;

n is 0, 1, 2, or 3;

with the proviso that, if $Y^2$ is N(Ar) or O, $Ar^a$ does not comprise any carbazole group, including any $R^1$, $R^2$, and $R^3$ substituents bonded to $Ar^a$.

28. The compound of claim 27, wherein the compound comprises a compound of formula (I), (II), or (III):

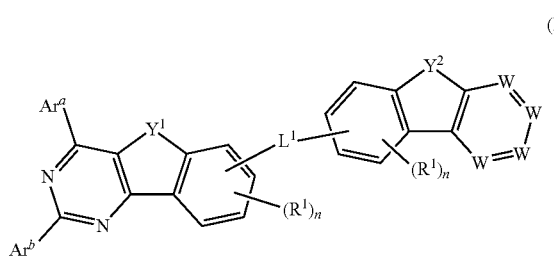
(I)

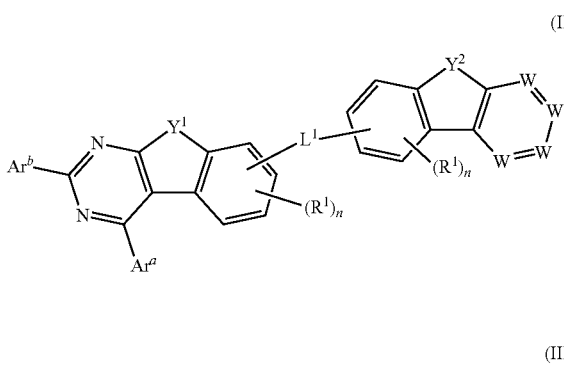
(II)

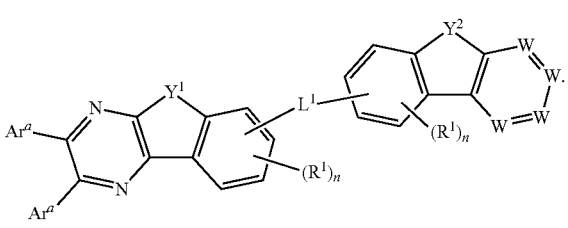
(III)

29. The compound of claim 27, wherein the compound is a compound of formulae (Ia), (IIa), or (IIIa):

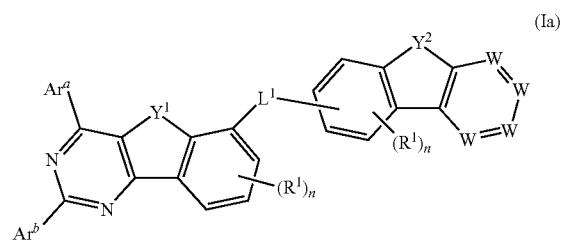
(Ia)

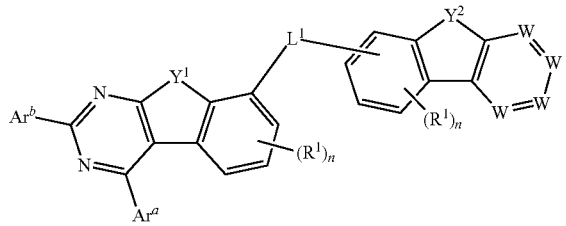
(IIa)

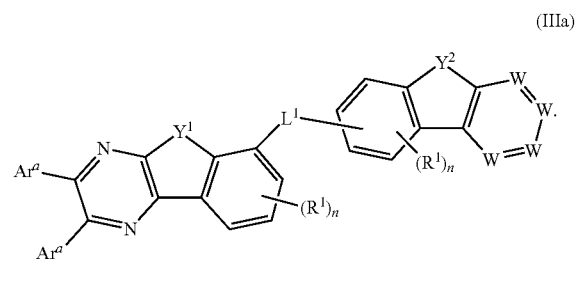
(IIIa)

30. The compound of claim 27, wherein the compound is a compound of formulae (Ib), (IIb), or (IIIb):

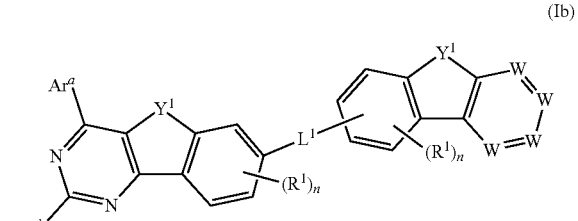
(Ib)

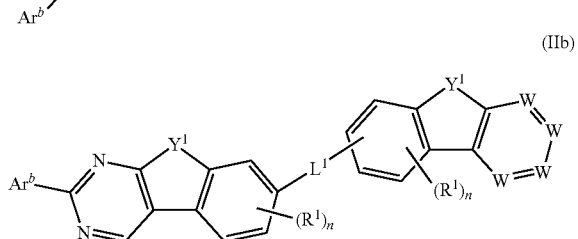
(IIb)

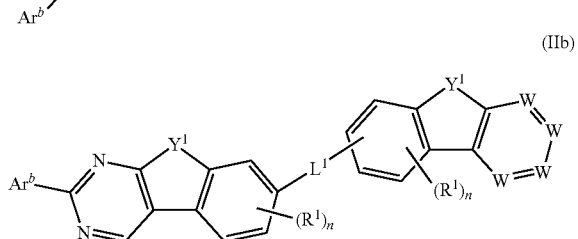
(IIIb)

31. The compound of claim 27, wherein the compound is a compound of formulae (Ic), (IIc), or (IIIc):

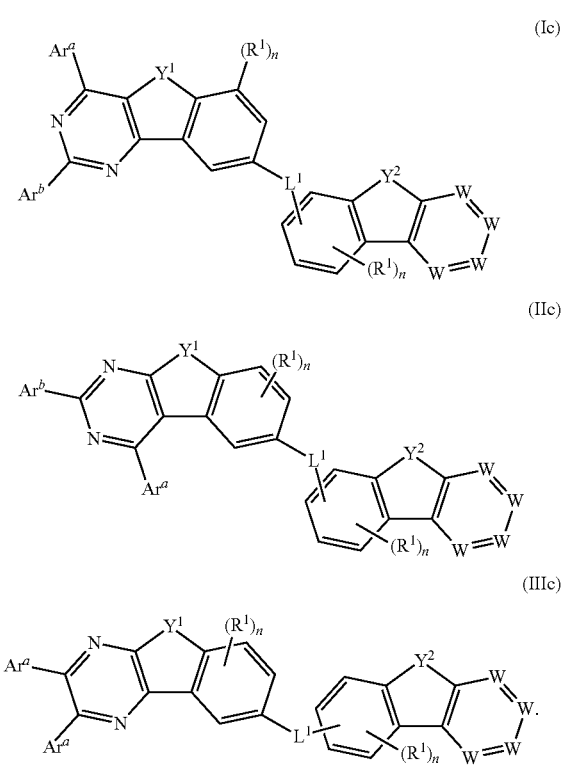
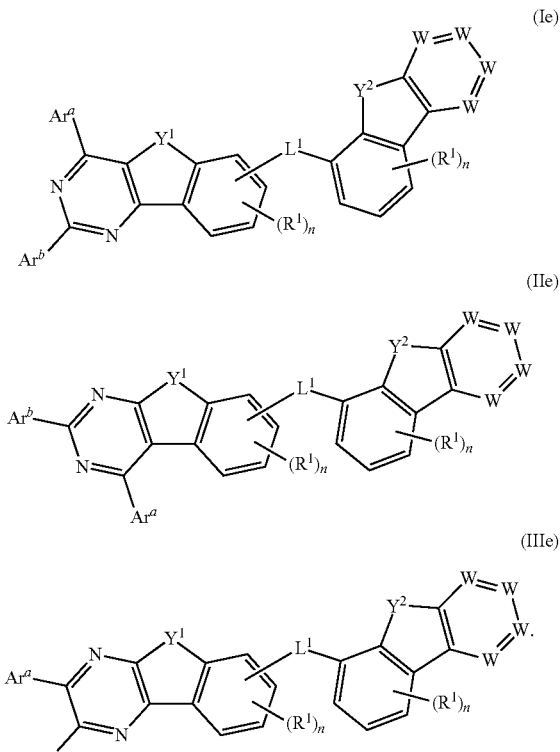
32. The compound of claim 27, wherein the compound is a compound of formulae (Id), (IId), or (IIId):
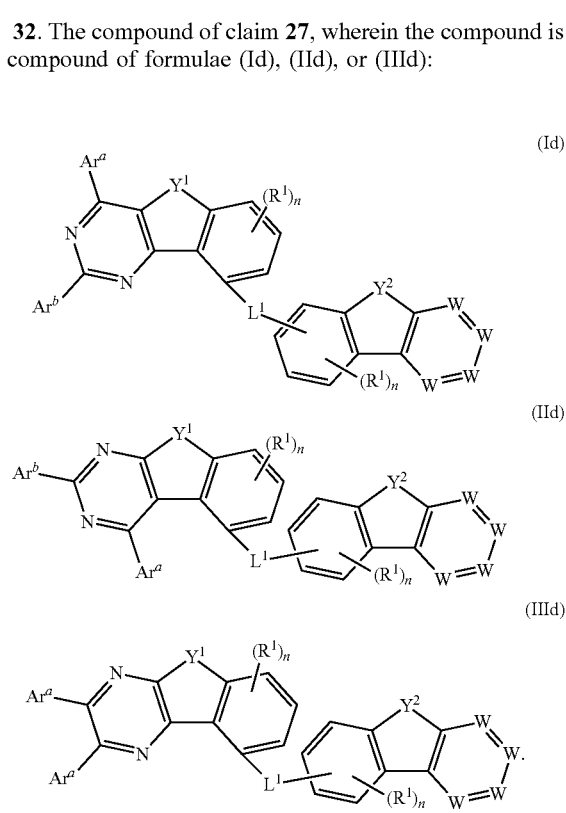
33. The compound of claim 27, wherein the compound is a compound of formulae (Ie), (IIe), or (IIIe):
34. The compound of claim 27, wherein the compound is a compound of formulae (If), (IIf), or (IIIf)
35. The compound of claim 27, wherein the compound is a compound of formulae (Ig), (IIg), or (IIIg):

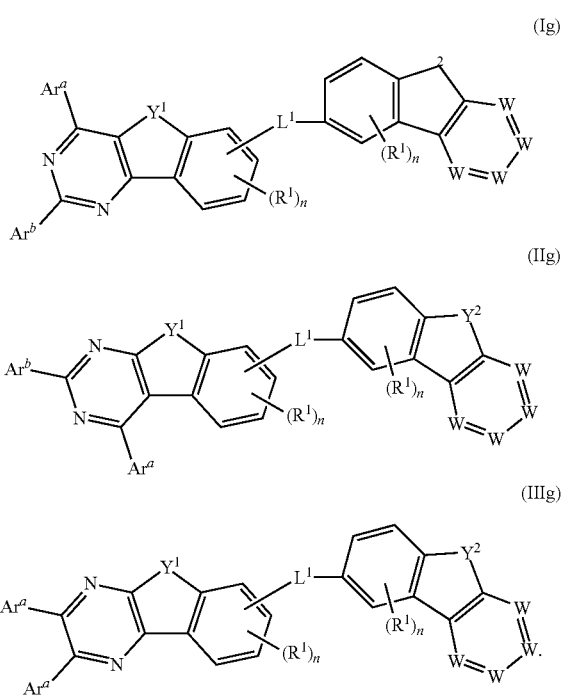

(Ig)
(IIg)
(IIIg)

36. The compound of claim 27, wherein the compound is a compound of formulae (Ih), (IIh), or (IIIh):

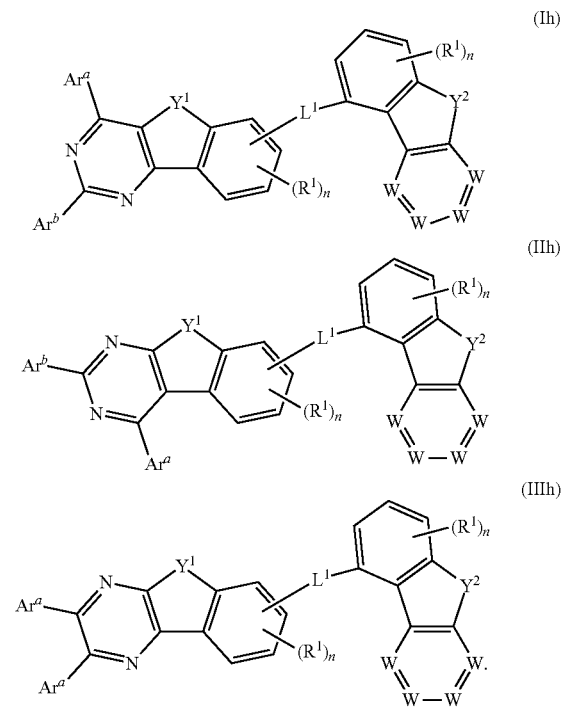

(Ih)
(IIh)
(IIIh)

37. The compound of claim 27, wherein $Y^2$ is $C(R^1)_2$ and $R^1$ is the same or different in each instance and is an aromatic or heteroaromatic ring system having 5 to 40 aromatic ring atoms and which are optionally substituted in each case by one or more $R^2$ radicals.

38. The compound of claim 27, wherein $Y^2$ is a group of formula ($Y^2$-2):

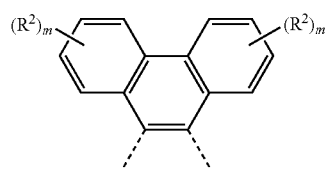

wherein the dotted lines denote the bonds to the adjacent atoms and m is 0, 1, 2, 3, or 4.

39. An oligomer, polymer, or dendrimer comprising one or more compounds according to claim 27, wherein one or more bonds of the compound to the polymer, oligomer, or dendrimer are present.

40. A composition comprising at least one compound of claim 27 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

41. A composition comprising at least one oligomer, polymer, or dendrimer of claim 39 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

42. A formulation comprising at least one compound of claim 27 and at least one solvent.

43. A formulation comprising at least one oligomer, polymer, or dendrimer of claim 39 and at least one solvent.

44. A formulation comprising at least one composition of claim 40 and at least one solvent.

45. A formulation comprising at least one composition of claim 41 and at least one solvent.

46. A process for preparing a compound of claim 27, comprising joining a compound comprising at least one diazadibenzofuran or diazadibenzothiophene group to a group comprising at least one carbazole, fluorene, phenanthrene and/or benzofuran radical in a coupling reaction.

47. A process for preparing an oligomer, polymer, or dendrimer of claim 39, comprising joining a compound comprising at least one diazadibenzofuran or diazadibenzothiophene group to a group comprising at least one carbazole, fluorene, phenanthrene, and/or benzofuran radical in a coupling reaction.

48. An electronic device comprising at least one compound of claim 27.

49. An electronic device comprising at least one oligomer, polymer, or dendrimer of claim 39.

50. The electronic device of claim 48, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

51. The electronic device of claim 49, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells, and organic laser diodes.

52. A process for preparing the compound of claim 2, comprising joining a compound comprising at least one diazadibenzofuran or diazadibenzothiophene group to a group comprising at least one, fluorene, and/or phenanthrene radical in a coupling reaction.

* * * * *